US008088604B2

(12) United States Patent
DeAngelis et al.

(10) Patent No.: US 8,088,604 B2
(45) Date of Patent: Jan. 3, 2012

(54) PRODUCTION OF DEFINED MONODISPERSE HEPAROSAN POLYMERS AND UNNATURAL POLYMERS WITH POLYSACCHARIDE SYNTHASES

(75) Inventors: Paul L. DeAngelis, Edmond, OK (US); Alison Sismey-Ragatz, Cassville, WI (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 579 days.

(21) Appl. No.: 11/906,704

(22) Filed: Oct. 3, 2007

(65) Prior Publication Data

US 2008/0109236 A1 May 8, 2008

Related U.S. Application Data

(63) Continuation-in-part of application No. 11/165,379, filed on Jan. 9, 2007, now Pat. No. 7,579,173, which is a continuation of application No. 10/642,248, filed on Aug. 15, 2003, now Pat. No. 7,223,571, which is a continuation-in-part of application No. 10/195,908, filed on Jul. 15, 2002, now abandoned, which is a continuation-in-part of application No. 09/437,277, filed on Nov. 10, 1999, now Pat. No. 6,444,447, which is a continuation-in-part of application No. 09/283,402, filed on Apr. 1, 1999, now abandoned, said application No. 10/195,908 is a continuation-in-part of application No. 09/842,484, filed on Apr. 25, 2001, now abandoned, said application No. 10/195,908 is a continuation-in-part of application No. 10/142,143, filed on May 8, 2002, now Pat. No. 7,307,159.

(60) Provisional application No. 60/849,034, filed on Oct. 3, 2006, provisional application No. 60/404,356, filed on Aug. 16, 2002, provisional application No. 60/479,432, filed on Jun. 18, 2003, provisional application No. 60/491,362, filed on Jul. 31, 2003, provisional application No. 60/107,929, filed on Nov. 11, 1998, provisional application No. 60/080,414, filed on Apr. 2, 1998, provisional application No. 60/199,538, filed on Apr. 25, 2000, provisional application No. 60/289,554, filed on May 8, 2001, provisional application No. 60/921,296, filed on Mar. 30, 2007.

(51) Int. Cl.

| | |
|---|---|
| ***C12P 19/18*** | (2006.01) |
| ***C12P 19/00*** | (2006.01) |
| ***C12P 19/04*** | (2006.01) |

(52) U.S. Cl. .......................................... 435/97; 435/101

(58) Field of Classification Search ........................ None
See application file for complete search history.

(56) References Cited

U.S. PATENT DOCUMENTS

| | | |
|---|---|---|
| 5,314,876 A | 5/1994 | Lormeau et al. |
| 5,384,398 A | 1/1995 | Lormeau et al. |
| 5,876,433 A | 3/1999 | Lunn |
| 5,958,899 A | 9/1999 | Zoppetti et al. |
| 6,120,536 A | 9/2000 | Ding et al. |
| 6,156,373 A | 12/2000 | Zhong et al. |
| 6,162,797 A | 12/2000 | Zoppetti et al. |

FOREIGN PATENT DOCUMENTS

| | | |
|---|---|---|
| WO | WO 02/89742 A2 | 5/2002 |
| WO | WO 03/029261 A2 | 10/2003 |

OTHER PUBLICATIONS

Ausubel, F. Current Protocols in Molecular Biology, Hybridization Analysis of DNA Blots, pp. 2-10.8.-2.10.11.*
Chica et al. (Curr Opin Biotechnol. Aug. 2005;16(4):378-84.*
Witkowski et al. (Biochemistry. Sep. 7, 1999; 38(36): 11643-50.*
Seffernick et al. (J Bacteriol. Apr. 2001; 183 (8): 2405-10.*
May, B.J. et al. Complete genomic sequence of *Pasteurella multocida*, Pm70. Proc. Natl. Acad. Sci. (USA) Mar. 2001, vol. 98. No. 6, pp. 3460-3465.
Townsend, K.M. et al. Genetic organization of *Pasteurella multocida* cap loci and development of a multiplex capsular typing system. J. Clin. Microbiol. Mar. 2001. vol. 39. No. 3, pp. 924-929.
Hill, A.L., et al.: Identification of the *Xenopus laevis* cDNA for EXT1: A Phylogenetic Perspective. DNA Sequence, 2002 vol. 13 (2), pp. 85-92; ISSN: 10472-5179; Taylor & Francis, Ltd. (USA).
Rimler, R.B.: Presumptive Identification of *Pasteurella multocida serogroups* A, D and F by capsule depolymerisation with mucopolysaccharidases. Veterinary Record (1994) 134, 191-192 (USA).
Poggi A., et al.: Inhibition of B16-BL6 melanoma lung colonies by semisynthetic sulfaminoheparosan sulfates from *E. coli* K5 polysaccharide. Semin Thromb Hemost. Aug. 2002; 28(4): 383-92. vol. 28, No. 4.
Kim, B.T., et al.: Human tumor suppressor EXT gene family members EXTL1 and EXTL3 encode alpha 1,4-N-acetylglucosaminyltransferases that likely are involved in heparan sulfate/heparin biosynthesis. Proc. Natl. Acad. Sci. U.S.A. 2001 Jun. 19, 1998 (13):7176-81.
Vicenzi, E., et al.: Broad spectrum inhibition of HIV-1 infection by sulfated K5 *Escherichia coli* polysaccharide derivatives. AIDS. Jan. 24, 2003; 17 (2): 177-81; ISSN: 0269-9370 Lippincott Williams & Wilkins; Italy.
Lin, X, et al.: Expression and functional analysis of mouse EXT1, a homolog exostoses type 1 gene. Biochem Biophys Res Commun. Jul. 30, 1998; 248(3): 738-43; Academic Press.
Legeai-Mallet L., et al.: EXT 1 Gene Mutation Induces Chondrocyte Cytoskeletal Abnormalities and Defective Collagen Expression in the Exostoses. J Bone Miner Res. Aug. 2000; 15(8):1489-500.

(Continued)

*Primary Examiner* — Tekchand Saidha
*Assistant Examiner* — Younus Meah
(74) *Attorney, Agent, or Firm* — Dunlap Codding, P.C.

(57) ABSTRACT

The present invention relates to methodology for polymer grafting by a polysaccharide synthase and, more particularly, polymer grafting using the hyaluronate or chondroitin or heparin/heparosan synthases from *Pasteurella*, in order to create a variety of glycosaminoglycan oligosaccharides having a natural or chimeric or hybrid sugar structure with a targeted size that are substantially monodisperse in size. The present invention also relates to methodology for polymer grafting by a polysaccharide synthase to form glycosaminoglycan polymers having an unnatural structure.

17 Claims, 21 Drawing Sheets

OTHER PUBLICATIONS

McCormick, C., et al.: The putative tumor suppressor EXT1 alters the expression of cell-surface heparan sulfate. Nat. Genet. Jun. 1998; 19(2):158-61. (Canada).
Ahn, J., et al.: Cloning of the putative tumor suppressor gene for hereditary multiple exostoses (EXT1). Nat. Genet. Oct. 1995; 11(2):137-43.
Stickens, D., et al.: The EXT2 multiple exostoses gene defines a family of putative tumor suppressor genes. Nat. Genet. Sep. 1996; 14(1):25-32.
Simmons, A.D., et al.: A direct interaction between EXT proteins and glycosyltransferases is defective in hereditary multple exostoses. Hum. Mol. Genet. Nov. 1999; 8(12):2155-64.
Hagner-McWhirter A., et al.: Biosynthesis of heparin/heparan sulfate: kinetic studies of the glucuronyl C5-epimerase with N-sulfated derivatives of the *Escherichia coli* K5 capsular polysaccharide as substrates. Glycobiology. Feb. 2000; 10(2):159-71. Oxford University Press. (USA).
Lidholt, K., et al.: Biosynthesis of heparin. The D-glucuronosyl- and N-acetyl-D-glucosaminyltransferase reactions and their relation to polymer modification. Biochem J. Oct. 1, 1992;287 (pt 1):21-9 (Sweden).
Lin, X, et al.: Disruption of gastrulation and heparan sulfate biosynthesis in EXT1-Deficient Mice. Dev. Biol. Aug. 15, 2000; 224(2):299-311. Academic Press. (USA).
Van Hul, W., et al.: Identification of a Third EXT-like Gene (EXTL3) Belonging to the EXT Gene Family; Genomics. Jan. 15, 1998;47(2):230-7. Academic Press. (Belgium).
Nader, H.B., et al.: New insights on the specificity of heparin and haparan sulfate lyases from *Flavobacterium heparinum* revealed by the use of synthetic derivatives of K5 polysaccharide from *E. coli* and 2-O-desulfated heparin. Glycoconj J. Jun. 1999; 16(6):265-70. Kluwer Academic Publishers. Manufactured in The Netherlands. (Brazil).
DeAngelis, P.L., et al.: Identification and Molecular Cloning of a Heparosan Synthase from *Pasteurella multocida* Type D. The Journal of Biological Chemistry. vol. 277, No. 9, ISSN: Mar. 1, pp. 7209-7213, 2002. (USA).
Naggi, A., et al.: Toward a Biotechnological Heparin through Combined Chemical and Enzymatic Modification of the *Escherichia coli* K5 Polysaccharide. Seminars in Thrombosis and Hemostasis, vol. 27, No. 5, 2001; pp. 437-443. (Italy).
Leali, D., et al.: Fibroblast Growth Factor-2 Antagonist Activity and Angiostatic Capacity of Sulfated *Escherichia coli* K5 Polysaccharide Derivatives. The Journal of Biological Chemistry, vol. 276, No. 41. ISSN: Oct. 12, pp. 37900-37908, 2001. (Italy).
Duncan, G., et al.: The link between heparan sulfate and hereditary bone disease: finding a function for the EXT family of putative tumor suppressor proteins. The Journal of Clinical Investigation, Aug. 2001, vol. 108, No. 4, pp. 511-516. (USA).
Kim, B-T, et al.: Demonstration of a Novel Gene DEXT3 of *Drosophila melanogaster* as the Essential *N*-Acetylglucosamine Transferase in the Heparan Sulfate Biosynthesis. The Journal of Biological Chemistry, vol. 277, No. 16, ISSN: Apr. 19, pp. 13659-13665, 2002. (Sweden).
Sugahara, K., et al.: Heparin and Heparan Sulfate Biosynthesis. Life, 54:163-175, 2002. (Japan).
Lind, T., et al.: Biosynthesis of Heparin/Heparan Sulfate. The Journal of Biological Chemistry, vol. 268, No. 28, ISSN: Oct. 5, pp. 20705-20708, 1993. (Sweden).
Wei, G., et al.: Location of the Glucuronosyltransferase Domain in the Heparan Sulfate Copolymerase EXT1 by Analysis of Chinese Hamster Ovary Cell Mutants. The Journal of Biological Chemistry, vol. 275, No. 36, ISSN: Sep. 8, pp. 27733-27740, 2000. (USA).
Razi, N., et al.: Structural and functional properties of heparin analogues obtained by chemical sulphation of *Escherichia coli* K5 capsular polysaccharide. Biochem J. Jul. 15, 1995;309 (pt2):465-72. (Sweden).
Kusche, M., et al.: Biosynthesis of heparin. Use of *Escherichia coli* K5 capsular polysaccharide as a model substrate in enzymic polymer-modification reactions. Biochem J. Apr. 1, 1991;275 (pt1):151-8. (Sweden).
Casu, B., et al.: Heparin-like compounds prepared by chemical modification of capsular polysaccharide from *E. coli*. Elsevier Science 1994; pp. 271-284. (Italy).
Vann, W.F., et al.: The Structure of the Capsular Polysaccharide (K5 Antigen) of Urinary-Tract-Infective *Escherichia coli* 010:K5:H4. Biochem J. 1981; 116; pp. 359-364. (Germany).
Toyoda, H., et al.: Structural Analysis of Glycosaminoglycans in *Drosophila* and *Caenorhabditis elegans* and Demonstrations That *tout-velu*, a *Drosophila* Gene Related to EXT Tumor Suppressors, Affects Heparan Sulfate in Vivo. The Journal of Biological Chemistry, vol. 275, No. 4; ISSN: Jan. 28, pp. 2269-2275, 2000. (Japan).
Zak, B.M., et al.: Hereditary multiple exostoses and heparan sulfate polymerization. Biochimica et Biophysica Acta 1573 (2002) 346-355. (USA).
Katada, T., et al.: cDNA cloning and distribution of XEXT1, the *Xenopus* homologue of EXT1. Dev Genese Evol. (2002) 212:248-250. (Japan).
Kitagawa, H., et al.: The Tumor Suppressor EXT-like Gene EXTL2 Encodes an 1, 4-N-Acety1hexosaminylatransferase That Transfers N-Acetylgalactosamine and N-Acetylglucosamine to the Common Clycosaminoglycan-Protein Linkage Region. The Journal of Biological Chemistry. 263(20):13933-139337.
Kitagawa, H., et al.: rib-2, a *Caenorhabditis elegans* Homolog of the Human Tumor Suppressor EXT Genes Encodes a Novel 1,4-N-Acetylglucosaminyltransferase Involved in the Biosynthetic Initiation and Elongation of Heparan Sulfate. The Journal of Biological Chemistry, vol. 276, No. 7; ISSN: Feb. 16, pp. 4834-4838, 2001. (Japan).
Song, G., et al.: Identification of mutations in the human EXT1 and EXT2 genes. Chin J. Med. Genet., Aug. 1999, vol. 16. No. 4, pp. 208-210. (China).
Clines, G.A., et al.: The Structure of the Human Multiple *Exostoses 2* Gene and Characterization of Homologs in Mouse and *Caenorhabditis elegans*. Cold Spring Harbor Laboratory Press 1997; ISSN: 1057-9803, pp. 359-367. (USA).
Wise, C.A., et al.: Identification and Localization of the Gene for EXTL, a Third Member of the Multiple Exostoses Gene Family. Cold Spring Harbor Laboratory Press 1997; ISSN: 1057-9803, pp. 10-16. (USA).
Linhardt, R.J., et al.: Production and Chemical Processing of Low Molecular Weight Heparins. Thieme Medical Publishers, Inc. 1999, vol. 25, Suppl. 3, pp. 5-16. (USA).
Fareed, J.: Heparin, Its Fractions, Fragments and Derivatives. Some Newer Perspectives. Seminars in Thrombosis and Hemostasis, vol. 11, No. 1, 1985, pp. 1-9.
Lind, T., et al.: The Putative Tumor Suppressors EXT1 and EXT2 Are Glycosyltransferases Required for the Biosynthesis of Heparan Sulfate. The Journal of Biological Chemistry, vol. 273, No. 41, ISSN: Oct. 9, pp. 26265-26268, 1998. (Sweden).
Senay, C., et al.: The EXT1/EXT2 tumor suppressors: catalytic activities and role in heparan sulfate biosynthesis. EMBO Reports vol. 1, No. 3, pp. 282-286, 2000. ((Sweden).
Bio Tie Therapies; BioHeparin—Prospectus; Jun. 2001. (Finland).
Sasisekharan, R., et al.: Heparin and heparan sulfate: biosynthesis, structure and function. Elsevier Science, Ltd. 2000; 1367-5931; pp. 626-631. (USA).
Pedersen, L.C., et al.: Heparan/Chondroitin Sulfate Biosynthesis. The Journal of Biological Chemistry, vol. 275, No. 44; ISSN: Nov. 3, pp. 34580-34585, 2000. (USA).
Finke, A., et al.: Biosynthesis of the *Escherichia coli* K5 Polysaccharide, a Representative of Group II Polysaccharides: Polymerization In Vitro and Characterization of the Product. Journal of Bacteriology, Jul. 1999, pp. 4088-4094. (Germany).
Griffiths, G., et al.: Characterization of the Glycosyltransferase Enzyme from the *Escherichia coli* K5 Capsule Gene Cluster and Identification and Charaterization of the Glucuronyl Active Site. The Journal of Biological Chemistry, vol. 273, No. 19, ISSN: May 8, pp. 11752-11757, 1998. (United Kingdom).
Hodson, N., et al.: Identification That KfiA, a Protein Essential for the Biosynthesis of the *Escherichia coli* K5 Capsular Polysaccharide, Is a UDP-GlcNAc Glycosyltransferase. The Journal of Biological Chemistry, vol. 275, No. 35, ISSN: Sep. 1, pp. 27311-27315, 2000. (United Kingdom).

Boyce, J.D., et al.: *Pasteurella multocida* capsule: composition, function and genetics. Journal of Biotechnology 83 (2000) pp. 153-160. (Australia).
Rimler, R.B., et al.: Influence of chondroitinase on direct hemagglutination titers and phagocytosis of *Pasteurella multocida* serogroups A, D and F. Veterinary Microbiology 47 (1995) pp. 287-294. (USA).
Rigg, G.P., et al.: The localization of KpsC, S and T, and KfiA, C and D Proteins Involved in the biosynthesis of the *Escherichia coli* K5 capsular polysaccharide: evidence for a membrane-bound complex. Microbiology (1998), 144, 2905-2914. (United Kingdom).
DeAngelis, P.L., et al.: Identification of the capsular polysaccharides of Type D and F *Pasteurella multocida* as unmodified heparin and chondroitin, respectively. Carbohydrate Research 337 (2002) pp. 1547-1552. (USA).
Jing, W., et al.: Structure function analysis of *Pasteurella* glycosaminoglycan synthesis. Glycobiology 2002 12: abstract 188. (USA).
McCormick, C., et al.: The putative tumor suppressors EXT1 and EXT2 form a stable complex that accumulates in the Golgi apparatus and catalyzes the synthesis of heparan sulfate. PNAS, Jan. 18, 2000, vol. 97, No. 2, pp. 668-673. (Canada).
Cheung, P.K., et al.: Etiological Point Mutations in the Hereditary Multiple Exostoses Gene EXT1: A Functional Analysis of Heparan Sulfate Polymerase Activity. Am. J. Hum. Genet. 69:55-66, 2001. (Canada).
Wyatt Technology Corporation: Heparin Characterization. Apr. 5, 1997; www.tigc.org.
Soldani, G., et al.: Experimental and Clinical Pharmacology of Glycosaminoglycans (GAGs). Drugs Exptl. Clin. Res. XVII(1) 81-85 (1991). (Italy).
Van Aken, H., et al.: Anticoagulation: The Present and Future. Clin. Appl. Thrombosis/Hemostasis, 7(3): 195-204, 2001. (Germany).
Lidholt, K., et al.: Substrate specificities of glycosyltransferases involved in formation of heparin precursor and *E. Coli* K5 capsular polysaccharides. Carbohydrate Research, 255 (1994) 87-101. (Sweden).
Roberts, I., et al.: Molecular Cloning and Analysis of Genes for Production of K5, K7, K12, and K92 Capsular Polysaccharides in *Escherichia coli*. J. Bacteriology; Dec. 1986, pp. 1228-1233. (Germany).
Kroncke, K.D., et al.: Expression of the *Escherichia coli* K5 Capsular Antigen: Immunoelectron Microscopic and Biochemical Studies with Recombinant *E. coli*. J. Bacteriology, Feb. 1990, pp. 1085-1091. (Germany).
Roberts, I.S., et al.: Common Organization of Gene Clusters for Production of Different Capsular Polysaccharides (K Antigens) in *Escherichia coli*. J. Bacteriology, Mar. 1988, pp. 1305-1310. (United Kingdom).
Petit, C., et al.: Region 2 of the *Escherichia coli* K5 capsule gene cluster encoding proteins for the biosynthesis of the K5 polysaccharide. Molecular Microbiology (1995) 17(4), pp. 611-620. (United Kingdom).
Smith, A.N., et al.: Molecular analysis of the *Escherichia coli* K5 *kps* locus: identification and characterization of an inner-membrane capsular polysaccharide transport system. Molecular Microbiology (1990) 4(11), pp. 1863-1869. (United Kingdom).
Bronner, D., et al.: Synthesis of the K5 (group II) capsular polysaccharide in transport-deficient recombinant *Escherichia coli*. FEMS Microbiology Letters 113 (1993), pp. 273-284. (Germany).
Pandit, K.K., et al.: Capsular hyaluronic acid in *Pasteurella multocida* type A and its counterpart in type D. Research in Veterinary Science. 54:20-24 (1993).
DeAngelis, P.; "Microbial glycosaminoglycan glycosyltransferases". Glysobiology, vol. 12(1): 9R-16R (2002).

* cited by examiner

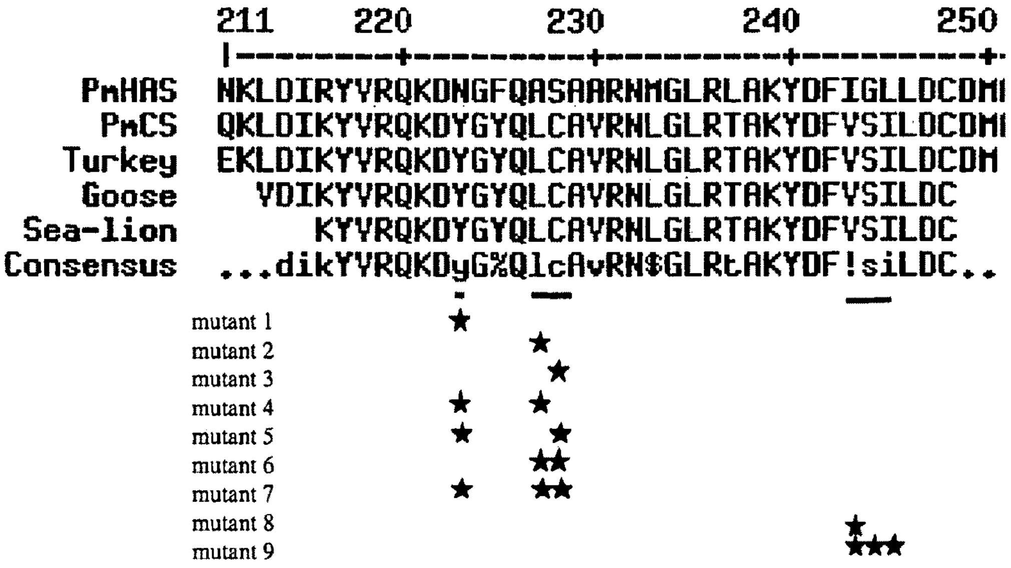

Figure 1

```
           211       220       230       240       250
        |---------+---------+---------+---------+---------+-
   PmHAS   NKLDIRYVRQKDNGFQASAARNMGLRLAKYDFIGLLDCDMI
   PmCS    QKLDIKYVRQKDYGYQLCAVRNLGLRTAKYDFVSILDCDMI
   Turkey  EKLDIKYVRQKDYGYQLCAVRNLGLRTAKYDFVSILDCDM
   Goose       VDIKYVRQKDYGYQLCAVRNLGLRTAKYDFVSILDC
   Sea-lion      KYVRQKDYGYQLCAVRNLGLRTAKYDFVSILDC
   Consensus  ...dikYVRQKDyG%QlcAvRN$GLRtAKYDF!siLDC..
```

mutant 1
mutant 2
mutant 3
mutant 4
mutant 5
mutant 6
mutant 7
mutant 8
mutant 9 pm-EG pm-FH pmCS$^{1-214}$-HAS$^{222-265}$-CS$^{258-704}$ pmHAS$^{1-221}$-CS$^{215-258}$-HAS$^{266-703}$

| enzyme | activity: HAS | CS | GlcUA-Tase |
|---|---|---|---|
| pm-BD | - | + | + |
| pm-AC | + | - | + |
| pm-FH | - | + | + |
| pm-EG | - | - | + |
| Pm-JL | + | - | + |
| pm-IK | - | - | + |
| pmCHC | + | + | + |
| pmHCH | not expressed | | |

**Model of *Pasteurella* Synthase Polymerization**

Model of Reaction Synchronization

Model of Stoichiometric Control of Polymer Size

A.

B.

| Sample No | *Mn* | *Mw* | polydispersity |
|---|---|---|---|
| #1 | 283400 | 283800 | 1.001 |
| #2 | 346400 | 347000 | 1.002 |
| #3 | 422200 | 423700 | 1.004 |
| #4 | 490000 | 493100 | 1.006 |
| #5 | 569700 | 575200 | 1.010 |

FIGURE 11.
Agarose Gels of Ladders and Migration
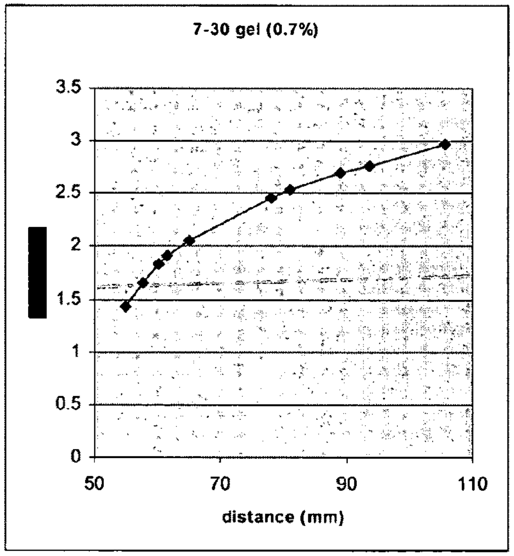
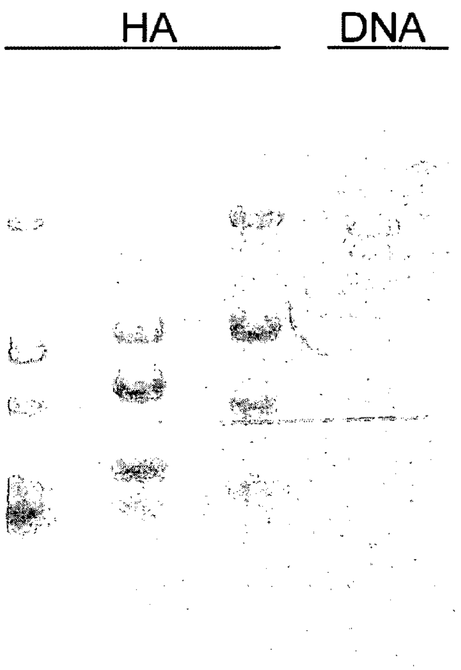

SEQUENCE LISTING

```
<160> NUMBER OF SEQ ID NOS: 75

<210> SEQ ID NO 1
<211> LENGTH: 2920
<212> TYPE: DNA
<213> ORGANISM: Pasteurella multocida

<400> SEQUENCE: 1

atgaatacat tatcacaagc aataaaagca tataacagca atgactatca attagcactc      60

aaattatttg aaaagtcggc ggaaatctat ggacggaaaa ttgttgaatt tcaaattacc     120

aaatgcaaag aaaaactctc agcacatcct tctgttaatt cagcacatct ttctgtaaat     180

aaagaagaaa aagtcaatgt ttgcgatagt ccgttagata ttgcaacaca actgttactt     240

tccaacgtaa aaaaattagt actttctgac tcggaaaaaa acacgttaaa aaataaatgg     300

aaattgctca ctgagaagaa atctgaaaat gcggaggtaa gagcggtcgc ccttgtacca     360

aaagattttc ccaaagatct ggttttagcg cctttacctg atcatgttaa tgattttaca     420

tggtacaaaa agcgaaagaa aagacttggc ataaaacctg aacatcaaca tgttggtctt     480

tctattatcg ttacaacatt caatcgacca gcaattttat cgattacatt agcctgttta     540

gtaaaccaaa aaacacatta cccgtttgaa gttatcgtga cagatgatgg tagtcaggaa     600

gatctatcac cgatcattcg ccaatatgaa aataaattgg atattcgcta cgtcagacaa     660

aaagataacg gttttcaagc cagtgccgct cggaatatgg gattacgctt agcaaaatat     720
```

```
gactttattg gcttactcga ctgtgatatg gcgccaaatc cattatgggt tcattcttat    780
gttgcagagc tattagaaga tgatgattta acaatcattg gtccaagaaa atacatcgat    840
acacaacata ttgacccaaa agacttctta aataacgcga gtttgcttga atcattacca    900
gaagtgaaaa ccaataatag tgttgccgca aaaggggaag gaacagtttc tctggattgg    960
cgcttagaac aattcgaaaa aacagaaaat ctccgcttat ccgattcgcc tttccgtttt   1020
tttgcggcgg gtaatgttgc tttcgctaaa aaatggctaa ataaatccgg tttctttgat   1080
gaggaattta atcactgggg tggagaagat gtggaatttg gatatcgctt attccgttac   1140
ggtagtttct ttaaaactat tgatggcatt atggcctacc atcaagagcc accaggtaaa   1200
gaaaatgaaa ccgatcgtga agcgggaaaa aatattacgc tcgatattat gagagaaaag   1260
gtcccttata tctatagaaa acttttacca atagaagatt cgcatatcaa tagagtacct   1320
ttagtttcaa tttatatccc agcttataac tgtgcaaact atattcaacg ttgcgtagat   1380
agtgcactga atcagactgt tgttgatctc gaggtttgta tttgtaacga tggttcaaca   1440
gataatacct tagaagtgat caataagctt tatggtaata atcctagggt acgcatcatg   1500
tctaaaccaa atggcggaat agcctcagca tcaaatgcag ccgtttcttt tgctaaaggt   1560
tattacattg ggcagttaga ttcagatgat tatcttgagc ctgatgcagt tgaactgtgt   1620
ttaaaagaat ttttaaaaga taaaacgcta gcttgtgttt ataccactaa tagaaacgtc   1680
aatccggatg gtagcttaat cgctaatggt tacaattggc cagaattttc acgagaaaaa   1740
ctcacaacgg ctatgattgc tcaccacttt agaatgttca cgattagagc ttggcattta   1800
actgatggat tcaatgaaaa aattgaaaat gccgtagact atgacatgtt cctcaaactc   1860
agtgaagttg gaaaatttaa acatcttaat aaaatctgct ataaccgtgt attacatggt   1920
gataacacat caattaagaa acttggcatt caaaagaaaa accattttgt tgtagtcaat   1980
cagtcattaa atagacaagg cataacttat tataattatg acgaatttga tgatttagat   2040
gaaagtagaa agtatatttt caataaaacc gctgaatatc aagaagagat tgatatctta   2100
aaagatatta aaatcatcca gaataaagat gccaaaatcg cagtcagtat tttttatccc   2160
aatacattaa acggcttagt gaaaaaacta aacaatatta ttgaatataa taaaaatata   2220
ttcgttattg ttctacatgt tgataagaat catcttacac cagatatcaa aaaagaaata   2280
ctagccttct atcataaaca tcaagtgaat attttactaa ataatgatat ctcatattac   2340
acgagtaata gattaataaa aactgaggcg catttaagta atattaataa attaagtcag   2400
ttaaatctaa attgtgaata catcattttt gataatcatg acagcctatt cgttaaaaat   2460
gacagctatg cttatatgaa aaaatatgat gtcggcatga atttctcagc attaacacat   2520
gattggatcg agaaaatcaa tgcgcatcca ccatttaaaa agctcattaa aacttatttt   2580
aatgacaatg acttaaaaag tatgaatgtg aaaggggcat cacaaggtat gtttatgacg   2640
tatgcgctag cgcatgagct tctgacgatt attaaagaag tcatcacatc ttgccagtca   2700
attgatagtg tgccagaata taacactgag gatatttggt tccaatttgc acttttaatc   2760
ttagaaaaga aaaccggcca tgtatttaat aaaacatcga ccctgactta tatgccttgg   2820
gaacgaaaat tacaatggac aaatgaacaa attgaaagtg caaaaagagg agaaaatata   2880
cctgttaaca agttcattat taatagtata actctataaa                         2920
```

<210> SEQ ID NO 2
<211> LENGTH: 972
<212> TYPE: PRT
<213> ORGANISM: Pasteurella multocida

<400> SEQUENCE: 2

```
Met Asn Thr Leu Ser Gln Ala Ile Lys Ala Tyr Asn Ser Asn Asp Tyr
1               5                   10                  15

Gln Leu Ala Leu Lys Leu Phe Glu Lys Ser Ala Glu Ile Tyr Gly Arg
            20                  25                  30

Lys Ile Val Glu Phe Gln Ile Thr Lys Cys Lys Glu Lys Leu Ser Ala
        35                  40                  45

His Pro Ser Val Asn Ser Ala His Leu Ser Val Asn Lys Glu Glu Lys
    50                  55                  60

Val Asn Val Cys Asp Ser Pro Leu Asp Ile Ala Thr Gln Leu Leu Leu
65                  70                  75                  80

Ser Asn Val Lys Lys Leu Val Leu Ser Asp Ser Glu Lys Asn Thr Leu
                85                  90                  95

Lys Asn Lys Trp Lys Leu Leu Thr Glu Lys Lys Ser Glu Asn Ala Glu
            100                 105                 110

Val Arg Ala Val Ala Leu Val Pro Lys Asp Phe Pro Lys Asp Leu Val
        115                 120                 125

Leu Ala Pro Leu Pro Asp His Val Asn Asp Phe Thr Trp Tyr Lys Lys
    130                 135                 140

Arg Lys Lys Arg Leu Gly Ile Lys Pro Glu His Gln His Val Gly Leu
145                 150                 155                 160

Ser Ile Ile Val Thr Thr Phe Asn Arg Pro Ala Ile Leu Ser Ile Thr
                165                 170                 175

Leu Ala Cys Leu Val Asn Gln Lys Thr His Tyr Pro Phe Glu Val Ile
            180                 185                 190

Val Thr Asp Asp Gly Ser Gln Glu Asp Leu Ser Pro Ile Ile Arg Gln
        195                 200                 205

Tyr Glu Asn Lys Leu Asp Ile Arg Tyr Val Arg Gln Lys Asp Asn Gly
    210                 215                 220

Phe Gln Ala Ser Ala Ala Arg Asn Met Gly Leu Arg Leu Ala Lys Tyr
225                 230                 235                 240

Asp Phe Ile Gly Leu Leu Asp Cys Asp Met Ala Pro Asn Pro Leu Trp
                245                 250                 255

Val His Ser Tyr Val Ala Glu Leu Leu Glu Asp Asp Asp Leu Thr Ile
            260                 265                 270

Ile Gly Pro Arg Lys Tyr Ile Asp Thr Gln His Ile Asp Pro Lys Asp
        275                 280                 285

Phe Leu Asn Asn Ala Ser Leu Leu Glu Ser Leu Pro Glu Val Lys Thr
    290                 295                 300

Asn Asn Ser Val Ala Ala Lys Gly Glu Gly Thr Val Ser Leu Asp Trp
305                 310                 315                 320

Arg Leu Glu Gln Phe Glu Lys Thr Glu Asn Leu Arg Leu Ser Asp Ser
                325                 330                 335

Pro Phe Arg Phe Phe Ala Ala Gly Asn Val Ala Phe Ala Lys Lys Trp
            340                 345                 350

Leu Asn Lys Ser Gly Phe Phe Asp Glu Glu Phe Asn His Trp Gly Gly
        355                 360                 365

Glu Asp Val Glu Phe Gly Tyr Arg Leu Phe Arg Tyr Gly Ser Phe Phe
    370                 375                 380

Lys Thr Ile Asp Gly Ile Met Ala Tyr His Gln Glu Pro Pro Gly Lys
385                 390                 395                 400

Glu Asn Glu Thr Asp Arg Glu Ala Gly Lys Asn Ile Thr Leu Asp Ile
                405                 410                 415
```

```
Met Arg Glu Lys Val Pro Tyr Ile Tyr Arg Lys Leu Leu Pro Ile Glu
            420                 425                 430

Asp Ser His Ile Asn Arg Val Pro Leu Val Ser Ile Tyr Ile Pro Ala
        435                 440                 445

Tyr Asn Cys Ala Asn Tyr Ile Gln Arg Cys Val Asp Ser Ala Leu Asn
    450                 455                 460

Gln Thr Val Val Asp Leu Glu Val Cys Ile Cys Asn Asp Gly Ser Thr
465                 470                 475                 480

Asp Asn Thr Leu Glu Val Ile Asn Lys Leu Tyr Gly Asn Asn Pro Arg
                485                 490                 495

Val Arg Ile Met Ser Lys Pro Asn Gly Gly Ile Ala Ser Ala Ser Asn
            500                 505                 510

Ala Ala Val Ser Phe Ala Lys Gly Tyr Tyr Ile Gly Gln Leu Asp Ser
        515                 520                 525

Asp Asp Tyr Leu Glu Pro Asp Ala Val Glu Leu Cys Leu Lys Glu Phe
    530                 535                 540

Leu Lys Asp Lys Thr Leu Ala Cys Val Tyr Thr Thr Asn Arg Asn Val
545                 550                 555                 560

Asn Pro Asp Gly Ser Leu Ile Ala Asn Gly Tyr Asn Trp Pro Glu Phe
                565                 570                 575

Ser Arg Glu Lys Leu Thr Thr Ala Met Ile Ala His His Phe Arg Met
            580                 585                 590

Phe Thr Ile Arg Ala Trp His Leu Thr Asp Gly Phe Asn Glu Lys Ile
        595                 600                 605

Glu Asn Ala Val Asp Tyr Asp Met Phe Leu Lys Leu Ser Glu Val Gly
    610                 615                 620

Lys Phe Lys His Leu Asn Lys Ile Cys Tyr Asn Arg Val Leu His Gly
625                 630                 635                 640

Asp Asn Thr Ser Ile Lys Lys Leu Gly Ile Gln Lys Lys Asn His Phe
                645                 650                 655

Val Val Val Asn Gln Ser Leu Asn Arg Gln Gly Ile Thr Tyr Tyr Asn
            660                 665                 670

Tyr Asp Glu Phe Asp Asp Leu Asp Glu Ser Arg Lys Tyr Ile Phe Asn
        675                 680                 685

Lys Thr Ala Glu Tyr Gln Glu Glu Ile Asp Ile Leu Lys Asp Ile Lys
    690                 695                 700

Ile Ile Gln Asn Lys Asp Ala Lys Ile Ala Val Ser Ile Phe Tyr Pro
705                 710                 715                 720

Asn Thr Leu Asn Gly Leu Val Lys Lys Leu Asn Asn Ile Ile Glu Tyr
                725                 730                 735

Asn Lys Asn Ile Phe Val Ile Val Leu His Val Asp Lys Asn His Leu
            740                 745                 750

Thr Pro Asp Ile Lys Lys Glu Ile Leu Ala Phe Tyr His Lys His Gln
        755                 760                 765

Val Asn Ile Leu Leu Asn Asn Asp Ile Ser Tyr Tyr Thr Ser Asn Arg
    770                 775                 780

Leu Ile Lys Thr Glu Ala His Leu Ser Asn Ile Asn Lys Leu Ser Gln
785                 790                 795                 800

Leu Asn Leu Asn Cys Glu Tyr Ile Ile Phe Asp Asn His Asp Ser Leu
                805                 810                 815

Phe Val Lys Asn Asp Ser Tyr Ala Tyr Met Lys Lys Tyr Asp Val Gly
            820                 825                 830

Met Asn Phe Ser Ala Leu Thr His Asp Trp Ile Glu Lys Ile Asn Ala
```

```
        835                 840                 845

His Pro Pro Phe Lys Lys Leu Ile Lys Thr Tyr Phe Asn Asp Asn Asp
    850                 855                 860

Leu Lys Ser Met Asn Val Lys Gly Ala Ser Gln Gly Met Phe Met Thr
865                 870                 875                 880

Tyr Ala Leu Ala His Glu Leu Leu Thr Ile Ile Lys Glu Val Ile Thr
                885                 890                 895

Ser Cys Gln Ser Ile Asp Ser Val Pro Glu Tyr Asn Thr Glu Asp Ile
            900                 905                 910

Trp Phe Gln Phe Ala Leu Leu Ile Leu Glu Lys Lys Thr Gly His Val
        915                 920                 925

Phe Asn Lys Thr Ser Thr Leu Thr Tyr Met Pro Trp Glu Arg Lys Leu
    930                 935                 940

Gln Trp Thr Asn Glu Gln Ile Glu Ser Ala Lys Arg Gly Glu Asn Ile
945                 950                 955                 960

Pro Val Asn Lys Phe Ile Ile Asn Ser Ile Thr Leu
                965                 970


<210> SEQ ID NO 3
<211> LENGTH: 2979
<212> TYPE: DNA
<213> ORGANISM: Pasteurella multocida

<400> SEQUENCE: 3

ttataaactg attaaagaag gtaaacgatt caagcaaggt taatttttaa aggaaagaaa     60

atgaatacat tatcacaagc aataaaagca tataacagca atgactatga attagcactc    120

aaattatttg agaagtctgc tgaaacctac gggcgaaaaa tcgttgaatt ccaaattatc    180

aaatgtaaag aaaaactctc gaccaattct tatgtaagtg aagataaaaa aaacagtgtt    240

tgcgatagct cattagatat cgcaacacag ctcttacttt ccaacgtaaa aaaattaact    300

ctatccgaat cagaaaaaaa cagtttaaaa aataaatgga aatctatcac tgggaaaaaa    360

tcggagaacg cagaaatcag aaaggtggaa ctagtaccca aagattttcc taaagatctt    420

gttcttgctc cattgccaga tcatgttaat gattttacat ggtacaaaaa tcgaaaaaaa    480

agcttaggta taaagcctgt aaataagaat atcggtcttt ctattattat tcctacattt    540

aatcgtagcc gtattttaga tataacgtta gcctgtttgg tcaatcagaa aacaaactac    600

ccatttgaag tcgttgttgc agatgatggt agtaaggaaa acttacttac cattgtgcaa    660

aaatacgaac aaaaacttga cataaagtat gtaagacaaa aagattatgg atatcaattg    720

tgtgcagtca gaaacttagg tttacgtaca gcaaagtatg attttgtctc gattctagac    780

tgcgatatgg caccacaaca attatgggtt cattcttatc ttacagaact attagaagac    840

aatgatattg ttttaattgg acctagaaaa tatgtggata ctcataatat taccgcagaa    900

caattcctta acgatccata tttaatagaa tcactacctg aaaccgctac aaataacaat    960

ccttcgatta catcaaaagg aaatatatcg ttggattgga gattagaaca tttcaaaaaa   1020

accgataatc tacgtctatg tgattctccg tttcgttatt ttagttgcgg taatgttgca   1080

ttttctaaag aatggctaaa taaagtaggt tggttcgatg aagaatttaa tcattggggg   1140

ggcgaagatg tagaatttgg ttacagatta tttgccaaag gctgtttttt cagagtaatt   1200

gacggcggaa tggcatacca tcaagaacca cctggtaaag aaaatgaaac agaccgcgaa   1260

gctggtaaaa gtattacgct taaaattgtg aaagaaaagg taccttacat ctatagaaag   1320

cttttaccaa tagaagattc acatattcat agaatacctt tagtttctat ttatatcccc   1380
```

```
gcttataact gtgcaaatta tattcaaaga tgtgtagata gtgctcttaa tcaaactgtt   1440
gtcgatctcg aggtttgtat ttgtaacgat ggttcaacag ataatacctt agaagtgatc   1500
aataagcttt atggtaataa tcctagggta cgcatcatgt ctaaaccaaa tggcggaata   1560
gcctcagcat caaatgcagc cgtttctttt gctaaaggtt attacattgg gcagttagat   1620
tcagatgatt atcttgagcc tgatgcagtt gaactgtgtt taaaagaatt tttaaaagat   1680
aaaacgctag cttgtgttta taccactaat agaaacgtca atccggatgg tagcttaatc   1740
gctaatggtt acaattggcc agaattttca cgagaaaaac tcacaacggc tatgattgct   1800
caccatttta gaatgtttac gattagagct tggcatttaa cggatggatt taacgaaaat   1860
attgaaaacg ccgtggatta tgacatgttc cttaaactca gtgaagttgg aaaatttaaa   1920
catcttaata aaatctgcta taaccgcgta ttacatggtg ataacacatc cattaagaaa   1980
ctcggcattc aaaagaaaaa ccattttgtt gtagtcaatc agtcattaaa tagacaaggc   2040
atcaattatt ataattatga caaatttgat gatttagatg aaagtagaaa gtatatcttc   2100
aataaaaccg ctgaatatca agaagaaatg gatattttaa aagatcttaa actcattcaa   2160
aataaagatg ccaaaatcgc agtcagtatt ttctatccca atacattaaa cggcttagtg   2220
aaaaaactaa acaatattat tgaatataat aaaaatatat tcgttattat tctacatgtt   2280
gataagaatc atcttacacc agacatcaaa aaagaaatat tggctttcta tcataagcac   2340
caagtgaata ttttactaaa taatgacatc tcatattaca cgagtaatag actaataaaa   2400
actgaggcac atttaagtaa tattaataaa ttaagtcagt taaatctaaa ttgtgaatac   2460
atcatttttg ataatcatga cagcctattc gttaaaaatg acagctatgc ttatatgaaa   2520
aaatatgatg tcggcatgaa tttctcagca ttaacacatg attggatcga gaaaatcaat   2580
gcgcatccac catttaaaaa gctgattaaa acctatttta atgacaatga cttaagaagt   2640
atgaatgtga aaggggcatc acaaggtatg tttatgaagt atgcgctacc gcatgagctt   2700
ctgacgatta ttaaagaagt catcacatcc tgccaatcaa ttgatagtgt gccagaatat   2760
aacactgagg atatttggtt ccaatttgca cttttaatct tagaaaagaa aaccggccat   2820
gtatttaata aaacatcgac cctgacttat atgccttggg aacgaaaatt acaatggaca   2880
aatgaacaaa ttcaaagtgc aaaaaaaggc gaaaatatcc ccgttaacaa gttcattatt   2940
aatagtataa cgctataaaa catttgcatt ttattaaaa                          2979
```

<210> SEQ ID NO 4
<211> LENGTH: 965
<212> TYPE: PRT
<213> ORGANISM: Pasteurella multocida

<400> SEQUENCE: 4

```
Met Asn Thr Leu Ser Gln Ala Ile Lys Ala Tyr Asn Ser Asn Asp Tyr
1               5                   10                  15

Glu Leu Ala Leu Lys Leu Phe Glu Lys Ser Ala Glu Thr Tyr Gly Arg
            20                  25                  30

Lys Ile Val Glu Phe Gln Ile Ile Lys Cys Lys Glu Lys Leu Ser Thr
        35                  40                  45

Asn Ser Tyr Val Ser Glu Asp Lys Lys Asn Ser Val Cys Asp Ser Ser
    50                  55                  60

Leu Asp Ile Ala Thr Gln Leu Leu Leu Ser Asn Val Lys Lys Leu Thr
65                  70                  75                  80

Leu Ser Glu Ser Glu Lys Asn Ser Leu Lys Asn Lys Trp Lys Ser Ile
                85                  90                  95
```

```
Thr Gly Lys Lys Ser Glu Asn Ala Glu Ile Arg Lys Val Glu Leu Val
            100                 105                 110

Pro Lys Asp Phe Pro Lys Asp Leu Val Leu Ala Pro Leu Pro Asp His
        115                 120                 125

Val Asn Asp Phe Thr Trp Tyr Lys Asn Arg Lys Lys Ser Leu Gly Ile
    130                 135                 140

Lys Pro Val Asn Lys Asn Ile Gly Leu Ser Ile Ile Ile Pro Thr Phe
145                 150                 155                 160

Asn Arg Ser Arg Ile Leu Asp Ile Thr Leu Ala Cys Leu Val Asn Gln
                165                 170                 175

Lys Thr Asn Tyr Pro Phe Glu Val Val Val Ala Asp Asp Gly Ser Lys
            180                 185                 190

Glu Asn Leu Leu Thr Ile Val Gln Lys Tyr Glu Gln Lys Leu Asp Ile
        195                 200                 205

Lys Tyr Val Arg Gln Lys Asp Tyr Gly Tyr Gln Leu Cys Ala Val Arg
    210                 215                 220

Asn Leu Gly Leu Arg Thr Ala Lys Tyr Asp Phe Val Ser Ile Leu Asp
225                 230                 235                 240

Cys Asp Met Ala Pro Gln Gln Leu Trp Val His Ser Tyr Leu Thr Glu
                245                 250                 255

Leu Leu Glu Asp Asn Asp Ile Val Leu Ile Gly Pro Arg Lys Tyr Val
            260                 265                 270

Asp Thr His Asn Ile Thr Ala Glu Gln Phe Leu Asn Asp Pro Tyr Leu
        275                 280                 285

Ile Glu Ser Leu Pro Glu Thr Ala Thr Asn Asn Asn Pro Ser Ile Thr
    290                 295                 300

Ser Lys Gly Asn Ile Ser Leu Asp Trp Arg Leu Glu His Phe Lys Lys
305                 310                 315                 320

Thr Asp Asn Leu Arg Leu Cys Asp Ser Pro Phe Arg Tyr Phe Ser Cys
                325                 330                 335

Gly Asn Val Ala Phe Ser Lys Glu Trp Leu Asn Lys Val Gly Trp Phe
            340                 345                 350

Asp Glu Glu Phe Asn His Trp Gly Gly Glu Asp Val Glu Phe Gly Tyr
        355                 360                 365

Arg Leu Phe Ala Lys Gly Cys Phe Phe Arg Val Ile Asp Gly Gly Met
    370                 375                 380

Ala Tyr His Gln Glu Pro Pro Gly Lys Glu Asn Glu Thr Asp Arg Glu
385                 390                 395                 400

Ala Gly Lys Ser Ile Thr Leu Lys Ile Val Lys Glu Lys Val Pro Tyr
                405                 410                 415

Ile Tyr Arg Lys Leu Leu Pro Ile Glu Asp Ser His Ile His Arg Ile
            420                 425                 430

Pro Leu Val Ser Ile Tyr Ile Pro Ala Tyr Asn Cys Ala Asn Tyr Ile
        435                 440                 445

Gln Arg Cys Val Asp Ser Ala Leu Asn Gln Thr Val Val Asp Leu Glu
    450                 455                 460

Val Cys Ile Cys Asn Asp Gly Ser Thr Asp Asn Thr Leu Glu Val Ile
465                 470                 475                 480

Asn Lys Leu Tyr Gly Asn Asn Pro Arg Val Arg Ile Met Ser Lys Pro
                485                 490                 495

Asn Gly Gly Ile Ala Ser Ala Ser Asn Ala Ala Val Ser Phe Ala Lys
            500                 505                 510

Gly Tyr Tyr Ile Gly Gln Leu Asp Ser Asp Asp Tyr Leu Glu Pro Asp
        515                 520                 525
```

-continued

```
Ala Val Glu Leu Cys Leu Lys Glu Phe Leu Lys Asp Lys Thr Leu Ala
    530                 535                 540

Cys Val Tyr Thr Thr Asn Arg Asn Val Asn Pro Asp Gly Ser Leu Ile
545                 550                 555                 560

Ala Asn Gly Tyr Asn Trp Pro Glu Phe Ser Arg Glu Lys Leu Thr Thr
                565                 570                 575

Ala Met Ile Ala His His Phe Arg Met Phe Thr Ile Arg Ala Trp His
            580                 585                 590

Leu Thr Asp Gly Phe Asn Glu Asn Ile Glu Asn Ala Val Asp Tyr Asp
        595                 600                 605

Met Phe Leu Lys Leu Ser Glu Val Gly Lys Phe Lys His Leu Asn Lys
    610                 615                 620

Ile Cys Tyr Asn Arg Val Leu His Gly Asp Asn Thr Ser Ile Lys Lys
625                 630                 635                 640

Leu Gly Ile Gln Lys Lys Asn His Phe Val Val Val Asn Gln Ser Leu
                645                 650                 655

Asn Arg Gln Gly Ile Asn Tyr Tyr Asn Tyr Asp Lys Phe Asp Asp Leu
            660                 665                 670

Asp Glu Ser Arg Lys Tyr Ile Phe Asn Lys Thr Ala Glu Tyr Gln Glu
        675                 680                 685

Glu Met Asp Ile Leu Lys Asp Leu Lys Leu Ile Gln Asn Lys Asp Ala
    690                 695                 700

Lys Ile Ala Val Ser Ile Phe Tyr Pro Asn Thr Leu Asn Gly Leu Val
705                 710                 715                 720

Lys Lys Leu Asn Asn Ile Ile Glu Tyr Asn Lys Asn Ile Phe Val Ile
                725                 730                 735

Ile Leu His Val Asp Lys Asn His Leu Thr Pro Asp Ile Lys Lys Glu
            740                 745                 750

Ile Leu Ala Phe Tyr His Lys His Gln Val Asn Ile Leu Leu Asn Asn
        755                 760                 765

Asp Ile Ser Tyr Tyr Thr Ser Asn Arg Leu Ile Lys Thr Glu Ala His
    770                 775                 780

Leu Ser Asn Ile Asn Lys Leu Ser Gln Leu Asn Leu Asn Cys Glu Tyr
785                 790                 795                 800

Ile Ile Phe Asp Asn His Asp Ser Leu Phe Val Lys Asn Asp Ser Tyr
                805                 810                 815

Ala Tyr Met Lys Lys Tyr Asp Val Gly Met Asn Phe Ser Ala Leu Thr
            820                 825                 830

His Asp Trp Ile Glu Lys Ile Asn Ala His Pro Pro Phe Lys Lys Leu
        835                 840                 845

Ile Lys Thr Tyr Phe Asn Asp Asn Asp Leu Arg Ser Met Asn Val Lys
    850                 855                 860

Gly Ala Ser Gln Gly Met Phe Met Lys Tyr Ala Leu Pro His Glu Leu
865                 870                 875                 880

Leu Thr Ile Ile Lys Glu Val Ile Thr Ser Cys Gln Ser Ile Asp Ser
                885                 890                 895

Val Pro Glu Tyr Asn Thr Glu Asp Ile Trp Phe Gln Phe Ala Leu Leu
            900                 905                 910

Ile Leu Glu Lys Lys Thr Gly His Val Phe Asn Lys Thr Ser Thr Leu
        915                 920                 925

Thr Tyr Met Pro Trp Glu Arg Lys Leu Gln Trp Thr Asn Glu Gln Ile
    930                 935                 940

Gln Ser Ala Lys Lys Gly Glu Asn Ile Pro Val Asn Lys Phe Ile Ile
```

-continued 945 950 955 960

Asn Ser Ile Thr Leu
965

<210> SEQ ID NO 5
<211> LENGTH: 1851
<212> TYPE: DNA
<213> ORGANISM: Pasteurella multocida

<400> SEQUENCE: 5
atgagcttat ttaaacgtgc tactgagcta tttaagtcag gaaactataa agatgcacta 60
actctatatg aaaatatagc taaaatttat ggttcagaaa gccttgttaa atataatatt 120
gatatatgta aaaaaaatat aacacaatca aaaagtaata aaatagaaga agataatatt 180
tctggagaaa acaaattttc agtatcaata aaagatctat ataacgaaat aagcaatagt 240
gaattaggga ttacaaaaga aagactagga gccccccctc tagtcagtat tataatgact 300
tctcataata cagaaaaatt cattgaagcc tcaattaatt cactattatt gcaaacatac 360
aataacttag aagttatcgt tgtagatgat tatagcacag ataaaacatt tcagatcgca 420
tccagaatag caaactctac aagtaaagta aaaacattcc gattaaactc aaatctaggg 480
acatactttg cgaaaaatac aggaatttta aagtctaaag gagatattat tttctttcag 540
gatagcgatg atgtatgtca ccatgaaaga atcgaaagat gtgttaatgc attattatcg 600
aataaagata atatagctgt tagatgtgca tattctagaa taaatctaga aacacaaaat 660
ataataaaag ttaatgataa taaatacaaa ttaggattaa taactttagg cgtttataga 720
aaagtattta atgaaattgg ttttttttaac tgcacaacca aagcatcgga tgatgaattt 780
tatcatagaa taattaaata ctatggtaaa aataggataa ataacttatt tctaccactg 840
tattataaca caatgcgtga agattcatta ttttctgata tggttgagtg ggtagatgaa 900
aataatataa agcaaaaaac ctctgatgct agacaaaatt atctccatga attccaaaaa 960
atacacaatg aaaggaaatt aaatgaatta aaagagattt ttagctttcc tagaattcat 1020
gacgccttac ctatatcaaa agaaatgagt aagctcagca accctaaaat tcctgtttat 1080
ataaatatat gctcaatacc ttcaagaata aaacaacttc aatacactat tggagtacta 1140
aaaaaccaat gcgatcattt tcatatttat cttgatggat atccagaagt acctgatttt 1200
ataaaaaaac tagggaataa agcgaccgtt attaattgtc aaaacaaaaa tgagtctatt 1260
agagataatg gaaagtttat tctattagaa aaacttataa aggaaaataa agatggatat 1320
tatataactt gtgatgatga tatccggtat cctgctgact acacaaacac tatgataaaa 1380
aaaattaata aatacaatga taaagcagca attggattac atggtgttat attcccaagt 1440
agagtcaaca agtattttc atcagacaga attgtctata attttcaaaa acctttagaa 1500
aatgatactg ctgtaaatat attaggaact ggaactgttg cctttagagt atctatttt 1560 aataaatttt ctctatctga ttttgagcat cctggcatgg tagatatcta tttttctata 1620
ctatgtaaga aaaacaatat actccaagtt tgtatatcac gaccatcgaa ttggctaaca 1680
gaagataaca aaaacactga gaccttattt catgaattcc aaaatagaga tgaaatacaa 1740
agtaaactca ttatttcaaa caacccttgg ggatactcaa gtatatatcc actattaaat 1800
aataatgcta attattctga acttattccg tgtttatctt tttataacga g 1851

<210> SEQ ID NO 6
<211> LENGTH: 615
<212> TYPE: PRT
<213> ORGANISM: Pasteurella multocida -continued

<400> SEQUENCE: 6

```
Met Ser Leu Phe Lys Arg Ala Thr Glu Leu Phe Lys Ser Gly Asn Tyr
1               5                   10                  15

Lys Asp Ala Leu Thr Leu Tyr Glu Asn Ile Ala Lys Ile Tyr Gly Ser
            20                  25                  30

Glu Ser Leu Val Lys Tyr Asn Ile Asp Ile Cys Lys Lys Asn Ile Thr
        35                  40                  45

Gln Ser Lys Ser Asn Lys Ile Glu Glu Asp Asn Ile Ser Gly Glu Asn
    50                  55                  60

Lys Phe Ser Val Ser Ile Lys Asp Leu Tyr Asn Glu Ile Ser Asn Ser
65                  70                  75                  80

Glu Leu Gly Ile Thr Lys Glu Arg Leu Gly Ala Pro Pro Leu Val Ser
                85                  90                  95

Ile Ile Met Thr Ser His Asn Thr Glu Lys Phe Ile Glu Ala Ser Ile
            100                 105                 110

Asn Ser Leu Leu Leu Gln Thr Tyr Asn Leu Glu Val Ile Val Val Asp
        115                 120                 125

Asp Tyr Ser Thr Asp Lys Thr Phe Gln Ile Ala Ser Arg Ile Ala Asn
    130                 135                 140

Ser Thr Ser Lys Val Lys Thr Phe Arg Leu Asn Ser Asn Leu Gly Thr
145                 150                 155                 160

Tyr Phe Ala Lys Asn Thr Gly Ile Leu Lys Ser Lys Gly Asp Ile Ile
                165                 170                 175

Phe Phe Gln Ser Asp Asp Val Cys His His Glu Arg Ile Glu Arg Cys
            180                 185                 190

Val Asn Ala Leu Leu Ser Asn Lys Asp Asn Ile Ala Val Arg Cys Ala
        195                 200                 205

Tyr Ser Arg Ile Asn Leu Glu Thr Gln Asn Ile Ile Lys Val Asn Asp
    210                 215                 220

Asn Lys Tyr Lys Leu Gly Leu Ile Thr Leu Gly Val Tyr Arg Lys Val
225                 230                 235                 240

Phe Asn Glu Ile Gly Phe Phe Asn Cys Thr Thr Lys Ala Ser Asp Asp
                245                 250                 255

Glu Phe Tyr His Arg Ile Ile Lys Tyr Tyr Gly Lys Asn Arg Ile Asn
            260                 265                 270

Asn Leu Phe Leu Pro Leu Tyr Tyr Asn Thr Met Arg Glu Asp Ser Leu
        275                 280                 285

Phe Ser Asp Met Val Glu Trp Val Asp Glu Asn Asn Ile Lys Gln Lys
    290                 295                 300

Thr Ser Asp Ala Arg Gln Asn Tyr Leu His Glu Phe Gln Lys Ile His
305                 310                 315                 320

Asn Glu Arg Lys Leu Asn Glu Leu Lys Glu Ile Phe Ser Phe Pro Arg
                325                 330                 335

Ile His Asp Ala Leu Pro Ile Ser Lys Glu Met Ser Lys Leu Ser Asn
            340                 345                 350

Pro Lys Ile Pro Val Tyr Ile Asn Ile Cys Ser Ile Pro Ser Arg Ile
        355                 360                 365

Lys Gln Leu Gln Tyr Thr Ile Gly Val Leu Lys Asn Gln Cys Asp His
    370                 375                 380

Phe His Ile Tyr Leu Asp Gly Tyr Pro Glu Val Pro Asp Phe Ile Lys
385                 390                 395                 400

Lys Leu Gly Asn Lys Ala Thr Val Ile Asn Cys Gln Asn Lys Asn Glu
                405                 410                 415
```

```
Ser Ile Arg Asp Asn Gly Lys Phe Ile Leu Leu Glu Lys Leu Ile Lys
            420                 425                 430

Glu Asn Lys Asp Gly Tyr Tyr Ile Thr Cys Asp Asp Asp Ile Arg Tyr
        435                 440                 445

Pro Ala Asp Tyr Thr Asn Thr Met Ile Lys Lys Ile Asn Lys Tyr Asn
    450                 455                 460

Asp Lys Ala Ala Ile Gly Leu His Gly Val Ile Phe Pro Ser Arg Val
465                 470                 475                 480

Asn Lys Tyr Phe Ser Ser Asp Arg Ile Val Tyr Asn Phe Gln Lys Pro
                485                 490                 495

Leu Glu Asn Asp Thr Ala Val Asn Ile Leu Gly Thr Gly Thr Val Ala
            500                 505                 510

Phe Arg Val Ser Ile Phe Asn Lys Phe Ser Leu Ser Asp Phe Glu His
        515                 520                 525

Pro Gly Met Val Asp Ile Tyr Phe Ser Ile Leu Cys Lys Lys Asn Asn
    530                 535                 540

Ile Leu Gln Val Cys Ile Ser Arg Pro Ser Asn Trp Leu Thr Glu Asp
545                 550                 555                 560

Asn Lys Asn Thr Glu Thr Leu Phe His Glu Phe Gln Asn Arg Asp Glu
                565                 570                 575

Ile Gln Ser Lys Leu Ile Ile Ser Asn Asn Pro Trp Gly Tyr Ser Ser
            580                 585                 590

Ile Tyr Pro Leu Leu Asn Asn Asn Ala Asn Tyr Ser Glu Leu Ile Pro
        595                 600                 605

Cys Leu Ser Phe Tyr Asn Glu
    610                 615
```

<210> SEQ ID NO 7
<211> LENGTH: 1940
<212> TYPE: DNA
<213> ORGANISM: Pasteurella multocida

<400> SEQUENCE: 7

```
aacaggggat aaggtcagta aatttaggat gatttttgac taatggataa atacttgaat      60

atccccatgg accgttttcc atgatcagct gagtttgttg ctcatcattg tctcgatatt     120

gatgatagag tgtttcgctg tctctattat cttccgttag ccagtttgct ggtcttgaaa     180

tacaaatctg aagaatatta tttttcttac acaagagaga gaaatagata tcagccatgc     240

ctgaatgggt aaagtcagaa agagaaaatt gattaaagag actgactcta aagctaacag     300

ttcctgtacc taatacattg accgctttgt ctttttccag aggtttatag aagctatata     360

ccagtctatc cgccgaaaaa tatttggtca ttctacttgg aaagagaatg ccgtgtaaac     420

caataaccgc tttatcatcg tattcattca gcttcttgat catcgtattg atgtaatcgc     480

ttggatagat aatgtcatca tcacaggtta tataatatcc atcttgattt ttttcaatca     540

actcttccag taaaatgaat ttgccattat ctctaatgga gttatcttta tctttgcaat     600

gaacaacggt tgctttatta cctaaatttt ttatgaagtc agggatttct acatagccat     660

caagataaat atgaaaatga tcacattgat tttttagtat gccgataata cgtcgtaatt     720

gcgctattct tgagggaata gaacaaatat tgatataaac aggaatctta ggattggaca     780

acttactcat ttcttgtggt actggtaagg catcgtaaat acgagggaat tgaaaaagat     840

ttttgaaatc atgtgaggca gtttcgttat gcatcgcttg aaacagggtt gcataatgtt     900

gtctggtatc agacattttc tgtattatgt tatgattgtc tatccattca accatatcag     960
```

```
taaataaaga gttttctctc attgtgttgt agtataacgg caagagtaaa ttttttattt   1020

tttcttttcc ataatatttc gcaattctat gaaaaaactc atcatctgag cctttagtcg   1080

tacaattgaa gaaaccaatt tcttgaaata cttttctgtg catacccaag gttataaaac   1140

ctaatctata atccatatta ttgactttaa tgatatgttg tgtttctggt gctagtcttg   1200

agtatgcaca acgaacagca atagtttctt tattagctaa taatatattt acacatcttt   1260

ctattctttc atgatgacat acatcatcac tatcttgaaa gaaaataatg tcacctttag   1320

attttaatat gcctgtattt ttcgcaaagt aagttcctag gtttgaattt aatctaaata   1380

ctctgacttt gcttgttgta ttcgctattc tcgaggcaat ttcaaatgta ttatccgagc   1440

tatcatcatc tacaataata atttctatgt ttttatatgt ttgtaacaat aatgaattaa   1500

tagaagcttc gataaattgc gctgtattgt gagatgtcat gataatactg actaatggat   1560

ttacgctgtt ggtttctttg actaacccta aatcactttt agcgacttca ttatataaat   1620

ctgttattga tgttgtttgc ttatcttttt ctagctttgc ttctaatgct tgattatagg   1680

tatatatttt ttcaaattct tgcagaacca attggagttg ttttaataaa agtttatttt   1740

cgttttcaag ggatgcggat agcggatgtt tactgtcctg ttttgccaat aaagtttgtt   1800

gagaaataat gtctttgttt aaagttgttt ttagactatc aattttattt tgaaaggtgt   1860

tgagttcatt ttctttttca tgttgggggg gatttttagt catttgtttt tgagtcatct   1920

cttttttct cttcatttca                                                 1940


<210> SEQ ID NO 8
<211> LENGTH: 651
<212> TYPE: PRT
<213> ORGANISM: Pasteurella multocida

<400> SEQUENCE: 8

Met Lys Arg Lys Lys Glu Met Thr Gln Lys Gln Met Thr Lys Asn Pro
1               5                   10                  15

Pro Gln His Glu Lys Glu Asn Glu Leu Asn Thr Phe Gln Asn Lys Ile
            20                  25                  30

Asp Ser Leu Lys Thr Thr Leu Asn Lys Asp Ile Ile Ser Gln Gln Thr
        35                  40                  45

Leu Leu Ala Lys Gln Asp Ser Lys His Pro Leu Ser Ala Ser Leu Glu
    50                  55                  60

Asn Glu Asn Lys Leu Leu Leu Lys Gln Leu Gln Leu Val Leu Gln Glu
65                  70                  75                  80

Phe Glu Lys Ile Tyr Thr Tyr Asn Gln Ala Leu Glu Ala Lys Leu Glu
                85                  90                  95

Lys Asp Lys Gln Thr Thr Ser Ile Thr Asp Leu Tyr Asn Glu Val Ala
            100                 105                 110

Lys Ser Asp Leu Gly Leu Val Lys Glu Thr Asn Ser Val Asn Pro Leu
        115                 120                 125

Val Ser Ile Ile Met Thr Ser His Asn Thr Ala Gln Phe Ile Glu Ala
    130                 135                 140

Ser Ile Asn Ser Leu Leu Leu Gln Thr Tyr Lys Asn Ile Glu Ile Ile
145                 150                 155                 160

Ile Val Asp Asp Asp Ser Ser Asp Asn Thr Phe Glu Ile Ala Ser Arg
                165                 170                 175

Ile Ala Asn Thr Thr Ser Lys Val Arg Val Phe Arg Leu Asn Ser Asn
            180                 185                 190

Leu Gly Thr Tyr Phe Ala Lys Asn Thr Gly Ile Leu Lys Ser Lys Gly
        195                 200                 205
```

```
Asp Ile Ile Phe Phe Gln Asp Ser Asp Asp Val Cys His His Glu Arg
    210                 215                 220

Ile Glu Arg Cys Val Asn Ile Leu Leu Ala Asn Lys Glu Thr Ile Ala
225                 230                 235                 240

Val Arg Cys Ala Tyr Ser Arg Leu Ala Pro Glu Thr Gln His Ile Ile
                245                 250                 255

Lys Val Asn Asn Met Asp Tyr Arg Leu Gly Phe Ile Thr Leu Gly Met
            260                 265                 270

His Arg Lys Val Phe Gln Glu Ile Gly Phe Phe Asn Cys Thr Thr Lys
        275                 280                 285

Gly Ser Asp Asp Glu Phe Phe His Arg Ile Ala Lys Tyr Tyr Gly Lys
    290                 295                 300

Glu Lys Ile Lys Asn Leu Leu Leu Pro Leu Tyr Tyr Asn Thr Met Arg
305                 310                 315                 320

Glu Asn Ser Leu Phe Thr Asp Met Val Glu Trp Ile Asp Asn His Asn
                325                 330                 335

Ile Ile Gln Lys Met Ser Asp Thr Arg Gln His Tyr Ala Thr Leu Phe
            340                 345                 350

Gln Ala Met His Asn Glu Thr Ala Ser His Asp Phe Lys Asn Leu Phe
        355                 360                 365

Gln Phe Pro Arg Ile Tyr Asp Ala Leu Pro Val Pro Gln Glu Met Ser
    370                 375                 380

Lys Leu Ser Asn Pro Lys Ile Pro Val Tyr Ile Asn Ile Cys Ser Ile
385                 390                 395                 400

Pro Ser Arg Ile Ala Gln Leu Arg Arg Ile Ile Gly Ile Leu Lys Asn
                405                 410                 415

Gln Cys Asp His Phe His Ile Tyr Leu Asp Gly Tyr Val Glu Ile Pro
            420                 425                 430

Asp Phe Ile Lys Asn Leu Gly Asn Lys Ala Thr Val Val His Cys Lys
        435                 440                 445

Asp Lys Asp Asn Ser Ile Arg Asp Asn Gly Lys Phe Ile Leu Leu Glu
    450                 455                 460

Glu Leu Ile Glu Lys Asn Gln Asp Gly Tyr Tyr Ile Thr Cys Asp Asp
465                 470                 475                 480

Asp Ile Ile Tyr Pro Ser Asp Tyr Ile Asn Thr Met Ile Lys Lys Leu
                485                 490                 495

Asn Glu Tyr Asp Asp Lys Ala Val Ile Gly Leu His Gly Ile Leu Phe
            500                 505                 510

Pro Ser Arg Met Thr Lys Tyr Phe Ser Ala Asp Arg Leu Val Tyr Ser
        515                 520                 525

Phe Tyr Lys Pro Leu Glu Lys Asp Lys Ala Val Asn Val Leu Gly Thr
    530                 535                 540

Gly Thr Val Ser Phe Arg Val Ser Leu Phe Asn Gln Phe Ser Leu Ser
545                 550                 555                 560

Asp Phe Thr His Ser Gly Met Ala Asp Ile Tyr Phe Ser Leu Leu Cys
                565                 570                 575

Lys Lys Asn Asn Ile Leu Gln Ile Cys Ile Ser Arg Pro Ala Asn Trp
            580                 585                 590

Leu Thr Glu Asp Asn Arg Asp Ser Glu Thr Leu Tyr His Gln Tyr Arg
        595                 600                 605

Asp Asn Asp Glu Gln Gln Thr Gln Leu Ile Met Glu Asn Gly Pro Trp
    610                 615                 620

Gly Tyr Ser Ser Ile Tyr Pro Leu Val Lys Asn His Pro Lys Phe Thr
```

-continued

```
625                 630                 635                 640

Asp Leu Ile Pro Cys Leu Pro Phe Tyr Phe Leu
                645                 650


<210> SEQ ID NO 9
<211> LENGTH: 703
<212> TYPE: PRT
<213> ORGANISM: Pasteurella multocida

<400> SEQUENCE: 9

Met Asn Thr Leu Ser Gln Ala Ile Lys Ala Tyr Asn Ser Asn Asp Tyr
1               5                   10                  15

Gln Leu Ala Leu Lys Leu Phe Glu Lys Ser Ala Glu Ile Tyr Gly Arg
            20                  25                  30

Lys Ile Val Glu Phe Gln Ile Thr Lys Cys Lys Glu Lys Leu Ser Ala
        35                  40                  45

His Pro Ser Val Asn Ser Ala His Leu Ser Val Asn Lys Glu Glu Lys
    50                  55                  60

Val Asn Val Cys Asp Ser Pro Leu Asp Ile Ala Thr Gln Leu Leu Leu
65                  70                  75                  80

Ser Asn Val Lys Lys Leu Val Leu Ser Asp Ser Glu Lys Asn Thr Leu
                85                  90                  95

Lys Asn Lys Trp Lys Leu Leu Thr Glu Lys Lys Ser Glu Asn Ala Glu
            100                 105                 110

Val Arg Ala Val Ala Leu Val Pro Lys Asp Phe Pro Lys Asp Leu Val
        115                 120                 125

Leu Ala Pro Leu Pro Asp His Val Asn Asp Phe Thr Trp Tyr Lys Lys
    130                 135                 140

Arg Lys Lys Arg Leu Gly Ile Lys Pro Glu His Gln His Val Gly Leu
145                 150                 155                 160

Ser Ile Ile Val Thr Thr Phe Asn Arg Pro Ala Ile Leu Ser Ile Thr
                165                 170                 175

Leu Ala Cys Leu Val Asn Gln Lys Thr His Tyr Pro Phe Glu Val Ile
            180                 185                 190

Val Thr Asp Asp Gly Ser Gln Glu Asp Leu Ser Pro Ile Ile Arg Gln
        195                 200                 205

Tyr Glu Asn Lys Leu Asp Ile Arg Tyr Val Arg Gln Lys Asp Asn Gly
    210                 215                 220

Phe Gln Ala Ser Ala Ala Arg Asn Met Gly Leu Arg Leu Ala Lys Tyr
225                 230                 235                 240

Asp Phe Ile Gly Leu Leu Asp Cys Asp Met Ala Pro Asn Pro Leu Trp
                245                 250                 255

Val His Ser Tyr Val Ala Glu Leu Leu Glu Asp Asp Asp Leu Thr Ile
            260                 265                 270

Ile Gly Pro Arg Lys Tyr Ile Asp Thr Gln His Ile Asp Pro Lys Asp
        275                 280                 285

Phe Leu Asn Asn Ala Ser Leu Leu Glu Ser Leu Pro Glu Val Lys Thr
    290                 295                 300

Asn Asn Ser Val Ala Ala Lys Gly Glu Gly Thr Val Ser Leu Asp Trp
305                 310                 315                 320

Arg Leu Glu Gln Phe Glu Lys Thr Glu Asn Leu Arg Leu Ser Asp Ser
                325                 330                 335

Pro Phe Arg Phe Phe Ala Ala Gly Asn Val Ala Phe Ala Lys Lys Trp
            340                 345                 350

Leu Asn Lys Ser Gly Phe Phe Asp Glu Glu Phe Asn His Trp Gly Gly
```

```
        355                 360                 365

Glu Asp Val Glu Phe Gly Tyr Arg Leu Phe Arg Tyr Gly Ser Phe Phe
    370                 375                 380

Lys Thr Ile Asp Gly Ile Met Ala Tyr His Gln Glu Pro Pro Gly Lys
385                 390                 395                 400

Glu Asn Glu Thr Asp Arg Glu Ala Gly Lys Asn Ile Thr Leu Asp Ile
                405                 410                 415

Met Arg Glu Lys Val Pro Tyr Ile Tyr Arg Lys Leu Leu Pro Ile Glu
            420                 425                 430

Asp Ser His Ile Asn Arg Val Pro Leu Val Ser Ile Tyr Ile Pro Ala
        435                 440                 445

Tyr Asn Cys Ala Asn Tyr Ile Gln Arg Cys Val Asp Ser Ala Leu Asn
    450                 455                 460

Gln Thr Val Val Asp Leu Glu Val Cys Ile Cys Asn Asp Gly Ser Thr
465                 470                 475                 480

Asp Asn Thr Leu Glu Val Ile Asn Lys Leu Tyr Gly Asn Asn Pro Arg
                485                 490                 495

Val Arg Ile Met Ser Lys Pro Asn Gly Gly Ile Ala Ser Ala Ser Asn
            500                 505                 510

Ala Ala Val Ser Phe Ala Lys Gly Tyr Tyr Ile Gly Gln Leu Asp Ser
        515                 520                 525

Asp Asp Tyr Leu Glu Pro Asp Ala Val Glu Leu Cys Leu Lys Glu Phe
    530                 535                 540

Leu Lys Asp Lys Thr Leu Ala Cys Val Tyr Thr Thr Asn Arg Asn Val
545                 550                 555                 560

Asn Pro Asp Gly Ser Leu Ile Ala Asn Gly Tyr Asn Trp Pro Glu Phe
                565                 570                 575

Ser Arg Glu Lys Leu Thr Thr Ala Met Ile Ala His His Phe Arg Met
            580                 585                 590

Phe Thr Ile Arg Ala Trp His Leu Thr Asp Gly Phe Asn Glu Lys Ile
        595                 600                 605

Glu Asn Ala Val Asp Tyr Asp Met Phe Leu Lys Leu Ser Glu Val Gly
    610                 615                 620

Lys Phe Lys His Leu Asn Lys Ile Cys Tyr Asn Arg Val Leu His Gly
625                 630                 635                 640

Asp Asn Thr Ser Ile Lys Lys Leu Gly Ile Gln Lys Lys Asn His Phe
                645                 650                 655

Val Val Val Asn Gln Ser Leu Asn Arg Gln Gly Ile Thr Tyr Tyr Asn
            660                 665                 670

Tyr Asp Glu Phe Asp Asp Leu Asp Glu Ser Arg Lys Tyr Ile Phe Asn
        675                 680                 685

Lys Thr Ala Glu Tyr Gln Glu Glu Ile Asp Ile Leu Lys Asp Ile
    690                 695                 700


<210> SEQ ID NO 10
<211> LENGTH: 1953
<212> TYPE: DNA
<213> ORGANISM: Pasteurella multocida

<400> SEQUENCE: 10

atgaatacat tatcacaagc aataaaagca tataacagca atgactatca attagcactc      60

aaattatttg aaaagtcggc ggaaatctat ggacggaaaa ttgttgaatt tcaaattacc     120

aaatgcaaag aaaaactctc agcacatcct tctgttaatt cagcacatct ttctgtaaat     180

aaagaagaaa aagtcaatgt ttgcgatagt ccgttagata ttgcaacaca actgttactt     240
```

tccaacgtaa aaaaattagt actttctgac tcggaaaaaa acacgttaaa aaataaatgg 300
aaattgctca ctgagaagaa atctgaaaat gcggaggtaa gagcggtcgc ccttgtacca 360
aaagattttc ccaaagatct ggttttagcg cctttacctg atcatgttaa tgattttaca 420
tggtacaaaa agcgaaagaa aagacttggc ataaaacctg aacatcaaca tgttggtctt 480
tctattatcg ttacaacatt caatcgacca gcaattttat cgattacatt agcctgttta 540
gtaaaccaaa aaacacatta cccgtttgaa gttatcgtga cagatgatgg tagtcaggaa 600
gatctatcac cgatcattcg ccaatatgaa aataaattgg atattcgcta cgtcagacaa 660
aaagataacg gttttcaagc cagtgccgct cggaatatgg gattacgctt agcaaaatat 720
gactttattg gcttactcga ctgtgatatg gcgccaaatc cattatgggt tcattcttat 780
gttgcagagc tattagaaga tgatgattta acaatcattg gtccaagaaa atacatcgat 840
acacaacata ttgacccaaa agacttctta aataacgcga gtttgcttga atcattacca 900
gaagtgaaaa ccaataatag tgttgccgca aaaggggaag gaacagtttc tctggattgg 960
cgcttagaac aattcgaaaa aacagaaaat ctccgcttat ccgattcgcc tttccgtttt 1020
tttgcggcgg gtaatgttgc tttcgctaaa aaatggctaa ataaatccgg tttctttgat 1080
gaggaattta atcactgggg tggagaagat gtggaatttg gatatcgctt attccgttac 1140
ggtagtttct ttaaaactat tgatggcatt atggcctacc atcaagagcc accaggtaaa 1200
gaaaatgaaa ccgatcgtga agcgggaaaa aatattacgc tcgatattat gagagaaaag 1260
gtcccttata tctatagaaa acttttacca atagaagatt cgcatatcaa tagagtacct 1320
ttagtttcaa tttatatccc agcttataac tgtgcaaact atattcaacg ttgcgtagat 1380
agtgcactga atcagactgt tgttgatctc gaggtttgta tttgtaacga tggttcaaca 1440
gataatacct tagaagtgat caataagctt tatggtaata atcctagggt acgcatcatg 1500
tctaaaccaa atggcggaat agcctcagca tcaaatgcag ccgtttcttt tgctaaaggt 1560
tattacattg ggcagttaga ttcagatgat tatcttgagc ctgatgcagt tgaactgtgt 1620
ttaaaagaat ttttaaaaga taaaacgcta gcttgtgttt ataccactaa tagaaacgtc 1680
aatccggatg gtagcttaat cgctaatggt tacaattggc cagaattttc acgagaaaaa 1740
ctcacaacgg ctatgattgc tcaccacttt agaatgttca cgattagagc ttggcattta 1800
actgatggat tcaatgaaaa aattgaaaat gccgtagact atgacatgtt cctcaaactc 1860
agtgaagttg gaaaatttaa acatcttaat aaaatctgct ataaccgtgt attacatggt 1920
gataacacat caattaagaa acttggcatt caa 1953

<210> SEQ ID NO 11
<211> LENGTH: 2112
<212> TYPE: DNA
<213> ORGANISM: Pasteurella multocida

<400> SEQUENCE: 11
atgaatacat tatcacaagc aataaaagca tataacagca atgactatca attagcactc 60
aaattatttg aaaagtcggc ggaaatctat ggacggaaaa ttgttgaatt tcaaattacc 120
aaatgcaaag aaaaactctc agcacatcct tctgttaatt cagcacatct ttctgtaaat 180
aaagaagaaa aagtcaatgt ttgcgatagt ccgttagata ttgcaacaca actgttactt 240
tccaacgtaa aaaaattagt actttctgac tcggaaaaaa acacgttaaa aaataaatgg 300
aaattgctca ctgagaagaa atctgaaaat gcggaggtaa gagcggtcgc ccttgtacca 360
aaagattttc ccaaagatct ggttttagcg cctttacctg atcatgttaa tgattttaca 420

-continued

```
tggtacaaaa agcgaaagaa aagacttggc ataaaacctg aacatcaaca tgttggtctt    480
tctattatcg ttacaacatt caatcgacca gcaattttat cgattacatt agcctgttta    540
gtaaaccaaa aaacacatta cccgtttgaa gttatcgtga cagatgatgg tagtcaggaa    600
gatctatcac cgatcattcg ccaatatgaa aataaattgg atattcgcta cgtcagacaa    660
aaagataacg gttttcaagc cagtgccgct cggaatatgg gattacgctt agcaaaatat    720
gactttattg gcttactcga ctgtgatatg gcgccaaatc cattatgggt tcattcttat    780
gttgcagagc tattagaaga tgatgattta acaatcattg gtccaagaaa atacatcgat    840
acacaacata ttgacccaaa agacttctta aataacgcga gtttgcttga atcattacca    900
gaagtgaaaa ccaataatag tgttgccgca aaaggggaag gaacagtttc tctggattgg    960
cgcttagaac aattcgaaaa aacagaaaat ctccgcttat ccgattcgcc tttccgtttt   1020
tttgcggcgg gtaatgttgc tttcgctaaa aaatggctaa ataaatccgg tttctttgat   1080
gaggaattta atcactgggg tggagaagat gtggaatttg gatatcgctt attccgttac   1140
ggtagtttct ttaaaactat tgatggcatt atggcctacc atcaagagcc accaggtaaa   1200
gaaaatgaaa ccgatcgtga agcgggaaaa aatattacgc tcgatattat gagagaaaag   1260
gtcccttata tctatagaaa acttttacca atagaagatt cgcatatcaa tagagtacct   1320
ttagtttcaa tttatatccc agcttataac tgtgcaaact atattcaacg ttgcgtagat   1380
agtgcactga atcagactgt tgttgatctc gaggtttgta tttgtaacaa tggttcaaca   1440
gataatacct tagaagtgat caataagctt tatggtaata atcctagggt acgcatcatg   1500
tctaaaccaa atggcggaat agcctcagca tcaaatgcag ccgtttcttt tgctaaaggt   1560
tattacattg ggcagttaga ttcagatgat tatcttgagc ctgatgcagt tgaactgtgt   1620
ttaaaagaat ttttaaaaga taaaacgcta gcttgtgttt ataccactaa tagaaacgtc   1680
aatccggatg gtagcttaat cgctaatggt tacaattggc cagaattttc acgagaaaaa   1740
ctcacaacgg ctatgattgc tcaccacttt agaatgttca cgattagagc ttggcattta   1800
actgatggat tcaatgaaaa aattgaaaat gccgtagact atgacatgtt cctcaaactc   1860
agtgaagttg gaaaatttaa acatcttaat aaaatctgct ataaccgtgt attacatggt   1920
gataacacat caattaagaa acttggcatt caaaagaaaa accattttgt tgtagtcaat   1980
cagtcattaa atagacaagg cataacttat tataattatg acgaatttga tgatttagat   2040
gaaagtagaa agtatatttt caataaaacc gctgaatatc aagaagagat tgatatctta   2100
aaagatattt aa                                                       2112
```

<210> SEQ ID NO 12
<211> LENGTH: 2112
<212> TYPE: DNA
<213> ORGANISM: Pasteurella multocida

<400> SEQUENCE: 12

```
atgaatacat tatcacaagc aataaaagca tataacagca atgactatca attagcactc     60
aaattatttg aaaagtcggc ggaaatctat ggacggaaaa ttgttgaatt tcaaattacc    120
aaatgcaaag aaaaactctc agcacatcct tctgttaatt cagcacatct ttctgtaaat    180
aaagaagaaa aagtcaatgt ttgcgatagt ccgttagata ttgcaacaca actgttactt    240
tccaacgtaa aaaaattagt actttctgac tcggaaaaaa acacgttaaa aaataaatgg    300
aaattgctca ctgagaagaa atctgaaaat gcggaggtaa gagcggtcgc ccttgtacca    360
aaagattttc ccaaagatct ggttttagcg cctttacctg atcatgttaa tgattttaca    420
```

```
tggtacaaaa agcgaaagaa aagacttggc ataaaacctg aacatcaaca tgttggtctt    480
tctattatcg ttacaacatt caatcgacca gcaattttat cgattacatt agcctgttta    540
gtaaaccaaa aaacacatta cccgtttgaa gttatcgtga cagataatgg tagtcaggaa    600
gatctatcac cgatcattcg ccaatatgaa aataaattgg atattcgcta cgtcagacaa    660
aaagataacg gttttcaagc cagtgccgct cggaatatgg gattacgctt agcaaaatat    720
gactttattg gcttactcga ctgtgatatg gcgccaaatc cattatgggt tcattcttat    780
gttgcagagc tattagaaga tgatgattta acaatcattg gtccaagaaa atacatcgat    840
acacaacata ttgacccaaa agacttctta aataacgcga gtttgcttga atcattacca    900
gaagtgaaaa ccaataatag tgttgccgca aaaggggaag gaacagtttc tctggattgg    960
cgcttagaac aattcgaaaa aacagaaaat ctccgcttat ccgattcgcc tttccgtttt   1020
tttgcggcgg gtaatgttgc tttcgctaaa aaatggctaa ataaatccgg tttctttgat   1080
gaggaattta atcactgggg tggagaagat gtggaatttg gatatcgctt attccgttac   1140
ggtagtttct ttaaaactat tgatggcatt atggcctacc atcaagagcc accaggtaaa   1200
gaaaatgaaa ccgatcgtga agcgggaaaa aatattacgc tcgatattat gagagaaaag   1260
gtcccttata tctatagaaa acttttacca atagaagatt cgcatatcaa tagagtacct   1320
ttagtttcaa tttatatccc agcttataac tgtgcaaact atattcaacg ttgcgtagat   1380
agtgcactga atcagactgt tgttgatctc gaggtttgta tttgtaacga tggttcaaca   1440
gataatacct tagaagtgat caataagctt tatggtaata atcctagggt acgcatcatg   1500
tctaaaccaa atggcggaat agcctcagca tcaaatgcag ccgtttcttt tgctaaaggt   1560
tattacattg ggcagttaga ttcagatgat tatcttgagc ctgatgcagt tgaactgtgt   1620
ttaaaagaat ttttaaaaga taaaacgcta gcttgtgttt ataccactaa tagaaacgtc   1680
aatccggatg gtagcttaat cgctaatggt tacaattggc cagaattttc acgagaaaaa   1740
ctcacaacgg ctatgattgc tcaccacttt agaatgttca cgattagagc ttggcattta   1800
actgatggat tcaatgaaaa aattgaaaat gccgtagact atgacatgtt cctcaaactc   1860
agtgaagttg gaaaatttaa acatcttaat aaaatctgct ataaccgtgt attacatggt   1920
gataacacat caattaagaa acttggcatt caaaagaaaa accattttgt tgtagtcaat   1980
cagtcattaa atagacaagg cataacttat tataattatg acgaatttga tgatttagat   2040
gaaagtagaa agtatatttt caataaaacc gctgaatatc aagaagagat tgatatctta   2100
aaagatattt aa                                                       2112
```

```
<210> SEQ ID NO 13
<211> LENGTH: 1614
<212> TYPE: DNA
<213> ORGANISM: Pasteurella multocida

<400> SEQUENCE: 13

atcaatagag tacctttagt ttcaatttat atcccagctt ataactgtgc aaactatatt     60
caacgttgcg tagatagtgc actgaatcag actgttgttg atctcgaggt ttgtatttgt    120
aacgatggtt caacagataa taccttagaa gtgatcaata agctttatgg taataatcct    180
agggtacgca tcatgtctaa accaaatggc ggaatagcct cagcatcaaa tgcagccgtt    240
tcttttgcta aaggttatta cattgggcag ttagattcag atgattatct tgagcctgat    300
gcagttgaac tgtgtttaaa agaattttta aaagataaaa cgctagcttg tgtttatacc    360
actaatagaa acgtcaatcc ggatggtagc ttaatcgcta atggttacaa ttggccagaa    420
```

ttttcacgag aaaaactcac aacggctatg attgctcacc actttagaat gttcacgatt 480
agagcttggc atttaactga tggattcaat gaaaaaattg aaaatgccgt agactatgac 540
atgttcctca aactcagtga agttggaaaa tttaaacatc ttaataaaat ctgctataac 600
cgtgtattac atggtgataa cacatcaatt aagaaacttg gcattcaaaa gaaaaaccat 660
tttgttgtag tcaatcagtc attaaataga caaggcataa cttattataa ttatgacgaa 720
tttgatgatt tagatgaaag tagaaagtat attttcaata aaaccgctga atatcaagaa 780
gagattgata tcttaaaaga tattaaaatc atccagaata aagatgccaa aatcgcagtc 840
agtatttttt atcccaatac attaaacggc ttagtgaaaa aactaaacaa tattattgaa 900
tataataaaa atatattcgt tattgttcta catgttgata agaatcatct tacaccagat 960
atcaaaaaag aaatactagc cttctatcat aaacatcaag tgaatatttt actaaataat 1020
gatatctcat attacacgag taatagatta ataaaaactg aggcgcattt aagtaatatt 1080
aataaattaa gtcagttaaa tctaaattgt gaatacatca tttttgataa tcatgacagc 1140
ctattcgtta aaaatgacag ctatgcttat atgaaaaaat atgatgtcgg catgaatttc 1200
tcagcattaa cacatgattg gatcgagaaa atcaatgcgc atccaccatt taaaaagctc 1260
attaaaactt attttaatga caatgactta aaaagtatga atgtgaaagg ggcatcacaa 1320
ggtatgttta tgacgtatgc gctagcgcat gagcttctga cgattattaa agaagtcatc 1380
acatcttgcc agtcaattga tagtgtgcca gaatataaca ctgaggatat ttggttccaa 1440
tttgcacttt taatcttaga aaagaaaacc ggccatgtat ttaataaaac atcgaccctg 1500
acttatatgc cttgggaacg aaaattacaa tggacaaatg aacaaattga aagtgcaaaa 1560
agaggagaaa atatacctgt taacaagttc attattaata gtataactct ataa 1614

<210> SEQ ID NO 14
<211> LENGTH: 966
<212> TYPE: DNA
<213> ORGANISM: Pasteurella multocida

<400> SEQUENCE: 14
atcaatagag tacctttagt ttcaatttat atcccagctt ataactgtgc aaactatatt 60
caacgttgcg tagatagtgc actgaatcag actgttgttg atctcgaggt ttgtatttgt 120
aacgatggtt caacagataa taccttagaa gtgatcaata agctttatgg taataatcct 180
agggtacgca tcatgtctaa accaaatggc ggaatagcct cagcatcaaa tgcagccgtt 240
tcttttgcta aaggttatta cattgggcag ttagattcag atgattatct tgagcctgat 300
gcagttgaac tgtgtttaaa agaattttta aaagataaaa cgctagcttg tgtttatacc 360
actaatagaa acgtcaatcc ggatggtagc ttaatcgcta atggttacaa ttggccagaa 420
ttttcacgag aaaaactcac aacggctatg attgctcacc actttagaat gttcacgatt 480
agagcttggc atttaactga tggattcaat gaaaaaattg aaaatgccgt agactatgac 540
atgttcctca aactcagtga agttggaaaa tttaaacatc ttaataaaat ctgctataac 600
cgtgtattac atggtgataa cacatcaatt aagaaacttg gcattcaaaa gaaaaaccat 660
tttgttgtag tcaatcagtc attaaataga caaggcataa cttattataa ttatgacgaa 720
tttgatgatt tagatgaaag tagaaagtat attttcaata aaaccgctga atatcaagaa 780
gagattgata tcttaaaaga tattaaaatc atccagaata aagatgccaa aatcgcagtc 840
agtatttttt atcccaatac attaaacggc ttagtgaaaa aactaaacaa tattattgaa 900
tataataaaa atatattcgt tattgttcta catgttgata agaatcatct tacaccagat 960
atctaa 966

<210> SEQ ID NO 15
<211> LENGTH: 1821
<212> TYPE: DNA
<213> ORGANISM: Pasteurella multocida

<400> SEQUENCE: 15
atgaaacctg aacatcaaca tgttggtctt tctattatcg ttacaacatt caatcgacca 60
gcaattttat cgattacatt agcctgttta gtaaaccaaa aaacacatta cccgtttgaa 120
gttatcgtga cagatgatgg tagtcaggaa gatctatcac cgatcattcg ccaatatgaa 180
aataaattgg atattcgcta cgtcagacaa aaagataacg gttttcaagc cagtgccgct 240
cggaatatgg gattacgctt agcaaaatat gactttattg gcttactcga ctgtgatatg 300
gcgccaaatc cattatgggt tcattcttat gttgcagagc tattagaaga tgatgattta 360
acaatcattg gtccaagaaa atacatcgat acacaacata ttgacccaaa agacttctta 420
aataacgcga gtttgcttga atcattacca gaagtgaaaa ccaataatag tgttgccgca 480
aaaggggaag gaacagtttc tctggattgg cgcttagaac aattcgaaaa aacagaaaat 540
ctccgcttat ccgattcgcc tttccgtttt tttgcggcgg gtaatgttgc tttcgctaaa 600
aaatggctaa ataaatccgg tttctttgat gaggaattta atcactgggg tggagaagat 660
gtggaatttg gatatcgctt attccgttac ggtagtttct ttaaaactat tgatggcatt 720
atggcctacc atcaagagcc accaggtaaa gaaaatgaaa ccgatcgtga agcgggaaaa 780
aatattacgc tcgatattat gagagaaaag gtcccttata tctatagaaa acttttacca 840
atagaagatt cgcatatcaa tagagtacct ttagtttcaa tttatatccc agcttataac 900
tgtgcaaact atattcaacg ttgcgtagat agtgcactga atcagactgt tgttgatctc 960
gaggtttgta tttgtaacga tggttcaaca gataatacct tagaagtgat caataagctt 1020
tatggtaata atcctagggt acgcatcatg tctaaaccaa atggcggaat agcctcagca 1080
tcaaatgcag ccgtttcttt tgctaaaggt tattacattg ggcagttaga ttcagatgat 1140
tatcttgagc ctgatgcagt tgaactgtgt ttaaaagaat ttttaaaaga taaaacgcta 1200
gcttgtgttt ataccactaa tagaaacgtc aatccggatg gtagcttaat cgctaatggt 1260
tacaattggc cagaattttc acgagaaaaa ctcacaacgg ctatgattgc tcaccacttt 1320
agaatgttca cgattagagc ttggcattta actgatggat tcaatgaaaa aattgaaaat 1380
gccgtagact atgacatgtt cctcaaactc agtgaagttg gaaaatttaa acatcttaat 1440
aaaatctgct ataaccgtgt attacatggt gataacacat caattaagaa acttggcatt 1500
caaaagaaaa accattttgt tgtagtcaat cagtcattaa atagacaagg cataacttat 1560
tataattatg acgaatttga tgatttagat gaaagtagaa agtatatttt caataaaacc 1620
gctgaatatc aagaagagat tgatatctta aaagatatta aaatcatcca gaataaagat 1680
gccaaaatcg cagtcagtat tttttatccc aatacattaa acggcttagt gaaaaaacta 1740
aacaatatta ttgaatataa taaaaatata ttcgttattg ttctacatgt tgataagaat 1800
catcttacac cagatatcta a 1821

<210> SEQ ID NO 16
<211> LENGTH: 2112
<212> TYPE: DNA
<213> ORGANISM: Pasteurella multocida

<400> SEQUENCE: 16
atgaatacat tatcacaagc aataaaagca tataacagca atgactatca attagcactc 60
aaattatttg aaaagtcggc ggaaatctat ggacggaaaa ttgttgaatt tcaaattacc 120
aaatgcaaag aaaaactctc agcacatcct tctgttaatt cagcacatct ttctgtaaat 180
aaagaagaaa aagtcaatgt ttgcgatagt ccgttagata ttgcaacaca actgttactt 240
tccaacgtaa aaaaattagt actttctgac tcggaaaaaa acacgttaaa aaataaatgg 300
aaattgctca ctgagaagaa atctgaaaat gcggaggtaa gagcggtcgc ccttgtacca 360
aaagattttc ccaaagatct ggttttagcg cctttacctg atcatgttaa tgattttaca 420
tggtacaaaa agcgaaagaa aagacttggc ataaaacctg aacatcaaca tgttggtctt 480
tctattatcg ttacaacatt caatcgacca gcaattttat cgattacatt agcctgttta 540
gtaaaccaaa aaacacatta cccgtttgaa gttatcgtga cagatgaagg tagtcaggaa 600
gatctatcac cgatcattcg ccaatatgaa aataaattgg atattcgcta cgtcagacaa 660
aaagataacg gttttcaagc cagtgccgct cggaatatgg gattacgctt agcaaaatat 720
gactttattg gcttactcga ctgtgatatg gcgccaaatc cattatgggt tcattcttat 780
gttgcagagc tattagaaga tgatgattta acaatcattg gtccaagaaa atacatcgat 840
acacaacata ttgacccaaa agacttctta aataacgcga gtttgcttga atcattacca 900
gaagtgaaaa ccaataatag tgttgccgca aaaggggaag gaacagtttc tctggattgg 960
cgcttagaac aattcgaaaa aacagaaaat ctccgcttat ccgattcgcc tttccgtttt 1020
tttgcggcgg gtaatgttgc tttcgctaaa aaatggctaa ataaatccgg tttctttgat 1080
gaggaattta atcactgggg tggagaagat gtggaatttg gatatcgctt attccgttac 1140
ggtagtttct ttaaaactat tgatggcatt atggcctacc atcaagagcc accaggtaaa 1200
gaaaatgaaa ccgatcgtga agcgggaaaa aatattacgc tcgatattat gagagaaaag 1260
gtcccttata tctatagaaa acttttacca atagaagatt cgcatatcaa tagagtacct 1320
ttagtttcaa tttatatccc agcttataac tgtgcaaact atattcaacg ttgcgtagat 1380
agtgcactga atcagactgt tgttgatctc gaggtttgta tttgtaacga tggttcaaca 1440
gataatacct tagaagtgat caataagctt tatggtaata atcctagggt acgcatcatg 1500
tctaaaccaa atggcggaat agcctcagca tcaaatgcag ccgtttcttt tgctaaaggt 1560
tattacattg ggcagttaga ttcagatgat tatcttgagc ctgatgcagt tgaactgtgt 1620
ttaaaagaat ttttaaaaga taaaacgcta gcttgtgttt ataccactaa tagaaacgtc 1680
aatccggatg gtagcttaat cgctaatggt tacaattggc cagaattttc acgagaaaaa 1740
ctcacaacgg ctatgattgc tcaccacttt agaatgttca cgattagagc ttggcattta 1800
actgatggat tcaatgaaaa aattgaaaat gccgtagact atgacatgtt cctcaaactc 1860
agtgaagttg gaaaatttaa acatcttaat aaaatctgct ataaccgtgt attacatggt 1920
gataacacat caattaagaa acttggcatt caaaagaaaa accattttgt tgtagtcaat 1980
cagtcattaa atagacaagg cataacttat tataattatg acgaatttga tgatttagat 2040
gaaagtagaa agtatatttt caataaaacc gctgaatatc aagaagagat tgatatctta 2100
aaagatattt aa 2112

<210> SEQ ID NO 17
<211> LENGTH: 2112
<212> TYPE: DNA
<213> ORGANISM: Pasteurella multocida

<400> SEQUENCE: 17

-continued

```
atgaatacat tatcacaagc aataaaagca tataacagca atgactatca attagcactc     60
aaattatttg aaaagtcggc ggaaatctat ggacggaaaa ttgttgaatt tcaaattacc    120
aaatgcaaag aaaaactctc agcacatcct tctgttaatt cagcacatct ttctgtaaat    180
aaagaagaaa aagtcaatgt ttgcgatagt ccgttagata ttgcaacaca actgttactt    240
tccaacgtaa aaaaattagt actttctgac tcggaaaaaa acacgttaaa aaataaatgg    300
aaattgctca ctgagaagaa atctgaaaat gcggaggtaa gagcggtcgc ccttgtacca    360
aaagattttc ccaaagatct ggttttagcg cctttacctg atcatgttaa tgattttaca    420
tggtacaaaa agcgaaagaa aagacttggc ataaaacctg aacatcaaca tgttggtctt    480
tctattatcg ttacaacatt caatcgacca gcaattttat cgattacatt agcctgttta    540
gtaaaccaaa aaacacatta cccgtttgaa gttatcgtga cagataaagg tagtcaggaa    600
gatctatcac cgatcattcg ccaatatgaa aataaattgg atattcgcta cgtcagacaa    660
aaagataacg gttttcaagc cagtgccgct cggaatatgg gattacgctt agcaaaatat    720
gactttattg gcttactcga ctgtgatatg gcgccaaatc cattatgggt tcattcttat    780
gttgcagagc tattagaaga tgatgattta acaatcattg gtccaagaaa atacatcgat    840
acacaacata ttgacccaaa agacttctta aataacgcga gtttgcttga atcattacca    900
gaagtgaaaa ccaataatag tgttgccgca aaaggggaag gaacagtttc tctggattgg    960
cgcttagaac aattcgaaaa aacagaaaat ctccgcttat ccgattcgcc tttccgtttt   1020
tttgcggcgg gtaatgttgc tttcgctaaa aaatggctaa ataaatccgg tttctttgat   1080
gaggaattta atcactgggg tggagaagat gtggaatttg gatatcgctt attccgttac   1140
ggtagtttct ttaaaactat tgatggcatt atggcctacc atcaagagcc accaggtaaa   1200
gaaaatgaaa ccgatcgtga agcgggaaaa aatattacgc tcgatattat gagagaaaag   1260
gtcccttata tctatagaaa acttttacca atagaagatt cgcatatcaa tagagtacct   1320
ttagtttcaa tttatatccc agcttataac tgtgcaaact atattcaacg ttgcgtagat   1380
agtgcactga atcagactgt tgttgatctc gaggtttgta tttgtaacga tggttcaaca   1440
gataatacct tagaagtgat caataagctt tatggtaata atcctagggt acgcatcatg   1500
tctaaaccaa atggcggaat agcctcagca tcaaatgcag ccgtttcttt tgctaaaggt   1560
tattacattg ggcagttaga ttcagatgat tatcttgagc ctgatgcagt tgaactgtgt   1620
ttaaaagaat ttttaaaaga taaaacgcta gcttgtgttt ataccactaa tagaaacgtc   1680
aatccggatg gtagcttaat cgctaatggt tacaattggc cagaattttc acgagaaaaa   1740
ctcacaacgg ctatgattgc tcaccacttt agaatgttca cgattagagc ttggcattta   1800
actgatggat tcaatgaaaa aattgaaaat gccgtagact atgacatgtt cctcaaactc   1860
agtgaagttg gaaaatttaa acatcttaat aaaatctgct ataaccgtgt attacatggt   1920
gataacacat caattaagaa acttggcatt caaaagaaaa accattttgt tgtagtcaat   1980
cagtcattaa atagacaagg cataacttat tataattatg acgaatttga tgatttagat   2040
gaaagtagaa agtatatttt caataaaacc gctgaatatc aagaagagat tgatatctta   2100
aaagatattt aa                                                       2112
```

<210> SEQ ID NO 18
<211> LENGTH: 2112
<212> TYPE: DNA
<213> ORGANISM: Pasteurella multocida

<400> SEQUENCE: 18

-continued atgaatacat tatcacaagc aataaaagca tataacagca atgactatca attagcactc 60
aaattatttg aaaagtcggc ggaaatctat ggacggaaaa ttgttgaatt tcaaattacc 120
aaatgcaaag aaaaactctc agcacatcct tctgttaatt cagcacatct ttctgtaaat 180
aaagaagaaa aagtcaatgt ttgcgatagt ccgttagata ttgcaacaca actgttactt 240
tccaacgtaa aaaaattagt actttctgac tcggaaaaaa acacgttaaa aaataaatgg 300
aaattgctca ctgagaagaa atctgaaaat gcggaggtaa gagcggtcgc ccttgtacca 360
aaagattttc ccaaagatct ggttttagcg cctttacctg atcatgttaa tgattttaca 420
tggtacaaaa agcgaaagaa aagacttggc ataaaacctg aacatcaaca tgttggtctt 480
tctattatcg ttacaacatt caatcgacca gcaattttat cgattacatt agcctgttta 540
gtaaaccaaa aaacacatta cccgtttgaa gttatcgtga cagatgatgg tagtcaggaa 600
gatctatcac cgatcattcg ccaatatgaa aataaattgg atattcgcta cgtcagacaa 660
aaagataacg gttttcaagc cagtgccgct cggaatatgg gattacgctt agcaaaatat 720
gactttattg gcttactcga ctgtgatatg gcgccaaatc cattatgggt tcattcttat 780
gttgcagagc tattagaaga tgatgattta acaatcattg gtccaagaaa atacatcgat 840
acacaacata ttgacccaaa agacttctta aataacgcga gtttgcttga atcattacca 900
gaagtgaaaa ccaataatag tgttgccgca aaaggggaag gaacagtttc tctggattgg 960
cgcttagaac aattcgaaaa aacagaaaat ctccgcttat ccgattcgcc tttccgtttt 1020
tttgcggcgg gtaatgttgc tttcgctaaa aaatggctaa ataaatccgg tttctttgat 1080
gaggaattta atcactgggg tggagaagat gtggaatttg gatatcgctt attccgttac 1140
ggtagtttct ttaaaactat tgatggcatt atggcctacc atcaagagcc accaggtaaa 1200
gaaaatgaaa ccgatcgtga agcgggaaaa aatattacgc tcgatattat gagagaaaag 1260
gtcccttata tctatagaaa acttttacca atagaagatt cgcatatcaa tagagtacct 1320
ttagtttcaa tttatatccc agcttataac tgtgcaaact atattcaacg ttgcgtagat 1380
agtgcactga atcagactgt tgttgatctc gaggtttgta tttgtaacga aggttcaaca 1440
gataatacct tagaagtgat caataagctt tatggtaata atcctagggt acgcatcatg 1500
tctaaaccaa atggcggaat agcctcagca tcaaatgcag ccgtttcttt tgctaaaggt 1560
tattacattg ggcagttaga ttcagatgat tatcttgagc ctgatgcagt tgaactgtgt 1620
ttaaaagaat ttttaaaaga taaaacgcta gcttgtgttt ataccactaa tagaaacgtc 1680
aatccggatg gtagcttaat cgctaatggt tacaattggc cagaattttc acgagaaaaa 1740
ctcacaacgg ctatgattgc tcaccacttt agaatgttca cgattagagc ttggcattta 1800
actgatggat tcaatgaaaa aattgaaaat gccgtagact atgacatgtt cctcaaactc 1860
agtgaagttg gaaaatttaa acatcttaat aaaatctgct ataaccgtgt attacatggt 1920
gataacacat caattaagaa acttggcatt caaaagaaaa accattttgt tgtagtcaat 1980
cagtcattaa atagacaagg cataacttat tataattatg acgaatttga tgatttagat 2040
gaaagtagaa agtatatttt caataaaacc gctgaatatc aagaagagat tgatatctta 2100
aaagatattt aa 2112

<210> SEQ ID NO 19
<211> LENGTH: 2112
<212> TYPE: DNA
<213> ORGANISM: Pasteurella multocida

<400> SEQUENCE: 19

-continued

```
atgaatacat tatcacaagc aataaaagca tataacagca atgactatca attagcactc     60
aaattatttg aaaagtcggc ggaaatctat ggacggaaaa ttgttgaatt tcaaattacc    120
aaatgcaaag aaaaactctc agcacatcct tctgttaatt cagcacatct ttctgtaaat    180
aaagaagaaa aagtcaatgt ttgcgatagt ccgttagata ttgcaacaca actgttactt    240
tccaacgtaa aaaaattagt actttctgac tcggaaaaaa acacgttaaa aaataaatgg    300
aaattgctca ctgagaagaa atctgaaaat gcggaggtaa gagcggtcgc ccttgtacca    360
aaagattttc ccaaagatct ggttttagcg cctttacctg atcatgttaa tgattttaca    420
tggtacaaaa agcgaaagaa aagacttggc ataaaacctg aacatcaaca tgttggtctt    480
tctattatcg ttacaacatt caatcgacca gcaattttat cgattacatt agcctgttta    540
gtaaaccaaa aaacacatta cccgtttgaa gttatcgtga cagatgatgg tagtcaggaa    600
gatctatcac cgatcattcg ccaatatgaa aataaattgg atattcgcta cgtcagacaa    660
aaagataacg gttttcaagc cagtgccgct cggaatatgg gattacgctt agcaaaatat    720
gactttattg gcttactcga ctgtgatatg gcgccaaatc cattatgggt tcattcttat    780
gttgcagagc tattagaaga tgatgattta acaatcattg gtccaagaaa atacatcgat    840
acacaacata ttgacccaaa agacttctta aataacgcga gtttgcttga atcattacca    900
gaagtgaaaa ccaataatag tgttgccgca aaaggggaag gaacagtttc tctggattgg    960
cgcttagaac aattcgaaaa aacagaaaat ctccgcttat ccgattcgcc tttccgtttt   1020
tttgcggcgg gtaatgttgc tttcgctaaa aaatggctaa ataaatccgg tttctttgat   1080
gaggaattta atcactgggg tggagaagat gtggaatttg gatatcgctt attccgttac   1140
ggtagtttct ttaaaactat tgatggcatt atggcctacc atcaagagcc accaggtaaa   1200
gaaaatgaaa ccgatcgtga agcgggaaaa aatattacgc tcgatattat gagagaaaag   1260
gtcccttata tctatagaaa acttttacca atagaagatt cgcatatcaa tagagtacct   1320
ttagtttcaa tttatatccc agcttataac tgtgcaaact atattcaacg ttgcgtagat   1380
agtgcactga atcagactgt tgttgatctc gaggtttgta tttgtaacaa aggttcaaca   1440
gataatacct tagaagtgat caataagctt tatggtaata atcctagggt acgcatcatg   1500
tctaaaccaa atggcggaat agcctcagca tcaaatgcag ccgtttcttt tgctaaaggt   1560
tattacattg ggcagttaga ttcagatgat tatcttgagc ctgatgcagt tgaactgtgt   1620
ttaaaagaat ttttaaaaga taaaacgcta gcttgtgttt ataccactaa tagaaacgtc   1680
aatccggatg gtagcttaat cgctaatggt tacaattggc cagaattttc acgagaaaaa   1740
ctcacaacgg ctatgattgc tcaccacttt agaatgttca cgattagagc ttggcattta   1800
actgatggat tcaatgaaaa aattgaaaat gccgtagact atgacatgtt cctcaaactc   1860
agtgaagttg gaaaatttaa acatcttaat aaaatctgct ataaccgtgt attacatggt   1920
gataacacat caattaagaa acttggcatt caaaagaaaa accattttgt tgtagtcaat   1980
cagtcattaa atagacaagg cataacttat tataattatg acgaatttga tgatttagat   2040
gaaagtagaa agtatatttt caataaaacc gctgaatatc aagaagagat tgatatctta   2100
aaagatattt aa                                                        2112
```

<210> SEQ ID NO 20
<211> LENGTH: 2271
<212> TYPE: DNA
<213> ORGANISM: Pasteurella multocida

<400> SEQUENCE: 20

-continued

```
atgaatacat tatcacaagc aataaaagca tataacagca atgactatca attagcactc     60
aaattatttg aaaagtcggc ggaaatctat ggacggaaaa ttgttgaatt tcaaattacc    120
aaatgcaaag aaaaactctc agcacatcct tctgttaatt cagcacatct ttctgtaaat    180
aaagaagaaa aagtcaatgt ttgcgatagt ccgttagata ttgcaacaca actgttactt    240
tccaacgtaa aaaaattagt actttctgac tcggaaaaaa acacgttaaa aaataaatgg    300
aaattgctca ctgagaagaa atctgaaaat gcggaggtaa gagcggtcgc ccttgtacca    360
aaagatttc ccaaagatct ggttttagcg cctttacctg atcatgttaa tgattttaca    420
tggtacaaaa agcgaaagaa aagacttggc ataaaacctg aacatcaaca tgttggtctt    480
tctattatcg ttacaacatt caatcgacca gcaattttat cgattacatt agcctgttta    540
gtaaaccaaa aaacacatta cccgtttgaa gttatcgtga cagatgatgg tagtcaggaa    600
gatctatcac cgatcattcg ccaatatgaa aataaattgg atattcgcta cgtcagacaa    660
aaagataacg gttttcaagc cagtgccgct cggaatatgg gattacgctt agcaaaatat    720
gactttattg gcttactcga ctgtgatatg gcgccaaatc cattatgggt tcattcttat    780
gttgcagagc tattagaaga tgatgattta acaatcattg gtccaagaaa atacatcgat    840
acacaacata ttgacccaaa agacttctta aataacgcga gtttgcttga atcattacca    900
gaagtgaaaa ccaataatag tgttgccgca aaaggggaag gaacagtttc tctggattgg    960
cgcttagaac aattcgaaaa aacagaaaat ctccgcttat ccgattcgcc tttccgtttt   1020
tttgcggcgg gtaatgttgc tttcgctaaa aaatggctaa ataaatccgg tttctttgat   1080
gaggaattta atcactgggg tggagaagat gtggaatttg gatatcgctt attccgttac   1140
ggtagtttct ttaaaactat tgatggcatt atggcctacc atcaagagcc accaggtaaa   1200
gaaaatgaaa ccgatcgtga agcgggaaaa aatattacgc tcgatattat gagagaaaag   1260
gtcccttata tctatagaaa acttttacca atagaagatt cgcatatcaa tagagtacct   1320
ttagtttcaa tttatatccc agcttataac tgtgcaaact atattcaacg ttgcgtagat   1380
agtgcactga atcagactgt tgttgatctc gaggtttgta tttgtaacga tggttcaaca   1440
gataatacct tagaagtgat caataagctt tatggtaata atcctagggt acgcatcatg   1500
tctaaaccaa atggcggaat agcctcagca tcaaatgcag ccgtttcttt tgctaaaggt   1560
tattacattg ggcagttaga ttcagatgat tatcttgagc ctgatgcagt tgaactgtgt   1620
ttaaaagaat ttttaaaaga taaaacgcta gcttgtgttt ataccactaa tagaaacgtc   1680
aatccggatg gtagcttaat cgctaatggt tacaattggc cagaattttc acgagaaaaa   1740
ctcacaacgg ctatgattgc tcaccacttt agaatgttca cgattagagc ttggcattta   1800
actgatggat tcaatgaaaa aattgaaaat gccgtagact atgacatgtt cctcaaactc   1860
agtgaagttg gaaaatttaa acatcttaat aaaatctgct ataaccgtgt attacatggt   1920
gataacacat caattaagaa acttggcatt caaaagaaaa accattttgt tgtagtcaat   1980
cagtcattaa atagacaagg cataacttat tataattatg acgaatttga tgatttagat   2040
gaaagtagaa agtatatttt caataaaacc gctgaatatc aagaagagat tgatatctta   2100
aaagatatta aaatcatcca gaataaagat gccaaaatcg cagtcagtat tttttatccc   2160
aatacattaa acggcttagt gaaaaaacta aacaatatta ttgaatataa taaaaatata   2220
ttcgttattg ttctacatgt tgataagaat catcttacac cagatatcta a             2271
```

<210> SEQ ID NO 21
<211> LENGTH: 1704

<212> TYPE: DNA
<213> ORGANISM: Pasteurella multocida

<400> SEQUENCE: 21

```
atgaatacat tatcacaagc aataaaagca tataacagca atgactatca attagcactc     60
aaattatttg aaaagtcggc ggaaatctat ggacggaaaa ttgttgaatt tcaaattacc    120
aaatgcaaag aaaaactctc agcacatcct tctgttaatt cagcacatct ttctgtaaat    180
aaagaagaaa aagtcaatgt ttgcgatagt ccgttagata ttgcaacaca actgttactt    240
tccaacgtaa aaaaattagt actttctgac tcggaaaaaa acacgttaaa aaataaatgg    300
aaattgctca ctgagaagaa atctgaaaat gcggaggtaa gagcggtcgc ccttgtacca    360
aaagatttc ccaaagatct ggttttagcg cctttacctg atcatgttaa tgattttaca     420
tggtacaaaa agcgaaagaa aagacttggc ataaaacctg aacatcaaca tgttggtctt    480
tctattatcg ttacaacatt caatcgacca gcaattttat cgattacatt agcctgttta    540
gtaaaccaaa aaacacatta cccgtttgaa gttatcgtga cagatgatgg tagtcaggaa    600
gatctatcac cgatcattcg ccaatatgaa aataaattgg atattcgcta cgtcagacaa    660
aaagataacg gttttcaagc cagtgccgct cggaatatgg gattacgctt agcaaaatat    720
gactttattg gcttactcga ctgtgatatg gcgccaaatc cattatgggt tcattcttat    780
gttgcagagc tattagaaga tgatgattta acaatcattg gtccaagaaa atacatcgat    840
acacaacata ttgacccaaa agacttctta aataacgcga gtttgcttga atcattacca    900
gaagtgaaaa ccaataatag tgttgccgca aaaggggaag gaacagtttc tctggattgg    960
cgcttagaac aattcgaaaa aacagaaaat ctccgcttat ccgattcgcc tttccgtttt   1020
tttgcggcgg gtaatgttgc tttcgctaaa aaatggctaa ataaatccgg tttctttgat   1080
gaggaattta atcactgggg tggagaagat gtggaatttg gatatcgctt attccgttac   1140
ggtagtttct ttaaaactat tgatggcatt atggcctacc atcaagagcc accaggtaaa   1200
gaaaatgaaa ccgatcgtga agcgggaaaa aatattacgc tcgatattat gagagaaaag   1260
gtcccttata tctatagaaa acttttacca atagaagatt cgcatatcaa tagagtacct   1320
ttagtttcaa tttatatccc agcttataac tgtgcaaact atattcaacg ttgcgtagat   1380
agtgcactga atcagactgt tgttgatctc gaggtttgta tttgtaacga tggttcaaca   1440
gataatacct tagaagtgat caataagctt tatggtaata atcctagggt acgcatcatg   1500
tctaaaccaa atggcggaat agcctcagca tcaaatgcag ccgtttcttt tgctaaaggt   1560
tattacattg ggcagttaga ttcagatgat tatcttgagc ctgatgcagt tgaactgtgt   1620
ttaaaagaat ttttaaaaga taaaacgcta gcttgtgttt ataccactaa tagaaacgtc   1680
aatccggatg gtagcttaat ctaa                                          1704
```

<210> SEQ ID NO 22
<211> LENGTH: 2115
<212> TYPE: DNA
<213> ORGANISM: Pasteurella multocida

<400> SEQUENCE: 22

```
atgaatacat tatcacaagc aataaaagca tataacagca atgactatga attagcactc     60
aaattatttg agaagtctgc tgaaacctac gggcgaaaaa tcgttgaatt ccaaattatc    120
aaatgtaaag aaaaactctc gaccaattct tatgtaagtg aagataaaaa aaacagtgtt    180
tgcgatagct cattagatat cgcaacacag ctcttacttt ccaacgtaaa aaaattaact    240
ctatccgaat cagaaaaaaa cagtttaaaa aataaatgga aatctatcac tgggaaaaaa    300
```

```
tcggagaacg cagaaatcag aaaggtggaa ctagtaccca aagattttcc taaagatctt    360
gttcttgctc cattgccaga tcatgttaat gattttacat ggtacaaaaa tcgaaaaaaa    420
agcttaggta taaagcctgt aaataagaat atcggtcttt ctattattat tcctacattt    480
aatcgtagcc gtattttaga tataacgtta gcctgtttgg tcaatcagaa aacaaactac    540
ccatttgaag tcgttgttgc agatgatggt agtaaggaaa acttacttac cattgtgcaa    600
aaatacgaac aaaaacttga cataaagtat gtaagacaaa aagattatgg atatcaattg    660
tgtgcagtca gaaacttagg tttacgtaca gcaaagtatg attttgtctc gattctagac    720
tgcgatatgg caccacaaca attatgggtt cattcttatc ttacagaact attagaagac    780
aatgatattg ttttaattgg acctagaaaa tatgtggata ctcataatat taccgcagaa    840
caattcctta acgatccata tttaatagaa tcactacctg aaaccgctac aaataacaat    900
ccttcgatta catcaaaagg aaatatatcg ttggattgga gattagaaca tttcaaaaaa    960
accgataatc tacgtctatg tgattctccg tttcgttatt ttagttgcgg taatgttgca   1020
ttttctaaag aatggctaaa taaagtaggt tggttcgatg aagaatttaa tcattggggg   1080
ggcgaagatg tagaatttgg ttacagatta tttgccaaag gctgtttttt cagagtaatt   1140
gacggcggaa tggcatacca tcaagaacca cctggtaaag aaaatgaaac agaccgcgaa   1200
gctggtaaaa gtattacgct taaaattgtg aaagaaaagg taccttacat ctatagaaag   1260
cttttaccaa tagaagattc acatattcat agaatacctt tagtttctat ttatatcccc   1320
gcttataact gtgcaaatta tattcaaaga tgtgtagata gtgctcttaa tcaaactgtt   1380
gtcgatctcg aggtttgtat ttgtaacgat ggttcaacag ataatacctt agaagtgatc   1440
aataagcttt atggtaataa tcctagggta cgcatcatgt ctaaaccaaa tggcggaata   1500
gcctcagcat caaatgcagc cgtttctttt gctaaaggtt attacattgg gcagttagat   1560
tcagatgatt atcttgagcc tgatgcagtt gaactgtgtt taaaagaatt tttaaaagat   1620
aaaacgctag cttgtgttta taccactaat agaaacgtca atccggatgg tagcttaatc   1680
gctaatggtt acaattggcc agaattttca cgagaaaaac tcacaacggc tatgattgct   1740
caccatttta gaatgtttac gattagagct tggcatttaa cggatggatt taacgaaaat   1800
attgaaaacg ccgtggatta tgacatgttc cttaaactca gtgaagttgg aaaatttaaa   1860
catcttaata aaatctgcta taaccgcgta ttacatggtg ataacacatc cattaagaaa   1920
ctcggcattc aaaagaaaaa ccatttttgtt gtagtcaatc agtcattaaa tagacaaggc   1980
atcaattatt ataattatga caaatttgat gatttagatg aaagtagaaa gtatatcttc   2040
aataaaaccg ctgaatatca agaagaaatg gatattttaa aagatcttaa actcattcaa   2100
aataaagatg cctaa                                                    2115
```

<210> SEQ ID NO 23
<211> LENGTH: 1980
<212> TYPE: DNA
<213> ORGANISM: Pasteurella multocida

<400> SEQUENCE: 23

```
atgctctcag cacatccttc tgttaattca gcacatcttt ctgtaaataa agaagaaaaa     60
gtcaatgttt gcgatagtcc gttagatatt gcaacacaac tgttactttc caacgtaaaa    120
aaattagtac tttctgactc ggaaaaaaac acgttaaaaa ataaatggaa attgctcact    180
gagaagaaat ctgaaaatgc ggaggtaaga gcggtcgccc ttgtaccaaa agattttccc    240
aaagatctgg ttttagcgcc tttacctgat catgttaatg attttacatg gtacaaaaag    300
```

cgaaagaaaa gacttggcat aaaacctgaa catcaacatg ttggtctttc tattatcgtt 360
acaacattca atcgaccagc aattttatcg attacattag cctgtttagt aaaccaaaaa 420
acacattacc cgtttgaagt tatcgtgaca gatgatggta gtcaggaaga tctatcaccg 480
atcattcgcc aatatgaaaa taaattggat attcgctacg tcagacaaaa agataacggt 540
tttcaagcca gtgccgctcg gaatatggga ttacgcttag caaaatatga ctttattggc 600
ttactcgact gtgatatggc gccaaatcca ttatgggttc attcttatgt tgcagagcta 660
ttagaagatg atgatttaac aatcattggt ccaagaaaat acatcgatac acaacatatt 720
gacccaaaag acttcttaaa taacgcgagt ttgcttgaat cattaccaga agtgaaaacc 780
aataatagtg ttgccgcaaa aggggaagga acagtttctc tggattggcg cttagaacaa 840
ttcgaaaaaa cagaaaatct ccgcttatcc gattcgcctt tccgtttttt tgcggcgggt 900
aatgttgctt tcgctaaaaa atggctaaat aaatccggtt tctttgatga ggaatttaat 960
cactggggtg gagaagatgt ggaatttgga tatcgcttat tccgttacgg tagtttcttt 1020
aaaactattg atggcattat ggcctaccat caagagccac caggtaaaga aaatgaaacc 1080
gatcgtgaag cgggaaaaaa tattacgctc gatattatga gagaaaaggt cccttatatc 1140
tatagaaaac ttttaccaat agaagattcg catatcaata gagtaccttt agtttcaatt 1200
tatatcccag cttataactg tgcaaactat attcaacgtt gcgtagatag tgcactgaat 1260
cagactgttg ttgatctcga ggtttgtatt tgtaacgatg gttcaacaga taatacctta 1320
gaagtgatca ataagcttta tggtaataat cctagggtac gcatcatgtc taaaccaaat 1380
ggcggaatag cctcagcatc aaatgcagcc gtttcttttg ctaaaggtta ttacattggg 1440
cagttagatt cagatgatta tcttgagcct gatgcagttg aactgtgttt aaaagaattt 1500
ttaaaagata aaacgctagc ttgtgtttat accactaata gaaacgtcaa tccggatggt 1560
agcttaatcg ctaatggtta caattggcca gaattttcac gagaaaaact cacaacggct 1620
atgattgctc accactttag aatgttcacg attagagctt ggcatttaac tgatggattc 1680
aatgaaaaaa ttgaaaatgc cgtagactat gacatgttcc tcaaactcag tgaagttgga 1740
aaatttaaac atcttaataa aatctgctat aaccgtgtat tacatggtga taacacatca 1800
attaagaaac ttggcattca aaagaaaaac catttttgtg tagtcaatca gtcattaaat 1860
agacaaggca taacttatta taattatgac gaatttgatg atttagatga aagtagaaag 1920
tatattttca ataaaaccgc tgaatatcaa gaagagattg atatcttaaa agatatttaa 1980

<210> SEQ ID NO 24
<211> LENGTH: 1902
<212> TYPE: DNA
<213> ORGANISM: Pasteurella multocida

<400> SEQUENCE: 24
atgttagata ttgcaacaca actgttactt tccaacgtaa aaaaattagt actttctgac 60
tcggaaaaaa acacgttaaa aaataaatgg aaattgctca ctgagaagaa atctgaaaat 120
gcggaggtaa gagcggtcgc ccttgtacca aaagattttc ccaaagatct ggttttagcg 180
cctttacctg atcatgttaa tgattttaca tggtacaaaa agcgaaagaa aagacttggc 240
ataaaacctg aacatcaaca tgttggtctt tctattatcg ttacaacatt caatcgacca 300
gcaattttat cgattacatt agcctgttta gtaaaccaaa aaacacatta cccgtttgaa 360
gttatcgtga cagatgatgg tagtcaggaa gatctatcac cgatcattcg ccaatatgaa 420
aataaattgg atattcgcta cgtcagacaa aaagataacg gttttcaagc cagtgccgct 480
cggaatatgg gattacgctt agcaaaatat gactttattg gcttactcga ctgtgatatg 540
gcgccaaatc cattatgggt tcattcttat gttgcagagc tattagaaga tgatgattta 600
acaatcattg gtccaagaaa atacatcgat acacaacata ttgacccaaa agacttctta 660
aataacgcga gtttgcttga atcattacca gaagtgaaaa ccaataatag tgttgccgca 720
aaaggggaag gaacagtttc tctggattgg cgcttagaac aattcgaaaa aacagaaaat 780
ctccgcttat ccgattcgcc tttccgtttt tttgcggcgg gtaatgttgc tttcgctaaa 840
aaatggctaa ataaatccgg tttctttgat gaggaattta atcactgggg tggagaagat 900
gtggaatttg gatatcgctt attccgttac ggtagtttct ttaaaactat tgatggcatt 960
atggcctacc atcaagagcc accaggtaaa gaaaatgaaa ccgatcgtga agcgggaaaa 1020
aatattacgc tcgatattat gagagaaaag gtcccttata tctatagaaa acttttacca 1080
atagaagatt cgcatatcaa tagagtacct ttagtttcaa tttatatccc agcttataac 1140
tgtgcaaact atattcaacg ttgcgtagat agtgcactga atcagactgt tgttgatctc 1200
gaggtttgta tttgtaacga tggttcaaca gataatacct tagaagtgat caataagctt 1260
tatggtaata atcctagggt acgcatcatg tctaaaccaa atggcggaat agcctcagca 1320
tcaaatgcag ccgtttcttt tgctaaaggt tattacattg ggcagttaga ttcagatgat 1380
tatcttgagc ctgatgcagt tgaactgtgt ttaaaagaat ttttaaaaga taaaacgcta 1440
gcttgtgttt ataccactaa tagaaacgtc aatccggatg gtagcttaat cgctaatggt 1500
tacaattggc cagaattttc acgagaaaaa ctcacaacgg ctatgattgc tcaccacttt 1560
agaatgttca cgattagagc ttggcattta actgatggat tcaatgaaaa aattgaaaat 1620
gccgtagact atgacatgtt cctcaaactc agtgaagttg gaaaatttaa acatcttaat 1680
aaaatctgct ataaccgtgt attacatggt gataacacat caattaagaa acttggcatt 1740
caaaagaaaa accattttgt tgtagtcaat cagtcattaa atagacaagg cataacttat 1800
tataattatg acgaatttga tgatttagat gaaagtagaa agtatatttt caataaaacc 1860
gctgaatatc aagaagagat tgatatctta aaagatattt aa 1902

<210> SEQ ID NO 25
<211> LENGTH: 1830
<212> TYPE: DNA
<213> ORGANISM: Pasteurella multocida

<400> SEQUENCE: 25
atgttaaaaa ataaatggaa attgctcact gagaagaaat ctgaaaatgc ggaggtaaga 60
gcggtcgccc ttgtaccaaa agattttccc aaagatctgg ttttagcgcc tttacctgat 120
catgttaatg attttacatg gtacaaaaag cgaaagaaaa gacttggcat aaaacctgaa 180
catcaacatg ttggtctttc tattatcgtt acaacattca atcgaccagc aattttatcg 240
attacattag cctgtttagt aaaccaaaaa acacattacc cgtttgaagt tatcgtgaca 300
gatgatggta gtcaggaaga tctatcaccg atcattcgcc aatatgaaaa taaattggat 360
attcgctacg tcagacaaaa agataacggt tttcaagcca gtgccgctcg gaatatggga 420
ttacgcttag caaaatatga ctttattggc ttactcgact gtgatatggc gccaaatcca 480
ttatgggttc attcttatgt tgcagagcta ttagaagatg atgatttaac aatcattggt 540
ccaagaaaat acatcgatac acaacatatt gacccaaaag acttcttaaa taacgcgagt 600
ttgcttgaat cattaccaga agtgaaaacc aataatagtg ttgccgcaaa aggggaagga 660
acagtttctc tggattggcg cttagaacaa ttcgaaaaaa cagaaaatct ccgcttatcc 720

-continued gattcgcctt tccgtttttt tgcggcgggt aatgttgctt tcgctaaaaa atggctaaat 780
aaatccggtt tctttgatga ggaatttaat cactggggtg gagaagatgt ggaatttgga 840
tatcgcttat tccgttacgg tagtttcttt aaaactattg atggcattat ggcctaccat 900
caagagccac caggtaaaga aaatgaaacc gatcgtgaag cgggaaaaaa tattacgctc 960
gatattatga gagaaaaggt cccttatatc tatagaaaac ttttaccaat agaagattcg 1020
catatcaata gagtaccttt agtttcaatt tatatcccag cttataactg tgcaaactat 1080
attcaacgtt gcgtagatag tgcactgaat cagactgttg ttgatctcga ggtttgtatt 1140
tgtaacgatg gttcaacaga taatacctta gaagtgatca ataagcttta tggtaataat 1200
cctagggtac gcatcatgtc taaaccaaat ggcggaatag cctcagcatc aaatgcagcc 1260
gtttcttttg ctaaaggtta ttacattggg cagttagatt cagatgatta tcttgagcct 1320
gatgcagttg aactgtgttt aaaagaattt ttaaaagata aaacgctagc ttgtgtttat 1380
accactaata gaaacgtcaa tccggatggt agcttaatcg ctaatggtta caattggcca 1440
gaattttcac gagaaaaact cacaacggct atgattgctc accactttag aatgttcacg 1500
attagagctt ggcatttaac tgatggattc aatgaaaaaa ttgaaaatgc cgtagactat 1560
gacatgttcc tcaaactcag tgaagttgga aaatttaaac atcttaataa aatctgctat 1620
aaccgtgtat tacatggtga taacacatca attaagaaac ttggcattca aaagaaaaac 1680
cattttgttg tagtcaatca gtcattaaat agacaaggca taacttatta taattatgac 1740
gaatttgatg atttagatga aagtagaaag tatattttca ataaaaccgc tgaatatcaa 1800
gaagagattg atatcttaaa agatatttaa 1830

<210> SEQ ID NO 26
<211> LENGTH: 1764
<212> TYPE: DNA
<213> ORGANISM: Pasteurella multocida

<400> SEQUENCE: 26
atgcttgtac caaaagattt tcccaaagat ctggttttag cgcctttacc tgatcatgtt 60
aatgatttta catggtacaa aaagcgaaag aaaagacttg gcataaaacc tgaacatcaa 120
catgttggtc tttctattat cgttacaaca ttcaatcgac cagcaatttt atcgattaca 180
ttagcctgtt tagtaaacca aaaaacacat tacccgtttg aagttatcgt gacagatgat 240
ggtagtcagg aagatctatc accgatcatt cgccaatatg aaaataaatt ggatattcgc 300
tacgtcagac aaaaagataa cggttttcaa gccagtgccg ctcggaatat gggattacgc 360
ttagcaaaat atgactttat tggcttactc gactgtgata tggcgccaaa tccattatgg 420
gttcattctt atgttgcaga gctattagaa gatgatgatt taacaatcat tggtccaaga 480
aaatacatcg atacacaaca tattgaccca aaagacttct taaataacgc gagtttgctt 540
gaatcattac cagaagtgaa aaccaataat agtgttgccg caaaagggga aggaacagtt 600
tctctggatt ggcgcttaga acaattcgaa aaaacagaaa atctccgctt atccgattcg 660
cctttccgtt tttttgcggc gggtaatgtt gctttcgcta aaaaatggct aaataaatcc 720
ggtttctttg atgaggaatt taatcactgg ggtggagaag atgtggaatt tggatatcgc 780
ttattccgtt acggtagttt ctttaaaact attgatggca ttatggccta ccatcaagag 840
ccaccaggta aagaaaatga aaccgatcgt gaagcgggaa aaaatattac gctcgatatt 900
atgagagaaa aggtccctta tatctataga aaacttttac caatagaaga ttcgcatatc 960
aatagagtac ctttagtttc aatttatatc ccagcttata actgtgcaaa ctatattcaa 1020
cgttgcgtag atagtgcact gaatcagact gttgttgatc tcgaggtttg tatttgtaac 1080
gatggttcaa cagataatac cttagaagtg atcaataagc tttatggtaa taatcctagg 1140
gtacgcatca tgtctaaacc aaatggcgga atagcctcag catcaaatgc agccgtttct 1200
tttgctaaag gttattacat tgggcagtta gattcagatg attatcttga gcctgatgca 1260
gttgaactgt gtttaaaaga atttttaaaa gataaaacgc tagcttgtgt ttataccact 1320
aatagaaacg tcaatccgga tggtagctta atcgctaatg gttacaattg gccagaattt 1380
tcacgagaaa aactcacaac ggctatgatt gctcaccact ttagaatgtt cacgattaga 1440
gcttggcatt taactgatgg attcaatgaa aaaattgaaa atgccgtaga ctatgacatg 1500
ttcctcaaac tcagtgaagt tggaaaattt aaacatctta ataaaatctg ctataaccgt 1560
gtattacatg gtgataacac atcaattaag aaacttggca ttcaaaagaa aaaccatttt 1620
gttgtagtca atcagtcatt aaatagacaa ggcataactt attataatta tgacgaattt 1680
gatgatttag atgaaagtag aaagtatatt ttcaataaaa ccgctgaata tcaagaagag 1740
attgatatct taaaagatat ttaa 1764

<210> SEQ ID NO 27
<211> LENGTH: 2007
<212> TYPE: DNA
<213> ORGANISM: Pasteurella multocida

<400> SEQUENCE: 27
atgaatacat tatcacaagc aataaaagca tataacagca atgactatca attagcactc 60
aaattatttg aaaagtcggc ggaaatctat ggacggaaaa ttgttgaatt tcaaattacc 120
aaatgcaaag aaaaactctc agcacatcct tctgttaatt cagcacatct ttctgtaaat 180
aaagaagaaa aagtcaatgt ttgcgatagt ccgttagata ttgcaacaca actgttactt 240
tccaacgtaa aaaaattagt actttctgac tcggaaaaaa acacgttaaa aaataaatgg 300
aaattgctca ctgagaagaa atctgaaaat gcggaggtaa gagcggtcgc ccttgtacca 360
aaagattttc ccaaagatct ggttttagcg cctttacctg atcatgttaa tgattttaca 420
tggtacaaaa agcgaaagaa aagacttggc ataaaacctg aacatcaaca tgttggtctt 480
tctattatcg ttacaacatt caatcgacca gcaattttat cgattacatt agcctgttta 540
gtaaaccaaa aaacacatta cccgtttgaa gttatcgtga cagatgatgg tagtcaggaa 600
gatctatcac cgatcattcg ccaatatgaa aataaattgg atattcgcta cgtcagacaa 660
aaagataacg gttttcaagc cagtgccgct cggaatatgg gattacgctt agcaaaatat 720
gactttattg gcttactcga ctgtgatatg gcgccaaatc cattatgggt tcattcttat 780
gttgcagagc tattagaaga tgatgattta acaatcattg gtccaagaaa atacatcgat 840
acacaacata ttgacccaaa agacttctta aataacgcga gtttgcttga atcattacca 900
gaagtgaaaa ccaataatag tgttgccgca aaaggggaag gaacagtttc tctggattgg 960
cgcttagaac aattcgaaaa aacagaaaat ctccgcttat ccgattcgcc tttccgtttt 1020
tttgcggcgg gtaatgttgc tttcgctaaa aaatggctaa ataaatccgg tttctttgat 1080
gaggaattta atcactgggg tggagaagat gtggaatttg gatatcgctt attccgttac 1140
ggtagtttct ttaaaactat tgatggcatt atggcctacc atcaagagcc accaggtaaa 1200
gaaaatgaaa ccgatcgtga agcgggaaaa aatattacgc tcgatattat gagagaaaag 1260
gtcccttata tctatagaaa acttttacca atagaagatt cgcatatcaa tagagtacct 1320
ttagtttcaa tttatatccc agcttataac tgtgcaaact atattcaacg ttgcgtagat 1380
agtgcactga atcagactgt tgttgatctc gaggtttgta tttgtaacga tggttcaaca 1440
gataatacct tagaagtgat caataagctt tatggtaata atcctagggt acgcatcatg 1500
tctaaaccaa atggcggaat agcctcagca tcaaatgcag ccgtttcttt tgctaaaggt 1560
tattacattg ggcagttaga ttcagatgat tatcttgagc ctgatgcagt tgaactgtgt 1620
ttaaaagaat ttttaaaaga taaaacgcta gcttgtgttt ataccactaa tagaaacgtc 1680
aatccggatg gtagcttaat cgctaatggt tacaattggc cagaattttc acgagaaaaa 1740
ctcacaacgg ctatgattgc tcaccacttt agaatgttca cgattagagc ttggcattta 1800
actgatggat tcaatgaaaa aattgaaaat gccgtagact atgacatgtt cctcaaactc 1860
agtgaagttg gaaaatttaa acatcttaat aaaatctgct ataaccgtgt attacatggt 1920
gataacacat caattaagaa acttggcatt caaaagaaaa accattttgt tgtagtcaat 1980
cagtcattaa atagacaagg catataa 2007

<210> SEQ ID NO 28
<211> LENGTH: 2061
<212> TYPE: DNA
<213> ORGANISM: Pasteurella multocida

<400> SEQUENCE: 28
atgaatacat tatcacaagc aataaaagca tataacagca atgactatca attagcactc 60
aaattatttg aaaagtcggc ggaaatctat ggacggaaaa ttgttgaatt tcaaattacc 120
aaatgcaaag aaaaactctc agcacatcct tctgttaatt cagcacatct ttctgtaaat 180
aaagaagaaa aagtcaatgt ttgcgatagt ccgttagata ttgcaacaca actgttactt 240
tccaacgtaa aaaaattagt actttctgac tcggaaaaaa acacgttaaa aaataaatgg 300
aaattgctca ctgagaagaa atctgaaaat gcggaggtaa gagcggtcgc ccttgtacca 360
aaagattttc ccaaagatct ggttttagcg cctttacctg atcatgttaa tgattttaca 420
tggtacaaaa agcgaaagaa aagacttggc ataaaacctg aacatcaaca tgttggtctt 480
tctattatcg ttacaacatt caatcgacca gcaattttat cgattacatt agcctgttta 540
gtaaaccaaa aaacacatta cccgtttgaa gttatcgtga cagatgatgg tagtcaggaa 600
gatctatcac cgatcattcg ccaatatgaa aataaattgg atattcgcta cgtcagacaa 660
aaagataacg gttttcaagc cagtgccgct cggaatatgg gattacgctt agcaaaatat 720
gactttattg gcttactcga ctgtgatatg gcgccaaatc cattatgggt tcattcttat 780
gttgcagagc tattagaaga tgatgattta acaatcattg gtccaagaaa atacatcgat 840
acacaacata ttgacccaaa agacttctta aataacgcga gtttgcttga atcattacca 900
gaagtgaaaa ccaataatag tgttgccgca aaaggggaag gaacagtttc tctggattgg 960
cgcttagaac aattcgaaaa aacagaaaat ctccgcttat ccgattcgcc tttccgtttt 1020
tttgcggcgg gtaatgttgc tttcgctaaa aaatggctaa ataaatccgg tttctttgat 1080
gaggaattta atcactgggg tggagaagat gtggaatttg gatatcgctt attccgttac 1140
ggtagtttct ttaaaactat tgatggcatt atggcctacc atcaagagcc accaggtaaa 1200
gaaaatgaaa ccgatcgtga agcgggaaaa aatattacgc tcgatattat gagagaaaag 1260
gtcccttata tctatagaaa acttttacca atagaagatt cgcatatcaa tagagtacct 1320
ttagtttcaa tttatatccc agcttataac tgtgcaaact atattcaacg ttgcgtagat 1380
agtgcactga atcagactgt tgttgatctc gaggtttgta tttgtaacga tggttcaaca 1440
gataatacct tagaagtgat caataagctt tatggtaata atcctagggt acgcatcatg 1500

-continued tctaaaccaa atggcggaat agcctcagca tcaaatgcag ccgtttcttt tgctaaaggt 1560
tattacattg ggcagttaga ttcagatgat tatcttgagc ctgatgcagt tgaactgtgt 1620
ttaaaagaat ttttaaaaga taaaacgcta gcttgtgttt ataccactaa tagaaacgtc 1680
aatccggatg gtagcttaat cgctaatggt tacaattggc cagaattttc acgagaaaaa 1740
ctcacaacgg ctatgattgc tcaccacttt agaatgttca cgattagagc ttggcattta 1800
actgatggat tcaatgaaaa aattgaaaat gccgtagact atgacatgtt cctcaaactc 1860
agtgaagttg gaaaatttaa acatcttaat aaaatctgct ataaccgtgt attacatggt 1920
gataacacat caattaagaa acttggcatt caaaagaaaa accattttgt tgtagtcaat 1980
cagtcattaa atagacaagg cataacttat tataattatg acgaatttga tgatttagat 2040
gaaagtagaa agtatattta a 2061

<210> SEQ ID NO 29
<211> LENGTH: 2112
<212> TYPE: DNA
<213> ORGANISM: Pasteurella multocida

<400> SEQUENCE: 29
atgaatacat tatcacaagc aataaaagca tataacagca atgactatca attagcactc 60
aaattatttg aaaagtcggc ggaaatctat ggacggaaaa ttgttgaatt tcaaattacc 120
aaatgcaaag aaaaactctc agcacatcct tctgttaatt cagcacatct ttctgtaaat 180
aaagaagaaa aagtcaatgt ttgcgatagt ccgttagata ttgcaacaca actgttactt 240
tccaacgtaa aaaaattagt actttctgac tcggaaaaaa acacgttaaa aaataaatgg 300
aaattgctca ctgagaagaa atctgaaaat gcggaggtaa gagcggtcgc ccttgtacca 360
aaagattttc ccaaagatct ggttttagcg cctttacctg atcatgttaa tgattttaca 420
tggtacaaaa agcgaaagaa aagacttggc ataaaacctg aacatcaaca tgttggtctt 480
tctattatcg ttacaacatt caatcgacca gcaattttat cgattacatt agcctgttta 540
gtaaaccaaa aaacacatta cccgtttgaa gttatcgtga cagatgatgg tagtcaggaa 600
gatctatcac cgatcattcg ccaatatgaa aataaattgg atattcgcta cgtcagacaa 660
aaagataacg gttttcaagc cagtgccgct cggaatatgg gattacgctt agcaaaatat 720
gactttattg gcttactcga atgtgatatg gcgccaaatc cattatgggt tcattcttat 780
gttgcagagc tattagaaga tgatgattta acaatcattg gtccaagaaa atacatcgat 840
acacaacata ttgacccaaa agacttctta aataacgcga gtttgcttga atcattacca 900
gaagtgaaaa ccaataatag tgttgccgca aaaggggaag gaacagtttc tctggattgg 960
cgcttagaac aattcgaaaa aacagaaaat ctccgcttat ccgattcgcc tttccgtttt 1020
tttgcggcgg gtaatgttgc tttcgctaaa aaatggctaa ataaatccgg tttctttgat 1080
gaggaattta atcactgggg tggagaagat gtggaatttg gatatcgctt attccgttac 1140
ggtagtttct ttaaaactat tgatggcatt atggcctacc atcaagagcc accaggtaaa 1200
gaaaatgaaa ccgatcgtga agcgggaaaa aatattacgc tcgatattat gagagaaaag 1260
gtcccttata tctatagaaa acttttacca atagaagatt cgcatatcaa tagagtacct 1320
ttagtttcaa tttatatccc agcttataac tgtgcaaact atattcaacg ttgcgtagat 1380
agtgcactga atcagactgt tgttgatctc gaggtttgta tttgtaacga tggttcaaca 1440
gataatacct tagaagtgat caataagctt tatggtaata atcctagggt acgcatcatg 1500
tctaaaccaa atggcggaat agcctcagca tcaaatgcag ccgtttcttt tgctaaaggt 1560
tattacattg ggcagttaga ttcagatgat tatcttgagc ctgatgcagt tgaactgtgt 1620
ttaaaagaat ttttaaaaga taaaacgcta gcttgtgttt ataccactaa tagaaacgtc 1680
aatccggatg gtagcttaat cgctaatggt tacaattggc cagaattttc acgagaaaaa 1740
ctcacaacgg ctatgattgc tcaccacttt agaatgttca cgattagagc ttggcattta 1800
actgatggat tcaatgaaaa aattgaaaat gccgtagact atgacatgtt cctcaaactc 1860
agtgaagttg gaaaatttaa acatcttaat aaaatctgct ataaccgtgt attacatggt 1920
gataacacat caattaagaa acttggcatt caaaagaaaa accattttgt tgtagtcaat 1980
cagtcattaa atagacaagg cataacttat tataattatg acgaatttga tgatttagat 2040
gaaagtagaa agtatatttt caataaaacc gctgaatatc aagaagagat tgatatctta 2100
aaagatattt aa 2112

<210> SEQ ID NO 30
<211> LENGTH: 2112
<212> TYPE: DNA
<213> ORGANISM: Pasteurella multocida

<400> SEQUENCE: 30
atgaatacat tatcacaagc aataaaagca tataacagca atgactatca attagcactc 60
aaattatttg aaaagtcggc ggaaatctat ggacggaaaa ttgttgaatt tcaaattacc 120
aaatgcaaag aaaaactctc agcacatcct tctgttaatt cagcacatct ttctgtaaat 180
aaagaagaaa aagtcaatgt ttgcgatagt ccgttagata ttgcaacaca actgttactt 240
tccaacgtaa aaaaattagt actttctgac tcggaaaaaa acacgttaaa aaataaatgg 300
aaattgctca ctgagaagaa atctgaaaat gcggaggtaa gagcggtcgc ccttgtacca 360
aaagattttc ccaaagatct ggttttagcg cctttacctg atcatgttaa tgattttaca 420
tggtacaaaa agcgaaagaa aagacttggc ataaaacctg aacatcaaca tgttggtctt 480
tctattatcg ttacaacatt caatcgacca gcaattttat cgattacatt agcctgttta 540
gtaaaccaaa aaacacatta cccgtttgaa gttatcgtga cagatgatgg tagtcaggaa 600
gatctatcac cgatcattcg ccaatatgaa aataaattgg atattcgcta cgtcagacaa 660
aaagataacg gttttcaagc cagtgccgct cggaatatgg gattacgctt agcaaaatat 720
gactttattg gcttactcaa ctgtgatatg gcgccaaatc cattatgggt tcattcttat 780
gttgcagagc tattagaaga tgatgattta acaatcattg gtccaagaaa atacatcgat 840
acacaacata ttgacccaaa agacttctta aataacgcga gtttgcttga atcattacca 900
gaagtgaaaa ccaataatag tgttgccgca aaaggggaag gaacagtttc tctggattgg 960
cgcttagaac aattcgaaaa aacagaaaat ctccgcttat ccgattcgcc tttccgtttt 1020
tttgcggcgg gtaatgttgc tttcgctaaa aaatggctaa ataaatccgg tttctttgat 1080
gaggaattta atcactgggg tggagaagat gtggaatttg gatatcgctt attccgttac 1140
ggtagtttct ttaaaactat tgatggcatt atggcctacc atcaagagcc accaggtaaa 1200
gaaaatgaaa ccgatcgtga agcgggaaaa aatattacgc tcgatattat gagagaaaag 1260
gtcccttata tctatagaaa acttttacca atagaagatt cgcatatcaa tagagtacct 1320
ttagtttcaa tttatatccc agcttataac tgtgcaaact atattcaacg ttgcgtagat 1380
agtgcactga atcagactgt tgttgatctc gaggtttgta tttgtaacga tggttcaaca 1440
gataatacct tagaagtgat caataagctt tatggtaata atcctagggt acgcatcatg 1500
tctaaaccaa atggcggaat agcctcagca tcaaatgcag ccgtttcttt tgctaaaggt 1560
tattacattg ggcagttaga ttcagatgat tatcttgagc ctgatgcagt tgaactgtgt 1620
ttaaaagaat ttttaaaaga taaaacgcta gcttgtgttt ataccactaa tagaaacgtc 1680
aatccggatg gtagcttaat cgctaatggt tacaattggc cagaattttc acgagaaaaa 1740
ctcacaacgg ctatgattgc tcaccacttt agaatgttca cgattagagc ttggcattta 1800
actgatggat tcaatgaaaa aattgaaaat gccgtagact atgacatgtt cctcaaactc 1860
agtgaagttg gaaaatttaa acatcttaat aaaatctgct ataaccgtgt attacatggt 1920
gataacacat caattaagaa acttggcatt caaaagaaaa accattttgt tgtagtcaat 1980
cagtcattaa atagacaagg cataacttat tataattatg acgaatttga tgatttagat 2040
gaaagtagaa agtatatttt caataaaacc gctgaatatc aagaagagat tgatatctta 2100
aaagatattt aa 2112

<210> SEQ ID NO 31
<211> LENGTH: 2112
<212> TYPE: DNA
<213> ORGANISM: Pasteurella multocida

<400> SEQUENCE: 31
atgaatacat tatcacaagc aataaaagca tataacagca atgactatca attagcactc 60
aaattatttg aaaagtcggc ggaaatctat ggacggaaaa ttgttgaatt tcaaattacc 120
aaatgcaaag aaaaactctc agcacatcct tctgttaatt cagcacatct ttctgtaaat 180
aaagaagaaa aagtcaatgt ttgcgatagt ccgttagata ttgcaacaca actgttactt 240
tccaacgtaa aaaaattagt actttctgac tcggaaaaaa acacgttaaa aaataaatgg 300
aaattgctca ctgagaagaa atctgaaaat gcggaggtaa gagcggtcgc ccttgtacca 360
aaagattttc ccaaagatct ggttttagcg cctttacctg atcatgttaa tgattttaca 420
tggtacaaaa agcgaaagaa aagacttggc ataaaacctg aacatcaaca tgttggtctt 480
tctattatcg ttacaacatt caatcgacca gcaattttat cgattacatt agcctgttta 540
gtaaaccaaa aaacacatta cccgtttgaa gttatcgtga cagatgatgg tagtcaggaa 600
gatctatcac cgatcattcg ccaatatgaa aataaattgg atattcgcta cgtcagacaa 660
aaagataacg gttttcaagc cagtgccgct cggaatatgg gattacgctt agcaaaatat 720
gactttattg gcttactcaa atgtgatatg gcgccaaatc cattatgggt tcattcttat 780
gttgcagagc tattagaaga tgatgattta acaatcattg gtccaagaaa atacatcgat 840
acacaacata ttgacccaaa agacttctta aataacgcga gtttgcttga atcattacca 900
gaagtgaaaa ccaataatag tgttgccgca aaaggggaag gaacagtttc tctggattgg 960
cgcttagaac aattcgaaaa aacagaaaat ctccgcttat ccgattcgcc tttccgtttt 1020
tttgcggcgg gtaatgttgc tttcgctaaa aaatggctaa ataaatccgg tttctttgat 1080
gaggaattta atcactgggg tggagaagat gtggaatttg gatatcgctt attccgttac 1140
ggtagtttct ttaaaactat tgatggcatt atggcctacc atcaagagcc accaggtaaa 1200
gaaaatgaaa ccgatcgtga agcgggaaaa aatattacgc tcgatattat gagagaaaag 1260
gtcccttata tctatagaaa acttttacca atagaagatt cgcatatcaa tagagtacct 1320
ttagtttcaa tttatatccc agcttataac tgtgcaaact atattcaacg ttgcgtagat 1380
agtgcactga atcagactgt tgttgatctc gaggtttgta tttgtaacga tggttcaaca 1440
gataatacct tagaagtgat caataagctt tatggtaata atcctagggt acgcatcatg 1500
tctaaaccaa atggcggaat agcctcagca tcaaatgcag ccgtttcttt tgctaaaggt 1560
tattacattg ggcagttaga ttcagatgat tatcttgagc ctgatgcagt tgaactgtgt 1620
ttaaaagaat ttttaaaaga taaaacgcta gcttgtgttt ataccactaa tagaaacgtc 1680
aatccggatg gtagcttaat cgctaatggt tacaattggc cagaattttc acgagaaaaa 1740
ctcacaacgg ctatgattgc tcaccacttt agaatgttca cgattagagc ttggcattta 1800
actgatggat tcaatgaaaa aattgaaaat gccgtagact atgacatgtt cctcaaactc 1860
agtgaagttg gaaaatttaa acatcttaat aaaatctgct ataaccgtgt attacatggt 1920
gataacacat caattaagaa acttggcatt caaaagaaaa accattttgt tgtagtcaat 1980
cagtcattaa atagacaagg cataacttat tataattatg acgaatttga tgatttagat 2040
gaaagtagaa agtatatttt caataaaacc gctgaatatc aagaagagat tgatatctta 2100
aaagatattt aa 2112

<210> SEQ ID NO 32
<211> LENGTH: 2112
<212> TYPE: DNA
<213> ORGANISM: Pasteurella multocida

<400> SEQUENCE: 32
atgaatacat tatcacaagc aataaaagca tataacagca atgactatca attagcactc 60
aaattatttg aaaagtcggc ggaaatctat ggacggaaaa ttgttgaatt tcaaattacc 120
aaatgcaaag aaaaactctc agcacatcct tctgttaatt cagcacatct ttctgtaaat 180
aaagaagaaa aagtcaatgt ttgcgatagt ccgttagata ttgcaacaca actgttactt 240
tccaacgtaa aaaaattagt actttctgac tcggaaaaaa acacgttaaa aaataaatgg 300
aaattgctca ctgagaagaa atctgaaaat gcggaggtaa gagcggtcgc ccttgtacca 360
aaagattttc ccaaagatct ggttttagcg cctttacctg atcatgttaa tgattttaca 420
tggtacaaaa agcgaaagaa aagacttggc ataaaacctg aacatcaaca tgttggtctt 480
tctattatcg ttacaacatt caatcgacca gcaattttat cgattacatt agcctgttta 540
gtaaaccaaa aaacacatta cccgtttgaa gttatcgtga cagatgatgg tagtcaggaa 600
gatctatcac cgatcattcg ccaatatgaa aataaattgg atattcgcta cgtcagacaa 660
aaagataacg gttttcaagc cagtgccgct cggaatatgg gattacgctt agcaaaatat 720
gactttattg gcttactcga ctgtgaaatg gcgccaaatc cattatgggt tcattcttat 780
gttgcagagc tattagaaga tgatgattta acaatcattg gtccaagaaa atacatcgat 840
acacaacata ttgacccaaa agacttctta aataacgcga gtttgcttga atcattacca 900
gaagtgaaaa ccaataatag tgttgccgca aaaggggaag gaacagtttc tctggattgg 960
cgcttagaac aattcgaaaa aacagaaaat ctccgcttat ccgattcgcc tttccgtttt 1020
tttgcggcgg gtaatgttgc tttcgctaaa aaatggctaa ataaatccgg tttctttgat 1080
gaggaattta atcactgggg tggagaagat gtggaatttg gatatcgctt attccgttac 1140
ggtagtttct ttaaaactat tgatggcatt atggcctacc atcaagagcc accaggtaaa 1200
gaaaatgaaa ccgatcgtga agcgggaaaa aatattacgc tcgatattat gagagaaaag 1260
gtcccttata tctatagaaa acttttacca atagaagatt cgcatatcaa tagagtacct 1320
ttagtttcaa tttatatccc agcttataac tgtgcaaact atattcaacg ttgcgtagat 1380
agtgcactga atcagactgt tgttgatctc gaggtttgta tttgtaacga tggttcaaca 1440
gataatacct tagaagtgat caataagctt tatggtaata atcctagggt acgcatcatg 1500
tctaaaccaa atggcggaat agcctcagca tcaaatgcag ccgtttcttt tgctaaaggt 1560

-continued

```
tattacattg ggcagttaga ttcagatgat tatcttgagc ctgatgcagt tgaactgtgt   1620

ttaaaagaat ttttaaaaga taaaacgcta gcttgtgttt ataccactaa tagaaacgtc   1680

aatccggatg gtagcttaat cgctaatggt tacaattggc cagaattttc acgagaaaaa   1740

ctcacaacgg ctatgattgc tcaccacttt agaatgttca cgattagagc ttggcattta   1800

actgatggat tcaatgaaaa aattgaaaat gccgtagact atgacatgtt cctcaaactc   1860

agtgaagttg gaaaatttaa acatcttaat aaaatctgct ataaccgtgt attacatggt   1920

gataacacat caattaagaa acttggcatt caaaagaaaa accattttgt tgtagtcaat   1980

cagtcattaa atagacaagg cataacttat tataattatg acgaatttga tgatttagat   2040

gaaagtagaa agtatatttt caataaaacc gctgaatatc aagaagagat tgatatctta   2100

aaagatattt aa                                                       2112
```

<210> SEQ ID NO 33
<211> LENGTH: 2112
<212> TYPE: DNA
<213> ORGANISM: Pasteurella multocida

<400> SEQUENCE: 33

```
atgaatacat tatcacaagc aataaaagca tataacagca atgactatca attagcactc     60

aaattatttg aaaagtcggc ggaaatctat ggacggaaaa ttgttgaatt tcaaattacc    120

aaatgcaaag aaaaactctc agcacatcct tctgttaatt cagcacatct ttctgtaaat    180

aaagaagaaa aagtcaatgt ttgcgatagt ccgttagata ttgcaacaca actgttactt    240

tccaacgtaa aaaaattagt actttctgac tcggaaaaaa acacgttaaa aaataaatgg    300

aaattgctca ctgagaagaa atctgaaaat gcggaggtaa gagcggtcgc ccttgtacca    360

aaagattttc ccaaagatct ggttttagcg cctttacctg atcatgttaa tgattttaca    420

tggtacaaaa agcgaaagaa aagacttggc ataaaacctg aacatcaaca tgttggtctt    480

tctattatcg ttacaacatt caatcgacca gcaattttat cgattacatt agcctgttta    540

gtaaaccaaa aaacacatta cccgtttgaa gttatcgtga cagatgatgg tagtcaggaa    600

gatctatcac cgatcattcg ccaatatgaa aataaattgg atattcgcta cgtcagacaa    660

aaagataacg gttttcaagc cagtgccgct cggaatatgg gattacgctt agcaaaatat    720

gactttattg gcttactcga ctgtaatatg gcgccaaatc cattatgggt tcattcttat    780

gttgcagagc tattagaaga tgatgattta acaatcattg gtccaagaaa atacatcgat    840

acacaacata ttgacccaaa agacttctta aataacgcga gtttgcttga atcattacca    900

gaagtgaaaa ccaataatag tgttgccgca aaaggggaag gaacagtttc tctggattgg    960

cgcttagaac aattcgaaaa aacagaaaat ctccgcttat ccgattcgcc tttccgtttt   1020

tttgcggcgg gtaatgttgc tttcgctaaa aaatggctaa ataaatccgg tttctttgat   1080

gaggaattta atcactgggg tggagaagat gtggaatttg gatatcgctt attccgttac   1140

ggtagtttct ttaaaactat tgatggcatt atggcctacc atcaagagcc accaggtaaa   1200

gaaaatgaaa ccgatcgtga agcgggaaaa aatattacgc tcgatattat gagagaaaag   1260

gtcccttata tctatagaaa acttttacca atagaagatt cgcatatcaa tagagtacct   1320

ttagtttcaa tttatatccc agcttataac tgtgcaaact atattcaacg ttgcgtagat   1380

agtgcactga atcagactgt tgttgatctc gaggtttgta tttgtaacga tggttcaaca   1440

gataatacct tagaagtgat caataagctt tatggtaata atcctagggt acgcatcatg   1500

tctaaaccaa atggcggaat agcctcagca tcaaatgcag ccgtttcttt tgctaaaggt   1560
```

```
tattacattg ggcagttaga ttcagatgat tatcttgagc ctgatgcagt tgaactgtgt   1620
ttaaaagaat ttttaaaaga taaaacgcta gcttgtgttt ataccactaa tagaaacgtc   1680
aatccggatg gtagcttaat cgctaatggt tacaattggc cagaattttc acgagaaaaa   1740
ctcacaacgg ctatgattgc tcaccacttt agaatgttca cgattagagc ttggcattta   1800
actgatggat tcaatgaaaa aattgaaaat gccgtagact atgacatgtt cctcaaactc   1860
agtgaagttg gaaaatttaa acatcttaat aaaatctgct ataaccgtgt attacatggt   1920
gataacacat caattaagaa acttggcatt caaaagaaaa accattttgt tgtagtcaat   1980
cagtcattaa atagacaagg cataacttat tataattatg acgaatttga tgatttagat   2040
gaaagtagaa agtatatttt caataaaacc gctgaatatc aagaagagat tgatatctta   2100
aaagatattt aa                                                       2112
```

<210> SEQ ID NO 34
<211> LENGTH: 2112
<212> TYPE: DNA
<213> ORGANISM: Pasteurella multocida

<400> SEQUENCE: 34

```
atgaatacat tatcacaagc aataaaagca tataacagca atgactatca attagcactc     60
aaattatttg aaaagtcggc ggaaatctat ggacggaaaa ttgttgaatt tcaaattacc    120
aaatgcaaag aaaaactctc agcacatcct tctgttaatt cagcacatct ttctgtaaat    180
aaagaagaaa aagtcaatgt ttgcgatagt ccgttagata ttgcaacaca actgttactt    240
tccaacgtaa aaaaattagt actttctgac tcggaaaaaa acacgttaaa aaataaatgg    300
aaattgctca ctgagaagaa atctgaaaat gcggaggtaa gagcggtcgc ccttgtacca    360
aaagattttc ccaaagatct ggttttagcg cctttacctg atcatgttaa tgattttaca    420
tggtacaaaa agcgaaagaa aagacttggc ataaaacctg aacatcaaca tgttggtctt    480
tctattatcg ttacaacatt caatcgacca gcaattttat cgattacatt agcctgttta    540
gtaaaccaaa aaacacatta cccgtttgaa gttatcgtga cagatgatgg tagtcaggaa    600
gatctatcac cgatcattcg ccaatatgaa aataaattgg atattcgcta cgtcagacaa    660
aaagataacg gttttcaagc cagtgccgct cggaatatgg gattacgctt agcaaaatat    720
gactttattg gcttactcga ctgtaaaatg gcgccaaatc cattatgggt tcattcttat    780
gttgcagagc tattagaaga tgatgattta acaatcattg gtccaagaaa atacatcgat    840
acacaacata ttgacccaaa agacttctta aataacgcga gtttgcttga atcattacca    900
gaagtgaaaa ccaataatag tgttgccgca aaaggggaag gaacagtttc tctggattgg    960
cgcttagaac aattcgaaaa aacagaaaat ctccgcttat ccgattcgcc tttccgtttt   1020
tttgcggcgg gtaatgttgc tttcgctaaa aaatggctaa ataaatccgg tttctttgat   1080
gaggaattta atcactgggg tggagaagat gtggaatttg gatatcgctt attccgttac   1140
ggtagtttct ttaaaactat tgatggcatt atggcctacc atcaagagcc accaggtaaa   1200
gaaaatgaaa ccgatcgtga agcgggaaaa aatattacgc tcgatattat gagagaaaag   1260
gtcccttata tctatagaaa acttttacca atagaagatt cgcatatcaa tagagtacct   1320
ttagtttcaa tttatatccc agcttataac tgtgcaaact atattcaacg ttgcgtagat   1380
agtgcactga atcagactgt tgttgatctc gaggtttgta tttgtaacga tggttcaaca   1440
gataatacct tagaagtgat caataagctt tatggtaata atcctagggt acgcatcatg   1500
tctaaaccaa atggcggaat agcctcagca tcaaatgcag ccgtttcttt tgctaaaggt   1560
```

tattacattg ggcagttaga ttcagatgat tatcttgagc ctgatgcagt tgaactgtgt 1620
ttaaaagaat ttttaaaaga taaaacgcta gcttgtgttt ataccactaa tagaaacgtc 1680
aatccggatg gtagcttaat cgctaatggt tacaattggc cagaattttc acgagaaaaa 1740
ctcacaacgg ctatgattgc tcaccacttt agaatgttca cgattagagc ttggcattta 1800
actgatggat tcaatgaaaa aattgaaaat gccgtagact atgacatgtt cctcaaactc 1860
agtgaagttg gaaaatttaa acatcttaat aaaatctgct ataaccgtgt attacatggt 1920
gataacacat caattaagaa acttggcatt caaaagaaaa accattttgt tgtagtcaat 1980
cagtcattaa atagacaagg cataacttat tataattatg acgaatttga tgatttagat 2040
gaaagtagaa agtatatttt caataaaacc gctgaatatc aagaagagat tgatatctta 2100
aaagatattt aa 2112

<210> SEQ ID NO 35
<211> LENGTH: 2112
<212> TYPE: DNA
<213> ORGANISM: Pasteurella multocida

<400> SEQUENCE: 35
atgaatacat tatcacaagc aataaaagca tataacagca atgactatca attagcactc 60
aaattatttg aaaagtcggc ggaaatctat ggacggaaaa ttgttgaatt tcaaattacc 120
aaatgcaaag aaaaactctc agcacatcct tctgttaatt cagcacatct ttctgtaaat 180
aaagaagaaa aagtcaatgt ttgcgatagt ccgttagata ttgcaacaca actgttactt 240
tccaacgtaa aaaaattagt actttctgac tcggaaaaaa acacgttaaa aaataaatgg 300
aaattgctca ctgagaagaa atctgaaaat gcggaggtaa gagcggtcgc ccttgtacca 360
aaagattttc ccaaagatct ggttttagcg cctttacctg atcatgttaa tgattttaca 420
tggtacaaaa agcgaaagaa aagacttggc ataaaacctg aacatcaaca tgttggtctt 480
tctattatcg ttacaacatt caatcgacca gcaattttat cgattacatt agcctgttta 540
gtaaaccaaa aaacacatta cccgtttgaa gttatcgtga cagatgatgg tagtcaggaa 600
gatctatcac cgatcattcg ccaatatgaa aataaattgg atattcgcta cgtcagacaa 660
aaagataacg gttttcaagc cagtgccgct cggaatatgg gattacgctt agcaaaatat 720
gactttattg gcttactcga ctgtgatatg gcgccaaatc cattatgggt tcattcttat 780
gttgcagagc tattagaaga tgatgattta acaatcattg gtccaagaaa atacatcgat 840
acacaacata ttgacccaaa agacttctta aataacgcga gtttgcttga atcattacca 900
gaagtgaaaa ccaataatag tgttgccgca aaaggggaag gaacagtttc tctggattgg 960
cgcttagaac aattcgaaaa aacagaaaat ctccgcttat ccgattcgcc tttccgtttt 1020
tttgcggcgg gtaatgttgc tttcgctaaa aaatggctaa ataaatccgg tttctttgat 1080
gaggaattta atcactgggg tggagaagat gtggaatttg gatatcgctt attccgttac 1140
ggtagtttct ttaaaactat tgatggcatt atggcctacc atcaagagcc accaggtaaa 1200
gaaaatgaaa ccgatcgtga agcgggaaaa aatattacgc tcgatattat gagagaaaag 1260
gtcccttata tctatagaaa acttttacca atagaagatt cgcatatcaa tagagtacct 1320
ttagtttcaa tttatatccc agcttataac tgtgcaaact atattcaacg ttgcgtagat 1380
agtgcactga atcagactgt tgttgatctc gaggtttgta tttgtaacga tggttcaaca 1440
gataatacct tagaagtgat caataagctt tatggtaata atcctagggt acgcatcatg 1500
tctaaaccaa atggcggaat agcctcagca tcaaatgcag ccgtttcttt tgctaaaggt 1560
tattacattg ggcagttaaa ttcagatgat tatcttgagc ctgatgcagt tgaactgtgt 1620
ttaaaagaat ttttaaaaga taaaacgcta gcttgtgttt ataccactaa tagaaacgtc 1680
aatccggatg gtagcttaat cgctaatggt tacaattggc cagaattttc acgagaaaaa 1740
ctcacaacgg ctatgattgc tcaccacttt agaatgttca cgattagagc ttggcattta 1800
actgatggat tcaatgaaaa aattgaaaat gccgtagact atgacatgtt cctcaaactc 1860
agtgaagttg gaaaatttaa acatcttaat aaaatctgct ataaccgtgt attacatggt 1920
gataacacat caattaagaa acttggcatt caaaagaaaa accattttgt tgtagtcaat 1980
cagtcattaa atagacaagg cataacttat tataattatg acgaatttga tgatttagat 2040
gaaagtagaa agtatatttt caataaaacc gctgaatatc aagaagagat tgatatctta 2100
aaagatattt aa 2112

<210> SEQ ID NO 36
<211> LENGTH: 2112
<212> TYPE: DNA
<213> ORGANISM: Pasteurella multocida

<400> SEQUENCE: 36
atgaatacat tatcacaagc aataaaagca tataacagca atgactatca attagcactc 60
aaattatttg aaaagtcggc ggaaatctat ggacggaaaa ttgttgaatt tcaaattacc 120
aaatgcaaag aaaaactctc agcacatcct tctgttaatt cagcacatct ttctgtaaat 180
aaagaagaaa aagtcaatgt ttgcgatagt ccgttagata ttgcaacaca actgttactt 240
tccaacgtaa aaaaattagt actttctgac tcggaaaaaa acacgttaaa aaataaatgg 300
aaattgctca ctgagaagaa atctgaaaat gcggaggtaa gagcggtcgc ccttgtacca 360
aaagattttc ccaaagatct ggttttagcg cctttacctg atcatgttaa tgattttaca 420
tggtacaaaa agcgaaagaa aagacttggc ataaaacctg aacatcaaca tgttggtctt 480
tctattatcg ttacaacatt caatcgacca gcaattttat cgattacatt agcctgttta 540
gtaaaccaaa aaacacatta cccgtttgaa gttatcgtga cagatgatgg tagtcaggaa 600
gatctatcac cgatcattcg ccaatatgaa aataaattgg atattcgcta cgtcagacaa 660
aaagataacg gttttcaagc cagtgccgct cggaatatgg gattacgctt agcaaaatat 720
gactttattg gcttactcga ctgtgatatg gcgccaaatc cattatgggt tcattcttat 780
gttgcagagc tattagaaga tgatgattta acaatcattg gtccaagaaa atacatcgat 840
acacaacata ttgacccaaa agacttctta aataacgcga gtttgcttga atcattacca 900
gaagtgaaaa ccaataatag tgttgccgca aaaggggaag gaacagtttc tctggattgg 960
cgcttagaac aattcgaaaa aacagaaaat ctccgcttat ccgattcgcc tttccgtttt 1020
tttgcggcgg gtaatgttgc tttcgctaaa aaatggctaa ataaatccgg tttctttgat 1080
gaggaattta atcactgggg tggagaagat gtggaatttg gatatcgctt attccgttac 1140
ggtagtttct ttaaaactat tgatggcatt atggcctacc atcaagagcc accaggtaaa 1200
gaaaatgaaa ccgatcgtga agcgggaaaa aatattacgc tcgatattat gagagaaaag 1260
gtcccttata tctatagaaa acttttacca atagaagatt cgcatatcaa tagagtacct 1320
ttagtttcaa tttatatccc agcttataac tgtgcaaact atattcaacg ttgcgtagat 1380
agtgcactga atcagactgt tgttgatctc gaggtttgta tttgtaacga tggttcaaca 1440
gataatacct tagaagtgat caataagctt tatggtaata atcctagggt acgcatcatg 1500
tctaaaccaa atggcggaat agcctcagca tcaaatgcag ccgtttcttt tgctaaaggt 1560

```
tattacattg ggcagttaga atcagatgat tatcttgagc ctgatgcagt tgaactgtgt   1620

ttaaaagaat ttttaaaaga taaaacgcta gcttgtgttt ataccactaa tagaaacgtc   1680

aatccggatg gtagcttaat cgctaatggt tacaattggc cagaattttc acgagaaaaa   1740

ctcacaacgg ctatgattgc tcaccacttt agaatgttca cgattagagc ttggcattta   1800

actgatggat tcaatgaaaa aattgaaaat gccgtagact atgacatgtt cctcaaactc   1860

agtgaagttg gaaaatttaa acatcttaat aaaatctgct ataaccgtgt attacatggt   1920

gataacacat caattaagaa acttggcatt caaaagaaaa accattttgt tgtagtcaat   1980

cagtcattaa atagacaagg cataacttat tataattatg acgaatttga tgatttagat   2040

gaaagtagaa agtatatttt caataaaacc gctgaatatc aagaagagat tgatatctta   2100

aaagatattt aa                                                      2112
```

<210> SEQ ID NO 37
<211> LENGTH: 2112
<212> TYPE: DNA
<213> ORGANISM: Pasteurella multocida

<400> SEQUENCE: 37

```
atgaatacat tatcacaagc aataaaagca tataacagca atgactatca attagcactc     60

aaattatttg aaaagtcggc ggaaatctat ggacggaaaa ttgttgaatt tcaaattacc    120

aaatgcaaag aaaaactctc agcacatcct tctgttaatt cagcacatct ttctgtaaat    180

aaagaagaaa aagtcaatgt ttgcgatagt ccgttagata ttgcaacaca actgttactt    240

tccaacgtaa aaaaattagt actttctgac tcggaaaaaa acacgttaaa aaataaatgg    300

aaattgctca ctgagaagaa atctgaaaat gcggaggtaa gagcggtcgc ccttgtacca    360

aaagattttc ccaaagatct ggttttagcg cctttacctg atcatgttaa tgattttaca    420

tggtacaaaa agcgaaagaa aagacttggc ataaaacctg aacatcaaca tgttggtctt    480

tctattatcg ttacaacatt caatcgacca gcaattttat cgattacatt agcctgttta    540

gtaaaccaaa aaacacatta cccgtttgaa gttatcgtga cagatgatgg tagtcaggaa    600

gatctatcac cgatcattcg ccaatatgaa aataaattgg atattcgcta cgtcagacaa    660

aaagataacg gttttcaagc cagtgccgct cggaatatgg gattacgctt agcaaaatat    720

gactttattg gcttactcga ctgtgatatg gcgccaaatc cattatgggt tcattcttat    780

gttgcagagc tattagaaga tgatgattta acaatcattg gtccaagaaa atacatcgat    840

acacaacata ttgacccaaa agacttctta aataacgcga gtttgcttga atcattacca    900

gaagtgaaaa ccaataatag tgttgccgca aaaggggaag gaacagtttc tctggattgg    960

cgcttagaac aattcgaaaa aacagaaaat ctccgcttat ccgattcgcc tttccgtttt   1020

tttgcggcgg gtaatgttgc tttcgctaaa aaatggctaa ataaatccgg tttctttgat   1080

gaggaattta atcactgggg tggagaagat gtggaatttg gatatcgctt attccgttac   1140

ggtagtttct ttaaaactat tgatggcatt atggcctacc atcaagagcc accaggtaaa   1200

gaaaatgaaa ccgatcgtga agcgggaaaa aatattacgc tcgatattat gagagaaaag   1260

gtcccttata tctatagaaa acttttacca atagaagatt cgcatatcaa tagagtacct   1320

ttagtttcaa tttatatccc agcttataac tgtgcaaact atattcaacg ttgcgtagat   1380

agtgcactga atcagactgt tgttgatctc gaggtttgta tttgtaacga tggttcaaca   1440

gataatacct tagaagtgat caataagctt tatggtaata atcctagggt acgcatcatg   1500

tctaaaccaa atggcggaat agcctcagca tcaaatgcag ccgtttcttt tgctaaaggt   1560
```

tattacattg ggcagttaaa atcagatgat tatcttgagc ctgatgcagt tgaactgtgt 1620
ttaaaagaat ttttaaaaga taaaacgcta gcttgtgttt ataccactaa tagaaacgtc 1680
aatccggatg gtagcttaat cgctaatggt tacaattggc cagaattttc acgagaaaaa 1740
ctcacaacgg ctatgattgc tcaccacttt agaatgttca cgattagagc ttggcattta 1800
actgatggat tcaatgaaaa aattgaaaat gccgtagact atgacatgtt cctcaaactc 1860
agtgaagttg gaaaatttaa acatcttaat aaaatctgct ataaccgtgt attacatggt 1920
gataacacat caattaagaa acttggcatt caaaagaaaa accattttgt tgtagtcaat 1980
cagtcattaa atagacaagg cataacttat tataattatg acgaatttga tgatttagat 2040
gaaagtagaa agtatatttt caataaaacc gctgaatatc aagaagagat tgatatctta 2100
aaagatattt aa 2112

<210> SEQ ID NO 38
<211> LENGTH: 2112
<212> TYPE: DNA
<213> ORGANISM: Pasteurella multocida

<400> SEQUENCE: 38
atgaatacat tatcacaagc aataaaagca tataacagca atgactatca attagcactc 60
aaattatttg aaaagtcggc ggaaatctat ggacggaaaa ttgttgaatt tcaaattacc 120
aaatgcaaag aaaaactctc agcacatcct tctgttaatt cagcacatct ttctgtaaat 180
aaagaagaaa aagtcaatgt ttgcgatagt ccgttagata ttgcaacaca actgttactt 240
tccaacgtaa aaaaattagt actttctgac tcggaaaaaa acacgttaaa aaataaatgg 300
aaattgctca ctgagaagaa atctgaaaat gcggaggtaa gagcggtcgc ccttgtacca 360
aaagattttc ccaaagatct ggttttagcg cctttacctg atcatgttaa tgattttaca 420
tggtacaaaa agcgaaagaa aagacttggc ataaaacctg aacatcaaca tgttggtctt 480
tctattatcg ttacaacatt caatcgacca gcaattttat cgattacatt agcctgttta 540
gtaaaccaaa aaacacatta cccgtttgaa gttatcgtga cagatgatgg tagtcaggaa 600
gatctatcac cgatcattcg ccaatatgaa aataaattgg atattcgcta cgtcagacaa 660
aaagataacg gttttcaagc cagtgccgct cggaatatgg gattacgctt agcaaaatat 720
gactttattg gcttactcga ctgtgatatg gcgccaaatc cattatgggt tcattcttat 780
gttgcagagc tattagaaga tgatgattta acaatcattg gtccaagaaa atacatcgat 840
acacaacata ttgacccaaa agacttctta aataacgcga gtttgcttga atcattacca 900
gaagtgaaaa ccaataatag tgttgccgca aaaggggaag gaacagtttc tctggattgg 960
cgcttagaac aattcgaaaa aacagaaaat ctccgcttat ccgattcgcc tttccgtttt 1020
tttgcggcgg gtaatgttgc tttcgctaaa aaatggctaa ataaatccgg tttctttgat 1080
gaggaattta atcactgggg tggagaagat gtggaatttg gatatcgctt attccgttac 1140
ggtagtttct ttaaaactat tgatggcatt atggcctacc atcaagagcc accaggtaaa 1200
gaaaatgaaa ccgatcgtga agcgggaaaa aatattacgc tcgatattat gagagaaaag 1260
gtcccttata tctatagaaa acttttacca atagaagatt cgcatatcaa tagagtacct 1320
ttagtttcaa tttatatccc agcttataac tgtgcaaact atattcaacg ttgcgtagat 1380
agtgcactga atcagactgt tgttgatctc gaggtttgta tttgtaacga tggttcaaca 1440
gataatacct tagaagtgat caataagctt tatggtaata atcctagggt acgcatcatg 1500
tctaaaccaa atggcggaat agcctcagca tcaaatgcag ccgtttcttt tgctaaaggt 1560
tattacattg ggcagttaga ttcagaagat tatcttgagc ctgatgcagt tgaactgtgt 1620
ttaaaagaat ttttaaaaga taaaacgcta gcttgtgttt ataccactaa tagaaacgtc 1680
aatccggatg gtagcttaat cgctaatggt tacaattggc cagaattttc acgagaaaaa 1740
ctcacaacgg ctatgattgc tcaccacttt agaatgttca cgattagagc ttggcattta 1800
actgatggat tcaatgaaaa aattgaaaat gccgtagact atgacatgtt cctcaaactc 1860
agtgaagttg gaaaatttaa acatcttaat aaaatctgct ataaccgtgt attacatggt 1920
gataacacat caattaagaa acttggcatt caaaagaaaa accattttgt tgtagtcaat 1980
cagtcattaa atagacaagg cataacttat tataattatg acgaatttga tgatttagat 2040
gaaagtagaa agtatatttt caataaaacc gctgaatatc aagaagagat tgatatctta 2100
aaagatattt aa 2112

<210> SEQ ID NO 39
<211> LENGTH: 2112
<212> TYPE: DNA
<213> ORGANISM: Pasteurella multocida

<400> SEQUENCE: 39
atgaatacat tatcacaagc aataaaagca tataacagca atgactatca attagcactc 60
aaattatttg aaaagtcggc ggaaatctat ggacggaaaa ttgttgaatt tcaaattacc 120
aaatgcaaag aaaaactctc agcacatcct tctgttaatt cagcacatct ttctgtaaat 180
aaagaagaaa aagtcaatgt ttgcgatagt ccgttagata ttgcaacaca actgttactt 240
tccaacgtaa aaaaattagt actttctgac tcggaaaaaa acacgttaaa aaataaatgg 300
aaattgctca ctgagaagaa atctgaaaat gcggaggtaa gagcggtcgc ccttgtacca 360
aaagattttc ccaaagatct ggttttagcg cctttacctg atcatgttaa tgattttaca 420
tggtacaaaa agcgaaagaa aagacttggc ataaaacctg aacatcaaca tgttggtctt 480
tctattatcg ttacaacatt caatcgacca gcaattttat cgattacatt agcctgttta 540
gtaaaccaaa aaacacatta cccgtttgaa gttatcgtga cagatgatgg tagtcaggaa 600
gatctatcac cgatcattcg ccaatatgaa aataaattgg atattcgcta cgtcagacaa 660
aaagataacg gttttcaagc cagtgccgct cggaatatgg gattacgctt agcaaaatat 720
gactttattg gcttactcga ctgtgatatg gcgccaaatc cattatgggt tcattcttat 780
gttgcagagc tattagaaga tgatgattta acaatcattg gtccaagaaa atacatcgat 840
acacaacata ttgacccaaa agacttctta aataacgcga gtttgcttga atcattacca 900
gaagtgaaaa ccaataatag tgttgccgca aaaggggaag gaacagtttc tctggattgg 960
cgcttagaac aattcgaaaa aacagaaaat ctccgcttat ccgattcgcc tttccgtttt 1020
tttgcggcgg gtaatgttgc tttcgctaaa aaatggctaa ataaatccgg tttctttgat 1080
gaggaattta atcactgggg tggagaagat gtggaatttg gatatcgctt attccgttac 1140
ggtagtttct ttaaaactat tgatggcatt atggcctacc atcaagagcc accaggtaaa 1200
gaaaatgaaa ccgatcgtga agcgggaaaa aatattacgc tcgatattat gagagaaaag 1260
gtcccttata tctatagaaa acttttacca atagaagatt cgcatatcaa tagagtacct 1320
ttagtttcaa tttatatccc agcttataac tgtgcaaact atattcaacg ttgcgtagat 1380
agtgcactga atcagactgt tgttgatctc gaggtttgta tttgtaacga tggttcaaca 1440
gataatacct tagaagtgat caataagctt tatggtaata atcctagggt acgcatcatg 1500
tctaaaccaa atggcggaat agcctcagca tcaaatgcag ccgtttcttt tgctaaaggt 1560

```
tattacattg ggcagttaga ttcaaatgat tatcttgagc ctgatgcagt tgaactgtgt   1620

ttaaaagaat ttttaaaaga taaaacgcta gcttgtgttt ataccactaa tagaaacgtc   1680

aatccggatg gtagcttaat cgctaatggt tacaattggc cagaattttc acgagaaaaa   1740

ctcacaacgg ctatgattgc tcaccacttt agaatgttca cgattagagc ttggcattta   1800

actgatggat tcaatgaaaa aattgaaaat gccgtagact atgacatgtt cctcaaactc   1860

agtgaagttg gaaaatttaa acatcttaat aaaatctgct ataaccgtgt attacatggt   1920

gataacacat caattaagaa acttggcatt caaaagaaaa accattttgt tgtagtcaat   1980

cagtcattaa atagacaagg cataacttat tataattatg acgaatttga tgatttagat   2040

gaaagtagaa agtatatttt caataaaacc gctgaatatc aagaagagat tgatatctta   2100

aaagatattt aa                                                       2112
```

<210> SEQ ID NO 40
<211> LENGTH: 2112
<212> TYPE: DNA
<213> ORGANISM: Pasteurella multocida

<400> SEQUENCE: 40

```
atgaatacat tatcacaagc aataaaagca tataacagca atgactatca attagcactc     60

aaattatttg aaaagtcggc ggaaatctat ggacggaaaa ttgttgaatt tcaaattacc    120

aaatgcaaag aaaaactctc agcacatcct tctgttaatt cagcacatct ttctgtaaat    180

aaagaagaaa aagtcaatgt ttgcgatagt ccgttagata ttgcaacaca actgttactt    240

tccaacgtaa aaaaattagt actttctgac tcggaaaaaa acacgttaaa aaataaatgg    300

aaattgctca ctgagaagaa atctgaaaat gcggaggtaa gagcggtcgc ccttgtacca    360

aaagattttc ccaaagatct ggttttagcg cctttacctg atcatgttaa tgattttaca    420

tggtacaaaa agcgaaagaa aagacttggc ataaaacctg aacatcaaca tgttggtctt    480

tctattatcg ttacaacatt caatcgacca gcaattttat cgattacatt agcctgttta    540

gtaaaccaaa aaacacatta cccgtttgaa gttatcgtga cagatgatgg tagtcaggaa    600

gatctatcac cgatcattcg ccaatatgaa aataaattgg atattcgcta cgtcagacaa    660

aaagataacg gttttcaagc cagtgccgct cggaatatgg gattacgctt agcaaaatat    720

gactttattg gcttactcga ctgtgatatg gcgccaaatc cattatgggt tcattcttat    780

gttgcagagc tattagaaga tgatgattta acaatcattg gtccaagaaa atacatcgat    840

acacaacata ttgacccaaa agacttctta aataacgcga gtttgcttga atcattacca    900

gaagtgaaaa ccaataatag tgttgccgca aaaggggaag gaacagtttc tctggattgg    960

cgcttagaac aattcgaaaa aacagaaaat ctccgcttat ccgattcgcc tttccgtttt   1020

tttgcggcgg gtaatgttgc tttcgctaaa aaatggctaa ataaatccgg tttctttgat   1080

gaggaattta atcactgggg tggagaagat gtggaatttg gatatcgctt attccgttac   1140

ggtagtttct ttaaaactat tgatggcatt atggcctacc atcaagagcc accaggtaaa   1200

gaaaatgaaa ccgatcgtga agcgggaaaa aatattacgc tcgatattat gagagaaaag   1260

gtcccttata tctatagaaa acttttacca atagaagatt cgcatatcaa tagagtacct   1320

ttagtttcaa tttatatccc agcttataac tgtgcaaact atattcaacg ttgcgtagat   1380

agtgcactga atcagactgt tgttgatctc gaggtttgta tttgtaacga tggttcaaca   1440

gataatacct tagaagtgat caataagctt tatggtaata atcctagggt acgcatcatg   1500

tctaaaccaa atggcggaat agcctcagca tcaaatgcag ccgtttcttt tgctaaaggt   1560
```

tattacattg ggcagttaga ttcaaaagat tatcttgagc ctgatgcagt tgaactgtgt 1620
ttaaaagaat ttttaaaaga taaaacgcta gcttgtgttt ataccactaa tagaaacgtc 1680
aatccggatg gtagcttaat cgctaatggt tacaattggc cagaattttc acgagaaaaa 1740
ctcacaacgg ctatgattgc tcaccacttt agaatgttca cgattagagc ttggcattta 1800
actgatggat tcaatgaaaa aattgaaaat gccgtagact atgacatgtt cctcaaactc 1860
agtgaagttg gaaaatttaa acatcttaat aaaatctgct ataaccgtgt attacatggt 1920
gataacacat caattaagaa acttggcatt caaaagaaaa accattttgt tgtagtcaat 1980
cagtcattaa atagacaagg cataacttat tataattatg acgaatttga tgatttagat 2040
gaaagtagaa agtatatttt caataaaacc gctgaatatc aagaagagat tgatatctta 2100
aaagatattt aa 2112

<210> SEQ ID NO 41
<211> LENGTH: 2112
<212> TYPE: DNA
<213> ORGANISM: Pasteurella multocida

<400> SEQUENCE: 41
atgaatacat tatcacaagc aataaaagca tataacagca atgactatca attagcactc 60
aaattatttg aaaagtcggc ggaaatctat ggacggaaaa ttgttgaatt tcaaattacc 120
aaatgcaaag aaaaactctc agcacatcct tctgttaatt cagcacatct ttctgtaaat 180
aaagaagaaa aagtcaatgt ttgcgatagt ccgttagata ttgcaacaca actgttactt 240
tccaacgtaa aaaaattagt actttctgac tcggaaaaaa acacgttaaa aaataaatgg 300
aaattgctca ctgagaagaa atctgaaaat gcggaggtaa gagcggtcgc ccttgtacca 360
aaagattttc ccaaagatct ggttttagcg cctttacctg atcatgttaa tgattttaca 420
tggtacaaaa agcgaaagaa aagacttggc ataaaacctg aacatcaaca tgttggtctt 480
tctattatcg ttacaacatt caatcgacca gcaattttat cgattacatt agcctgttta 540
gtaaaccaaa aaacacatta cccgtttgaa gttatcgtga cagatgatgg tagtcaggaa 600
gatctatcac cgatcattcg ccaatatgaa aataaattgg atattcgcta cgtcagacaa 660
aaagataacg gttttcaagc cagtgccgct cggaatatgg gattacgctt agcaaaatat 720
gactttattg gcttactcga ctgtgatatg gcgccaaatc cattatgggt tcattcttat 780
gttgcagagc tattagaaga tgatgattta acaatcattg gtccaagaaa atacatcgat 840
acacaacata ttgacccaaa agacttctta aataacgcga gtttgcttga atcattacca 900
gaagtgaaaa ccaataatag tgttgccgca aaaggggaag gaacagtttc tctggattgg 960
cgcttagaac aattcgaaaa aacagaaaat ctccgcttat ccgattcgcc tttccgtttt 1020
tttgcggcgg gtaatgttgc tttcgctaaa aaatggctaa ataaatccgg tttctttgat 1080
gaggaattta atcactgggg tggagacgat gtggaatttg gatatcgctt attccgttac 1140
ggtagtttct ttaaaactat tgatggcatt atggcctacc atcaagagcc accaggtaaa 1200
gaaaatgaaa ccgatcgtga agcgggaaaa aatattacgc tcgatattat gagagaaaag 1260
gtcccttata tctatagaaa acttttacca atagaagatt cgcatatcaa tagagtacct 1320
ttagtttcaa tttatatccc agcttataac tgtgcaaact atattcaacg ttgcgtagat 1380
agtgcactga atcagactgt tgttgatctc gaggtttgta tttgtaacga tggttcaaca 1440
gataatacct tagaagtgat caataagctt tatggtaata atcctagggt acgcatcatg 1500
tctaaaccaa atggcggaat agcctcagca tcaaatgcag ccgtttcttt tgctaaaggt 1560
tattacattg ggcagttaga ttcagatgat tatcttgagc ctgatgcagt tgaactgtgt 1620
ttaaaagaat ttttaaaaga taaaacgcta gcttgtgttt ataccactaa tagaaacgtc 1680
aatccggatg gtagcttaat cgctaatggt tacaattggc cagaattttc acgagaaaaa 1740
ctcacaacgg ctatgattgc tcaccacttt agaatgttca cgattagagc ttggcattta 1800
actgatggat tcaatgaaaa aattgaaaat gccgtagact atgacatgtt cctcaaactc 1860
agtgaagttg gaaaatttaa acatcttaat aaaatctgct ataaccgtgt attacatggt 1920
gataacacat caattaagaa acttggcatt caaaagaaaa accattttgt tgtagtcaat 1980
cagtcattaa atagacaagg cataacttat tataattatg acgaatttga tgatttagat 2040
gaaagtagaa agtatatttt caataaaacc gctgaatatc aagaagagat tgatatctta 2100
aaagatattt aa 2112

<210> SEQ ID NO 42
<211> LENGTH: 2112
<212> TYPE: DNA
<213> ORGANISM: Pasteurella multocida

<400> SEQUENCE: 42
atgaatacat tatcacaagc aataaaagca tataacagca atgactatca attagcactc 60
aaattatttg aaaagtcggc ggaaatctat ggacggaaaa ttgttgaatt tcaaattacc 120
aaatgcaaag aaaaactctc agcacatcct tctgttaatt cagcacatct ttctgtaaat 180
aaagaagaaa aagtcaatgt ttgcgatagt ccgttagata ttgcaacaca actgttactt 240
tccaacgtaa aaaaattagt actttctgac tcggaaaaaa acacgttaaa aaataaatgg 300
aaattgctca ctgagaagaa atctgaaaat gcggaggtaa gagcggtcgc ccttgtacca 360
aaagattttc ccaaagatct ggttttagcg cctttacctg atcatgttaa tgattttaca 420
tggtacaaaa agcgaaagaa aagacttggc ataaaacctg aacatcaaca tgttggtctt 480
tctattatcg ttacaacatt caatcgacca gcaattttat cgattacatt agcctgttta 540
gtaaaccaaa aaacacatta cccgtttgaa gttatcgtga cagatgatgg tagtcaggaa 600
gatctatcac cgatcattcg ccaatatgaa aataaattgg atattcgcta cgtcagacaa 660
aaagataacg gttttcaagc cagtgccgct cggaatatgg gattacgctt agcaaaatat 720
gactttattg gcttactcga ctgtgatatg gcgccaaatc cattatgggt tcattcttat 780
gttgcagagc tattagaaga tgatgattta acaatcattg gtccaagaaa atacatcgat 840
acacaacata ttgacccaaa agacttctta aataacgcga gtttgcttga atcattacca 900
gaagtgaaaa ccaataatag tgttgccgca aaaggggaag gaacagtttc tctggattgg 960
cgcttagaac aattcgaaaa aacagaaaat ctccgcttat ccgattcgcc tttccgtttt 1020
tttgcggcgg gtaatgttgc tttcgctaaa aaatggctaa ataaatccgg tttctttgat 1080
gaggaattta atcactgggg tggacaagat gtggaatttg gatatcgctt attccgttac 1140
ggtagtttct ttaaaactat tgatggcatt atggcctacc atcaagagcc accaggtaaa 1200
gaaaatgaaa ccgatcgtga agcgggaaaa aatattacgc tcgatattat gagagaaaag 1260
gtcccttata tctatagaaa acttttacca atagaagatt cgcatatcaa tagagtacct 1320
ttagtttcaa tttatatccc agcttataac tgtgcaaact atattcaacg ttgcgtagat 1380
agtgcactga atcagactgt tgttgatctc gaggtttgta tttgtaacga tggttcaaca 1440
gataatacct tagaagtgat caataagctt tatggtaata atcctagggt acgcatcatg 1500
tctaaaccaa atggcggaat agcctcagca tcaaatgcag ccgtttcttt tgctaaaggt 1560

-continued

```
tattacattg ggcagttaga ttcagatgat tatcttgagc ctgatgcagt tgaactgtgt   1620

ttaaaagaat ttttaaaaga taaaacgcta gcttgtgttt ataccactaa tagaaacgtc   1680

aatccggatg gtagcttaat cgctaatggt tacaattggc cagaattttc acgagaaaaa   1740

ctcacaacgg ctatgattgc tcaccacttt agaatgttca cgattagagc ttggcattta   1800

actgatggat tcaatgaaaa aattgaaaat gccgtagact atgacatgtt cctcaaactc   1860

agtgaagttg gaaaatttaa acatcttaat aaaatctgct ataaccgtgt attacatggt   1920

gataacacat caattaagaa acttggcatt caaaagaaaa accattttgt tgtagtcaat   1980

cagtcattaa atagacaagg cataacttat tataattatg acgaatttga tgatttagat   2040

gaaagtagaa agtatatttt caataaaacc gctgaatatc aagaagagat tgatatctta   2100

aaagatattt aa                                                       2112
```

<210> SEQ ID NO 43
<211> LENGTH: 2112
<212> TYPE: DNA
<213> ORGANISM: Pasteurella multocida

<400> SEQUENCE: 43

```
atgaatacat tatcacaagc aataaaagca tataacagca atgactatca attagcactc     60

aaattatttg aaaagtcggc ggaaatctat ggacggaaaa ttgttgaatt tcaaattacc    120

aaatgcaaag aaaaactctc agcacatcct tctgttaatt cagcacatct ttctgtaaat    180

aaagaagaaa aagtcaatgt ttgcgatagt ccgttagata ttgcaacaca actgttactt    240

tccaacgtaa aaaaattagt actttctgac tcggaaaaaa acacgttaaa aaataaatgg    300

aaattgctca ctgagaagaa atctgaaaat gcggaggtaa gagcggtcgc ccttgtacca    360

aaagattttc ccaaagatct ggttttagcg cctttacctg atcatgttaa tgattttaca    420

tggtacaaaa agcgaaagaa aagacttggc ataaaacctg aacatcaaca tgttggtctt    480

tctattatcg ttacaacatt caatcgacca gcaattttat cgattacatt agcctgttta    540

gtaaaccaaa aaacacatta cccgtttgaa gttatcgtga cagatgatgg tagtcaggaa    600

gatctatcac cgatcattcg ccaatatgaa aataaattgg atattcgcta cgtcagacaa    660

aaagataacg gttttcaagc cagtgccgct cggaatatgg gattacgctt agcaaaatat    720

gactttattg gcttactcga ctgtgatatg gcgccaaatc cattatgggt tcattcttat    780

gttgcagagc tattagaaga tgatgattta acaatcattg gtccaagaaa atacatcgat    840

acacaacata ttgacccaaa agacttctta aataacgcga gtttgcttga atcattacca    900

gaagtgaaaa ccaataatag tgttgccgca aaaggggaag gaacagtttc tctggattgg    960

cgcttagaac aattcgaaaa aacagaaaat ctccgcttat ccgattcgcc tttccgtttt   1020

tttgcggcgg gtaatgttgc tttcgctaaa aaatggctaa ataaatccgg tttctttgat   1080

gaggaattta atcactgggg tggacacgat gtggaatttg gatatcgctt attccgttac   1140

ggtagtttct ttaaaactat tgatggcatt atggcctacc atcaagagcc accaggtaaa   1200

gaaaatgaaa ccgatcgtga agcgggaaaa aatattacgc tcgatattat gagagaaaag   1260

gtcccttata tctatagaaa acttttacca atagaagatt cgcatatcaa tagagtacct   1320

ttagtttcaa tttatatccc agcttataac tgtgcaaact atattcaacg ttgcgtagat   1380

agtgcactga atcagactgt tgttgatctc gaggtttgta tttgtaacga tggttcaaca   1440

gataatacct tagaagtgat caataagctt tatggtaata atcctagggt acgcatcatg   1500

tctaaaccaa atggcggaat agcctcagca tcaaatgcag ccgtttcttt tgctaaaggt   1560
```

```
tattacattg ggcagttaga ttcagatgat tatcttgagc ctgatgcagt tgaactgtgt   1620

ttaaaagaat ttttaaaaga taaaacgcta gcttgtgttt ataccactaa tagaaacgtc   1680

aatccggatg gtagcttaat cgctaatggt tacaattggc cagaattttc acgagaaaaa   1740

ctcacaacgg ctatgattgc tcaccacttt agaatgttca cgattagagc ttggcattta   1800

actgatggat tcaatgaaaa aattgaaaat gccgtagact atgacatgtt cctcaaactc   1860

agtgaagttg gaaaatttaa acatcttaat aaaatctgct ataaccgtgt attacatggt   1920

gataacacat caattaagaa acttggcatt caaaagaaaa accattttgt tgtagtcaat   1980

cagtcattaa atagacaagg cataacttat tataattatg acgaatttga tgatttagat   2040

gaaagtagaa agtatatttt caataaaacc gctgaatatc aagaagagat tgatatctta   2100

aaagatattt aa                                                       2112
```

<210> SEQ ID NO 44
<211> LENGTH: 2112
<212> TYPE: DNA
<213> ORGANISM: Pasteurella multocida

<400> SEQUENCE: 44

```
atgaatacat tatcacaagc aataaaagca tataacagca atgactatca attagcactc     60

aaattatttg aaaagtcggc ggaaatctat ggacggaaaa ttgttgaatt tcaaattacc    120

aaatgcaaag aaaaactctc agcacatcct tctgttaatt cagcacatct ttctgtaaat    180

aaagaagaaa aagtcaatgt ttgcgatagt ccgttagata ttgcaacaca actgttactt    240

tccaacgtaa aaaaattagt actttctgac tcggaaaaaa acacgttaaa aaataaatgg    300

aaattgctca ctgagaagaa atctgaaaat gcggaggtaa gagcggtcgc ccttgtacca    360

aaagattttc ccaaagatct ggttttagcg cctttacctg atcatgttaa tgattttaca    420

tggtacaaaa agcgaaagaa aagacttggc ataaaacctg aacatcaaca tgttggtctt    480

tctattatcg ttacaacatt caatcgacca gcaattttat cgattacatt agcctgttta    540

gtaaaccaaa aaacacatta cccgtttgaa gttatcgtga cagatgatgg tagtcaggaa    600

gatctatcac cgatcattcg ccaatatgaa aataaattgg atattcgcta cgtcagacaa    660

aaagataacg gttttcaagc cagtgccgct cggaatatgg gattacgctt agcaaaatat    720

gactttattg gcttactcga ctgtgatatg gcgccaaatc cattatgggt tcattcttat    780

gttgcagagc tattagaaga tgatgattta acaatcattg gtccaagaaa atacatcgat    840

acacaacata ttgacccaaa agacttctta aataacgcga gtttgcttga atcattacca    900

gaagtgaaaa ccaataatag tgttgccgca aaaggggaag gaacagtttc tctggattgg    960

cgcttagaac aattcgaaaa aacagaaaat ctccgcttat ccgattcgcc tttccgtttt   1020

tttgcggcgg gtaatgttgc tttcgctaaa aaatggctaa ataaatccgg tttctttgat   1080

gaggaattta atcactgggg tggagaagaa gtggaatttg gatatcgctt attccgttac   1140

ggtagtttct ttaaaactat tgatggcatt atggcctacc atcaagagcc accaggtaaa   1200

gaaaatgaaa ccgatcgtga agcgggaaaa aatattacgc tcgatattat gagagaaaag   1260

gtcccttata tctatagaaa acttttacca atagaagatt cgcatatcaa tagagtacct   1320

ttagtttcaa tttatatccc agcttataac tgtgcaaact atattcaacg ttgcgtagat   1380

agtgcactga atcagactgt tgttgatctc gaggtttgta tttgtaacga tggttcaaca   1440

gataatacct tagaagtgat caataagctt tatggtaata atcctagggt acgcatcatg   1500

tctaaaccaa atggcggaat agcctcagca tcaaatgcag ccgtttcttt tgctaaaggt   1560
```

tattacattg ggcagttaga ttcagatgat tatcttgagc ctgatgcagt tgaactgtgt 1620
ttaaaagaat ttttaaaaga taaaacgcta gcttgtgttt ataccactaa tagaaacgtc 1680
aatccggatg gtagcttaat cgctaatggt tacaattggc cagaattttc acgagaaaaa 1740
ctcacaacgg ctatgattgc tcaccacttt agaatgttca cgattagagc ttggcattta 1800
actgatggat tcaatgaaaa aattgaaaat gccgtagact atgacatgtt cctcaaactc 1860
agtgaagttg gaaaatttaa acatcttaat aaaatctgct ataaccgtgt attacatggt 1920
gataacacat caattaagaa acttggcatt caaaagaaaa accattttgt tgtagtcaat 1980
cagtcattaa atagacaagg cataacttat tataattatg acgaatttga tgatttagat 2040
gaaagtagaa agtatatttt caataaaacc gctgaatatc aagaagagat tgatatctta 2100
aaagatattt aa 2112

<210> SEQ ID NO 45
<211> LENGTH: 2112
<212> TYPE: DNA
<213> ORGANISM: Pasteurella multocida

<400> SEQUENCE: 45
atgaatacat tatcacaagc aataaaagca tataacagca atgactatca attagcactc 60
aaattatttg aaaagtcggc ggaaatctat ggacggaaaa ttgttgaatt tcaaattacc 120
aaatgcaaag aaaaactctc agcacatcct tctgttaatt cagcacatct ttctgtaaat 180
aaagaagaaa aagtcaatgt ttgcgatagt ccgttagata ttgcaacaca actgttactt 240
tccaacgtaa aaaaattagt actttctgac tcggaaaaaa acacgttaaa aaataaatgg 300
aaattgctca ctgagaagaa atctgaaaat gcggaggtaa gagcggtcgc ccttgtacca 360
aaagattttc ccaaagatct ggttttagcg cctttacctg atcatgttaa tgattttaca 420
tggtacaaaa agcgaaagaa aagacttggc ataaaacctg aacatcaaca tgttggtctt 480
tctattatcg ttacaacatt caatcgacca gcaattttat cgattacatt agcctgttta 540
gtaaaccaaa aaacacatta cccgtttgaa gttatcgtga cagatgatgg tagtcaggaa 600
gatctatcac cgatcattcg ccaatatgaa aataaattgg atattcgcta cgtcagacaa 660
aaagataacg gttttcaagc cagtgccgct cggaatatgg gattacgctt agcaaaatat 720
gactttattg gcttactcga ctgtgatatg gcgccaaatc cattatgggt tcattcttat 780
gttgcagagc tattagaaga tgatgattta acaatcattg gtccaagaaa atacatcgat 840
acacaacata ttgacccaaa agacttctta aataacgcga gtttgcttga atcattacca 900
gaagtgaaaa ccaataatag tgttgccgca aaaggggaag gaacagtttc tctggattgg 960
cgcttagaac aattcgaaaa aacagaaaat ctccgcttat ccgattcgcc tttccgtttt 1020
tttgcggcgg gtaatgttgc tttcgctaaa aaatggctaa ataaatccgg tttctttgat 1080
gaggaattta atcactgggg tggagaaaat gtggaatttg gatatcgctt attccgttac 1140
ggtagtttct ttaaaactat tgatggcatt atggcctacc atcaagagcc accaggtaaa 1200
gaaaatgaaa ccgatcgtga agcgggaaaa aatattacgc tcgatattat gagagaaaag 1260
gtcccttata tctatagaaa acttttacca atagaagatt cgcatatcaa tagagtacct 1320
ttagtttcaa tttatatccc agcttataac tgtgcaaact atattcaacg ttgcgtagat 1380
agtgcactga atcagactgt tgttgatctc gaggtttgta tttgtaacga tggttcaaca 1440
gataatacct tagaagtgat caataagctt tatggtaata atcctagggt acgcatcatg 1500
tctaaaccaa atggcggaat agcctcagca tcaaatgcag ccgtttcttt tgctaaaggt 1560
tattacattg ggcagttaga ttcagatgat tatcttgagc ctgatgcagt tgaactgtgt 1620
ttaaaagaat ttttaaaaga taaaacgcta gcttgtgttt ataccactaa tagaaacgtc 1680
aatccggatg gtagcttaat cgctaatggt tacaattggc cagaattttc acgagaaaaa 1740
ctcacaacgg ctatgattgc tcaccacttt agaatgttca cgattagagc ttggcattta 1800
actgatggat tcaatgaaaa aattgaaaat gccgtagact atgacatgtt cctcaaactc 1860
agtgaagttg gaaaatttaa acatcttaat aaaatctgct ataaccgtgt attacatggt 1920
gataacacat caattaagaa acttggcatt caaaagaaaa accattttgt tgtagtcaat 1980
cagtcattaa atagacaagg cataacttat tataattatg acgaatttga tgatttagat 2040
gaaagtagaa agtatatttt caataaaacc gctgaatatc aagaagagat tgatatctta 2100
aaagatattt aa 2112

<210> SEQ ID NO 46
<211> LENGTH: 2112
<212> TYPE: DNA
<213> ORGANISM: Pasteurella multocida

<400> SEQUENCE: 46
atgaatacat tatcacaagc aataaaagca tataacagca atgactatca attagcactc 60
aaattatttg aaaagtcggc ggaaatctat ggacggaaaa ttgttgaatt tcaaattacc 120
aaatgcaaag aaaaactctc agcacatcct tctgttaatt cagcacatct ttctgtaaat 180
aaagaagaaa aagtcaatgt ttgcgatagt ccgttagata ttgcaacaca actgttactt 240
tccaacgtaa aaaaattagt actttctgac tcggaaaaaa acacgttaaa aaataaatgg 300
aaattgctca ctgagaagaa atctgaaaat gcggaggtaa gagcggtcgc ccttgtacca 360
aaagattttc ccaaagatct ggttttagcg cctttacctg atcatgttaa tgattttaca 420
tggtacaaaa agcgaaagaa aagacttggc ataaaacctg aacatcaaca tgttggtctt 480
tctattatcg ttacaacatt caatcgacca gcaattttat cgattacatt agcctgttta 540
gtaaaccaaa aaacacatta cccgtttgaa gttatcgtga cagatgatgg tagtcaggaa 600
gatctatcac cgatcattcg ccaatatgaa aataaattgg atattcgcta cgtcagacaa 660
aaagataacg gttttcaagc cagtgccgct cggaatatgg gattacgctt agcaaaatat 720
gactttattg gcttactcga ctgtgatatg gcgccaaatc cattatgggt tcattcttat 780
gttgcagagc tattagaaga tgatgattta acaatcattg gtccaagaaa atacatcgat 840
acacaacata ttgacccaaa agacttctta aataacgcga gtttgcttga atcattacca 900
gaagtgaaaa ccaataatag tgttgccgca aaaggggaag gaacagtttc tctggattgg 960
cgcttagaac aattcgaaaa aacagaaaat ctccgcttat ccgattcgcc tttccgtttt 1020
tttgcggcgg gtaatgttgc tttcgctaaa aaatggctaa ataaatccgg tttctttgat 1080
gaggaattta atcactgggg tggagaaaaa gtggaatttg gatatcgctt attccgttac 1140
ggtagtttct ttaaaactat tgatggcatt atggcctacc atcaagagcc accaggtaaa 1200
gaaaatgaaa ccgatcgtga agcgggaaaa aatattacgc tcgatattat gagagaaaag 1260
gtcccttata tctatagaaa acttttacca atagaagatt cgcatatcaa tagagtacct 1320
ttagtttcaa tttatatccc agcttataac tgtgcaaact atattcaacg ttgcgtagat 1380
agtgcactga atcagactgt tgttgatctc gaggtttgta tttgtaacga tggttcaaca 1440
gataatacct tagaagtgat caataagctt tatggtaata atcctagggt acgcatcatg 1500
tctaaaccaa atggcggaat agcctcagca tcaaatgcag ccgtttcttt tgctaaaggt 1560
tattacattg ggcagttaga ttcagatgat tatcttgagc ctgatgcagt tgaactgtgt 1620
ttaaaagaat ttttaaaaga taaaacgcta gcttgtgttt ataccactaa tagaaacgtc 1680
aatccggatg gtagcttaat cgctaatggt tacaattggc cagaattttc acgagaaaaa 1740
ctcacaacgg ctatgattgc tcaccacttt agaatgttca cgattagagc ttggcattta 1800
actgatggat tcaatgaaaa aattgaaaat gccgtagact atgacatgtt cctcaaactc 1860
agtgaagttg gaaaatttaa acatcttaat aaaatctgct ataaccgtgt attacatggt 1920
gataacacat caattaagaa acttggcatt caaaagaaaa accattttgt tgtagtcaat 1980
cagtcattaa atagacaagg cataacttat tataattatg acgaatttga tgatttagat 2040
gaaagtagaa agtatatttt caataaaacc gctgaatatc aagaagagat tgatatctta 2100
aaagatattt aa 2112

<210> SEQ ID NO 47
<211> LENGTH: 2136
<212> TYPE: DNA
<213> ORGANISM: Pasteurella multocida

<400> SEQUENCE: 47
atgaacacat tatcacaagc aataaaagca tataacagca atgactatca attagcactc 60
aaattatttg aaaagtcggc ggaaatctat ggacggaaaa ttgttgaatt tcaaattacc 120
aaatgccaag aaaaactctc agcacatcct tctgttaatt cagcacatct ttctgtaaat 180
aaagaagaaa aagtcaatgt ttgcgatagt ccgttagata ttgcaacaca actgttactt 240
tccaacgtaa aaaaattagt actttctgac tcggaaaaaa acacgttaaa aaataaatgg 300
aaattgctca ctgagaagaa atctgaaaat gcggaggtaa gagcggtcgc ccttgtacca 360
aaagattttc ccaaagatct ggttttagcg cctttacctg atcatgttaa tgattttaca 420
tggtacaaaa agcgaaagaa aagacttggc ataaaacctg aacatcaaca tgttggtctt 480
tctattatcg ttacaacatt caatcgacca gcaattttat cgattacatt agcctgttta 540
gtaaaccaaa aaacacatta cccgtttgaa gttatcgtga cagatgatgg tagtcaggaa 600
gatctatcac cgatcattcg ccaatatgaa aataaattgg atattcgcta cgtcagacaa 660
aaagataacg gttttcaagc cagtgccgct cggaatatgg gattacgctt agcaaaatat 720
gactttattg gcttactcga ctgtgatatg gcgccaaatc cattatgggt tcattcttat 780
gttgcagagc tattagaaga tgatgattta acaatcattg gtccaagaaa atacatcgat 840
acacaacata ttgacccaaa agacttctta aataacgcga gtttgcttga atcattacca 900
gaagtgaaaa ccaataatag tgttgccgca aaaggggaag gaacagtttc tctggattgg 960
cgcttagaac aattcgaaaa aacagaaaat ctccgcttat ccgattcgcc tttccgtttt 1020
tttgcggcgg gtaatgttgc tttcgctaaa aaatggctaa ataaatccgg tttctttgat 1080
gaggaattta atcactgggg tggagaagat gtggaatttg gatatcgctt attccgttac 1140
ggtagtttct ttaaaactat tgatggcatt atggcctacc atcaagagcc accaggtaaa 1200
gaaaatgaaa ccgatcgtga agcgggaaaa aatattacgc tcgatattat gagagaaaag 1260
gtcccttata tctatagaaa acttttacca atagaagatt cgcatattca tagaatacct 1320
ttagtttcta tttatatccc cgcttataac tgtgcaaatt atattcaaag atgtgtagat 1380
agtgctctta atcaaactgt tgtcgatctc gaggtttgta tttgtaacga tggttcaaca 1440
gataatacct tagaagtgat caataagctt tatggtaata atcctagggt acgcatcatg 1500
tctaaaccaa atggcggaat agcctcagca tcaaatgcag ccgtttcttt tgctaaaggt 1560
tattacattg ggcagttaga ttcagatgat tatcttgagc ctgatgcagt tgaactgtgt 1620
ttaaaagaat ttttaaaaga taaaacgcta gcttgtgttt ataccactaa tagaaacgtc 1680
aatccggatg gtagcttaat cgctaatggt tacaattggc cagaattttc acgagaaaaa 1740
ctcacaacgg ctatgattgc tcaccatttt agaatgttta cgattagagc ttggcattta 1800
acggatggat ttaacgaaaa tattgaaaac gccgtggatt atgacatgtt ccttaaactc 1860
agtgaagttg gaaaatttaa acatcttaat aaaatctgct ataaccgcgt attacatggt 1920
gataacacat ccattaagaa actcggcatt caaaagaaaa accattttgt tgtagtcaat 1980
cagtcattaa atagacaagg catcaattat tataattatg acaaatttga tgatttagat 2040
gaaagtagaa agtatatctt caataaaacc gctgaatatc aagaagaaat ggatatttta 2100
aaagatctta aactcattca gaataaagat gcctaa 2136

<210> SEQ ID NO 48
<211> LENGTH: 2091
<212> TYPE: DNA
<213> ORGANISM: Pasteurella multocida

<400> SEQUENCE: 48
atgaatacat tatcacaagc aataaaagca tataacagca atgactatga attagcactc 60
aaattatttg agaagtctgc tgaaacctac gggcgaaaaa tcgttgaatt ccaaattatc 120
aaatgtaaag aaaaactctc gaccaattct tatgtaagtg aagataaaaa aaacagtgtt 180
tgcgatagct cattagatat cgcaacacag ctcttacttt ccaacgtaaa aaaattaact 240
ctatccgaat cagaaaaaaa cagtttaaaa aataaatgga aatctatcac tgggaaaaaa 300
tcggagaacg cagaaatcag aaaggtggaa ctagtaccca aagattttcc taaagatctt 360
gttcttgctc cattgccaga tcatgttaat gattttacat ggtacaaaaa tcgaaaaaaa 420
agcttaggta taaagcctgt aaataagaat atcggtcttt ctattattat tcctacattt 480
aatcgtagcc gtattttaga tataacgtta gcctgtttgg tcaatcagaa aacaaactac 540
ccatttgaag tcgttgttgc agatgatggt agtaaggaaa acttacttac cattgtgcaa 600
aaatacgaac aaaaacttga cataaagtat gtaagacaaa aagattatgg atatcaattg 660
tgtgcagtca gaaacttagg tttacgtaca gcaaagtatg attttgtctc gattctagac 720
tgcgatatgg caccacaaca attatgggtt cattcttatc ttacagaact attagaagac 780
aatgatattg ttttaattgg acctagaaaa tatgtggata ctcataatat taccgcagaa 840
caattcctta acgatccata tttaatagaa tcactacctg aaaccgctac aaataacaat 900
ccttcgatta catcaaaagg aaatatatcg ttggattgga gattagaaca tttcaaaaaa 960
accgataatc tacgtctatg tgattcaccg tttcgttatt ttagttgcgg taatgttgca 1020
ttttctaaag aatggctaaa taaagtaggt tggttcgatg aagaatttaa tcattggggg 1080
ggcgaagatg tagaatttgg ttacagatta tttgccaaag gctgtttttt cagagtaatt 1140
gacggcggaa tggcatacca tcaagaacca cctggtaaag aaaatgaaac agaccgcgaa 1200
gctggtaaaa gtattacgct taaaattgtg aaagaaaagg taccttacat ctatagaaaa 1260
cttttaccaa tagaagattc gcatatcaat agagtacctt tagtttcaat ttatatccca 1320
gcttataact gtgcaaacta tattcaacgt tgcgtagata gtgcactgaa tcagactgtt 1380
gttgatctcg aggtttgtat ttgtaacgat ggttcaacag ataatacctt agaagtgatc 1440
aataagcttt atggtaataa tcctagggta cgcatcatgt ctaaaccaaa tggcggaata 1500
gcctcagcat caaatgcagc cgtttctttt gctaaaggtt attacattgg gcagttagat 1560
tcagatgatt atcttgagcc tgatgcagtt gaactgtgtt taaaagaatt tttaaaagat 1620
aaaacgctag cttgtgttta taccactaat agaaacgtca atccggatgg tagcttaatc 1680
gctaatggtt acaattggcc agaattttca cgagaaaaac tcacaacggc tatgattgct 1740
caccacttta gaatgttcac gattagagct tggcatttaa ctgatggatt caatgaaaaa 1800
attgaaaatg ccgtagacta tgacatgttc ctcaaactca gtgaagttgg aaaatttaaa 1860
catcttaata aaatctgcta taaccgtgta ttacatggtg ataacacatc aattaagaaa 1920
cttggcattc aaaagaaaaa ccatttttgtt gtagtcaatc agtcattaaa tagacaaggc 1980
ataacttatt ataattatga cgaatttgat gatttagatg aaagtagaaa gtatattttc 2040
aataaaaccg ctgaatatca agaagagatt gatatcttaa aagatattta a 2091

<210> SEQ ID NO 49
<211> LENGTH: 29
<212> TYPE: DNA
<213> ORGANISM: Artificial Sequence
<220> FEATURE:
<223> OTHER INFORMATION: primer

<400> SEQUENCE: 49
atgaacacat tatcacaagc aataaaagc 29

<210> SEQ ID NO 50
<211> LENGTH: 27
<212> TYPE: DNA
<213> ORGANISM: Artificial Sequence
<220> FEATURE:
<223> OTHER INFORMATION: primer

<400> SEQUENCE: 50
gcgaatcttc tattggtaaa agytttc 27

<210> SEQ ID NO 51
<211> LENGTH: 26
<212> TYPE: DNA
<213> ORGANISM: Artificial sequence
<220> FEATURE:
<223> OTHER INFORMATION: primer

<400> SEQUENCE: 51
cttttaccaa tagaagattc gcatat 26

<210> SEQ ID NO 52
<211> LENGTH: 33
<212> TYPE: DNA
<213> ORGANISM: Artificial Sequence
<220> FEATURE:
<223> OTHER INFORMATION: primer

<400> SEQUENCE: 52
gaagacgtct taggcatctt tattctgaat gag 33

<210> SEQ ID NO 53
<211> LENGTH: 43
<212> TYPE: DNA
<213> ORGANISM: Artificial Sequence
<220> FEATURE:
<223> OTHER INFORMATION: primer

<400> SEQUENCE: 53
gggaattctg cagttaaata tcttttaaga tatcaatctc ttc 43

<210> SEQ ID NO 54
<211> LENGTH: 33
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (9)..(9)
<223> OTHER INFORMATION: inosine
<220> FEATURE:
<221> NAME/KEY: misc_feature
<222> LOCATION: (12)..(12)
<223> OTHER INFORMATION: inosine
<220> FEATURE:
<221> NAME/KEY: misc_feature
<222> LOCATION: (18)..(18)
<223> OTHER INFORMATION: inosine
<220> FEATURE:
<221> NAME/KEY: misc_feature
<222> LOCATION: (24)..(24)
<223> OTHER INFORMATION: inosine
<220> FEATURE:
<221> NAME/KEY: misc_feature
<222> LOCATION: (27)..(27)
<223> OTHER INFORMATION: inosine

<400> SEQUENCE: 54
garttybtnm rngarggnaa rgcnytntay gay 33

<210> SEQ ID NO 55
<211> LENGTH: 39
<212> TYPE: DNA
<213> ORGANISM: Artificial sequence
<220> FEATURE:
<223> OTHER INFORMATION: primer
<220> FEATURE:
<221> NAME/KEY: misc_feature
<222> LOCATION: (7)..(7)
<223> OTHER INFORMATION: inosine
<220> FEATURE:
<221> NAME/KEY: misc_feature
<222> LOCATION: (10)..(10)
<223> OTHER INFORMATION: inosine
<220> FEATURE:
<221> NAME/KEY: misc_feature
<222> LOCATION: (16)..(16)
<223> OTHER INFORMATION: inosine
<220> FEATURE:
<221> NAME/KEY: misc_feature
<222> LOCATION: (22)..(22)
<223> OTHER INFORMATION: inosine
<220> FEATURE:
<221> NAME/KEY: misc_feature
<222> LOCATION: (25)..(25)
<223> OTHER INFORMATION: A, C, G or T

<400> SEQUENCE: 55
rcartanccn ccrtanccra answnggrtt rttrtartg 39

<210> SEQ ID NO 56
<211> LENGTH: 30
<212> TYPE: DNA
<213> ORGANISM: Artificial Sequence
<220> FEATURE:
<223> OTHER INFORMATION: primer

<400> SEQUENCE: 56
tatatttaca gcagtatcat tttctaaagg 30

<210> SEQ ID NO 57
<211> LENGTH: 501
<212> TYPE: PRT
<213> ORGANISM: Pasteurella multocida

<400> SEQUENCE: 57

Met Ser Leu Phe Lys Arg Ala Thr Glu Leu Phe Lys Ser Gly Asn Tyr
1 5 10 15

Lys Asp Ala Leu Thr Leu Tyr Glu Asn Ile Ala Lys Ile Tyr Gly Ser
20 25 30

Glu Ser Leu Val Lys Tyr Asn Ile Asp Ile Cys Lys Lys Asn Ile Thr
35 40 45

Gln Ser Lys Ser Asn Lys Ile Glu Glu Asp Asn Ile Ser Gly Glu Asn
50 55 60

Glu Phe Ser Val Ser Ile Lys Asp Leu Tyr Asn Glu Ile Ser Asn Ser
65 70 75 80

Glu Leu Gly Ile Thr Lys Glu Arg Leu Gly Ala Pro Pro Leu Val Ser
85 90 95

Ile Ile Met Thr Ser His Asn Thr Glu Lys Phe Ile Glu Ala Ser Ile
100 105 110

Asn Ser Leu Leu Leu Gln Thr Tyr Asn Asn Leu Glu Val Ile Val Val
115 120 125

Asp Asp Tyr Ser Thr Asp Lys Thr Phe Gln Ile Ala Ser Arg Ile Ala
130 135 140

Asn Ser Thr Ser Lys Val Lys Thr Phe Arg Leu Asn Ser Asn Leu Gly
145 150 155 160

Thr Tyr Phe Ala Lys Asn Thr Gly Ile Leu Lys Ser Lys Gly Asp Ile
165 170 175

Ile Phe Phe Gln Asp Ser Asp Asp Val Cys His His Glu Arg Ile Glu
180 185 190

Arg Cys Val Asn Ala Leu Leu Ser Asn Lys Asp Asn Ile Ala Val Arg
195 200 205

Cys Ala Tyr Ser Arg Ile Asn Leu Glu Thr Gln Asn Ile Ile Lys Val
210 215 220

Asn Asp Asn Lys Tyr Lys Leu Gly Leu Ile Thr Leu Gly Val Tyr Arg
225 230 235 240

Lys Val Phe Asn Glu Ile Gly Phe Phe Asn Cys Thr Thr Lys Ala Ser
245 250 255

Asp Asp Glu Phe Tyr His Arg Ile Ile Lys Tyr Tyr Gly Lys Asn Arg
260 265 270

Ile Asn Asn Leu Phe Leu Pro Leu Tyr Tyr Asn Thr Met Arg Glu Asp
275 280 285

Ser Leu Phe Ser Asp Met Val Glu Trp Val Asp Glu Asn Asn Ile Lys
290 295 300

Gln Lys Thr Ser Asp Ala Arg Gln Asn Tyr Leu His Glu Phe Gln Lys
305 310 315 320

Ile His Asn Glu Arg Lys Phe Asn Glu Leu Lys Glu Ile Phe Ser Phe
325 330 335

Pro Arg Ile His Asp Ala Leu Pro Ile Ser Lys Glu Met Ser Lys Leu
340 345 350

Ser Asn Pro Lys Ile Pro Val Tyr Ile Asn Ile Cys Ser Ile Pro Ser
355 360 365

Arg Ile Lys Gln Leu Gln Tyr Thr Ile Gly Val Leu Lys Asn Gln Cys
370 375 380

Asp His Phe His Ile Tyr Leu Asp Gly Tyr Pro Glu Val Pro Asp Phe
385 390 395 400

Ile Lys Lys Leu Gly Asn Lys Ala Thr Val Ile Asn Cys Gln Asn Lys
405 410 415

```
Asn Glu Ser Ile Arg Asp Asn Gly Lys Phe Ile Leu Leu Glu Lys Leu
            420                 425                 430

Ile Lys Glu Asn Lys Asp Gly Tyr Tyr Ile Thr Cys Asp Asp Asp Ile
        435                 440                 445

Arg Tyr Pro Ala Asp Tyr Ile Asn Thr Met Ile Lys Lys Ile Asn Lys
    450                 455                 460

Tyr Asn Asp Lys Ala Ala Ile Gly Leu His Gly Val Ile Phe Pro Ser
465                 470                 475                 480

Arg Val Asn Lys Tyr Phe Ser Ser Asp Arg Ile Val Tyr Asn Phe Gln
                485                 490                 495

Lys Thr Phe Arg Lys
            500


<210> SEQ ID NO 58
<211> LENGTH: 1510
<212> TYPE: DNA
<213> ORGANISM: Pasteurella multocida

<400> SEQUENCE: 58

aatgagctta tttaaacgtg ctactgagct atttaagtca ggaaactata aagatgcact      60

aactctatat gaaaatatag ctaaaattta tggttcagaa agccttgtta aatataatat     120

tgatatatgt aaaaaaaata taacacaatc aaaaagtaat aaaatagaag aagataatat     180

ttctggagaa aacgaatttt cagtatcaat aaaagatcta tataacgaaa taagcaatag     240

tgaattaggg attacaaaag aaagactagg agcccccccct ctagtcagta ttataatgac     300

ttctcataat acagaaaaat tcattgaagc ctcaattaat tcactattat tgcaaacata     360

caataactta gaagttatcg ttgtagatga ttatagcaca gataaaacat ttcagatcgc     420

atccagaata gcaaactcta caagtaaagt aaaaacattc cgattaaact caaatctagg     480

gacatacttt gcgaaaaata caggaatttt aaagtctaaa ggagatatta ttttctttca     540

ggatagcgat gatgtatgtc accatgaaag aatcgaaaga tgtgttaatg cattattatc     600

gaataaagat aatatagctg ttagatgtgc atattctaga ataaatctag aaacacaaaa     660

tataataaaa gttaatgata ataaatacaa attaggatta ataactttag gcgtttatag     720

aaaagtattt aatgaaattg gtttttttaa ctgcacaacc aaagcatcgg atgatgaatt     780

ttatcataga ataattaaat actatggtaa aaataggata aataacttat ttctaccact     840

gtattataac acaatgcgtg aagattcatt attttctgat atggttgagt gggtagatga     900

aaataatata aagcaaaaaa cctctgatgc tagacaaaat tatctccatg aattccaaaa     960

aatacacaat gaaaggaaat ttaatgaatt aaaagagatt tttagctttc ctagaattca    1020

tgacgcctta cctatatcaa aagaaatgag taagctcagc aaccctaaaa ttcctgttta    1080

tataaatata tgctcaatac cttcaagaat aaaacaactt caatacacta ttggagtact    1140

aaaaaaccaa tgcgatcatt ttcatattta tcttgatgga tatccagaag tacctgattt    1200

tataaaaaaa ctagggaata aagcgaccgt tattaattgt caaaacaaaa atgagtctat    1260

tagagataat ggaaagttta ttctattaga aaaacttata aaggaaaata aagatggata    1320

ttatataact tgtgatgatg atatccggta tcctgctgac tacataaaca ctatgataaa    1380

aaaaattaat aaatacaatg ataaagcagc aattggatta catggtgtta tattcccaag    1440

tagagtcaac aagtattttt catcagacag aattgtctat aattttcaaa aaacctttag    1500

aaaatgatac                                                           1510
```

<210> SEQ ID NO 59
<211> LENGTH: 238
<212> TYPE: PRT
<213> ORGANISM: Escherichia coli

<400> SEQUENCE: 59

Met Ile Val Ala Asn Met Ser Ser Tyr Pro Pro Arg Lys Lys Glu Leu
1               5                   10                  15

Val His Ser Ile Gln Ser Leu His Ala Gln Val Asp Lys Ile Asn Leu
            20                  25                  30

Cys Leu Asn Glu Phe Glu Glu Ile Pro Glu Glu Leu Asp Gly Phe Ser
        35                  40                  45

Lys Leu Asn Pro Val Ile Pro Asp Lys Asp Tyr Lys Asp Val Gly Lys
    50                  55                  60

Phe Ile Phe Pro Cys Ala Lys Asn Asp Met Ile Val Leu Thr Asp Asp
65                  70                  75                  80

Asp Ile Ile Tyr Pro Pro Asp Tyr Val Glu Lys Met Leu Asn Phe Tyr
                85                  90                  95

Asn Ser Phe Ala Ile Phe Asn Cys Ile Val Gly Ile His Gly Cys Ile
            100                 105                 110

Tyr Ile Asp Ala Phe Asp Gly Asp Gln Ser Lys Arg Lys Val Phe Ser
        115                 120                 125

Phe Thr Gln Gly Leu Leu Arg Pro Arg Val Val Asn Gln Leu Gly Thr
    130                 135                 140

Gly Thr Val Phe Leu Lys Ala Asp Gln Leu Pro Ser Leu Lys Tyr Met
145                 150                 155                 160

Asp Gly Ser Gln Arg Phe Val Asp Val Arg Phe Ser Arg Tyr Met Leu
                165                 170                 175

Glu Asn Glu Ile Gly Met Ile Cys Val Pro Arg Glu Lys Asn Trp Leu
            180                 185                 190

Arg Glu Val Ser Ser Gly Ser Met Glu Gly Leu Trp Asn Thr Phe Thr
        195                 200                 205

Lys Lys Trp Pro Leu Asp Ile Ile Lys Glu Thr Gln Ala Ile Ala Gly
    210                 215                 220

Tyr Ser Lys Leu Asn Leu Glu Leu Val Tyr Asn Val Glu Gly
225                 230                 235

<210> SEQ ID NO 60
<211> LENGTH: 520
<212> TYPE: PRT
<213> ORGANISM: Escherichia coli

<400> SEQUENCE: 60

Met Asn Ala Glu Tyr Ile Asn Leu Val Glu Arg Lys Lys Lys Leu Gly
1               5                   10                  15

Thr Asn Ile Gly Ala Leu Asp Phe Leu Leu Ser Ile His Lys Glu Lys
            20                  25                  30

Val Asp Leu Gln His Lys Asn Ser Pro Leu Lys Gly Asn Asp Asn Leu
        35                  40                  45

Ile His Lys Arg Ile Asn Glu Tyr Asp Asn Val Leu Glu Leu Ser Lys
    50                  55                  60

Asn Val Ser Ala Gln Asn Ser Gly Asn Glu Phe Ser Tyr Leu Leu Gly
65                  70                  75                  80

Tyr Ala Asp Ser Leu Arg Lys Val Gly Met Leu Asp Thr Tyr Ile Lys
                85                  90                  95

Ile Val Cys Tyr Leu Thr Ile Gln Ser Arg Tyr Phe Lys Asn Gly Glu
            100                 105                 110

-continued

```
Arg Val Lys Leu Phe Glu His Ile Ser Asn Ala Leu Arg Tyr Ser Arg
        115                 120                 125

Ser Asp Phe Leu Ile Asn Leu Ile Phe Glu Arg Tyr Ile Glu Tyr Ile
    130                 135                 140

Asn His Leu Lys Leu Ser Pro Lys Gln Lys Asp Phe Tyr Phe Cys Thr
145                 150                 155                 160

Lys Phe Ser Lys Phe His Asp Tyr Thr Lys Asn Gly Tyr Lys Tyr Leu
                165                 170                 175

Ala Phe Asp Asn Gln Ala Asp Ala Gly Tyr Gly Leu Thr Leu Leu Leu
            180                 185                 190

Asn Ala Asn Asp Asp Met Gln Asp Ser Tyr Asn Leu Leu Pro Glu Gln
        195                 200                 205

Glu Leu Phe Ile Cys Asn Ala Val Ile Asp Asn Met Asn Ile Tyr Arg
    210                 215                 220

Ser Gln Phe Asn Lys Cys Leu Arg Lys Tyr Asp Leu Ser Glu Ile Thr
225                 230                 235                 240

Asp Ile Tyr Pro Asn Lys Ile Ile Leu Gln Gly Ile Lys Phe Asp Lys
                245                 250                 255

Lys Lys Asn Val Tyr Gly Lys Asp Leu Val Ser Ile Ile Met Ser Val
            260                 265                 270

Phe Asn Ser Glu Asp Thr Ile Ala Tyr Ser Leu His Ser Leu Leu Asn
        275                 280                 285

Gln Thr Tyr Glu Asn Ile Glu Ile Leu Val Cys Asp Asp Cys Ser Ser
    290                 295                 300

Asp Lys Ser Leu Glu Ile Ile Lys Ser Ile Ala Tyr Ser Ser Ser Arg
305                 310                 315                 320

Val Lys Val Tyr Ser Ser Arg Lys Asn Gln Gly Pro Tyr Asn Ile Arg
                325                 330                 335

Asn Glu Leu Ile Lys Lys Ala His Gly Asn Phe Ile Thr Phe Gln Asp
            340                 345                 350

Ala Asp Asp Leu Ser His Pro Glu Arg Ile Gln Arg Gln Val Glu Val
        355                 360                 365

Leu Arg Asn Asn Lys Ala Val Ile Cys Met Ala Asn Trp Ile Arg Val
    370                 375                 380

Ala Ser Asn Gly Lys Ile Gln Phe Phe Tyr Asp Asp Lys Ala Thr Arg
385                 390                 395                 400

Met Ser Val Val Ser Ser Met Ile Lys Lys Asp Ile Phe Ala Thr Val
                405                 410                 415

Gly Gly Tyr Arg Gln Ser Leu Ile Gly Ala Asp Thr Glu Phe Tyr Glu
            420                 425                 430

Thr Val Ile Met Arg Tyr Gly Arg Glu Ser Ile Val Arg Leu Leu Gln
        435                 440                 445

Pro Leu Ile Leu Gly Leu Trp Gly Asp Ser Gly Leu Thr Arg Asn Lys
    450                 455                 460

Gly Thr Glu Ala Leu Pro Asp Gly Tyr Ile Ser Gln Ser Arg Arg Glu
465                 470                 475                 480

Tyr Ser Asp Ile Ala Ala Arg Gln Arg Val Leu Gly Lys Ser Ile Val
                485                 490                 495

Ser Asp Lys Asp Val Arg Gly Leu Leu Ser Arg Tyr Gly Leu Phe Lys
            500                 505                 510

Asp Val Ser Gly Ile Ile Glu Gln
        515                 520
```

<210> SEQ ID NO 61
<211> LENGTH: 746
<212> TYPE: PRT
<213> ORGANISM: Mus musculus

<400> SEQUENCE: 61

```
Met Gln Ala Lys Lys Arg Tyr Phe Ile Leu Leu Ser Ala Gly Ser Cys
1               5                   10                  15

Leu Ala Leu Leu Phe Tyr Phe Gly Gly Val Gln Phe Arg Ala Ser Arg
            20                  25                  30

Ser His Ser Arg Arg Glu Glu His Ser Gly Arg Asn Gly Leu His Gln
        35                  40                  45

Pro Ser Pro Asp His Phe Trp Pro Arg Phe Pro Asp Ala Leu Arg Pro
    50                  55                  60

Phe Phe Pro Trp Asp Gln Leu Glu Asn Glu Asp Ser Ser Val His Ile
65                  70                  75                  80

Ser Pro Arg Gln Lys Arg Asp Ala Asn Ser Ser Ile Tyr Lys Gly Lys
                85                  90                  95

Lys Cys Arg Met Glu Ser Cys Phe Asp Phe Thr Leu Cys Lys Lys Asn
            100                 105                 110

Gly Phe Lys Val Tyr Val Tyr Pro Gln Gln Lys Gly Glu Lys Ile Ala
        115                 120                 125

Glu Ser Tyr Gln Asn Ile Leu Ala Ala Ile Glu Gly Ser Arg Phe Tyr
    130                 135                 140

Thr Ser Asp Pro Ser Gln Ala Cys Leu Phe Val Leu Ser Leu Asp Thr
145                 150                 155                 160

Leu Asp Arg Asp Gln Leu Ser Pro Gln Tyr Val His Asn Leu Arg Ser
                165                 170                 175

Lys Val Gln Ser Leu His Leu Trp Asn Asn Gly Arg Asn His Leu Ile
            180                 185                 190

Phe Asn Leu Tyr Ser Gly Thr Trp Pro Asp Tyr Thr Glu Asp Val Gly
        195                 200                 205

Phe Asp Ile Gly Gln Ala Met Leu Ala Lys Ala Ser Ile Ser Thr Glu
    210                 215                 220

Asn Phe Arg Pro Asn Phe Asp Val Ser Ile Pro Leu Phe Ser Lys Asp
225                 230                 235                 240

His Pro Arg Thr Gly Gly Glu Arg Gly Phe Leu Lys Phe Asn Thr Ile
                245                 250                 255

Pro Pro Leu Arg Lys Tyr Met Leu Val Phe Lys Gly Lys Arg Tyr Leu
            260                 265                 270

Thr Gly Ile Gly Ser Asp Thr Arg Asn Ala Leu Tyr His Val His Asn
        275                 280                 285

Gly Glu Asp Val Leu Leu Leu Thr Thr Cys Lys His Gly Lys Asp Trp
    290                 295                 300

Gln Lys His Lys Asp Ser Arg Cys Asp Arg Asp Asn Thr Glu Tyr Glu
305                 310                 315                 320

Lys Tyr Asp Tyr Arg Glu Met Leu His Asn Ala Thr Phe Cys Leu Val
                325                 330                 335

Pro Arg Gly Arg Arg Leu Gly Ser Phe Arg Phe Leu Glu Ala Leu Gln
            340                 345                 350

Ala Ala Cys Val Pro Val Met Leu Ser Asn Gly Trp Glu Leu Pro Phe
        355                 360                 365

Ser Glu Val Ile Asn Trp Asn Gln Ala Ala Val Ile Gly Asp Glu Arg
    370                 375                 380

Leu Leu Leu Gln Ile Pro Ser Thr Ile Arg Ser Ile His Gln Asp Lys
```

```
385                 390                 395                 400

Ile Leu Ala Leu Arg Gln Gln Thr Gln Phe Leu Trp Glu Ala Tyr Phe
                405                 410                 415

Ser Ser Val Glu Lys Ile Val Leu Thr Thr Leu Glu Ile Ile Gln Asp
            420                 425                 430

Arg Ile Phe Lys His Ile Ser Arg Asn Ser Leu Ile Trp Asn Lys His
        435                 440                 445

Pro Gly Gly Leu Phe Val Leu Pro Gln Tyr Ser Ser Tyr Leu Gly Asp
    450                 455                 460

Phe Pro Tyr Tyr Tyr Ala Asn Leu Gly Leu Lys Pro Pro Ser Lys Phe
465                 470                 475                 480

Thr Ala Val Ile His Ala Val Thr Pro Leu Val Ser Gln Ser Gln Pro
                485                 490                 495

Val Leu Lys Leu Leu Val Ala Ala Ala Lys Ser Gln Tyr Cys Ala Gln
            500                 505                 510

Ile Ile Val Leu Trp Asn Cys Asp Lys Pro Leu Pro Ala Lys His Arg
        515                 520                 525

Trp Pro Ala Thr Ala Val Pro Val Ile Val Ile Glu Gly Glu Ser Lys
    530                 535                 540

Val Met Ser Ser Arg Phe Leu Pro Tyr Asp Asn Ile Ile Thr Asp Ala
545                 550                 555                 560

Val Leu Ser Leu Asp Glu Asp Thr Val Leu Ser Thr Thr Glu Val Asp
                565                 570                 575

Phe Ala Phe Thr Val Trp Gln Ser Phe Pro Glu Arg Ile Val Gly Tyr
            580                 585                 590

Pro Ala Arg Ser His Phe Trp Asp Asn Ser Lys Glu Arg Trp Gly Tyr
        595                 600                 605

Thr Ser Lys Trp Thr Asn Asp Tyr Ser Met Val Leu Thr Gly Ala Ala
    610                 615                 620

Ile Tyr His Lys Tyr Tyr His Tyr Leu Tyr Ser His Tyr Leu Pro Ala
625                 630                 635                 640

Ser Leu Lys Asn Met Val Asp Gln Leu Ala Asn Cys Glu Asp Ile Leu
                645                 650                 655

Met Asn Phe Leu Val Ser Ala Val Thr Lys Leu Pro Pro Ile Lys Val
            660                 665                 670

Thr Gln Lys Lys Gln Tyr Lys Glu Thr Met Met Gly Gln Thr Ser Arg
        675                 680                 685

Ala Ser Arg Trp Ala Asp Pro Asp His Phe Ala Gln Arg Gln Ser Cys
    690                 695                 700

Met Asn Thr Phe Ala Ser Trp Phe Gly Tyr Met Pro Leu Ile His Ser
705                 710                 715                 720

Gln Met Arg Leu Asp Pro Val Leu Phe Lys Asp Gln Val Ser Ile Leu
                725                 730                 735

Arg Lys Lys Tyr Arg Asp Ile Glu Arg Leu
            740                 745


<210> SEQ ID NO 62
<211> LENGTH: 718
<212> TYPE: PRT
<213> ORGANISM: Mus musculus

<400> SEQUENCE: 62

Met Cys Ala Ser Val Lys Ser Asn Ile Arg Gly Pro Ala Leu Ile Pro
1               5                   10                  15

Arg Met Lys Thr Lys His Arg Ile Tyr Tyr Val Thr Leu Phe Ser Ile
```

-continued

```
            20                  25                  30

Val Leu Leu Gly Leu Ile Ala Thr Gly Met Phe Gln Phe Trp Pro His
        35                  40                  45

Ser Ile Glu Ser Ser Ser Asp Gly Gly Val Glu Lys Arg Ser Ile Arg
    50                  55                  60

Glu Val Pro Val Val Arg Leu Pro Thr Asp Ser Pro Ile Pro Glu Arg
65                  70                  75                  80

Gly Asp Leu Ser Cys Arg Met His Thr Cys Phe Asp Val Tyr Arg Cys
                85                  90                  95

Gly Phe Asn Pro Lys Asn Lys Ile Lys Val Tyr Ile Tyr Pro Leu Lys
            100                 105                 110

Lys Tyr Val Asp Asp Ala Gly Val Pro Val Ser Ser Ala Ile Ser Arg
        115                 120                 125

Glu Tyr Asn Glu Leu Leu Thr Ala Ile Ser Asp Ser Asp Tyr Tyr Thr
    130                 135                 140

Asp Asp Ile Asn Arg Ala Cys Leu Phe Val Pro Ser Ile Asp Val Leu
145                 150                 155                 160

Asn Gln Asn Pro Leu Arg Ile Lys Glu Thr Ala Gln Ala Leu Ala Gln
                165                 170                 175

Leu Ser Arg Trp Asp Arg Gly Thr Asn His Leu Leu Phe Asn Met Leu
            180                 185                 190

Pro Gly Ala Pro Pro Asp Tyr Asn Thr Ala Leu Asp Val Pro Arg Asp
        195                 200                 205

Arg Ala Leu Leu Ala Gly Gly Gly Phe Ser Thr Trp Thr Tyr Arg Gln
    210                 215                 220

Gly Tyr Asp Val Ser Ile Pro Val Phe Ser Pro Leu Ser Ala Glu Met
225                 230                 235                 240

Ala Leu Pro Glu Lys Ala Pro Gly Pro Arg Arg Tyr Phe Leu Leu Ser
                245                 250                 255

Ser Gln Met Ala Ile His Pro Glu Tyr Arg Glu Glu Leu Glu Ala Leu
            260                 265                 270

Gln Ala Lys His Gln Glu Ser Val Leu Val Leu Asp Lys Cys Thr Asn
        275                 280                 285

Leu Ser Glu Gly Val Leu Ser Val Arg Lys Arg Cys His Gln His Gln
    290                 295                 300

Val Phe Asp Tyr Pro Gln Val Leu Gln Glu Ala Thr Phe Cys Thr Val
305                 310                 315                 320

Leu Arg Arg Ala Arg Leu Gly Gln Ala Val Leu Ser Asp Val Leu Gln
                325                 330                 335

Ala Gly Cys Val Pro Val Val Ile Ala Asp Ser Tyr Ile Leu Pro Phe
            340                 345                 350

Ser Glu Val Leu Asp Trp Lys Lys Ala Ser Val Val Val Pro Glu Glu
        355                 360                 365

Lys Met Ser Asp Val Tyr Ser Ile Leu Gln Asn Ile Pro Gln Arg Gln
    370                 375                 380

Ile Glu Glu Met Gln Arg Gln Ala Arg Trp Phe Trp Glu Ala Tyr Phe
385                 390                 395                 400

Gln Ser Ile Lys Ala Ile Ala Leu Ala Thr Leu Gln Ile Ile Asn Asp
                405                 410                 415

Arg Ile Tyr Pro Tyr Ala Ala Ile Ser Tyr Glu Glu Trp Asn Asp Pro
            420                 425                 430

Pro Ala Val Lys Trp Ala Ser Val Ser Asn Pro Leu Phe Leu Pro Leu
        435                 440                 445
```

```
Ile Pro Pro Gln Ser Gln Gly Phe Thr Ala Ile Val Leu Thr Tyr Asp
    450                 455                 460

Arg Val Glu Ser Leu Phe Arg Val Ile Thr Glu Val Ser Lys Val Pro
465                 470                 475                 480

Ser Leu Ser Lys Leu Leu Val Val Trp Asn Asn Gln Asn Lys Asn Pro
                485                 490                 495

Pro Glu Glu Ser Leu Trp Pro Lys Ile Arg Val Pro Leu Lys Val Val
            500                 505                 510

Arg Thr Ala Glu Asn Lys Leu Ser Asn Arg Phe Phe Pro Tyr Asp Glu
        515                 520                 525

Ile Glu Thr Glu Ala Val Leu Ala Ile Asp Asp Asp Ile Ile Met Leu
    530                 535                 540

Thr Ser Asp Glu Leu Gln Phe Gly Tyr Glu Val Trp Arg Glu Phe Pro
545                 550                 555                 560

Asp Arg Leu Val Gly Tyr Pro Gly Arg Leu His Leu Trp Asp His Glu
                565                 570                 575

Met Asn Lys Trp Lys Tyr Glu Ser Glu Trp Thr Asn Glu Val Ser Met
            580                 585                 590

Val Leu Thr Gly Ala Ala Phe Tyr His Lys Tyr Phe Asn Tyr Leu Tyr
        595                 600                 605

Thr Tyr Lys Met Pro Gly Asp Ile Lys Asn Trp Val Asp Ala His Met
    610                 615                 620

Asn Cys Glu Asp Ile Ala Met Asn Phe Leu Val Ala Asn Val Thr Gly
625                 630                 635                 640

Lys Ala Val Ile Lys Val Thr Pro Arg Lys Lys Phe Lys Cys Pro Glu
                645                 650                 655

Cys Thr Ala Ile Asp Gly Leu Ser Leu Asp Gln Thr His Met Val Glu
            660                 665                 670

Arg Ser Glu Cys Ile Asn Lys Phe Ala Ser Val Phe Gly Thr Met Pro
        675                 680                 685

Leu Lys Val Val Glu His Arg Ala Asp Pro Val Leu Tyr Lys Asp Asp
    690                 695                 700

Phe Pro Glu Lys Leu Lys Ser Phe Pro Asn Ile Gly Ser Leu
705                 710                 715
```

<210> SEQ ID NO 63
<211> LENGTH: 76
<212> TYPE: PRT
<213> ORGANISM: Artificial Sequence
<220> FEATURE:
<223> OTHER INFORMATION: motif
<220> FEATURE:
<221> NAME/KEY: MISC_FEATURE
<222> LOCATION: (4)..(4)
<223> OTHER INFORMATION: any amino acid
<220> FEATURE:
<221> NAME/KEY: MISC_FEATURE
<222> LOCATION: (6)..(6)
<223> OTHER INFORMATION: Leu or Ile
<220> FEATURE:
<221> NAME/KEY: MISC_FEATURE
<222> LOCATION: (8)..(11)
<223> OTHER INFORMATION: Any amino acid
<220> FEATURE:
<221> NAME/KEY: MISC_FEATURE
<222> LOCATION: (14)..(14)
<223> OTHER INFORMATION: Any amino acid
<220> FEATURE:
<221> NAME/KEY: MISC_FEATURE
<222> LOCATION: (15)..(15)
<223> OTHER INFORMATION: Ser or Thr
<220> FEATURE:
<221> NAME/KEY: MISC_FEATURE
<222> LOCATION: (16)..(16)
<223> OTHER INFORMATION: Ser or Thr
<220> FEATURE:
<221> NAME/KEY: MISC_FEATURE
<222> LOCATION: (18)..(18)
<223> OTHER INFORMATION: Lys or Asn
<220> FEATURE:
<221> NAME/KEY: MISC_FEATURE
<222> LOCATION: (19)..(19)
<223> OTHER INFORMATION: Thr or Ser
<220> FEATURE:
<221> NAME/KEY: MISC_FEATURE
<222> LOCATION: (20)..(25)
<223> OTHER INFORMATION: any amino acid
<220> FEATURE:
<221> NAME/KEY: MISC_FEATURE
<222> LOCATION: (28)..(28)
<223> OTHER INFORMATION: any amino acid
<220> FEATURE:
<221> NAME/KEY: MISC_FEATURE
<222> LOCATION: (29)..(31)
<223> OTHER INFORMATION: Ser or Thr
<220> FEATURE:
<221> NAME/KEY: MISC_FEATURE
<222> LOCATION: (32)..(32)
<223> OTHER INFORMATION: Lys or Arg
<220> FEATURE:
<221> NAME/KEY: MISC_FEATURE
<222> LOCATION: (34)..(34)
<223> OTHER INFORMATION: Lys or Arg
<220> FEATURE:
<221> NAME/KEY: MISC_FEATURE
<222> LOCATION: (35)..(40)
<223> OTHER INFORMATION: any amino acid
<220> FEATURE:
<221> NAME/KEY: MISC_FEATURE
<222> LOCATION: (42)..(42)
<223> OTHER INFORMATION: any amino acid
<220> FEATURE:
<221> NAME/KEY: MISC_FEATURE
<222> LOCATION: (44)..(44)
<223> OTHER INFORMATION: any amino acid
<220> FEATURE:
<221> NAME/KEY: MISC_FEATURE
<222> LOCATION: (46)..(61)
<223> OTHER INFORMATION: any amino acid
<220> FEATURE:
<221> NAME/KEY: MISC_FEATURE
<222> LOCATION: (65)..(65)
<223> OTHER INFORMATION: any amino acid
<220> FEATURE:
<221> NAME/KEY: MISC_FEATURE
<222> LOCATION: (68)..(68)
<223> OTHER INFORMATION: any amino acid
<220> FEATURE:
<221> NAME/KEY: MISC_FEATURE
<222> LOCATION: (69)..(69)
<223> OTHER INFORMATION: Cys or Ser
<220> FEATURE:
<221> NAME/KEY: MISC_FEATURE
<222> LOCATION: (71)..(71)
<223> OTHER INFORMATION: His or Pro
<220> FEATURE:
<221> NAME/KEY: MISC_FEATURE
<222> LOCATION: (75)..(75)
<223> OTHER INFORMATION: any amino acid

<400> SEQUENCE: 63

```
Gln Thr Tyr Xaa Asn Xaa Glu Xaa Xaa Xaa Xaa Asp Asp Xaa Xaa Xaa
1               5                   10                  15

Asp Xaa Xaa Xaa Xaa Xaa Xaa Xaa Xaa Ile Ala Xaa Xaa Xaa Xaa Xaa
            20                  25                  30

Val Xaa Xaa Xaa Xaa Xaa Xaa Xaa Asn Xaa Gly Xaa Tyr Xaa Xaa Xaa
        35                  40                  45

Xaa Xaa Xaa Xaa Xaa Xaa Xaa Xaa Xaa Xaa Xaa Xaa Xaa Phe Gln Asp
    50                  55                  60
```

```
Xaa Asp Asp Xaa Xaa His Xaa Glu Arg Ile Xaa Arg
65                  70                  75


<210> SEQ ID NO 64
<211> LENGTH: 102
<212> TYPE: PRT
<213> ORGANISM: Artificial Sequence
<220> FEATURE:
<223> OTHER INFORMATION: motif
<220> FEATURE:
<221> NAME/KEY: MISC_FEATURE
<222> LOCATION: (1)..(1)
<223> OTHER INFORMATION: Lys or Arg
<220> FEATURE:
<221> NAME/KEY: MISC_FEATURE
<222> LOCATION: (3)..(3)
<223> OTHER INFORMATION: any amino acid
<220> FEATURE:
<221> NAME/KEY: MISC_FEATURE
<222> LOCATION: (8)..(19)
<223> OTHER INFORMATION: any amino acid
<220> FEATURE:
<221> NAME/KEY: MISC_FEATURE
<222> LOCATION: (20)..(24)
<223> OTHER INFORMATION: may be missing from sequence; each portion (is
      present) may be any amino acid
<220> FEATURE:
<221> NAME/KEY: MISC_FEATURE
<222> LOCATION: (29)..(29)
<223> OTHER INFORMATION: Arg or Ile
<220> FEATURE:
<221> NAME/KEY: MISC_FEATURE
<222> LOCATION: (32)..(32)
<223> OTHER INFORMATION: any amino acid
<220> FEATURE:
<221> NAME/KEY: MISC_FEATURE
<222> LOCATION: (35)..(37)
<223> OTHER INFORMATION: any amino acid
<220> FEATURE:
<221> NAME/KEY: MISC_FEATURE
<222> LOCATION: (39)..(84)
<223> OTHER INFORMATION: any amino acid
<220> FEATURE:
<221> NAME/KEY: MISC_FEATURE
<222> LOCATION: (85)..(94)
<223> OTHER INFORMATION: all or part of sequence comprising residues
      85-94 may be missing; each position may be any amino acid
<220> FEATURE:
<221> NAME/KEY: MISC_FEATURE
<222> LOCATION: (96)..(96)
<223> OTHER INFORMATION: any amino acid

<400> SEQUENCE: 64

Xaa Asp Xaa Gly Lys Phe Ile Xaa Xaa Xaa Xaa Xaa Xaa Xaa Xaa Xaa
1               5                   10                  15

Xaa Xaa Xaa Xaa Xaa Xaa Xaa Xaa Asp Asp Asp Ile Xaa Tyr Pro Xaa
            20                  25                  30

Asp Tyr Xaa Xaa Xaa Met Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Val Asn Xaa
                85                  90                  95

Leu Gly Thr Gly Thr Val
            100


<210> SEQ ID NO 65
<211> LENGTH: 1854
```

<212> TYPE: DNA
<213> ORGANISM: Pasteurella multocida

<400> SEQUENCE: 65

```
atgagcttat ttaaacgtgc tactgagcta tttaagtcag gaaactataa agatgcacta     60
actctatatg aaaatatagc taaaatttat ggttcagaaa gccttgttaa atataatatt    120
gatatatgta aaaaaaatat aacacaatca aaaagtaata aaatagaaga agataatatt    180
tctggagaaa acaaattttc agtatcaata aaagatctat ataacgaaat aagcaatagt    240
gaattaggga ttacaaaaga aagactagga gcccccccctc tagtcagtat tataatgact    300
tctcataata cagaaaaatt cattgaagcc tcaattaatt cactattatt gcaaacatac    360
aataacttag aagttatcgt tgtagatgat tatagcacag ataaaacatt tcagatcgca    420
tccagaatag caaactctac aagtaaagta aaaacattcc gattaaactc aaatctaggg    480
acatactttg cgaaaaatac aggaatttta aagtctaaag gagatattat tttctttcag    540
gatagcgatg atgtatgtca ccatgaaaga atcgaaagat gtgttaatgc attattatcg    600
aataaagata atatagctgt tagatgtgca tattctagaa taaatctaga aacacaaaat    660
ataataaaag ttaatgataa taaatacaaa ttaggattaa taactttagg cgtttataga    720
aaagtattta atgaaattgg ttttttttaac tgcacaacca aagcatcgga tgatgaattt    780
tatcatagaa taattaaata ctatggtaaa aataggataa ataacttatt tctaccactg    840
tattataaca caatgcgtga agattcatta ttttctgata tggttgagtg ggtagatgaa    900
aataatataa agcaaaaaac ctctgatgct agacaaaatt atctccatga attccaaaaa    960
atacacaatg aaaggaaatt aaatgaatta aaagagattt ttagctttcc tagaattcat   1020
gacgccttac ctatatcaaa agaaatgagt aagctcagca accctaaaat tcctgtttat   1080
ataaatatat gctcaatacc ttcaagaata aaacaacttc aatacactat tggagtacta   1140
aaaaaccaat gcgatcattt tcatatttat cttgatggat atccagaagt acctgatttt   1200
ataaaaaaac tagggaataa agcgaccgtt attaattgtc aaaacaaaaa tgagtctatt   1260
agagataatg gaaagtttat tctattagaa aaacttataa aggaaaataa agatggatat   1320
tatataactt gtgatgatga tatccggtat cctgctgact acataaacac tatgataaaa   1380
aaaattaata aatacaatga taaagcagca attggattac atggtgttat attcccaagt   1440
agagtcaaca agtatttttc atcagacaga attgtctata attttcaaaa acctttagaa   1500
aatgatactg ctgtaaatat attaggaact ggaactgttg cctttagagt atctattttt   1560
aataaatttt ctctatctga ttttgagcat cctggcatgg tagatatcta tttttctata   1620
ctatgtaaga aaaacaatat actccaagtt tgtatatcac gaccatcgaa ttggctaaca   1680
gaagataaca aaaacactga gaccttattt catgaattcc aaaatagaga tgaaatacaa   1740
agtaaactca ttatttcaaa caacccttgg ggatactcaa gtatatatcc attattaaat   1800
aataatgcta attattctga acttattccg tgtttatctt tttataacga gtaa         1854
```

<210> SEQ ID NO 66
<211> LENGTH: 617
<212> TYPE: PRT
<213> ORGANISM: Pasteurella multocida

<400> SEQUENCE: 66

```
Met Ser Leu Phe Lys Arg Ala Thr Glu Leu Phe Lys Ser Gly Asn Tyr
1               5                   10                  15

Lys Asp Ala Leu Thr Leu Tyr Glu Asn Ile Ala Lys Ile Tyr Gly Ser
            20                  25                  30
```

```
Glu Ser Leu Val Lys Tyr Asn Ile Asp Ile Cys Lys Lys Asn Ile Thr
        35                  40                  45

Gln Ser Lys Ser Asn Lys Ile Glu Glu Asp Asn Ile Ser Gly Glu Asn
    50                  55                  60

Lys Phe Ser Val Ser Ile Lys Asp Leu Tyr Asn Glu Ile Ser Asn Ser
65                  70                  75                  80

Glu Leu Gly Ile Thr Lys Glu Arg Leu Gly Ala Pro Pro Leu Val Ser
                85                  90                  95

Ile Ile Met Thr Ser His Asn Thr Glu Lys Phe Ile Glu Ala Ser Ile
            100                 105                 110

Asn Ser Leu Leu Leu Gln Thr Tyr Asn Asn Leu Glu Val Ile Val Val
        115                 120                 125

Asp Asp Tyr Ser Thr Asp Lys Thr Phe Gln Ile Ala Ser Arg Ile Ala
    130                 135                 140

Asn Ser Thr Ser Lys Val Lys Thr Phe Arg Leu Asn Ser Asn Leu Gly
145                 150                 155                 160

Thr Tyr Phe Ala Lys Asn Thr Gly Ile Leu Lys Ser Lys Gly Asp Ile
                165                 170                 175

Ile Phe Phe Gln Asp Ser Asp Asp Val Cys His His Glu Arg Ile Glu
            180                 185                 190

Arg Cys Val Asn Ala Leu Leu Ser Asn Lys Asp Asn Ile Ala Val Arg
        195                 200                 205

Cys Ala Tyr Ser Arg Ile Asn Leu Glu Thr Gln Asn Ile Ile Lys Val
    210                 215                 220

Asn Asp Asn Lys Tyr Lys Leu Gly Leu Ile Thr Leu Gly Val Tyr Arg
225                 230                 235                 240

Lys Val Phe Asn Glu Ile Gly Phe Phe Asn Cys Thr Thr Lys Ala Ser
                245                 250                 255

Asp Asp Glu Phe Tyr His Arg Ile Ile Lys Tyr Tyr Gly Lys Asn Arg
            260                 265                 270

Ile Asn Asn Leu Phe Leu Pro Leu Tyr Tyr Asn Thr Met Arg Glu Asp
        275                 280                 285

Ser Leu Phe Ser Asp Met Val Glu Trp Val Asp Glu Asn Asn Ile Lys
    290                 295                 300

Gln Lys Thr Ser Asp Ala Arg Gln Asn Tyr Leu His Glu Phe Gln Lys
305                 310                 315                 320

Ile His Asn Glu Arg Lys Leu Asn Glu Leu Lys Glu Ile Phe Ser Phe
                325                 330                 335

Pro Arg Ile His Asp Ala Leu Pro Ile Ser Lys Glu Met Ser Lys Leu
            340                 345                 350

Ser Asn Pro Lys Ile Pro Val Tyr Ile Asn Ile Cys Ser Ile Pro Ser
        355                 360                 365

Arg Ile Lys Gln Leu Gln Tyr Thr Ile Gly Val Leu Lys Asn Gln Cys
    370                 375                 380

Asp His Phe His Ile Tyr Leu Asp Gly Tyr Pro Glu Val Pro Asp Phe
385                 390                 395                 400

Ile Lys Lys Leu Gly Asn Lys Ala Thr Val Ile Asn Cys Gln Asn Lys
                405                 410                 415

Asn Glu Ser Ile Arg Asp Asn Gly Lys Phe Ile Leu Leu Glu Lys Leu
            420                 425                 430

Ile Lys Glu Asn Lys Asp Gly Tyr Tyr Ile Thr Cys Asp Asp Asp Ile
        435                 440                 445

Arg Tyr Pro Ala Asp Tyr Ile Asn Thr Met Ile Lys Lys Ile Asn Lys
```

-continued

```
    450                 455                 460

Tyr Asn Asp Lys Ala Ala Ile Gly Leu His Gly Val Ile Phe Pro Ser
465                 470                 475                 480

Arg Val Asn Lys Tyr Phe Ser Ser Asp Arg Ile Val Tyr Asn Phe Gln
                485                 490                 495

Lys Pro Leu Glu Asn Asp Thr Ala Val Asn Ile Leu Gly Thr Gly Thr
            500                 505                 510

Val Ala Phe Arg Val Ser Ile Phe Asn Lys Phe Ser Leu Ser Asp Phe
        515                 520                 525

Glu His Pro Gly Met Val Asp Ile Tyr Phe Ser Ile Leu Cys Lys Lys
    530                 535                 540

Asn Asn Ile Leu Gln Val Cys Ile Ser Arg Pro Ser Asn Trp Leu Thr
545                 550                 555                 560

Glu Asp Asn Lys Asn Thr Glu Thr Leu Phe His Glu Phe Gln Asn Arg
                565                 570                 575

Asp Glu Ile Gln Ser Lys Leu Ile Ile Ser Asn Asn Pro Trp Gly Tyr
            580                 585                 590

Ser Ser Ile Tyr Pro Leu Leu Asn Asn Asn Ala Asn Tyr Ser Glu Leu
        595                 600                 605

Ile Pro Cys Leu Ser Phe Tyr Asn Glu
    610                 615


<210> SEQ ID NO 67
<211> LENGTH: 2112
<212> TYPE: DNA
<213> ORGANISM: Pasteurella multocida

<400> SEQUENCE: 67

atgaatacat tatcacaagc aataaaagca tataacagca atgactatca attagcactc      60

aaattatttg aaaagtcggc ggaaatctat ggacggaaaa ttgttgaatt tcaaattacc     120

aaatgcaaag aaaaactctc agcacatcct tctgttaatt cagcacatct ttctgtaaat     180

aaagaagaaa aagtcaatgt ttgcgatagt ccgttagata ttgcaacaca actgttactt     240

tccaacgtaa aaaaattagt actttctgac tcggaaaaaa acacgttaaa aaataaatgg     300

aaattgctca ctgagaagaa atctgaaaat gcggaggtaa gagcggtcgc ccttgtacca     360

aaagattttc ccaaagatct ggttttagcg cctttacctg atcatgttaa tgattttaca     420

tggtacaaaa agcgaaagaa aagacttggc ataaaacctg aacatcaaca tgttggtctt     480

tctattatcg ttacaacatt caatcgacca gcaattttat cgattacatt agcctgttta     540

gtaaaccaaa aaacacatta cccgtttgaa gttatcgtga cagatgatgg tagtcaggaa     600

gatctatcac cgatcattcg ccaatatgaa aataaattgg atattcgcta cgtcagacaa     660

aaagataacg gttttcaagc cagtgccgct cggaatatgg gattacgctt agcaaaatat     720

gactttattg gcttactcga ctgtgatatg gcgccaaatc cattatgggt tcattcttat     780

gttgcagagc tattagaaga tgatgattta acaatcattg gtccaagaaa atacatcgat     840

acacaacata ttgacccaaa agacttctta aataacgcga gtttgcttga atcattacca     900

gaagtgaaaa ccaataatag tgttgccgca aaaggggaag gaacagtttc tctggattgg     960

cgcttagaac aattcgaaaa aacagaaaat ctccgcttat ccgattcgcc tttccgtttt    1020

tttgcggcgg gtaatgttgc tttcgctaaa aaatggctaa ataaatccgg tttctttgat    1080

gaggaattta atcactgggg tggagaagat gtggaatttg gatatcgctt attccgttac    1140

ggtagtttct ttaaaactat tgatggcatt atggcctacc atcaagagcc accaggtaaa    1200
```

-continued

```
gaaaatgaaa ccgatcgtga agcgggaaaa aatattacgc tcgatattat gagagaaaag   1260

gtcccttata tctatagaaa acttttacca atagaagatt cgcatatcaa tagagtacct   1320

ttagtttcaa tttatatccc agcttataac tgtgcaaact atattcaacg ttgcgtagat   1380

agtgcactga atcagactgt tgttgatctc gaggtttgta tttgtaacga tggttcaaca   1440

gataatacct tagaagtgat caataagctt tatggtaata atcctagggt acgcatcatg   1500

tctaaaccaa atggcggaat agcctcagca tcaaatgcag ccgtttcttt tgctaaaggt   1560

tattacattg ggcagttaga ttcagatgat tatcttgagc ctgatgcagt tgaactgtgt   1620

ttaaaagaat ttttaaaaga taaaacgcta gcttgtgttt ataccactaa tagaaacgtc   1680

aatccggatg gtagcttaat cgctaatggt tacaattggc cagaattttc acgagaaaaa   1740

ctcacaacgg ctatgattgc tcaccacttt agaatgttca cgattagagc ttggcattta   1800

actgatggat tcaatgaaaa aattgaaaat gccgtagact atgacatgtt cctcaaactc   1860

agtgaagttg gaaaatttaa acatcttaat aaaatctgct ataaccgtgt attacatggt   1920

gataacacat caattaagaa acttggcatt caaaagaaaa accattttgt tgtagtcaat   1980

cagtcattaa atagacaagg cataacttat tataattatg acgaatttga tgatttagat   2040

gaaagtagaa agtatatttt caataaaacc gctgaatatc aagaagagat tgatatctta   2100

aaagatattt aa                                                       2112
```

```
<210> SEQ ID NO 68
<211> LENGTH: 5
<212> TYPE: PRT
<213> ORGANISM: Artificial Sequence
<220> FEATURE:
<223> OTHER INFORMATION: motif
<220> FEATURE:
<221> NAME/KEY: MISC_FEATURE
<222> LOCATION: (1)..(1)
<223> OTHER INFORMATION: Asp or Asn
<220> FEATURE:
<221> NAME/KEY: MISC_FEATURE
<222> LOCATION: (5)..(5)
<223> OTHER INFORMATION: Ser or Thr

<400> SEQUENCE: 68

Xaa Asp Gly Ser Xaa
1               5


<210> SEQ ID NO 69
<211> LENGTH: 5
<212> TYPE: PRT
<213> ORGANISM: Artificial Sequence
<220> FEATURE:
<223> OTHER INFORMATION: motif
<220> FEATURE:
<221> NAME/KEY: MISC_FEATURE
<222> LOCATION: (4)..(4)
<223> OTHER INFORMATION: Asp or Thr

<400> SEQUENCE: 69

Asp Ser Asp Xaa Tyr
1               5


<210> SEQ ID NO 70
<211> LENGTH: 565
<212> TYPE: PRT
<213> ORGANISM: Pasteurella multocida

<400> SEQUENCE: 70

Met Ser Leu Phe Lys Arg Ala Thr Glu Leu Phe Lys Ser Gly Asn Tyr
1               5                   10                  15
```

```
Lys Asp Ala Leu Thr Leu Tyr Glu Asn Ile Ala Lys Ile Tyr Gly Ser
            20                  25                  30

Glu Ser Leu Val Lys Tyr Asn Ile Asp Ile Cys Lys Lys Asn Ile Thr
        35                  40                  45

Gln Ser Lys Ser Asn Lys Ile Glu Glu Asp Asn Ile Ser Gly Glu Asn
    50                  55                  60

Lys Phe Ser Val Ser Ile Lys Asp Leu Tyr Asn Glu Ile Ser Asn Ser
65                  70                  75                  80

Glu Leu Gly Ile Thr Lys Glu Arg Leu Gly Ala Pro Pro Leu Val Ser
                85                  90                  95

Ile Ile Met Thr Ser His Asn Thr Glu Lys Phe Ile Glu Ala Ser Ile
            100                 105                 110

Asn Ser Leu Leu Leu Gln Thr Tyr Asn Leu Glu Val Ile Val Val Asp
        115                 120                 125

Asp Tyr Ser Thr Asp Lys Thr Phe Gln Ile Ala Ser Arg Ile Ala Asn
    130                 135                 140

Ser Thr Ser Lys Val Lys Thr Phe Arg Leu Asn Ser Asn Leu Gly Thr
145                 150                 155                 160

Tyr Phe Ala Lys Asn Thr Gly Ile Leu Lys Ser Lys Gly Asp Ile Ile
                165                 170                 175

Phe Phe Gln Ser Asp Asp Val Cys His His Glu Arg Ile Glu Arg Cys
            180                 185                 190

Val Asn Ala Leu Leu Ser Asn Lys Asp Asn Ile Ala Val Arg Cys Ala
        195                 200                 205

Tyr Ser Arg Ile Asn Leu Glu Thr Gln Asn Ile Ile Lys Val Asn Asp
    210                 215                 220

Asn Lys Tyr Lys Leu Gly Leu Ile Thr Leu Gly Val Tyr Arg Lys Val
225                 230                 235                 240

Phe Asn Glu Ile Gly Phe Phe Asn Cys Thr Thr Lys Ala Ser Asp Asp
                245                 250                 255

Glu Phe Tyr His Arg Ile Ile Lys Tyr Tyr Gly Lys Asn Arg Ile Asn
            260                 265                 270

Asn Leu Phe Leu Pro Leu Tyr Tyr Asn Thr Met Arg Glu Asp Ser Leu
        275                 280                 285

Phe Ser Asp Met Val Glu Trp Val Asp Glu Asn Asn Ile Lys Gln Lys
    290                 295                 300

Thr Ser Asp Ala Arg Gln Asn Tyr Leu His Glu Phe Gln Lys Ile His
305                 310                 315                 320

Asn Glu Arg Lys Leu Asn Glu Leu Lys Glu Ile Phe Ser Phe Pro Arg
                325                 330                 335

Ile His Asp Ala Leu Pro Ile Ser Lys Glu Met Ser Lys Leu Ser Asn
            340                 345                 350

Pro Lys Ile Pro Val Tyr Ile Asn Ile Cys Ser Ile Pro Ser Arg Ile
        355                 360                 365

Lys Gln Leu Gln Tyr Thr Ile Gly Val Leu Lys Asn Gln Cys Asp His
    370                 375                 380

Phe His Ile Tyr Leu Asp Gly Tyr Pro Glu Val Pro Asp Phe Ile Lys
385                 390                 395                 400

Lys Leu Gly Asn Lys Ala Thr Val Ile Asn Cys Gln Asn Lys Asn Glu
                405                 410                 415

Ser Ile Arg Asp Asn Gly Lys Phe Ile Leu Leu Glu Lys Leu Ile Lys
            420                 425                 430

Glu Asn Lys Asp Gly Tyr Tyr Ile Thr Cys Asp Asp Asp Ile Arg Tyr
```

```
        435                 440                 445

Pro Ala Asp Tyr Thr Asn Thr Met Ile Lys Lys Ile Asn Lys Tyr Asn
    450                 455                 460

Asp Lys Ala Ala Ile Gly Leu His Gly Val Ile Phe Pro Ser Arg Val
465                 470                 475                 480

Asn Lys Tyr Phe Ser Ser Asp Arg Ile Val Tyr Asn Phe Gln Lys Pro
                485                 490                 495

Leu Glu Asn Asp Thr Ala Val Asn Ile Leu Gly Thr Gly Thr Val Ala
            500                 505                 510

Phe Arg Val Ser Ile Phe Asn Lys Phe Ser Leu Ser Asp Phe Glu His
        515                 520                 525

Pro Gly Met Val Asp Ile Tyr Phe Ser Ile Leu Cys Lys Lys Asn Asn
    530                 535                 540

Ile Leu Gln Val Cys Ile Ser Arg Pro Ser Asn Trp Leu Thr Glu Asp
545                 550                 555                 560

Asn Lys Asn Thr Glu
                565


<210> SEQ ID NO 71
<211> LENGTH: 538
<212> TYPE: PRT
<213> ORGANISM: Pasteurella multocida

<400> SEQUENCE: 71

Ser Asn Ser Glu Leu Gly Ile Thr Lys Glu Arg Leu Gly Ala Pro Pro
1               5                   10                  15

Leu Val Ser Ile Ile Met Thr Ser His Asn Thr Glu Lys Phe Ile Glu
            20                  25                  30

Ala Ser Ile Asn Ser Leu Leu Leu Gln Thr Tyr Asn Leu Glu Val Ile
        35                  40                  45

Val Val Asp Asp Tyr Ser Thr Asp Lys Thr Phe Gln Ile Ala Ser Arg
    50                  55                  60

Ile Ala Asn Ser Thr Ser Lys Val Lys Thr Phe Arg Leu Asn Ser Asn
65                  70                  75                  80

Leu Gly Thr Tyr Phe Ala Lys Asn Thr Gly Ile Leu Lys Ser Lys Gly
                85                  90                  95

Asp Ile Ile Phe Phe Gln Ser Asp Asp Val Cys His His Glu Arg Ile
            100                 105                 110

Glu Arg Cys Val Asn Ala Leu Leu Ser Asn Lys Asp Asn Ile Ala Val
        115                 120                 125

Arg Cys Ala Tyr Ser Arg Ile Asn Leu Glu Thr Gln Asn Ile Ile Lys
    130                 135                 140

Val Asn Asp Asn Lys Tyr Lys Leu Gly Leu Ile Thr Leu Gly Val Tyr
145                 150                 155                 160

Arg Lys Val Phe Asn Glu Ile Gly Phe Phe Asn Cys Thr Thr Lys Ala
                165                 170                 175

Ser Asp Asp Glu Phe Tyr His Arg Ile Ile Lys Tyr Tyr Gly Lys Asn
            180                 185                 190

Arg Ile Asn Asn Leu Phe Leu Pro Leu Tyr Tyr Asn Thr Met Arg Glu
        195                 200                 205

Asp Ser Leu Phe Ser Asp Met Val Glu Trp Val Asp Glu Asn Asn Ile
    210                 215                 220

Lys Gln Lys Thr Ser Asp Ala Arg Gln Asn Tyr Leu His Glu Phe Gln
225                 230                 235                 240

Lys Ile His Asn Glu Arg Lys Leu Asn Glu Leu Lys Glu Ile Phe Ser
```

```
                245                 250                 255

Phe Pro Arg Ile His Asp Ala Leu Pro Ile Ser Lys Glu Met Ser Lys
            260                 265                 270

Leu Ser Asn Pro Lys Ile Pro Val Tyr Ile Asn Ile Cys Ser Ile Pro
        275                 280                 285

Ser Arg Ile Lys Gln Leu Gln Tyr Thr Ile Gly Val Leu Lys Asn Gln
    290                 295                 300

Cys Asp His Phe His Ile Tyr Leu Asp Gly Tyr Pro Glu Val Pro Asp
305                 310                 315                 320

Phe Ile Lys Lys Leu Gly Asn Lys Ala Thr Val Ile Asn Cys Gln Asn
                325                 330                 335

Lys Asn Glu Ser Ile Arg Asp Asn Gly Lys Phe Ile Leu Leu Glu Lys
            340                 345                 350

Leu Ile Lys Glu Asn Lys Asp Gly Tyr Tyr Ile Thr Cys Asp Asp Asp
        355                 360                 365

Ile Arg Tyr Pro Ala Asp Tyr Thr Asn Thr Met Ile Lys Lys Ile Asn
    370                 375                 380

Lys Tyr Asn Asp Lys Ala Ala Ile Gly Leu His Gly Val Ile Phe Pro
385                 390                 395                 400

Ser Arg Val Asn Lys Tyr Phe Ser Ser Asp Arg Ile Val Tyr Asn Phe
                405                 410                 415

Gln Lys Pro Leu Glu Asn Asp Thr Ala Val Asn Ile Leu Gly Thr Gly
            420                 425                 430

Thr Val Ala Phe Arg Val Ser Ile Phe Asn Lys Phe Ser Leu Ser Asp
        435                 440                 445

Phe Glu His Pro Gly Met Val Asp Ile Tyr Phe Ser Ile Leu Cys Lys
    450                 455                 460

Lys Asn Asn Ile Leu Gln Val Cys Ile Ser Arg Pro Ser Asn Trp Leu
465                 470                 475                 480

Thr Glu Asp Asn Lys Asn Thr Glu Thr Leu Phe His Glu Phe Gln Asn
                485                 490                 495

Arg Asp Glu Ile Gln Ser Lys Leu Ile Ile Ser Asn Asn Pro Trp Gly
            500                 505                 510

Tyr Ser Ser Ile Tyr Pro Leu Leu Asn Asn Asn Ala Asn Tyr Ser Glu
        515                 520                 525

Leu Ile Pro Cys Leu Ser Phe Tyr Asn Glu
    530                 535


<210> SEQ ID NO 72
<211> LENGTH: 40
<212> TYPE: PRT
<213> ORGANISM: turkey

<400> SEQUENCE: 72

Glu Lys Leu Asp Ile Lys Tyr Val Arg Gln Lys Asp Tyr Gly Tyr Gln
1               5                   10                  15

Leu Cys Ala Val Arg Asn Leu Gly Leu Arg Thr Ala Lys Tyr Asp Phe
            20                  25                  30

Val Ser Ile Leu Asp Cys Asp Met
        35                  40


<210> SEQ ID NO 73
<211> LENGTH: 36
<212> TYPE: PRT
<213> ORGANISM: goose

<400> SEQUENCE: 73
```

```
Val Asp Ile Lys Tyr Val Arg Gln Lys Asp Tyr Gly Tyr Gln Leu Cys
1               5                   10                  15

Ala Val Arg Asn Leu Gly Leu Arg Thr Ala Lys Tyr Asp Phe Val Ser
            20                  25                  30

Ile Leu Asp Cys
        35


<210> SEQ ID NO 74
<211> LENGTH: 33
<212> TYPE: PRT
<213> ORGANISM: sea lion

<400> SEQUENCE: 74

Lys Tyr Val Arg Gln Lys Asp Tyr Gly Tyr Gln Leu Cys Ala Val Arg
1               5                   10                  15

Asn Leu Gly Leu Arg Thr Ala Lys Tyr Asp Phe Val Ser Ile Leu Asp
            20                  25                  30

Cys


<210> SEQ ID NO 75
<211> LENGTH: 35
<212> TYPE: PRT
<213> ORGANISM: artificial sequence
<220> FEATURE:
<223> OTHER INFORMATION: consensus of alignment of PmHAS, PmCS, Turkey,
      Goose, and sea lion sequences.
<220> FEATURE:
<221> NAME/KEY: MISC_FEATURE
<222> LOCATION: (12)..(12)
<223> OTHER INFORMATION: F or Y
<220> FEATURE:
<221> NAME/KEY: MISC_FEATURE
<222> LOCATION: (20)..(20)
<223> OTHER INFORMATION: L or M
<220> FEATURE:
<221> NAME/KEY: MISC_FEATURE
<222> LOCATION: (30)..(30)
<223> OTHER INFORMATION: I or V

<400> SEQUENCE: 75

Asp Ile Lys Tyr Val Arg Gln Lys Asp Tyr Gly Xaa Gln Leu Cys Ala
1               5                   10                  15

Val Arg Asn Xaa Gly Leu Arg Thr Ala Lys Tyr Asp Phe Xaa Ser Ile
            20                  25                  30

Leu Asp Cys
        35
```

PRODUCTION OF DEFINED MONODISPERSE HEPAROSAN POLYMERS AND UNNATURAL POLYMERS WITH POLYSACCHARIDE SYNTHASES

CROSS-REFERENCE TO RELATED APPLICATIONS

This application claims benefit under 35 U.S.C. 119(e) of U.S. Ser. No. 60/849,034, filed Oct. 3, 2006; and U.S Ser. No. 60/921,296, filed Mar. 30, 2007.

This application is also a continuation-in-part of U.S. Ser. No. 11/651,379, filed Jan. 9, 2007, now U.S. Pat. No. 7,579,173; which is a continuation of U.S. Ser. No. 10/642,248, filed Aug. 15, 2003, now U.S. Pat. No. 7,223,571; which claims benefit under 35 U.S.C. 119(e) of provisional applications U.S. Ser. No. 60/404,356, filed Aug. 16, 2002; U.S. Ser. No. 60/479,432, filed Jun. 18, 2003; and U.S. Ser. No. 60/491,362, filed Jul. 31, 2003.

Said U.S. Ser. No. 10/642,248 is also a continuation-in-part of U.S. Ser. No. 10/195,908, filed Jul. 15, 2002, now abandoned; which is a continuation-in-part of U.S. Ser. No. 09/437,277, filed Nov. 10, 1999, now U.S. Pat. No. 6,444,447, issued Sep. 3, 2002; which claims benefit under 35 U.S.C. 119(e) of U.S. Provisional No. 60/107,929, filed Nov. 11, 1998.

Said U.S. Ser. No. 10/195,908 is also a continuation-in-part of U.S. Ser. No. 09/283,402, filed Apr. 1, 1999, now abandoned; which claims benefit under 35 U.S.C. 119(e) of U.S. Provisional No. 60/080,414, filed Apr. 2, 1998.

Said U.S. Ser. No. 10/195,908 is also a continuation-in-part of U.S. Ser. No. 09/842,484, filed Apr. 25, 2001, now abandoned; which claims benefit under 35 U.S.C. 119(e) of U.S. Ser. No. 60/199,538, filed Apr. 25, 2000.

Said U.S. Ser. No. 10/195,908 is also a continuation-in-part of U.S. Ser. No. 10/142,143, filed May 8, 2002, now U.S. Pat. No. 7,307,159; which claims benefit under 35 U.S.C. 119(e) of U.S. Ser. No. 60/289,554, filed May 8, 2001.

The contents of each of the above-referenced patents and patent applications are hereby expressly incorporated herein in their entirety by reference.

STATEMENT REGARDING FEDERALLY SPONSORED RESEARCH OR DEVELOPMENT

This application was supported in part by National Research Grant C2163601 from the National Science Foundation. The United States Government may have rights in and to this application by virtue of this funding.

BACKGROUND

1. Field of the Invention

The present invention relates to methodology for the production of polymers, such as polysaccharides or oligosaccharides, by a glycosaminoglycan synthase and, more particularly, polymer production utilizing glycosaminoglycan synthases from *Pasteurella multocida*.

Various glycosaminoglycans show potential as non-toxic therapeutic agents to modulate blood coagulation, cancer metastasis, or cell growth. Complex sugars cause biological effects by binding to target proteins including enzymes and receptors. Methodologies to synthesize many compounds, however, and to test for potency and selectivity are limiting steps in drug discovery. Moreover, glycosaminoglycans of different sizes can have dramatically different biological effects. As such, the presently claimed and disclosed invention also relates to a chemoenzymatic synthesis methodology to create both pure, chimeric, and hybrid polymers composed of hyaluronan, chondroitin, keratan, dermatan, heparin units, and combinations thereof (e.g., chimeric or hybrid polymers), wherein the pure, chimeric and hybrid polymers are substantially monodisperse in size.

In addition, new structures or chemical groups may be incorporated into the glycosaminoglycan chain for forming unnatural polymers.

2. Description of the Related Art

Polysaccharides are large carbohydrate molecules comprising from about 25 sugar units to thousands of sugar units. Oligosaccharides are smaller carbohydrate molecules comprising less than about 25 sugar units. Animals, plants, fungi and bacteria produce an enormous variety of polysaccharide structures that are involved in numerous important biological functions such as structural elements, energy storage, and cellular interaction mediation. Often, the polysaccharide's biological function is due to the interaction of the polysaccharide with proteins such as receptors and growth factors. The glycosaminoglycan class of polysaccharides and oligosaccharides, which includes heparin, chondroitin, dermatan, keratan, and hyaluronic acid, plays major roles in determining cellular behavior (e.g., migration, adhesion) as well as the rate of cell proliferation in mammals. These polysaccharides and oligosaccharides are, therefore, essential for the correct formation and maintenance of the organs of the human body.

Several species of pathogenic bacteria and fungi also take advantage of the polysaccharide's role in cellular communication. These pathogenic microbes form polysaccharide surface coatings or capsules that are identical or chemically similar to host molecules. For instance, Group A & C *Streptococcus* and Type A *Pasteurella multocida* produce authentic hyaluronic acid capsules, and other *Pasteurella multocida* (Type F and D) and pathogenic *Escherichia coli* (K4 and K5) are known to make capsules composed of polymers very similar to chondroitin and heparin. The pathogenic microbes form the polysaccharide surface coatings or capsules because such a coating is nonimmunogenic and protects the bacteria from host defenses, thereby providing the equivalent of molecular camouflage.

Enzymes alternatively called synthases, synthetases, or transferases, catalyze the polymerization of polysaccharides found in living organisms. Many of the known enzymes also polymerize activated sugar nucleotides. The most prevalent sugar donors contain UDP, but ADP, GDP, and CMP are also used depending on (1) the particular sugar to be transferred and (2) the organism. Many types of polysaccharides are found at, or outside of, the cell surface. Accordingly, most of the synthase activity is typically associated with either the plasma membrane on the cell periphery or the Golgi apparatus membranes that are involved in secretion. In general, these membrane-bound synthase proteins are difficult to manipulate by typical procedures, and only a few enzymes have been identified after biochemical purification.

A larger number of synthases have been cloned and sequenced at the nucleotide level using reverse genetic approaches in which the gene or the complementary DNA (cDNA) was obtained before the protein was characterized. Despite this sequence information, the molecular details concerning the three-dimensional native structures, the active sites, and the mechanisms of catalytic action of the polysaccharide synthases, in general, are very limited or absent. For example, the catalytic mechanism for glycogen synthesis is not yet known in detail even though the enzyme was discovered decades ago. In another example, it is still a matter of debate whether most of the enzymes that produce heteropolysaccharides utilize one UDP-sugar binding site to transfer both precursors, or alternatively, if there exists two dedicated regions for each substrate.

A wide variety of polysaccharides are commercially harvested from many sources, such as xanthan from bacteria, carrageenans from seaweed, and gums from trees. This substantial industry supplies thousands of tons of these raw materials for a multitude of consumer products ranging from ice cream desserts to skin cream cosmetics. Vertebrate tissues and pathogenic bacteria are the sources of more exotic polysaccharides utilized in the medical field e.g., as surgical aids, vaccines, and anticoagulants. For example, two glycosaminoglycan polysaccharides, heparin from pig intestinal mucosa and hyaluronic acid from rooster combs, are employed in several applications including clot prevention and eye surgery, respectively. Polysaccharides extracted from bacterial capsules (e.g., various *Streptococcus pneumoniae* strains) are utilized to vaccinate both children and adults against disease with varying levels of success. However, for the most part, one must use the existing structures found in the raw materials as obtained from nature. In many of the older industrial processes, chemical modification (e.g., hydrolysis, sulfation, deacetylation) is used to alter the structure and properties of the native polysaccharide. However, the synthetic control and the reproducibility of large-scale reactions are not always successful. Additionally, such polysaccharides are only available having a large molecular weight distribution, and oligosaccharides of the same repeat units are not available.

Some of the current methods for designing and constructing carbohydrate polymers in vitro utilize: (i) difficult, multistep sugar chemistry, or (ii) reactions driven by transferase enzymes involved in biosynthesis, or (iii) reactions harnessing carbohydrate degrading enzymes catalyzing transglycosylation or hydrolysis. The latter two methods are often restricted by the specificity and the properties of the available naturally occurring enzymes. Many of these enzymes are neither particularly abundant nor stable but are almost always expensive. Overall, the procedures currently employed yield polymers containing between 2 and about 12 sugars. Unfortunately, many of the physical and biological properties of polysaccharides do not become apparent until the polymer contains 25, 100, or even thousands of monomers.

As stated above, polysaccharides are the most abundant biomaterials on earth, yet many of the molecular details of their biosynthesis and function are not clear. Hyaluronic acid or HA is a linear polysaccharide of the glycosaminoglycan class and is composed of up to thousands of β(1,4)GlcUA-β(1,3)GlcNAc repeats. In vertebrates, HA is a major structural element of the extracellular matrix and plays roles in adhesion and recognition. HA has a high negative charge density and numerous hydroxyl groups, therefore, the molecule assumes an extended and hydrated conformation in solution. The viscoelastic properties of cartilage and synovial fluid are, in part, the result of the physical properties of the HA polysaccharide. HA also interacts with proteins such as CD44, RHAMM, and fibrinogen thereby influencing many natural processes such as angiogenesis, cancer, cell motility, wound healing, and cell adhesion.

There are numerous medical applications of HA. For example, HA has been widely used as a viscoelastic replacement for the vitreous humor of the eye in ophthalmic surgery during implantation of intraocular lenses in cataract patients. HA injection directly into joints is also used to alleviate pain associated with arthritis. Chemically cross-linked gels and films are also utilized to prevent deleterious adhesions after abdominal surgery. Other researchers using other methods have demonstrated that adsorbed HA coatings also improve the biocompatibility of medical devices such as catheters and sensors by reducing fouling and tissue abrasion.

HA is also made by certain microbes that cause disease in humans and animals. Some bacterial pathogens, namely Gram-negative *Pasteurella multocida* Type A and Gram-positive *Streptococcus* Group A and C, produce an extracellular HA capsule which protects the microbes from host defenses such as phagocytosis. Mutant bacteria that do not produce HA capsules are $10^2$- and $10^3$-fold less virulent in comparison to the encapsulated strains. Furthermore, the *Paramecium bursaria* Chlorella virus (PBCV-1) directs the algal host cells to produce a HA surface coating early in infection.

The various HA synthases (HAS), the enzymes that polymerize HA, utilize UDP-GlcUA and UDP-GlcNAc sugar nucleotide precursors in the presence of a divalent Mn, Mg, or Co ion to polymerize long chains of HA. The HA chains can be quite large ($n=10^2$ to $10^4$). In particular, the HASs are membrane proteins localized to the lipid bilayer at the cell surface. During HA biosynthesis, the HA polymer is transported across the bilayer into the extracellular space. In all HASs, a single species of polypeptide catalyzes the transfer of two distinct sugars. In contrast, the vast majority of other known glycosyltransferases transfer only one monosaccharide.

HasA (or spHAS) from Group A *Streptococcus pyogenes* was the first HA synthase to be described at the molecular level. The various vertebrate homologs (*Xenopus* DG42 or XlHAS1; murine and human HAS1, HAS2, and HAS3) and the viral enzyme, A98R, are quite similar at the amino acid level to certain regions of the HasA polypeptide chain (~30% identity overall) and were discovered only after the sequence of spHAS was disclosed in 1994. At least 7 short motifs (5-9 residues) interspersed throughout these Class I enzymes are identical or quite conserved. The evolutionary relationship among these HA synthases from such dissimilar sources is not clear at present. The enzymes are predicted to have a similar overall topology in the bilayer: membrane-associated regions at the amino and the carboxyl termini flank a large cytoplasmic central domain (~200 amino acids). The amino terminal region appears to contain two transmembrane segments, while the carboxyl terminal region appears to contain three to five membrane-associated or transmembrane segments, depending on the species. Very little of these HAS polypeptide chains are expected to be exposed to the outside of the cell.

With respect to the reaction pathway utilized by this group of enzymes, mixed findings have been reported from indirect experiments. The Group A streptococcal enzyme was reported to add sugars to the nonreducing terminus of the growing chain as determined by selective labeling and degradation studies. Using a similar approach, however, two laboratories working with the enzyme preparations from mammalian cells concluded that the new sugars were added to the reducing end of the nascent chain. In comparing these various studies, the analysis of the enzymatically-released sugars from the streptococcal system added more rigorous support for their interpretation. In another type of experiment, HA made in mammalian cells was reported to have a covalently attached UDP group as measured by an incorporation of low amounts of radioactivity derived from $^{32}$P-labeled UDP-sugar into an anionic polymer. This data implied that the last sugar was transferred to the reducing end of the polymer. Thus, it remains unclear if these rather similar HAS polypeptides from vertebrates and streptococci actually utilize different reaction pathways.

On the other hand, the Class II HAS, pmHAS, has many useful catalytic properties including the ability to elongate exogenous acceptors at the non-reducing end with HA chains. The chondroitin synthase, pmCS, and the heparosan synthases, pmHS1 and pmHS2, are also useful, but they add chondroitin or heparosan chains to the acceptors non-reducing terminus, respectively.

Chondroitin is one of the most prevalent glycosaminoglycans (GAGs) in vertebrates as well as part of the capsular polymer of Type F *P. multocida*, a minor fowl cholera pathogen. This bacterium produces unsulfated chondroitin (DeAngelis et al., 2002) but animals possess sulfated chondroitin polymers. The first chondroitin synthase from any source to be molecularly cloned was the *P. multocida* pmCS (DeAngelis and Padgett-McCue, 2000). The pmCS contains 965 amino acid residues and is about 90% identical to pmHAS. A soluble recombinant *Escherichia coli*-derived pmCS$^{1-704}$ catalyzes the repetitive addition of sugars from UDP-GalNAc and UDP-GlcUA to chondroitin oligosaccharide acceptors in vitro.

Heparosan [N-acetylheparosan], (-GlcUA-β1,4-GlcNAc-α1,4-), is the repeating sugar backbone of the polysaccharide found in the capsule of certain pathogenic bacteria as well as the biosynthetic precursor of heparin or heparan sulfate found in animals from hydra to vertebrates. In mammals, the sulfated forms bind to a variety of extremely important polypeptides including hemostasis factors (e.g., antithrombin III, thrombin), growth factors (e.g., EGF, VEGF), and chemokines (e.g., IL-8, platelet factor 4) as well as the adhesive proteins for viral pathogens (e.g., herpes, Dengue fever). Currently, heparin is extracted from animal tissue and used as an anticoagulant or antithrombotic drug. In the future, similar polymers and derivatives should also be useful for pharmacological intervention in a variety of pathologic conditions including neoplasia and viral infection.

Several enzyme systems have been identified that synthesize heparosan. In bacteria, either a pair of two separate glycosyltransferases (*Escherichia coli* KfiA and KfiC) or a single glycosyltransferase (*Pasteurella multocida* PmHS1 or PmHS2; DeAngelis & White, 2002, 2004) have been shown to polymerize heparosan; the enzymes from both species are homologous at the protein level. In vertebrates, a pair of enzymes, EXT 1 and EXT 2, that are not similar to the bacterial systems appear to be responsible for producing the repeating units of the polymer chain which is then subsequently modified by sulfation and epimerization.

The heparosan synthases from *P. multocida* possess both a hexosamine and a glucuronic acid transfer site in the same polypeptide chain, as shown by mutagenesis studies (Kane, T. A. et. al, J. Biol. Chem. 2006), and are therefore referred to as “dual-action” or bifunctional glycosyltransferases. These enzymes are complex because they employ both an inverting and a retaining mechanism when transferring the monosaccharide from UDP precursors to the non-reducing terminus of a growing chain. The two *Pasteurella* heparosan synthases, PmHS1 and PmHS2, are approximately 70% identical at the amino acid sequence level. The two genes are found in different regions of the bacterial chromosome: PmHS1 (hssA) is associated with the prototypical Gram-negative Type II carbohydrate biosynthesis gene locus but PmHS2 (hssB) resides far removed in an unspecialized region. As shown in this present invention, these catalysts have useful catalytic properties that may be harnessed by the hand of man.

To facilitate the development of biotechnological medical improvements, the present invention provides a method for the production of glycosaminoglycans of HA, chondroitin, heparosan, and chimeric or hybrid molecules incorporating multiple glycosaminoglycans, wherein the glycosaminoglycans are substantially monodisperse and thus have a defined size distribution.

Further, in order to overcome the disadvantages and defects of the prior art, the present invention also encompasses the use of one or more natural or modified synthases that have the ability to produce unnatural polymers. An advantage of these enzymes is that their altered specificity allows new useful groups or units to be added to the polymer. The present invention also encompasses the methodology of polysaccharide or oligosaccharide polymer grafting, i.e., HA, heparosan or chondroitin, using either a hyaluronan synthase (pmHAS) or a chondroitin synthase (pmCS) or a heparin synthase (pmHS, also referred to as pmHS1, and PglA, also referred to as pmHS2), respectively, from various types of *P. multocida*. Modified versions of the pmHAS or pmCS or pmHS1, or pmHS2 enzymes (whether genetically or chemically modified) can also be utilized to graft on polysaccharides of various size and composition. Thus, the present invention results in (1) the targeting of specific, desirable size distributions or size ranges; (2) the synthesis of monodisperse (narrow size distribution) polymers; and (3) the creation of new, unnatural polymers with altered chemical groups.

BRIEF DESCRIPTION OF THE SEVERAL VIEWS OF THE DRAWINGS

FIG. 1 depicts a comparison of partial primary sequences of pmHAS and different pmCSs. Primary sequences of presumably chondroitin synthases from different Type F *Pasteurella multocida* were obtained by directly sequencing the products of colony-lysis PCR. The MULTALIN alignment indicates that most of the differences between pmHAS and pmCS are conserved among these independent strains. Residues that were substituted in site-mutagenesis studies were underlined. The mutant polypeptides contain a single or combination of different mutations, indicated by star(s). None of these mutations changes the specificity of the original enzymes. PmHAS: residues 211-250 of SEQ ID NO:2; PmCS: residues 204-243 of SEQ ID NO:4; Turkey: SEQ ID NO:72; Goose: SEQ ID NO:73; Sea-Lion: SEQ ID NO:74; and consensus: SEQ ID NO:75.

FIG. 11 is an electrophoresis gel that illustrates the migration of a ladder constructed of HA of defined size distribution for use as a standard.

DETAILED DESCRIPTION OF THE INVENTION

Figure 2:
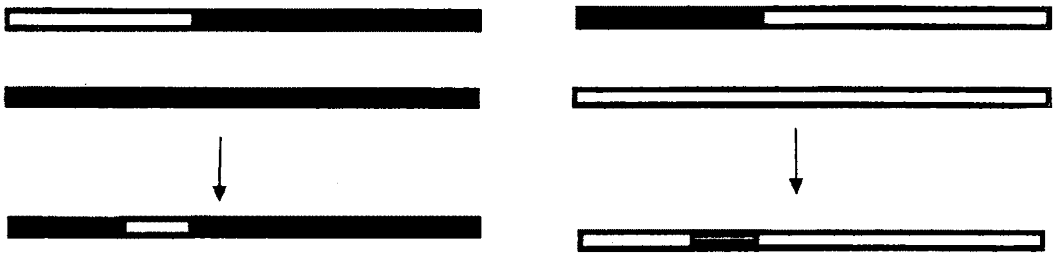
FIG. 2 depicts chimeric constructs of pmHAS$^{1-221}$-CS$^{215-258}$-HAS$^{266-703}$ and pmCS$^{1-214}$-HAS$^{222-265}$-CS$^{258-704}$. Pm-FH and pPm7A DNA were used to create pmHAS$^{1-221}$-CS$^{215-258}$-HAS$^{266-703}$. A very interesting result was that pmCS$^{1-214}$-HAS$^{222-265}$-CS$^{258-704}$ can transfer both GalNAc and GlcNAc to HA oligomer acceptor; this enzyme displays relaxed sugar specificity.

Before explaining at least one embodiment of the invention in detail, it is to be understood that the invention is not limited in its application to the details of construction and the arrangements of the components set forth in the following description or illustrated in the drawings. The invention is capable of other embodiments or of being practiced or carried out in various ways. Also, it is to be understood that the phraseology and terminology employed herein is for purpose of description and should not be regarded as limiting.

Glycosaminoglycans (GAGs) are linear polysaccharides composed of repeating disaccharide units containing a derivative of an amino sugar (either glucosamine or galactosamine). Hyaluronan [HA], chondroitin, and heparan sulfate/heparin contain a uronic acid as the other component of the disaccharide repeat while keratan contains a galactose. The GAGs are summarized in Table I.

TABLE I

| | | Post-Polymerization Modifications | |
|---|---|---|---|
| Polymer | Disaccharide Repeat | Vertebrates | Bacteria |
| Hyaluronan | β3GlcNAc β4GlcUA | none | none |
| Chondroitin | β3GalNAc β4GlcUA | O-sulfated/ epimerized | none |
| Heparin/heparan | β4GlcNAc α4GlcUA | O,N-sulfated/ epimerized | none |
| Keratan | β4GlcNAc β3Gal | O-sulfated | not reported |

An unnatural glycosaminoglycan (unnatural GAG) would be a composition of matter not normally found in known living vertebrates, animals or microbes; different arrangements or structures of chemical groups are added by the hand of man.

Vertebrates may contain all four types of GAGs, but the polysaccharide chain is often further modified after sugar polymerization. One or more modifications including O-sulfation of certain hydroxyls, deacetylation and subsequent N-sulfation, or epimerization of glucuronic acid to iduronic acid are found in most GAGs except HA. An amazing variety of distinct structures have been reported for chondroitin sulfate and heparan sulfate/heparin even within a single polymer chain. A few clever pathogenic microbes also produce unmodified GAG chains; the bacteria use extracellular polysaccharide coatings as molecular camouflage to avoid host defenses. The chondroitin and heparan sulfate/heparin chains in vertebrates are initially synthesized by elongation of a xylose-containing linkage tetrasaccharide attached to a variety of proteins. Keratan is either O-linked or N-linked to certain proteins depending on the particular molecule. HA and all of the known bacterial GAGs are not part of the classification of proteins known as glycoproteins. All GAGs except HA are found covalently linked to a core protein, and such combination is referred to as a proteoglycan. Glycoproteins are usually much smaller than proteoglycans and only contain from 1-60% carbohydrate by weight in the form of numerous relatively short, branched oligosaccharide chains, whereas a proteoglycan can contain as much as 95% carbohydrate by weight. The core protein in a proteoglycan is also usually a glycoprotein, therefore usually contains other oligosaccharide chains besides the GAGs.

GAGs and their derivatives are currently used in the medical field as ophthalmic and viscoelastic supplements, adhesion surgical aids to prevent post-operative adhesions, catheter and device coatings, and anticoagulants. Other current or promising future applications include anti-cancer medications, tissue engineering matrices, immune and neural cell modulators, anti-virals, proliferation modulators, and drug targeting agents.

Complex carbohydrates, such as GAGs, are information rich molecules. A major purpose of the sugars that make up GAGs is to allow communication between cells and extracellular components of multicellular organisms. Typically, certain proteins bind to particular sugar chains in a very selective fashion. A protein may simply adhere to the sugar, but quite often the protein's intrinsic activity may be altered and/or the protein transmits a signal to the cell to modulate its behavior. For example, in the blood coagulation cascade, heparin binding to inhibitory proteins helps shuts down the clotting response. In another case, HA binds to cells via the CD44 receptor that stimulates the cells to migrate and to proliferate. Even though long GAG polymers (i.e., $>10^2$ Da) are found naturally in the body, typically the protein's binding site interacts with a stretch of 4 to 10 monosaccharides. Therefore, oligosaccharides can be used to either (a) substitute for the polymer, or (b) to inhibit the polymer's action depending on the particular system.

HA polysaccharide plays structural roles in the eye, skin, and joint synovium. Large HA polymers ($\sim10^6$ Da) also stimulate cell motility and proliferation. On the other hand, shorter HA polymers ($\sim10^4$ Da) often have the opposite effect. HA-oligosaccharides composed of 10 to 14 sugars [$HA_{10-14}$] have promise for inhibition of cancer cell growth and metastasis. In an in vivo assay, mice injected with various invasive and virulent tumor cell lines (melanoma, glioma, carcinomas from lung, breast and ovary) develop a number of large tumors and die within weeks. Treatment with HA oligosaccharides greatly reduced the number and the size of tumors. Metastasis, the escape of cancer cells throughout the body, is one of the biggest fears of both the ailing patient and the physician. HA or HA-like oligosaccharides appear to serve as a supplemental treatment to inhibit cancer growth and metastasis.

The preliminary mode of action of the HA-oligosaccharide sugars is thought to be mediated by binding or interacting with one of several important HA-binding proteins (probably CD44 or RHAM) in the mammalian body. One proposed scenario for the anticancer action of HA-oligosaccharides is that multiple CD44 protein molecules in a cancer cell can bind simultaneously to a long HA polymer. This multivalent HA binding causes CD44 activation (perhaps mediated by dimerization or a receptor patching event) that triggers cancer cell activation and migration. However, if the cancer cell is flooded with small HA-oligosaccharides, then each CD44 molecule individually binds a different HA molecule in a monovalent manner such that no dimerization/patching event occurs. Thus no activation signal is transmitted to the cell. Currently, it is believed that the optimal HA-sugar size is 10 to 14 sugars. Although this size may be based more upon the size of HA currently available for testing rather than biological functionality—i.e., now that HA molecules and HA-like derivatives <10 sugars are available according to the methodologies of the present invention, the optimal HA size or oligosaccharide composition may be found to be different.

It has also been shown that treatment with certain anti-CD44 antibodies or CD44-antisense nucleic acid prevents the growth and metastasis of cancer cells in a fashion similar to HA-oligosaccharides; in comparison to the sugars, however, these protein-based and nucleic acid-based reagents are somewhat difficult to deliver in the body and/or may have long-term negative effects. A very desirable attribute of HA-oligosaccharides for therapeutics is that these sugar molecules are natural by-products that can occur in small amounts in the healthy human body during the degradation of HA polymer; no untoward innate toxicity, antigenicity, or allergenic concerns are obvious.

Other emerging areas for the potential therapeutic use of HA oligosaccharides are the stimulation of blood vessel formation and the stimulation of dendritic cell maturation. Enhancement of wound-healing and resupplying cardiac oxygenation may be additional applications that harness the ability of HA oligosaccharides to cause endothelial cells to form tubes and sprout new vessels. Dendritic cells possess adjuvant activity in stimulating specific CD4 and CD8 T cell responses. Therefore, dendritic cells are targets in vaccine development strategies for the prevention and treatment of infections, allograft reactions, allergic and autoimmune diseases, and cancer.

Heparin interacts with many proteins in the body, but two extremely interesting classes are coagulation cascade proteins and growth factors. Antithrombin III [ATIII] and certain other hemostasis proteins are 100,000-fold more potent inhibitors of blood cloning when complexed with heparin. Indeed, heparin is so potent it must be used in a hospital setting and requires careful monitoring in order to avoid hemorrhage. Newer, processed lower molecular weight forms of heparin are safer, but this material is still a complex mixture. It has been shown that a particular pentasaccharide (5 sugars long) found in heparin is responsible for the ATIII-anticoagulant effect. But since heparin is a very heterogeneous polymer, it is difficult to isolate the pentasaccharide (5 sugars long) in a pure state. The pentasaccharide can also be prepared in a conventional chemical synthesis involving ~50 to 60 steps. However, altering the synthesis or preparing an assortment of analogs in parallel is not always feasible—either chemically or financially.

Many growth factors, including VEGF (vascular endothelial growth factor), HBEGF (heparin-binding epidermal growth factor), and FGF (fibroblast growth factor), bind to cells by interacting simultaneously with the growth factor receptor and a cell-surface heparin proteoglycan; without the heparin moiety, the potency of the growth factor plummets. Cell proliferation is modulated in part by heparin; therefore, diseases such as cancer and atherosclerosis are potential targets. Abnormal or unwanted proliferation would be curtailed if the growth factor was prevented from stimulating target disease-state cells by interacting with a heparin-like oligosaccharide analog instead of a surface-bound receptor. Alternatively, in certain cases, the heparin oligosaccharides alone have been shown to have stimulatory effects.

Chondroitin is the most abundant GAG in the human body, but all of its specific biological roles are not yet clear. Phenomenon such as neural cell outgrowth appears to be modulated by chondroitin. Both stimulatory and inhibitory effects have been noted depending on the chondroitin form and the cell type. Therefore, chondroitin or similar molecules are of utility in re-wiring synaptic connections after degenerative diseases (e.g., Alzheimer's) or paralytic trauma. The epimerized form of chondroitin (GlcUA converted to the C5 isomer, iduronic acid or IdoUA), dermatan, selectively inhibits certain coagulation proteins such as heparin cofactor II. By modulating this protein in the coagulation pathway instead of ATIII, dermatan appears to allow for a larger safety margin than heparin treatment for reduction of thrombi or clots that provoke strokes and heart attacks.

Many details of GAG/protein interactions are not yet clear due to (a) the heterogeneity of GAGs (in part due to their biosynthesis pathway), and (b) the difficulty in analyzing long polysaccharides and membrane receptor proteins at the molecular level. Fortunately, many short oligosaccharides have biological activities that serve to assist research pursuits as well as to treat disease in the near future. Conventional chemical synthesis of short GAG oligosaccharides is possible, but the list of roadblocks includes: (i) difficult multistep syntheses that employ toxic catalysts, (ii) very low yield or high failure rates with products longer than ~6 monosaccharides, (iii) imperfect control of stereoselectivity (e.g., wrong anomer) and regioselectivity (e.g., wrong attachment site), and (iv) the possibility for residual protection groups (non-carbohydrate moieties) in the final product.

Chemoenzymatic synthesis, however, employing catalytic glycosyltransferases with exquisite control and superb efficiency is currently being developed by several universities and companies. A major obstacle is the production of useful catalyst because the vast majority of glycosyltransferases are rare membrane proteins that are not particularly robust. In the co-pending applications referenced herein and in the presently claimed and disclosed invention, several practical catalysts from *Pasteurella* bacteria that allow for the synthesis of the three most important human GAGs (i.e., the three known acidic GAGs) are described and enabled (e.g. HA, chondroitin, and heparin).

All of the known HA, chondroitin and heparosan/heparan sulfate/heparin glycosyltransferase enzymes that synthesize the alternating sugar repeat backbones in microbes and in vertebrates utilize UDP-sugar precursors and divalent metal cofactors (e.g., magnesium, cobalt, and/or manganese ion) near neutral pH according to the overall reaction:

nUDP-GlcUA+nUDP-HexNAc 2nUDP+$[\text{GlcUA-HexNAc}]_n$ where HexNAc=GlcNAc or GalNAc. Depending on the specific GAG and the particular organism or tissue examined, and the degree of polymerization, n, ranges from about 25 to about 10,000. Smaller molecules may be made in vitro, as desired. If the GAG is polymerized by a single polypeptide, the enzyme is called a synthase or co-polymerase.

As outlined in and incorporated by reference in the "Cross-Reference" section of this application hereinabove, the present Applicants have discovered four new dual-action enzyme catalysts from distinct isolates of the Gram-negative bacterium *Pasteurella multocida* using various molecular biology strategies. *P. multocida* infects fowl, swine, and cattle as well as many wildlife species. The enzymes are: a HA synthase, or (pmHAS); a chondroitin synthase, or (pmCS); and two heparosan synthases, or (pmHS1 and PmHS2). To date, no keratan synthase from any source has been identified or reported in the literature.

In U.S. Ser. No. 10/217,613, filed Aug. 12, 2002, the contents of which are hereby expressly incorporated herein by reference in their entirety, the molecular directionality of pmHAS synthesis was disclosed and claimed. pmHAS is unique in comparison to all other existing HA synthases of *Streptococcus* bacteria, humans and an algal virus. Specifically, recombinant pmHAS can elongate exogeneously-supplied short HA chains (e.g., 2-4 sugars) into longer HA chains (e.g., 3 to 150 sugars). The pmHAS synthase has been shown to add monosaccharides one at a time in a step-wise fashion to the growing chain. The pmHAS enzyme's exquisite sugar transfer specificity results in the repeating sugar backbone of the GAG chain. The pmCS enzyme, which is about 90% identical at the amino acid level to pmHAS, performs the same synthesis reactions but transfers GalNAc instead of GlcNAc. The pmCS enzyme was described and enabled in U.S. Ser. No. 09/842,484. The pmHS1 and PmHS2 enzymes are not very similar at the amino acid level to pmHAS, but perform the similar synthesis reactions; the composition of sugars is identical but the linkages differ because heparosan is (α-4GlcUA-β-4GlcNAc). The pmHS1 and PmHS2 enzymes were described and enabled in copending U.S. Ser. No. 10/142,143.

The explanation for the step-wise addition of sugars to the GAG chain during biosynthesis was determined by analyzing mutants of the pmHAS enzyme. pmHAS possesses two independent catalytic sites in one polypeptide. Mutants were created that transferred only GlcUA, and distinct mutants were also created that transferred only GlcNAc. These mutants cannot polymerize HA chains individually, but if the two types of mutants are mixed together in the same reaction with an acceptor molecule, then polymerization was rescued. The chondroitin synthase, pmCS, has a similar sequence and similar two-domain structure. The heparosan synthases, pmHS1 and PmHS2, also contain regions for the two active sites. Single action mutants have also been created for the chondroitin synthase, pmCS, and are described hereinafter in detail.

The naturally occurring *Pasteurella* GAG synthases are very specific glycosyltransferases with respect to the sugar transfer reaction; only the correct monosaccharide from the authentic UDP-sugar is added onto acceptors. The epimers or other closely structurally related precursor molecules (e.g., UDP-glucose) are usually not utilized. The GAG synthases do, however, utilize certain heterologous acceptor sugars. For example, pmHAS will elongate short chondroitin acceptors with long HA chains. pmHS1 will also add long heparosan chains onto HA acceptor oligosaccharides as well as heparin oligosaccharides (see hereinbelow). Therefore, the presently claimed and disclosed invention encompasses a wide range of hybrid or chimeric GAG oligosaccharides prepared utilizing these *P. multocida* GAG catalysts.

It has also been determined that the recombinant pmHAS, pmHS1, pmHS2, and pmCS synthases add sugars to the nonreducing end of a growing polymer chain. The correct monosaccharides are added sequentially in a stepwise fashion to the nascent chain or a suitable exogenous oligosaccharide or polysaccharide acceptor molecule. The pmHAS sequence, however, is significantly different from the other known HA synthases. There appears to be only two short potential sequence motifs ([D/N]DGS[S/T], SEQ ID NO:68; DSD[D/T]Y, SEQ ID NO:69) in common between pmHAS (Class II) and the Group A HAS spHAS (Class I). Instead, a portion of the central region of the pmHAS is more homologous to the amino termini of other bacterial glycosyltransferases that produce different capsular polysaccharides or lipopolysaccharides. Furthermore, pmHAS is about twice as long as any other HAS enzyme.

When the pmHAS is given long elongation reaction times, HA polymers of at least 400 sugars long are formed. Unlike the Class I HA synthases, recombinant versions of pmHAS and pmCS produced in certain foreign hosts also have the ability to extend exogenously supplied HA or chondroitin oligosaccharides with long HA and chondroitin polymers in vitro, respectively. The recombinant pmHS1 and pmHS2 enzymes produced in a foreign host have the ability to extend HA, chondroitin, or heparin oligosaccharides with long heparosan chains in vitro. See e.g., U.S. Ser. No. 10/195,908, filed Jul. 15, 2002, the contents of which are expressly incorporated herein by reference in their entirety. If recombinant versions of pmHAS or pmCS or pmHS1 or pmHS2 are supplied with functional acceptor oligosaccharides, total HA, chondroitin and heparin biosynthesis is increased up to 50-fold over reactions without the exogenous oligosaccharide. The native versions of the pmHAS, pmCS, pmHS1, and PmHS2 enzymes isolated from *P. multocida* do not perform such elongation reactions with exogenous acceptor (or perform with very low efficiency) due to the presence of a nascent HA, chondroitin, or heparin chain in the natural host. The nature of the polymer retention mechanism of the pmHAS, pmCS, pmHS1, and PmHS2 polypeptide might be the causative factor for this activity: i.e. a HA- or chondroitin- or heparin-binding site may exist that holds onto the HA or chondroitin or heparin chain during polymerization. Small HA or chondroitin or heparin oligosaccharides supplied by the hand of man are also capable of occupying this site of the recombinant enzyme and thereafter be extended into longer polysaccharide chains.

Most membrane proteins are relatively difficult to study due to their insolubility in aqueous solution, and the native HASs, CSs, HSs, and PmHS2s are no exception. The HAS enzyme from Group A and C *Streptococcus* bacteria has been detergent-solubilized and purified in an active state in small quantities. Once isolated in a relatively pure state, the streptococcal enzyme has very limited stability. A soluble recombinant form of the HAS enzyme from *P. multocida* called $pmHAS^{1-703}$ comprises residues 1-703 of the 972 residues of the native pmHAS enzyme. $pmHAS^{1-703}$ can be mass-produced in *E. coli* and purified by chromatography. The $pmHAS^{1-703}$ enzyme retains the ability of the parent enzyme to add onto either a long HA polymer, a short HA primer, a long chondroitin polymer, a short chondroitin primer, a short chondroitin polymer, as well as other exogenous acceptors. The chondroitin chain may also be sulfated. Furthermore, the purified $pmHAS^{1-703}$ enzyme is stable in an optimized buffer for days on ice and for hours at normal reaction temperatures. One formulation of the optimal buffer consists of 1M ethylene glycol, 0.1-0.2 M ammonium sulfate, 50 mM Tris, pH 7.2, and protease inhibitors which also allow the stability and specificity at typical reaction conditions for sugar transfer. For the reaction UDP-sugars and divalent manganese (10-20 mM) are added. $pmHAS^{1-703}$ will also add a HA polymer onto plastic beads with an immobilized short HA primer or any other substrate capable of having an acceptor molecule or acceptor group thereon.

Full-length, native sequence PmHS1 or PmHS2 can be converted into higher yield, soluble proteins that are purifiable by the addition of fusion protein partners, such as, but not limited to, maltose-binding protein (MBP).

pmCS, pmHAS, pmHS1, and PmHS2 possess two separate glycosyltransferase sites. Protein truncation studies demonstrated that residues 1-117 of pmHAS can be deleted without affecting catalytic activity; similar truncation of the homologous pmCS, pmHS1, and PmHS2 enzymes may also be preferred. The carboxyl-terminal boundary of the GlcUA-transferase of pmHAS resides within residues 686-703 and within residues 686-704 of pmCS. These sites each contain a DGS and DXD motif; all aspartate residues of these motifs are essential for HA synthase activity. D196, D247 and D249 mutants possessed only GlcUA-transferase activity while D477, D527 and D529 mutants possessed only GlcNAc-transferase activity. These results further confirm our previous assignment of the active sites within the synthase polypeptide. The WGGED sequence motif appears to be involved in GlcNAc-transferase activity because E396 mutants and D370 mutants possessed only GlcUA-transferase activity. The highly homologous (90% identical) pmCS can also be mutated in the same fashion. For example, mutating the homologous DXD motif in the GlcUA site of pmCS results in an enzyme with only GalNAc-transferase activity.

Type F *P. multocida* synthesizes an unsulfated chondroitin (β3N-acetylgalactosamine [GalNAc]-β4GlcUA) capsule. Domain swapping between pmHAS and the homologous chondroitin synthase, pmCS, has been performed. A chimeric or hybrid enzyme consisting of residues 1-427 of pmHAS and residues 421-704 of pmCS was an active HA synthase. On the other hand, the converse chimeric or hybrid enzyme consisting of residues 1-420 of pmCS and residues 428-703 of pmHAS was an active chondroitin synthase. Overall, these findings support the model of two independent transferase sites within a single polypeptide as well as further delineate the site boundaries of both enzymes. The hexosamine-transferase site resides in the N-terminal domain while the GlcUA-transferase site resides in the COOH-terminal domain of these GAG synthases. Thus, certain units or regions of the GAG synthase sequences are able to function (with novel or typical catalytic activity) in various unnatural or new combinations assembled by the hand of man.

The present invention encompasses methods of producing a variety of unique biocompatible molecules and coatings based on polysaccharides. Polysaccharides, especially those of the glycosaminoglycan class, serve numerous roles in the body as structural elements and signaling molecules. By grafting or making hybrid molecules composed of more than one polymer backbone, it is possible to meld distinct physical and biological properties into a single molecule without resorting to unnatural chemical reactions or residues. The present invention also incorporates the propensity of certain recombinant enzymes, when prepared in a virgin state, to utilize various acceptor molecules as the seed for further polymer growth: naturally occurring forms of the enzyme or existing living wild-type host organisms do not display this ability. Thus, the present invention results in (a) the production of hybrid oligosaccharides or polysaccharides and (b) the formation of polysaccharide coatings. Such hybrid polymers can serve as "molecular glue"—i.e., when two cell types or other biomaterials interact with each half of a hybrid molecule, then each of the two phases are bridged.

In addition, adding new chemical groups and thus forming unnatural glycosaminoglycan polymers, may facilitate coupling to other molecules or surfaces, even cells.

Such polysaccharide coatings are useful for integrating a foreign object within a surrounding tissue matrix. For example, a prosthetic device is more firmly attached to the body when the device is coated with a naturally adhesive polysaccharide. Additionally, the device's artificial components could be masked by the biocompatible coating to reduce immunoreactivity or inflammation. Another aspect of the present invention is the coating or grafting of GAGs onto various drug delivery matrices or bioadhesives or suitable medicaments to improve and/or alter delivery, half-life, persistence, targeting and/or toxicity.

Recombinant pmHAS, pmCS, pmHS1, and PmHS2 elongate exogenous functional oligosaccharide acceptors to form long or short polymers in vitro; thus far no other Class I HA synthase has displayed this capability. The directionality of synthesis was established definitively by testing the ability of pmHAS and pmCS and pmHS1 and PmHS2 to elongate defined oligosaccharide derivatives. The non-reducing end sugar addition allows the reducing end to be modified for other purposes; the addition of GAG chains to small molecules, polymers, or surfaces is thus readily performed. Analysis of the initial stages of synthesis demonstrated that pmHAS and pmCS and pmHS1 and PmHS2 added single monosaccharide units sequentially. Apparently the fidelity of the individual sugar transfer reactions is sufficient to generate the authentic repeating structure of HA or chondroitin or heparin. Therefore, simultaneous addition of disaccharide block units is not required as hypothesized in some recent models of polysaccharide biosynthesis. pmHAS and pmCS and pmHS1 and PmHS2 appear distinct from most other known HA and chondroitin and heparin synthases based on differences in sequence, topology in the membrane, and/or putative reaction mechanism.

As mentioned previously, pmHAS, the 972-residue membrane-associated hyaluronan synthase, catalyzes the transfer of both GlcNAc and GlcUA to form an HA polymer. In order to define the catalytic and membrane-associated domains, pmHAS and pmCS mutants have been analyzed. $pmHAS^{1-703}$ is a soluble, active HA synthase suggesting that the carboxyl-terminus is involved in membrane association of the native enzyme. $pmHAS^{1-650}$ is inactive as a HA synthase, but retains GlcNAc-transferase activity. Within the pmHAS sequence, there is a duplicated domain containing a short motif, DGS or Asp-Gly-Ser, that is conserved among many glycosyltransferases. Changing this aspartate in either domain to asparagine, glutamate, or lysine reduced the HA synthase activity to low levels. The mutants substituted at residue 196 possessed GlcUA-transferase activity while those substituted at residue 477 possessed GlcNAc-transferase activity. The Michaelis constants of the functional transferase activity of the various mutants, a measure of the apparent affinity of the enzymes for the precursors, were similar to wild-type values. Furthermore, mixing D196N and D477K mutant proteins in the same reaction allowed HA polymerization at levels similar to the wild-type enzyme. These results provide the first direct evidence that the synthase polypeptide utilizes two separate glycosyltransferase sites. Likewise, pmCS mutants were made and tested having the same functionality and sequence similarity to the mutants created for pmHAS.

*Pasteurella multocida* Type F, the minor fowl cholera pathogen, produces an extracellular polysaccharide capsule that is a putative virulence factor. As outlined in U.S. Ser. No. 09/842,484, filed Apr. 25, 2002, and entitled Chondroitin Synthase Gene and Methods of Making and Using Same, the contents of which are hereby expressly incorporated herein in their entirety, the capsule of *Pasteurella multocida* Type F was removed by treating microbes with chondroitin AC lyase. It was found by acid hydrolysis that the polysaccharide contained galactosamine and glucuronic acid. A Type F polysaccharide synthase was molecularly cloned and its enzymatic activity was characterized. The 965-residue enzyme, called pmCS, is 90% identical at the nucleotide and the amino acid level to the hyaluronan synthase, pmHAS, from *P. multocida* Type A. A recombinant *Escherichia coli*-derived, truncated, soluble version of pmCS (residues 1-704) was shown to catalyze the repetitive addition of sugars from UDP-GalNAc and UDP-GlcUA to chondroitin oligosaccharide acceptors in vitro. Other structurally related sugar nucleotide precursors did not substitute in the elongation reaction. Polymer molecules composed of $\sim10^3$ sugar residues were produced as measured by gel filtration chromatography. The polysaccharide synthesized in vitro was sensitive to the action of chondroitin AC lyase but resistant to the action of hyaluronan lyase. This was the first report identifying a glycosyltransferase that forms a polysaccharide composed of chondroitin disaccharide repeats, $[\beta(1,4)GlcUA-\beta(1,3)GalNAc]_n$. In analogy to known hyaluronan synthases, a single polypeptide species, pmCS, possesses both transferase activities. The heparin synthases, pmHS1 and PmHS2, from *P. multocida*, also are a single polypeptide species that possess both transferase activities to catalyze heparin/heparosan.

Promising initial target polymers for a variety of therapeutic uses are glycosaminoglycan chains composed of about 1 kDa to about 4 MDa (kDa is defined as $10^3$ Da, whereas MDa is defined as $10^6$ Da). The two current competing state-of-the-art techniques for creating the desired smaller size glycosaminoglycan [GAG] polymers are extremely limited and will not allow the medical potential of the sugars to be achieved. Small GAG molecules are presently made either by: (1) partially depolymerizing costly large polymers with degradative enzymes or with chemical means (e.g., heat, acid, sonication), or (2) highly demanding organic chemistry-based carbohydrate synthesis. The former method is difficult to control, inefficient, costly, and is in a relatively stagnant development stage. For example, the enzyme wants to degrade the polymer to the 2 or 4 sugar end stage product, but this sugar is inactive for many therapeutic treatments. The use of acid hydrolysis also removes a fraction of the acetyl groups from the GlcNAc or GalNAc groups thereby introducing a positive charge into an otherwise anionic molecule. The latter method, chemical synthesis, involves steps with low to moderate repetitive yield and has never been reported for a HA-oligosaccharide longer than 6 to 8 sugars in length. Also racemization (e.g., production of the wrong isomer) during chemical synthesis creates inactive or harmful molecules; the inclusion of the wrong isomer in a therapeutic preparation in the past has had tragic consequences as evidenced by the birth defects spawned by the drug Thalidomide. As sugars contain many similar reactive hydroxyl groups, in order to effect proper coupling between two sugars in a chemical synthesis, most hydroxyl groups must be blocked or protected. At the conclusion of the reaction, all of the protecting groups must be removed, but this process is not perfect; as a result, a fraction of the product molecules retain these unnatural moieties. The issues of racemization and side-products from chemical synthesis are not problems for the high-fidelity enzyme catalysts of the presently claimed and disclosed invention.

The partial depolymerization method only yields fragments of the original GAG polymer and is essentially useless for creating novel sugars beyond simple derivatizations (e.g., esterifying some fraction of GlcUA residues in an indiscriminate fashion). Chemical synthesis may suffice in theory to make novel sugars, but the strategy needs to be customized for adding a new sugar, plus the problems with side-reactions/isomerization and the ultimate oligosaccharide size still pose the same trouble as described earlier. Another distinct method using the degradative enzymes to generate small molecules by running in reverse on mixtures of two polymers (e.g., HA and chondroitin) has some potential for novel GAG polysaccharide synthesis. See e.g. J Biochem (Tokyo). 2000 April; 127(4):695-702, Chimeric glycosaminoglycan oligosaccharides synthesized by enzymatic reconstruction and their use in substrate specificity determination of *Streptococcus* hyaluronidase, Takagaki K, Munakata H, Majima M, Kakizaki I, Endo M.; and J Biol. Chem. 1995 Feb. 24; 270(8):3741-7, Enzymic reconstruction of glycosaminoglycan oligosaccharide chains using the transglycosylation reaction of bovine testicular hyaluronidase, Saitoh H, Takagaki K, Majima M, Nakamura T, Matsuki A, Kasai M, Narita H, Endo M. However, this technology can make only a very limited scope of products with a block pattern (no single or specifically spaced substitutions possible) using slow reactions that cannot easily be customized or controlled. No other technology is as versatile as the presently claimed and disclosed biocatalytic system with respect to flexibility of final polysaccharide structure in the about 1 kDa to about 4 MDa size range. Novel, designer molecules can be prepared with minimal re-tooling by use of the appropriate hyaluronic acid or chondroitin or heparin enzyme catalysts and substrates.

The size of the HA polysaccharide dictates its biological effect in many cellular and tissue systems based on many reports in the literature. However, no source of very defined, uniform HA polymers with sizes greater than 2-5 kDa is currently available. This situation is complicated by the observation that long and short HA polymers appear to have antagonistic or inverse effects on some biological systems. Therefore, HA preparations containing a mixture of both size populations may yield contradictory or paradoxical results. Thus, one of the objects of the present invention is to provide a method to produce HA with very narrow, substantially monodisperse size distributions that overcomes the disadvantages and defects of the prior art.

The methods for enzymatically producing defined glycosaminoglycan polymers of the present invention involves providing at least one functional acceptor and at least one recombinant glycosaminoglycan transferase capable of elongating the functional acceptor in a controlled and/or repetitive fashion to form extended glycosaminoglycan-like molecules. At least one UDP-sugar (such as but not limited to, UDP-GlcUA, UDP-GalUA UDP-GlcNAc, UDP-Glc, UDP-GalNAc, UDP-GlcN, UDP-GalN), or a structural variant or derivative thereof (including a monosaccharide with functional groups or combinations thereof not found in typical known organisms) is added in a stoichiometric ratio to the functional acceptor such that the recombinant glycosaminoglycan transferase elongates the at least one functional acceptor to provide glycosaminoglycan polymers having a desired size distribution and that are substantially monodisperse in size. Such desired size distribution is obtained by controlling the stroichiometric ratio of UDP-sugar to functional acceptor.

The term "substantially monodisperse in size" as used herein will be understood to refer to defined glycoasminoglycan polymers that have a very narrow size distribution. For example, substantially monodisperse glycosaminoglycan polymers having a molecular weight in a range of from about 3.5 kDa to about 0.5 MDa will have a polydispersity value (i.e., Mw/Mn, where Mw is the average molecular weight and Mn is the number average molecular weight) in a range of from about 1.0 to about 1.1, and preferably in a range from about 1.0 to about 1.05. In yet another example, substantially monodisperse glycosaminoglycan polymers having a molecular weight in a range of from about 0.5 MDa to about 4.5 MDa will have a polydispersity value in a range of from about 1.0 to about 1.5, and preferably in a range from about 1.0 to about 1.2.

The functional acceptor utilized in accordance with the present invention will have at least one sugar unit of uronic acid, hexosamine, and structural variants or derivatives thereof, wherein the uronic acid may be GlcUA, IdoUA (iduronic acid), GalUA, and structural variants or derivatives thereof; and the hexosamine may be GlcNAc, GalNAc, GlcN, GalN, and structural variants or derivatives thereof. In one embodiment, the functional acceptor may have at least two sugar units.

In one embodiment, the functional acceptor may be an HA oligosaccharide of about 3 sugar units to about 4.2 kDa, or an HA polymer having a mass of about 3.5 kDa to about 2 MDa. In another embodiment, the functional acceptor may be an HA oligosaccharide, polysaccharide or polymer; a chondroitin oligosaccharide, polysaccharide or polymer; a chondroitin sulfate oligosaccharide, polysaccharide or polymer; a heparosan oligosaccharide, polysaccharide or polymer; a heparin oligosaccharide, polysaccharide, or polymer; a heparin oligosaccharide, polysaccharide or polymer; a heparosan-like oligosaccharide, polysaccharide or polymer; or a sulfated or modified oligosaccharide, polysaccharide or polymer. In yet another embodiment, the functional acceptor may be an extended acceptor such as HA chains, chondroitin chains, heparosan chains, mixed glycosaminoglycan chains, analog containing chains or any combination thereof.

Another functional acceptor class that may be utilized in accordance with the present invention includes synthetic glycosides (i.e., sugars that have a non-sugar component at the reducing end) or similar synthetic carbohydrates. The synthetic portion substitutes for one of the natural sugar units; these molecules are less expensive and can possess useful groups.

The functional acceptor utilized in accordance with the present invention may further comprise a moiety selected from the group consisting of a fluorescent tag, a radioactive tag or therapeutic, an affinity tag, a detection probe, a medicant, a biologically active agent, a therapeutic agent, and combinations thereof. The UDP-sugar provided in accordance with the present invention may be radioactive or nuclear magnetic resonance-active.

Any recombinant glycosaminoglycan transferase described or incorporated by reference herein may be utilized in the methods of the present invention. For example, the recombinant glycosaminoglycan transferase utilized in accordance with the present invention may be a recombinant hyaluronan synthase, a recombinant chondroitin synthase, a recombinant heparosan synthase, or any active fragment or mutant thereof. The recombinant glycosaminglycan transferase may be capable of adding only one UDP-sugar described herein above or may be capable of adding two or more UDP-sugars described herein above.

In one embodiment of the present invention, the recombinant glycosaminglycan transferases utilized in accordance with the present invention may be selected from the group consisting of: a recombinant heparosan synthase having an amino acid sequence as set forth in SEQ ID NO: 6, 8, 66, 70 or 71; a recombinant heparosan synthase encoded by the nucleotide sequence of SEQ ID NO: 5, 7 or 65; a recombinant heparosan synthase encoded by a nucleotide sequence capable of hybridizing to a complement of the nucleotide sequence of SEQ ID NOS: 5, 7 or 65 under hybridization conditions comprising hybridization at a temperature of 68° C. in 5×SSC/5× Denhardt's solution/1.0% SDS, followed with washing in 3×SSC at 42° C.; a recombinant heparosan synthase encoded by a nucleotide sequence capable of hybridizing to a complement of a nucleotide sequence encoding an amino acid sequence as set forth in SEQ ID NO: 6, 8, 66, 70 or 71 under hybridization conditions comprising hybridization at a temperature of 68° C. in 5×SSC/5× Denhardt's solution/1.0% SDS, followed with washing in 3×SSC at 42° C.; a recombinant heparosan synthase encoded by a nucleotide sequence capable of hybridizing to a complement of the nucleotide sequence of SEQ ID NOS: 5, 7 or 65 under hybridization conditions comprising hybridization at a temperature of 30° C. in 5×SSC, 5× Denhardts reagent, 30% formamide for about 20 hours followed by washing twice in 2×SSC, 0.1% SDS at about 30° C. for about 15 min followed by 0.5×SSC, 0.1% SDS at about 30° C. for about 30 minutes; and a recombinant heparosan synthase encoded by a nucleotide sequence capable of hybridizing to a complement of a nucleotide sequence encoding an amino acid sequence as set forth in SEQ ID NO: 6, 8, 66, 70 or 71 under hybridization conditions comprising hybridization at a temperature of 30° C. in 5×SSC, 5× Denhardts reagent, 30% formamide for about 20 hours followed by washing twice in 2×SSC, 0.1% SDS at about 30° C. for about 15 min followed by 0.5×SSC, 0.1% SDS at about 30° C. for about 30 minutes.

The present invention further includes recombinantly produced, isolated glycosaminglycan polymers produced by the methods described herein above. Such recombinantly produced, isolated glycosaminoglycan polymers are substantially monodisperse in size.

In addition, the present invention further includes methods of doing business by producing the glycosaminoglycan polymers by the methods described herein above and selling and delivering such glycosaminoglycan polymers to a customer or providing such glycosaminoglycan polymers to a patient.

In another embodiment of the present invention, methods of enzymatically producing glycosaminoglycan polymers having unnatural structures are provided. The methods include providing at least one functional acceptor as described above, providing at least one recombinant glycosaminoglycan transferase as described above, and providing at least one UDP-sugar analog, wherein the at least one UDP-sugar analog is not found in mammals in a native state. The at least one recombinant glycosaminoglycan transferase then elongates the at least one functional acceptor to provide glycosaminoglycan polymers having the sugar analog incorporated therein, thereby providing glycosaminoglycan polymers having an unnatural structure.

In one embodiment, the at least one UDP-sugar analog is selected from the group consisting of UDP-GlcN, UDP-GlcNAcUA, UDP-GlcNAcNAc, UDP-GlcdiNAcUA, UDP-GlcN[TFA], UDP-GlcNBut, UDP-GlcNPro, UDP-6-F-6-deoxyGlcNAc, UDP-2-F-2-deoxyGlcUA, and combinations thereof. The at least one UDP-sugar analog may also further comprise a moiety selected from the group consisting of a fluorescent tag, a radioactive tag or therapeutic, an affinity tag, a detection probe, a medicant, a biologically active agent, a therapeutic agent, and combinations thereof.

In one embodiment, the at least one recombinant glycosaminoglycan transferase is selected from the group consisting of a recombinant hyaluronan synthase or active fragment or mutant thereof, a recombinant chondroitin synthase or active fragment or mutant thereof, a recombinant heparosan synthase or active fragment or mutant thereof and combinations thereof. In another embodiment, the at least one recombinant glycosaminoglycan transferase comprises a recombinant single action glycosyltransferase capable of adding only one of GlcUA, GlcNAc, Glc, GalNAc, GlcN, GalN or a structural variant or derivative thereof. In yet another embodiment, the at least one recombinant glycosaminoglycan transferase comprises a recombinant synthetic chimeric glycosaminoglycan transferase capable of adding two or more of GlcUA, GlcNAc, Glc, GalNAc, GlcN, GalN and a structural variant or derivative thereof. In yet another embodiment, the at least one recombinant glycosaminoglycan transferase is selected from the group consisting of: a recombinant glycosaminoglycan transferase having an amino acid sequence essentially as set forth in SEQ ID NO:2, 4, 6, 8, 9, 66, 70 or 71; a recombinant glycosaminoglycan transferase encoded by a nucleotide sequence essentially as set forth in SEQ ID NO:1, 3, 5, 7, 10-46, 65 or 67; a recombinant glycosaminoglycan transferase encoded by a nucleotide sequence capable of hybridizing to a complement of a nucleotide sequence selected from the group consisting of SEQ ID NOS:1, 3, 5, 7, 10-46, 65 or 67 under hybridization conditions comprising hybridization at a temperature of 68° C. in 5×SSC/5× Denhardt's solution/1.0% SDS, followed with washing in 3×SSC at 42° C.; and a chimeric recombinant glycosaminoglycan transferase having an amino acid sequence essentially as set forth in SEQ ID NO:47 or 48.

The present invention further includes a recombinantly produced, isolated glycosaminoglycan polymer having an unnatural structure, wherein the glycosaminoglycan polymer comprises at least one sugar analog that is not found in mammals in a native state, and wherein the recombinantly produced, isolated glycosaminoglycan polymer is produced by the methods described herein above. In on embodiment, the glycosaminoglycan polymer having an unnatural structure comprises a glycosaminoglycan selected from the group consisting of an HA oligosaccharide, an HA polymer, a chondroitin oligosaccharide, a chondroitin polymer, a chondroitin sulfate polymer, a heparosan oligosaccharide, a heparin polymer, a heparin polymer, a heparosan polymer, and combinations thereof; and at least one sugar analog that is not found in mammals in a native state, wherein the at least one sugar analog is selected from the group consisting of UDP-GlcN, UDP-GlcNAcUA, UDP-GlcNAcNAc, UDP-GlcdiNAcUA, UDP-GlcN[TFA], UDP-GlcNBut, UDP-GlcNPro, UDP-6-F-6-deoxyGlcNAc, UDP-2-F-2-deoxyGlcUA, and combinations thereof.

The present invention also includes methods of doing business by producing the glycosaminoglycan polymers having an unnatural structure by the methods described herein above and selling and delivering such glycosaminoglycan polymers to a customer or providing such glycosaminoglycan polymers to a patient.

As used herein, the term "nucleic acid segment" and "DNA segment" are used interchangeably and refer to a DNA molecule which has been isolated free of total genomic DNA of a particular species. Therefore, a "purified" DNA or nucleic acid segment as used herein, refers to a DNA segment which contains a Hyaluronate Synthase ("HAS") coding sequence or Chondroitin Synthase (CS) coding sequence or Heparin/Heparosan Synthase (HS) coding sequence yet is isolated away from, or purified free from, unrelated genomic DNA, for example, total *Pasteurella multocida*. Included within the term "DNA segment", are DNA segments and smaller fragments of such segments, and also recombinant vectors, including, for example, plasmids, cosmids, phage, viruses, and the like.

Similarly, a DNA segment comprising an isolated or purified pmHAS or pmCS or pmHS1 or PmHS2 gene refers to a DNA segment including HAS or CS or HS coding sequences isolated substantially away from other naturally occurring genes or protein encoding sequences. In this respect, the term "gene" is used for simplicity to refer to a functional protein-, polypeptide- or peptide-encoding unit. As will be understood by those in the art, this functional term includes genomic sequences, cDNA sequences or combinations thereof. "Isolated substantially away from other coding sequences" means that the gene of interest, in this case pmHAS or pmCS or pmHS1 or PmHS2 forms the significant part of the coding region of the DNA segment, and that the DNA segment does not contain other non-relevant large portions of naturally-occurring coding DNA, such as large chromosomal fragments or other functional genes or DNA coding regions. Of course, this refers to the DNA segment as originally isolated, and does not exclude genes or coding regions later added to, or intentionally left in, the segment by the hand of man.

Due to certain advantages associated with the use of prokaryotic sources, one will likely realize the most advantages upon isolation of the HAS or CS or HS gene from the prokaryote *P. multocida*. One such advantage is that, typically, eukaryotic genes may require significant post-transcriptional modifications that can only be achieved in a eukaryotic host. This will tend to limit the applicability of any eukaryotic HAS or CS or HS gene that is obtained. Moreover, those of ordinary skill in the art will likely realize additional advantages in terms of time and ease of genetic manipulation where a prokaryotic enzyme gene is sought to be employed. These additional advantages include (a) the ease of isolation of a prokaryotic gene because of the relatively small size of the genome and, therefore, the reduced amount of screening of the corresponding genomic library, and (b) the ease of manipulation because the overall size of the coding region of a prokaryotic gene is significantly smaller due to the absence of introns. Furthermore, if the product of the pmHAS or pmCS or pmHS1 or PmHS2 gene (i.e., the enzyme) requires posttranslational modifications, these would best be achieved in a similar prokaryotic cellular environment (host) from which the gene was derived.

Preferably, DNA sequences utilized in accordance with the present invention will further include genetic control regions which allow the expression of the sequence in a selected recombinant host. The genetic control region may be native to the cell from which the gene was isolated, or may be native to the recombinant host cell, or may be an exaggerous segment that is compatible with and recognized by the transcriptional machinery of the selected recbominant host cell. Of course, the nature of the control region employed will generally vary depending on the particular use (e.g., cloning host) envisioned.

In particular embodiments, the invention concerns the use of isolated DNA segments and recombinant vectors incorporating DNA sequences which encode a pmHAS or pmCS or pmHS1 or PmHS2 gene, that includes within its amino acid sequence an amino acid sequence in accordance with SEQ ID NO:2, 4, 6, 8, 9, or 70, respectively. Moreover, in other particular embodiments, the invention concerns the use of isolated DNA segments and recombinant vectors incorporating DNA sequences which encode a gene that includes within its nucleic acid sequence an amino acid sequence encoding HAS or CS or HS peptides or peptide fragment thereof, and in particular to a HAS or CS or HS peptide or peptide fragment thereof, corresponding to *Pasteurella multocida* HAS or CS or HS. For example, where the DNA segment or vector encodes a full length HAS or CS or HS protein, or is intended for use in expressing the HAS or CS or HS protein, preferred sequences are those which are essentially as set forth in SEQ ID NO:1, 3, 5, 7, 69, or 71, respectively.

Truncated glycosaminoglycan transferase genes (such as, but not limited to, pmHAS$^{1-703}$, SEQ ID NO:71) also fall within the definition of preferred sequences as set forth above. For instance, at the carboxyl terminus, approximately 270-272 amino acids may be removed from the PmHAS sequence and still have a functioning HAS. Likewise, the removal of the last 50 residues or the first 77 residues of PmHS1 (SEQ ID NOS: 70 and 71, respectively) does not inactivate its catalytic function (Kane et al., 2006). Those of ordinary skill in the art would appreciate that simple amino acid removal from either end of the GAG synthase sequence can be accomplished. The truncated versions of the sequence (as disclosed hereinafter) simply have to be checked for activity in order to determine if such a truncated sequence is still capable of producing GAGs. The other GAG synthases disclosed and claimed herein are also amenable to truncation or alteration with preservation of activity, and the uses of such truncated or alternated GAG synthases also fall within the scope of the present invention.

Nucleic acid segments having HAS or CS or HS activity may be isolated by the methods described herein. The term "a sequence essentially as set forth in SEQ ID NO:X means that the sequence substantially corresponds to a portion of SEQ ID NO:X and has relatively few amino acids or codons encoding amino acids which are not identical to, or a biologically functional equivalent of, the amino acids or codons encoding amino acids of SEQ ID NO:X. The term "biologically functional equivalent" is well understood in the art and is further defined in detail herein, as a gene having a sequence essentially as set forth in SEQ ID NO:X, and that is associated with the ability of prokaryotes to produce HA or a hyaluronic acid or chondroitin or heparin polymer in vitro or in vivo. In the above examples X refers to either SEQ ID NO:1, 2, 3, 4, 5, 6, 7, 8, 9, 65, 66 or 67 or any additional sequences set forth herein, such as the truncated or mutated versions of pmHAS$^{1-703}$ that are contained generally in SEQ ID NOS:10-48.

The art is replete with examples of practitioner's ability to make structural changes to a nucleic acid segment (i.e. encoding conserved or semi-conserved amino acid substitutions) and still preserve its enzymatic or functional activity when expressed. See for special example of literature attesting to such: (1) Risler et al. Amino Acid Substitutions in Structurally Related Proteins. A Pattern Recognition Approach. J. Mol. Biol. 204:1019-1029 (1988) [ . . . according to the observed exchangeability of amino acid side chains, only four groups could be delineated; (i) Ile and Val; (ii) Leu and Met, (iii) Lys, Arg, and Gln, and (iv) Tyr and Phe.]; (2) Niefind et al. Amino Acid Similarity Coefficients for Protein Modeling and Sequence Alignment Derived from Main-Chain Folding Anoles. J. Mol. Biol. 219:481-497 (1991) [similarity parameters allow amino acid substitutions to be designed]; and (3) Overington et al. Environment-Specific Amino Acid Substitution Tables Tertiary Templates and Prediction of Protein Folds, Protein Science 1:216-226 (1992) [Analysis of the pattern of observed substitutions as a function of local environment shows that there are distinct patterns . . . Compatible changes can be made.]

It is widely recognized that a pair of distinct enzymes with even 30, 50 or 70% identity or similarity at the active site (of functional regions) thereof can possess the same catalytic activity. As most of the protein sequence is a scaffold for the active site, it is not required that all regions of the enzymes be exactly the same between functional enzyme homologs or analogs. In addition, some extra (non-catalytic) sequences may also be present, thus lowering the total protein similarity levels. Thus, functional regions (and not entire sequences) should be the basis for similarity comparisons between two enzymes.

These references and countless others, indicate that one of ordinary skill in the art, given a nucleic acid sequence or an amino acid, could make substitutions and changes to the nucleic acid sequence without changing its functionality (specific examples of such changes are given hereinafter and are generally set forth in SEQ ID NOS: 10-48). Also, a substituted nucleic acid segment may be highly identical and retain its enzymatic activity with regard to its unadulterated parent, and yet still fail to hybridize thereto. Additionally, the present application discloses 4 enzymes and numerous mutants of these enzymes that still retain at least 50% of the enzymatic activity of the unmutated parent enzyme—i.e., ½ of the dual action transferase activity of the unadulterated parent. As such, variations of the sequences and enzymes that fall within the above-defined functional limitations have been disclosed and enabled. One of ordinary skill in the art, given the present specification, would be able to identify, isolate, create, and test DNA sequences and/or enzymes that produce natural or chimeric or hybrid GAG molecules. As such, the presently claimed and disclosed invention should not be regarded as being solely limited to the specific sequences disclosed herein.

The invention discloses nucleic acid segments encoding an enzymatically active HAS or CS or HS from *P. multocida*—pmHAS, pmCS, pmHS1, and PmHS2, respectively. One of ordinary skill in the art would appreciate that substitutions can be made to the pmHAS or pmCS or pmHS1 or PmHS2 nucleic acid segments listed in SEQ ID NO:1, 3, 5, 7, 65 and 67, respectively, without deviating outside the scope and claims of the present invention. Indeed, such changes have been made and are described hereinafter with respect to the mutants produced. Standardized and accepted functionally equivalent amino acid substitutions are presented in Table II. In addition, other analogous or homologous enzymes that are functionally equivalent to the disclosed synthase sequences would also be appreciated by those skilled in the art to be similarly useful in the methods of the present invention, that is, a new method to control precisely the size distribution of polysaccharides, namely glycosaminoglycans.

TABLE II

| Amino Acid Group | Conservative and Semi-Conservative Substitutions |
|---|---|
| NonPolar R Groups | Alanine, Valine, Leucine, Isoleucine, Proline, Methionine, Phenylalanine, Tryptophan |
| Polar, but uncharged, R Groups | Glycine, Serine, Threonine, Cysteine, Asparagine, Glutamine |
| Negatively Charged R Groups | Aspartic Acid, Glutamic Acid |
| Positively Charged R Groups | Lysine, Arginine, Histidine |

Another preferred embodiment of the present invention is a purified nucleic acid segment that encodes a protein in accordance with SEQ ID NO:1 or 3 or 5 or 7 or 67, respectively, further defined as a recombinant vector. As used herein, the term "recombinant vector" refers to a vector that has been modified to contain a nucleic acid segment that encodes an HAS or CS or HS protein, or fragment thereof. The recombinant vector may be further defined as an expression vector comprising a promoter operatively linked to said HAS- or CS- or HS-encoding nucleic acid segment.

A further preferred embodiment of the present invention is a host cell, made recombinant with a recombinant vector comprising an HAS or CS or HS gene. The preferred recombinant host cell may be a prokaryotic cell. In another embodiment, the recombinant host cell is an eukaryotic cell. As used herein, the term "engineered" or "recombinant" cell is intended to refer to a cell into which a recombinant gene, such as a gene encoding HAS or CS or HS, has been introduced mechanically or by the hand of man. Therefore, engineered cells are distinguishable from naturally occurring cells which do not contain a recombinantly introduced gene. Engineered cells are thus cells having a gene or genes introduced through the hand of man. Recombinantly introduced genes will either be in the form of a cDNA gene, a copy of a genomic gene, or will include genes positioned adjacent to a promoter associated or not naturally associated with the particular introduced gene.

In preferred embodiments, the HAS- or CS- or HS-encoding DNA segments further include DNA sequences, known in the art functionally as origins of replication or "replicons", which allow replication of contiguous sequences by the particular host. Such origins allow the preparation of extrachromosomally localized and replicating chimeric or hybrid segments or plasmids, to which HAS- or CS- or HS-encoding DNA sequences are ligated. In more preferred instances, the employed origin is one capable of replication in bacterial hosts suitable for biotechnology applications. However, for more versatility of cloned DNA segments, it may be desirable to alternatively or even additionally employ origins recognized by other host systems whose use is contemplated (such as in a shuttle vector).

The isolation and use of other replication origins such as the SV40, polyoma or bovine papilloma virus origins, which may be employed for cloning or expression in a number of higher organisms, are well known to those of ordinary skill in the art. In certain embodiments, the invention may thus be defined in terms of a recombinant transformation vector which includes the HAS- or CS- or HS-coding gene sequence together with an appropriate replication origin and under the control of selected control regions.

Thus, it will be appreciated by those of skill in the art that other means may be used to obtain the HAS or CS or HS gene or cDNA, in light of the present disclosure. For example, polymerase chain reaction or RT-PCR produced DNA fragments may be obtained which contain full complements of genes or cDNAs from a number of sources, including other strains of *Pasteurella* or from a prokaryot with similar glycosyltransferases or from eukaryotic sources, such as cDNA libraries. Virtually any molecular cloning approach may be employed for the generation of DNA fragments in accordance with the present invention. Thus, the only limitation generally on the particular method employed for DNA isolation is that the isolated nucleic acids should encode a biologically functional equivalent HAS or CS or HS.

Once the DNA has been isolated, it is ligated together with a selected vector. Virtually any cloning vector can be employed to realize advantages in accordance with the invention. Typical useful vectors include plasmids and phages for use in prokaryotic organisms and even viral vectors for use in eukaryotic organisms. Examples include pKK223-3, pMAL-c, pSA3, recombinant lambda, SV40, polyoma, adenovirus, bovine papilloma virus and retroviruses. However, it is believed that particular advantages will ultimately be realized where vectors capable of replication in both biotechnologically useful Gram-positive or Gram-negative bacteria (e.g., *Bacillus, Lactococcus*, or *E. coli*) are employed.

Vectors such as these, exemplified by the pSA3 vector of Dao and Ferretti or the pAT19 vector of Trieu-Cuot, et al., allow one to perform clonal colony selection in an easily manipulated host such as *E. coli*, followed by subsequent transfer back into a food grade *Lactococcus* or *Bacillus* strain for production of hyaluronan or chondroitin or heparin polymer. In another embodiment, the recombinant vector is employed to make the functional GAG synthase for in vitro use. These are benign and well studied organisms used in the production of certain foods and biotechnology products and are recognized as GRAS (generally recognized as safe) organisms. These are advantageous in that one can augment the *Lactococcus* or *Bacillus* strain's ability to synthesize HA or chondroitin or heparin through gene dosaging (i.e., providing extra copies of the HAS or CS or HS gene by amplification) and/or inclusion of additional genes to increase the availability of HA or chondroitin or heparin precursors. The inherent ability of a bacterium to synthesize HA or chondroitin or heparin can also be augmented through the formation of extra copies, or amplification, of the plasmid that carries the HAS or CS or HS gene. This amplification can account for up to a 10-fold increase in plasmid copy number and, therefore, the HAS or CS or HS gene copy number.

Another procedure to further augment HAS or CS or HS gene copy number is the insertion of multiple copies of the gene into the plasmid. Another technique would include integrating at least one copy of the HAS or CS or HS gene into chromosomal DNA. This extra amplification would be especially feasible, since the bacterial HAS or CS or HS gene size is small. In some scenarios, the chromosomal DNA-ligated vector is employed to transfect the host that is selected for clonal screening purposes such as *E. coli*, through the use of a vector that is capable of expressing the inserted DNA in the chosen host.

In certain other embodiments, the invention concerns isolated DNA segments and recombinant vectors that include within their sequence a nucleic acid sequence essentially as set forth in SEQ ID NO:1, 3, 5, 7, 65 or 67. The term "essentially as set forth in SEQ ID NO: 1, 3, 5, 7, 65 or 67 is used in the same sense as described above and means that the nucleic acid sequence substantially corresponds to a portion of SEQ ID NO: 1, 3, 5, 7, 65 or 67 and has relatively few codons which are not identical, or functionally equivalent, to the codons of SEQ ID NO: 1, 3, 5, 7, 65 or 67. The term "functionally equivalent codon" is used herein to refer to codons that encode the same amino acid, such as the six codons for arginine or serine, and also refers to codons that encode biologically equivalent amino acids, as set forth in Table II.

It will also be understood that amino acid and nucleic acid sequences may include additional residues, such as additional N- or C-terminal amino acids or 5' or 3' nucleic acid sequences, and yet still be essentially as set forth in one of the sequences disclosed herein, so long as the sequence meets the criteria set forth above, including the maintenance of biological protein activity where protein expression and enzyme activity is concerned. The addition of terminal sequences particularly applies to nucleic acid sequences which may, for example, include various non-coding sequences flanking either of the 5' or 3' portions of the coding region or may include various internal sequences, which are known to occur within genes. Furthermore, residues may be removed from the N- or C-terminal amino acids and yet still be essentially as set forth in one of the sequences disclosed herein, so long as the sequence meets the criteria set forth above, as well.

Allowing for the degeneracy of the genetic code as well as conserved and semi-conserved substitutions, sequences which have between about 40% and about 99%; or more preferably, between about 60% and about 99%; or more preferably, between about 70% and about 99%; or more preferably, between about 80% and about 99%; or even more preferably, between about 90% and about 99% identity to the nucleotides of SEQ ID NO: 1, 3, 5, 7, 65 or 67 will be sequences which are "essentially as set forth in SEQ ID NO: 1, 3, 5, 7, 65 or 67. Sequences which are essentially the same as those set forth in SEQ ID NO: 1, 3, 5, 7, 65 or 67 may also be functionally defined as sequences which are capable of hybridizing to a nucleic acid segment containing the complement of SEQ ID NO: 1, 3, 5, 7, 65 or 67 under standard stringent hybridization conditions, "moderately stringent hybridization conditions," "less stringent hybridization conditions," or "low stringency hybridization conditions." Suitable standard or less stringent hybridization conditions will be well known to those of skill in the art and are clearly set forth hereinbelow. In a preferred embodiment, standard stringent hybridization conditions or less stringent hybridization conditions are utilized.

The terms "standard stringent hybridization conditions," "moderately stringent conditions," and less stringent hybridization conditions or "low stringency hybridization conditions" are used herein, describe those conditions under which substantially complementary nucleic acid segments will form standard Watson-Crick base-pairing and thus "hybridize" to one another. A number of factors are known that determine the specificity of binding or hybridization, such as pH; temperature; salt concentration; the presence of agents, such as formamide and dimethyl sulfoxide; the length of the segments that are hybridizing; and the like. There are various protocols for standard hybridization experiments. Depending on the relative similarity of the target DNA and the probe or query DNA, then the hybridization is performed under stringent, moderate, or under low or less stringent conditions.

The hybridizing portion of the hybridizing nucleic acids is typically at least about 14 nucleotides in length, and preferably between about 14 and about 100 nucleotides in length. The hybridizing portion of the hybridizing nucleic acid is at least about 60%, e.g., at least about 80% or at least about 90%, identical to a portion or all of a nucleic acid sequence encoding a HAS or chondroitin or heparin synthase or its complement, such as SEQ ID NO: 1, 3, 5, 7, 65 or 67 or the complement thereof. Hybridization of the oligonucleotide probe to a nucleic acid sample typically is performed under standard or stringent hybridization conditions. Nucleic acid duplex or hybrid stability is expressed as the melting temperature or $T_m$, which is the temperature at which a probe nucleic acid sequence dissociates from a target DNA. This melting temperature is used to define the required stringency conditions. If sequences are to be identified that are related and substantially identical to the probe, rather than identical, then it is useful to first establish the lowest temperature at which only homologous hybridization occurs with a particular concentration of salt (e.g., SSC, SSPE, or HPB). Then, assuming that 1% mismatching results in a 1C decrease in the $T_m$, the temperature of the final wash in the hybridization reaction is reduced accordingly (for example, if sequences having >95% identity with the probe are sought, the final wash temperature is decreased by about 5C). In practice, the change in $T_m$ can be between about 0.5° and about 1.5° per 1% mismatch. Examples of standard stringent hybridization conditions include hybridizing at about 68C in 5×SSC/5× Denhardt's solution/1.0% SDS, followed with washing in 0.2×SSC/0.1% SDS at room temperature or hybridizing in 1.8×HPB at about 30C to about 45C followed by washing a 0.2-0.5×HPB at about 45°. Moderately stringent conditions include hybridizing as described above in 5×SSC\5× Denhardt's solution 1% SDS washing in 3×SSC at 42C. The parameters of salt concentration and temperature can be varied to achieve the optimal level of identity between the probe and the target nucleic acid. Additional guidance regarding such conditions is readily available in the art, for example, by Sambrook et al., 1989, Molecular Cloning, A Laboratory Manual, (Cold Spring Harbor Press, N.Y.); and Ausubel et al. (eds.), 1995, Current Protocols in Molecular Biology, (John Wiley & Sons, N.Y.). Several examples of low stringency protocols include: (A) hybridizing in 5×SSC, 5× Denhardts reagent, 30% formamide at about 30C for about 20 hours followed by washing twice in 2×SSC, 0.1% SDS at about 30C for about 15 min followed by 0.5×SSC, 0.1% SDS at about 30 C for about 30 min (FEMS Microbiology Letters, 2000, vol. 193, p. 99-103); (B) hybridizing in 5×SSC at about 45C overnight followed by washing with 2×SSC, then by 0.7×SSC at about 55°. (J.

Viological Methods, 1990, vol. 30, p. 141-150); or (C) hybridizing in 1.8×HPB at about 30° to about 45°; followed by washing in 1×HPB at 23°.

Naturally, the present invention also encompasses DNA segments which are complementary, or essentially complementary, to the sequences set forth in SEQ ID NO:1 or 3 or 5 or 7 or 65 or 67. Nucleic acid sequences which are "complementary" are those which are capable of base-pairing according to the standard Watson-Crick complementarity rules. For example, the sequence 5'-ATAGCG-3' is complementary to the sequence 5'-CGCTAT-3" because when the two sequences are aligned, each "T" is able to base-pair with an "A", which each "G" is able to base pair with a "C". As used herein, the term "complementary sequences" means nucleic acid sequences which are substantially complementary, as may be assessed by the nucleotide comparison set forth above, or as defined as being capable of hybridizing to the nucleic acid segment of SEQ ID NO: 1, 3, 5, 7, 65 or 67 under standard stringent, moderately stringent, or less stringent hybridizing conditions.

The nucleic acid segments of the present invention, regardless of the length of the coding sequence itself, may be combined with other DNA sequences, such as promoters, polyadenylation signals, additional restriction enzyme sites, multiple cloning sites, epitope tags, polyhistidine regions, other coding segments, and the like, such that their overall length may vary considerably. It is therefore contemplated that a nucleic acid fragment of almost any length may be employed, with the total length preferably being limited by the ease of preparation and use in the intended recombinant DNA protocol.

Naturally, it will also be understood that this invention is not limited to the particular amino acid and nucleic acid sequences of SEQ ID NO:1, 2, 3, 4, 5, 6, 7, 8, 9, 65, 66 or 67. Recombinant vectors and isolated DNA segments may therefore variously include the HAS or CS or HS coding regions themselves, coding regions bearing selected alterations or modifications in the basic coding region, or they may encode larger polypeptides which nevertheless include HAS or CS or HS coding regions or may encode biologically functional equivalent proteins or peptides which have variant amino acid sequences.

The DNA segments of the present invention encompass DNA segments encoding biologically functional equivalent HAS or CS or HS proteins and peptides. Such sequences may arise as a consequence of codon redundancy and functional equivalency which are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques, e.g., to introduce improvements to the enzyme activity or to antigenicity of the HAS or CS or HS protein or to test HAS or CS or HS mutants in order to examine HAS or CS or HS activity at the molecular level or to produce HAS or CS or HS mutants having changed or novel enzymatic activity and/or sugar substrate specificity.

Traditionally, chemical or physical treatments of polysaccharides were required to join two dissimilar materials. For example, a reactive nucleophile group of one polymer or surface was exposed to an activated acceptor group of the other material. Two main problems exist with this approach, however. First, the control of the chemical reaction cannot be refined, and differences in temperature and level of activation often result in a distribution of several final products that vary from lot to lot preparation. For instance, several chains may be cross-linked in a few random, ill-defined areas, and the resulting sample is not homogenous. Second, the use of chemical reactions to join molecules often leaves an unnatural or nonbiological residue at the junction of biomaterials. For example, the use of an amine and an activated carboxyl group would result in an amide linkage. This inappropriate residue buried in a carbohydrate may pose problems with biological systems such as the subsequent production of degradation products which accumulate to toxic levels or the triggering of an immune response.

The terms "unnatural sugar" and "sugar analog" are used herein interchangeably, and will be understood to refer to a sugar analog that is not found in mammals in a native state, that is, a sugar analog that is produced by the hand of man. This sugar unit may be a component of a precursor UDP-sugar, or an acceptor, or the monosaccharide itself.

Use of pmHAS for Polymer Grafting and Polysaccharide Production

Most polysaccharide polymers must be of a certain length before their physical or biological properties become apparent. Often the polysaccharide must comprise at least 20-100 sugar units. Certain enzymes that react with exogenous polymers have been previously available, but typically add only one sugar unit. The unique enzymes described in the present invention, (e.g., pmHAS, pmCS, pmHS1, and PmHS2), if desired, form polymers of at least 100-400 sugar units in length. Thus, one embodiment of the presently claimed and disclosed invention, results in long, defined linear polymers composed of only natural glycosidic linkages. In addition, the presently claimed and disclosed invention also includes the addition of 1 or 2 sugars, as well as the addition of 2-100 sugars.

The four known glycosaminoglycan synthesizing enzymes from *Pasteurella multocida* bacteria normally make polymers similar to or identical to vertebrate polymers. These bacteria employ the polysaccharide, either HA (Type A bacteria), chondroitin (Type F bacteria), or heparosan (unsulfated, unepimerized heparin; Type D bacteria) as an extracellular coating to serve as molecular camouflage. Native enzymes normally make polymer chains of a single type of sugar repeat. If a recombinant HAS or CS or HS enzyme is employed, however, the enzyme can be forced to work on an exogenous functional acceptor molecule. For instance, the recombinant enzyme may be incubated with a polymer acceptor, and the recombinant enzyme will then elongate the acceptor with UDP-sugar precursors. The known native enzymes do not perform this reaction since they already contain a growing polymer chain that was formed in the living cell; enzyme preparations from native cells typically retain the polymer following isolation.

pmHAS (SEQ ID NO:2), a 972 amino acid residue protein from *Pasteurella multocida*, is made in a functional state in recombinant *Escherichia coli*. The pmHAS gene is given in SEQ ID NO:1. Other functional derivatives of pmHAS, for example an enzyme called $pmHAS^{1-703}$ (SEQ ID NO:9) and the $pmHAS^{1-703}$ gene (SEQ ID NO:67), have been produced which are soluble. The soluble form can be prepared in larger quantities and in a purer state than the naturally occurring full-length enzyme. The preferred *E. coli* strains do not have an UDP-Glc dehydrogenase and therefore the recombinant enzyme does not make HA chain in the foreign host. Therefore, the enzyme is in a virgin state since the empty acceptor site can be occupied with foreign polymers. For example, the recombinant enzyme may be incubated in a mixture comprising from about 10 to about 50 mM Tris pH 7.2, from 0.5 to about 20 mM $MnCl_2$, from about 0.1 to about 30 mM UDP-GlcUA, from about 0.1 to about 30 mM UDP-GlcNAc, and a suitable acceptor at about 20-37° for from about 1 to about 600 minutes. Suitable acceptors can be any functional acceptor, such as a glycosaminoglycan acceptor or sugar acceptor, for example, but not by limitation, short HA chains (two or more sugar units such as $HA_4$) or short chondroitin sulfate chains (5 sugar units) or long chondroitin sulfate chains (~$10^2$ sugar units). In the case of the latter acceptors, pmHAS (or its derivatives), then elongates the foreign acceptors (i.e., long or short chondroitin polymers, plus or minus sulfation) at their nonreducing termini with authentic HA chains. The length of the HA chain added onto the acceptor is controlled by altering the concentration of UDP-sugars (thus changing the stoichiometry of UDP-sugar to acceptor) and/or the reaction time. Immobilized acceptors, such as beads or other solid objects with bound acceptor oligosaccharides, can also be extended by the pmHAS enzyme using UDP-sugars. In this manner, the pmHAS enzyme (or its derivatives) can be used to attach polysaccharide chains to any suitable acceptor molecule.

Type A *P. multocida* produces HA capsule [GlcUA-GlcNAc repeats] and possesses the pmHAS enzyme. On the other hand, Type F *P. multocida* produces a chondroitin or chondroitin-like polymer capsule [GlcUA-GalNAc repeats]. The DNA encoding an open reading frame (GenBank accession #AF195517) that is 90% identical to pmHAS at the protein level has been cloned; this enzyme is called PmCS, the *P. multocida* chondroitin synthase. The amino acid sequence of pmCS is set forth in SEQ ID NO:4 and the pmCS gene sequence is set forth in SEQ ID NO:3. As the PmCS enzyme's sequence is so similar to pmHAS, one of ordinary skill in the art, given the present specification, is able to manipulate the pmCS in the same manner as that for pmHAS and any manipulation that is successful with regard to the pmHAS would be performable with the pmCS, with the exception that chondroitin chains would be grafted instead of HA. Either HA or chondroitin chains can serve as acceptors for pmCS as both acceptors serve well for pmHAS. The PmHS1 and PmHS2 enzymes possess some similarities to these other GAG synthases, but elongate with heparosan, a distinct polymer, when supplied with UDP-GlcNAc and UDP-GlcUA. If the enzymes are supplied with analog sugar precursors, novel unnatural GAG extensions result.

Such hybrid polysaccharide materials composed of HA, chondroitin and/or heparin within a single polymer chain cannot be formed in a controlled fashion (targeted size and monodisperse) especially with regard to medium to large size polymers (i.e., greater than 2 to 5 KDa) by any other existing process without (1) leaving unnatural residues, and/or (2) producing undesirable crosslinking reactions. The testicular hyaluronidase method gives a variety of small products derived from quasi-random linkage of GAGs, HA and chondroitin. Very large polymers are not major or significant products. The chimeric or hybrid polysaccharide materials can serve as biocompatible molecular glue for cell/cell interactions in artificial tissues or organs and the HA/chondroitin/heparin hybrid mimics natural proteoglycans that normally contain an additional protein intermediate between polymer chains. The present invention, therefore, obviates the requirement for a protein intermediary. A recombinant HA/chondroitin/heparin chimeric or hybrid polysaccharide, devoid of such an intermediary protein, is desirous since molecules from animal sources are potentially immunogenic—the chimeric or hybrid polysaccharide, however, would not appear as foreign to the host, thus no immune response is generated.

Also, the recombinant polymers can be made free of adventitious agents (e.g., prions, viruses etc.). In addition, the molecules are not degraded by proteases.

An intrinsic and essential feature of polysaccharide synthesis is the repetitive addition of sugar monomer units to the growing polymer. The glycosyltransferase remains in association with the nascent chain. This feature is particularly relevant for HA biosynthesis as the HA polysaccharide product, in all known cases, is transported out of the cell; if the polymer was released, then the HAS would not have another chance to elongate that particular molecule. Four possible mechanisms for maintaining the growing polymer chain at the active site of the enzyme are immediately obvious. First, the enzyme possesses a carbohydrate polymer binding pocket or cleft. Second, the nascent chain is covalently attached to the enzyme during its synthesis. Third, the enzyme binds to the nucleotide base or the lipid moiety of the precursor while the nascent polymer chain is still covalently attached. Fourth, other molecules help retain the chain.

The HAS activity of the native pmHAS enzyme found in *P. multocida* membrane preparations is not stimulated by the addition of HA oligosaccharides; theoretically, the endogenous nascent HA chain initiated in vivo renders the exogenously supplied acceptor unnecessary. However, recombinant pmHAS produced in an *E. coli* strain that lacks the UDP-GlcUA precursor, and thus lacks a nascent HA chain, is able to bind and to elongate exogenous HA oligosaccharides. As mentioned above, there are four likely means for a nascent HA chain to be held at or near the active site. In the case of pmHAS, it appears that a HA-binding site exists near or at the sugar transferase catalytic site. In general, PmCS, PmHS1 and PmHS2 should have similar architectures for their substrates.

Defined oligosaccharides that vary in size and composition are used to discern the nature of the interaction between pmHAS and the sugar chain. For example, it appears that the putative HA-polymer binding pocket of pmHAS will bind and elongate at least an intact HA disaccharide with increased efficiency occurring when a trisaccharide is used (reduced tetramer or a synthetic trisaccharide). Synthetic mimics (i.e., glycosides) of disaccharides or trisaccharides are also functional acceptors. Oligosaccharide binding to pmHAS appears to be somewhat selective because the heparosan pentamer, which only differs in the glycosidic linkages from HA-derived oligosaccharides, does not serve as an acceptor. However, chondroitin [GlcUA-GalNAc repeat] does serve as an acceptor for pmHAS.

To date, no other HA synthase besides pmHAS has been shown to utilize an exogenous acceptor or primer sugar. In an early study of a cell-free HA synthesis system, preparations of native Group A Streptococcal HAS were neither inhibited nor stimulated by the addition of various HA oligosaccharides including the HA tetramer derived from testicular hyaluronidase digests. These membrane preparations were isolated from cultures that were producing copious amounts of HA polysaccharide. The cells were hyaluronidase-treated to facilitate handling. Therefore, it is quite likely that the native streptococcal enzyme was isolated with a small nascent HA chain attached to or bound to the protein much as suspected in the case of the native pmHAS. Theoretically, the existing nascent chain formed in vivo would block the entry and subsequent utilization of an exogenous acceptor by the isolated enzyme in vitro. With the advent of molecularly cloned HAS genes, it is possible to prepare virgin enzymes lacking a nascent HA chain if the proper host is utilized for expression. In these tests, recombinant yeast with spHAS did not use HA acceptors proving that the Class I enzyme intrinsically cannot elongate such acceptors.

Both heparin and chondroitin, in mammalian systems, are synthesized by the addition of sugar units to the nonreducing end of the polymer chain. In humans and animals in vivo, the glycosyltransferases initiate chain elongation on at least primer monosaccharides [more preferably tetrasaccharides such as xylose-galactose-galactose-GlcUA] that are attached to serine residues of proteoglycan core molecules. In vitro, enzyme extracts transfer a single sugar to exogenously added heparin or chondroitin oligosaccharides; unfortunately, the subsequent sugar of the disaccharide unit is usually not added and processive elongation to longer polymers does not occur. Therefore it is likely that some component is altered or missing in the in vitro system. In the case of heparin biosynthesis, it appears that a complexe of EXT 1 and 2 enzymes transfers both GlcUA and GlcNAc sugars to the glycosaminoglycan chain.

Recent work with the *E. coli* K5 KfiA and KfiC enzymes, which polymerize heparosan, indicates that a pair of proteins can transfer both sugars to the nonreducing end of acceptor molecules in vitro. Extensive processive elongation, however, was not demonstrated in these experiments; crude cell lysates transferred a single sugar to long defined even- or odd-numbered oligosaccharides.

Recombinant pmHAS adds single monosaccharides in a sequential fashion to the nonreducing termini of the nascent HA chain; elongation of HA polymers containing hundreds of sugars has been demonstrated in vitro. The simultaneous formation of the disaccharide repeat unit is not necessary for generating the alternating structure of the HA molecule. The intrinsic specificity and fidelity of each half-reaction (e.g., GlcUA added to a GlcNAc residue or vice versa) apparently is sufficient to synthesize authentic HA chains.

A great technical benefit resulting from the alternating disaccharide structure of HA is that the reaction can be dissected by controlling the availability of UDP-sugar nucleotides. By omitting or supplying precursors in a reaction mixture, the glycosyltransferase may be stopped and started at different stages of synthesis of the heteropolysaccharide. In contrast, there is no facile way to control in a step-wise fashion the glycosyltransferase enzymes that produce important homopolysaccharides such as chitin, cellulose, starch, and glycogen. This control also is possible for a targeted synthesis of GAGs with natural and/or unnatural sugars.

An alternative method for controlling polymerization has been accomplished by creating mutants that only add one sugar linkage onto a short HA oligosaccharide. For example, $pmHAS^{1-650}$ (SEQ. ID NO:10) can only add single GlcNAc sugars onto the non-reducing end (i.e., HA tetrasaccharide [GlcNAc-GlcUA-GlcNAc-GlcUA]) of an acceptor (i.e., forms the HA pentamer). On the other hand, a mutant has been created and called $pmHAS^{1-703}$-D477N (SEQ. ID NO:11) [pmHAS residues 1-703 with an asparagine substituted for the asparatate at position 477], that transfers only a single GlcNAc residue onto the non-reducing terminal GlcUa group of the short HA oligosaccharide. If extracts of two such single-action point mutants (e.g. D477N, SEQ ID NO:11 and D196N [i.e., pmHAS residues 1-703 with an asparagine substituted for the aspartate at position 196], SEQ ID NO:12) are mixed together with an acceptor in the presence of UDP-GlcNAc and UDP-GlcUA, then significant polymerization is achieved. It is also obvious that by carrying out the steps of GlcNAc or GlcUA transfer separately and sequentially, almost any HA chain length is possible. The same is also true with regard to PmCS either alone or in combination with pmHAS as well as pmHS1 (potential sites described in Kane et al., 2006) or PmHS2 either alone or in combination with pmCS and pmHAS, individually or as a group.

pmHS1 and PmHS2 Identification and Molecular Cloning

As stated hereinabove, *Pasteurella multocida* Type D, a causative agent of atrophic rhinitis in swine and pasteurellosis in other domestic animals, produces an extracellular polysaccharide capsule that is a putative virulence factor. It has been reported that the capsule of Type D was removed by treating microbes with heparin lyase III. A 617-residue enzyme, pmHS1 (SEQ ID NOS:5 and 66), and a 651-residue enzyme, PmHS2 (SEQ ID NO:8), which are both authentic heparosan (unsulfated, unepimerized heparin) synthase enzymes have been molecularly cloned and are presently claimed and disclosed in copending U.S. application Ser. No. 10/142,143, incorporated herein previously by reference. Recombinant *Escherichia coli*-derived pmHS1 or PmHS2 catalyzes the polymerization of the monosaccharides from UDP-GlcNAc and UDP-GlcUA. Other structurally related sugar nucleotides do not substitute. Synthase activity was stimulated about 7- to 25-fold by the addition of an exogenous polymer acceptor. Molecules composed of ~500 to 3,000 sugar residues were produced in vitro. The polysaccharide was sensitive to the action of heparin lyase III but resistant to hyaluronan lyase. The sequence of pmHS1 enzyme is not very similar to the vertebrate heparin/heparan sulfate glycosyltransferases, EXT1/2 (SEQ ID NOS:61/62), or to other *Pasteurella* glycosaminoglycan synthases that produce hyaluronan or chondroitin. Certain motifs do exist however, between the pmHS1, pmHS2, and KfiA (SEQ ID NO:59) and KfiC (SEQ ID NO:60) thereby leading to deduced amino acid motifs that are conserved throughout this class of GAG synthases for the production of heparin/heparosan. The pmHS1 and PmHS2 enzymes are the first microbial dual-action glycosyltransferase to be described that form a polysaccharide composed of β4GlcUA-α4GlcNAc disaccharide repeats. In contrast, heparosan biosynthesis in *E. coli* K5 requires at least two separate polypeptides, KfiA and KfiC, to catalyze the same polymerization reaction.

Molecular Cloning of the Type D *P. multocida* Heparosan Synthase—A PCR product which contained a portion of the Type D UDP-glucose dehydrogenase gene was used as a hybridization probe to obtain the rest of the Type D *P. multocida* capsular locus from a lambda library. We found a functional heparosan synthase, which we named pmHS1, in several distinct Type D strains from different host organisms isolated around the world (i.e., A2 clone SEQ ID NOS:5 and 6; bioclone SEQ ID NOS:65 and 66). In every case, an open reading frame of 617 residues with very similar amino acid sequence (98-99% identical) was obtained. In the latter stages of our experiments, another group deposited a sequence from the capsular locus of a Type D organism in GenBank[15]. In their annotation, the carboxyl terminus of the pmHS1 homolog is truncated and mutated to form a 501-residue protein that was called DcbF (GenBank Accession Number AAK17905) (SEQ ID NOS:57 and 58). No functional role for the protein except glycosyltransferase was described and no activity experiments were performed. As described herein, membranes or cell lysates prepared from *E. coli* with the recombinant dcbF gene do not possess heparosan synthase activity. The gene annotated as DcbF (SEQ ID NO:58) is truncated at the carboxyl terminus in comparison to the presently claimed and described *P. multocida* HS clones. The truncated (T) or the full-length (FL) open reading frames of DcbF were cloned into the expression system pETBlue-1 vector, as described hereinabove. Membranes isolated from the same host strain, *E. coli* Tuner with the various recombinant plasmids were tested in HS assays with both radiolabeled UDP-sugars. The results of these experiments are summarized in Table III.

TABLE III

| Clone | [14C]GlcUA Incorp. (dpm) | [3H]GlcNAc Incorp. (dpm) |
|---|---|---|
| Negative Control | 160 | 40 |
| B1(FL) | 710(*) | 1040(*) |
| 012(T) | 40 | 265 |
| 013(T) | 70 | 1610 |
| 019(T) | 55 | 1105 |
| N2(T) | 70 | 1910 |
| N4(T) | 70 | 880 |
| N5(T) | 80 | 650 |

Five-fold less FL enzyme than T enzymes were tested in these parallel assays. At most, only a single GlcNAc sugar is added to the exogenously supplied acceptor in the truncated enzymes (T). Full-length HS from Type D *P. multocida*, however, adds both sugars (*) to the nascent chain. Thus, the previously annotated and deposited DcbF gene is not a functional heparosan synthase.

Another deduced gene was recently uncovered by the University of Minnesota in their Type A *P. multocida* genome project, originally (and erronenously) called "PglA", but now correctly re-named PmHS2 (GenBank Accession Number AAK02498), encoding 651 amino acids that are similar to pmHS1 (73% identical in the major overlapping region). However, the PmHS2 gene (SEQ ID NO:7) is not located in the putative capsule locus. This group made no annotation of the function of PmHS2. Our studies show that this PmHS2 protein (SEQ ID NO:8) also polymerizes GlcUA and GlcNAc residues to form heparosan. We also found that a Type D strain and a Type F strain also appear to contain a homologous PmHS2 gene as shown by PCR and activity analysis.

As mentioned before, during the pmHS1 cloning project in the present Applicant(s)' laboratory, investigators at the University of Minnesota published the complete genome of a *Pasteurella multocida* isolate. The fragments of the presently claimed and disclosed pmHS1 gene were utilized as the query in a BLAST search against this *P. multocida* genome. A gene annotated as pglA, but with no ascribed, predicted or demonstrated function was found to be very similar to the pmHS1 gene. The pglA gene is not in the main capsule locus found by either the DeAngelis or the Adler groups. The pglA open reading frame was obtained from two different encapsulated strains: Type A (P-1059 from a turkey—this strain is not the same as the Univ. of Minnesota strain—clones denoted as "A") and Type D (P-3881 from a cow—clones denoted as "D"). The pmHS2 gene was amplified from chromosomal templates prepared by method of Pitcher et al (*Letters in Applied Microbiology,* 1989 which is expressly incorporated herein by reference in its entirety). PCR with Taq polymerase (18 cycles) using custom flanking oligonucleotide primers that correspond to the region of the start codon and the stop codon of pmHS2. An appropriate size amplicon corresponding to the pmHS2 gene was found in both Type A and D strains; this result was rather unexpected if one considers that the capsular compositions are HA and N-acetylheparosan polysaccharides, for Type A and Type D strains, respectively. The resulting ~1.9 kilobase PCR amplicons were ligated into an expression vector, pETBlue-1 (Novagen), transformed into the cloning host, *E. coli* Novablue (Novagen), and selected on LB carbenicillin and tetracycline plates at 30°. The colonies were screened for the presence of insert in the proper orientation by PCR with a combination of vector and insert primers. Clones were streak isolated, small cultures were grown, and preparations of the plasmid DNA were made. The plasmids were transformed into the expression host, *E. coli* Tuner (Novagen), and selected on LB with carbenicillin and chloramphenicol.

After streak isolation, small cultures were grown at 30° as the starting inoculum (1:100) for larger cultures (50 ml) for protein expression and activity assay. These cultures were grown in the same LB supplemented with 1% casein amino acids and trace element solution with vigorous shaking (250 rpm) at 30°. The cells were grown to mid-logarithmic phase (2.5 hours), induced with 0.5 mm IPTG, and grown for 4.5 hours. Cells were collected by centrifugation and frozen at −80° overnight. The membrane preparations were isolated by cold lysozyme/ultrasonication method of DeAngelis et. al. (*J. Biol. Chem.,* 1998; pmHAS isolation the contents of which are expressly incorporated herein in their entirety) except that 0.1 mM mercaptoethanol was used as the reducing agent. The membranes were assayed for radioactive sugar incorporation and descending paper chromatography (according to the methodology of DeAngelis and Padget-McCue, *J. Biol. Chem.,* 2000, the contents of which are expressly incorporated herein in their entirety). Later improvements on the PmHS catalysts included fusion to maltose-binding protein and growth in an *E. coli* strain that readily lyses.

In general, a mixture with membranes, 50 mM Tris, pH 7.2, 10 mM $MgCl_2$, 10 mM $MnCl_2$, 0.4 mM UDP-[$^3$H]GlcNAc, 0.2 mM UDP-[$^{14}$C]GlcUA, and heparin oligosaccharide acceptor (2 μg uronic acid) were incubated at 30° for 2.5 hours before analysis by paper chromatography. As expected for a polysaccharide synthase, both sugars were incorporated into polymer (Table IV). Negative controls using membranes from a plasmid with an irrelevant control insert did not show incorporation. Therefore, PmHS2 is a dual-action synthase capable of sugar biosynthesis as shown by functional expression of activity of one recombinant gene in a foreign host that normally does not make GlcUA/GlcNAc polymers. The relaxed specificity of UDP-sugar incorporation of PmHS2 should be of use for the design and production of new polymers with altered characteristics.

TABLE IV

In vitro incorporation of sugar by membranes containing recombinant pmHS2

| CLONE | [$^3$H]GlcNAc (dpm) | [$^{14}$C]GlcUA (dpm) |
|---|---|---|
| PmHS2-A2 | 50,400 | 54,900 |
| PmHS2-A4 | 39,100 | 41,000 |
| PmHS2-D4 | 32,500 | 34,200 |
| PmHS2-D7 | 44,800 | 46,600 |

The typical background for negative controls is less than 200 dpm incorporation. Type A and Type D isolates have the PmHS2, a synthase that incorporates both GlcUA and GlcNAc sugars. (A=Type A; D=Type D; #=independent clone number). Table V shows PmHS2 Sugar Specificity test results. The experiments summarized in Table V are similar to the experiments summarized in Table IV (with less enzyme) except that other UDP-sugars that are not normally found in heparin or heparosan were also tested (note—60 minute incubation times, 50 μl reactions). The Type A and the Type D enzymes behave in a similar fashion with relaxed sugar specificity in this test. The PmHS2 system can add a glucose instead of a GlcNAc sugar. The ability to co-polymerize the sugars that compose the authentic heparin backbone were tested by performing two parallel reactions:

UDP-[$^{14}$C]GlcUA+various combinations of $2^{nd}$ UDP-sugars.

UDP-[$^{3}$H]GlcNAc+various combinations of $2^{nd}$ UDP-sugars.

*P. multocida* Type F-derived recombinant pmHS2 is thus also a heparosan synthase. As shown in the following Table VII, the Type F PmHS2 can incorporate the authentic heparin sugars.

The pmHS2 homolog of *P. multocida* Type F strain P-4218 was amplified with flanking primers as described for the Type A and D strains. The ORF was subcloned into the pETBlue-1 system in *E. coli* Tuner cells for use as a source of membrane preparations as described. Three independent clones (F 3, 4, 18) were assayed under standard HS assay measuring radio-labeled sugar incorporation with paper chromatography. A negative control, membranes from "Blank" vector and a positive control, the Type D pmHS2 clone D7, were tested in parallel. Reactions plus/minus the Type D polymer acceptor were assayed.

TABLE V

| Panel I. Type A PmHS2-A2 | |
|---|---|
| $2^{nd}$ Sugar | [$^{3}$H]GlcNAc Incorporated into Polymer (dpm) |
| none | 450 |
| UDP-GlcUA | 12,900 |
| UDP-GalUA | 400 |
| UDP-Glc | 430 |
| $2^{nd}$ Sugar | [$^{14}$C]GlcUA Incorporated into Polymer (dpm) |
| none | 60 |
| UDP-GlcNAc | 7,700 |
| UDP-GalNAc | 60 |
| UDP-Glc | 985 |
| Panel II. Type D PmHS2-D7 | |
| $2^{nd}$ Sugar | [$^{3}$H]GlcNAc Incorporated into Polymer (dpm) |
| None | 570 |
| UDP-GlcUA | 13,500 |
| UDP-GalUA | 530 |
| UDP-Glc | 500 |
| $2^{nd}$ Sugar | [$^{14}$C]GlcUA Incorporated into Polymer (dpm) |
| None | 60 |
| UDP-GlcNAc | 6,500 |
| UDP-GalNAc | 40 |
| UDP-Glc | 660 |

TABLE VII

| Activity of pmHS2 from Type F | | | |
|---|---|---|---|
| Membranes | Acceptor | $^{3}$H-GlcNAc (dpm) | $^{14}$C-GlcUA (dpm) |
| Blank | 0 | 8 | 8 |
| PmHS2 F 3 | + | 7100 | 3100 |
| PmHS2 F 4 | 0 | 6100 | 3800 |
| PmHS2 F 4 | + | 11000 | 6400 |
| PmHS2 F 18 | 0 | 20000 | 10000 |
| PmHS2 F 18 | + | 23000 | 12000 |
| PmHS2 D 7 | 0 | 36000 | 17000 |

TABLE VI

| Acceptor Usage of PmHS2 from Types A and D [$^{14}$C-GlcUA] incorporation | | |
|---|---|---|
| Clone | Acceptor | NO Acceptor |
| A2 | 1560 | 1210 |
| D7 | 1240 | 1080 |

The Type A and the Type D clones were tested for stimulation by addition of the Type D polysaccharide acceptor (described hereinbefore with respect to pmHS1). Weaker stimulation of activity by acceptor on pmHS2 was observed in comparison to pmHS1 (comparison is not shown here).

The next best heterologous matches for the pmHS1 enzyme in the Genbank database are KfiA and KfiC proteins from *E. coli* K5; these two proteins work together to make the heparosan polymer. There is a good overall alignment of the enzyme sequences if smaller portions of pmHS1 ORF are aligned separately with KfiA (pmHS12, SEQ ID NO:59) and KfiC (pmHS11, SEQ ID NO:60). The MULTALIN alignment program (Corpet, 1988) identified regions that were very similar. Some of the most notable sequence similarities occur in the regions containing variants of the DXD amino acid sequence motif. Indeed, the first 1-360 residues of pmHS1 align with an approximate 38% identity to the *E. coli* KfiC, a single action GlcUA-transferase, while the 361-617 residues of pmHS12 align with an approximate 31% identity to the *E. coli* KfiA, a GlcNAc-transferase. Thus, the pmHS1 is a naturally occurring fusion of two different glycosyltransferase domains. The pmHS1 is a dual action enzyme that alone makes heparin/heparosan polymers because both sugar transferase sites exist in one polypeptide enzyme.

The amino acid sequence of the heparosan synthase, pmHS1, however, is very different from other *Pasteurella* GAG synthases, pmHAS and pmCS. The pmHAS and pmHS1 enzymes both perform the task of polymerizing the identical monosaccharides; HA and heparin only differ with respect to their linkages. The creation of different anomeric linkages probably requires very distinct active sites due to the disparity between a retaining (to form α-linkages) and an inverting (to form β-linkages) transfer mechanism. The putative dual-action vertebrate heparin synthases, EXT1 (SEQ ID NO:61) and EXT2 (SEQ ID NO:62), also appear to have two transferase domains, but the amino acid sequences are not similar to pmHS1. Thus, by aligning pmHS2, pmHS1 (B10 and A2 clones), KfiA, or KfiC, deduced amino acid sequence motifs have been identified. Such motifs are listed below.

Comparisons of the two known sets of heparin/heparosan biosynthesis enzymes from the *E. coli* K5 Kfi locus, the PmHS2 enzyme, and the pmHS1 from Type D capsular locus, allows for the initial assessment and bioinformatic prediction of new enzymes based on the amino acid sequence data. The closer the match (% identity) in a single polypeptide for the two sequence motifs described hereinafter (corresponding to the critical elements of the GlcUA-transferase and the GlcNAc-transferase), the higher the probability that the query enzyme is a new heparin/heparosan synthase (a single dual-action enzyme). The closer the match (% identity) in two polypeptides (especially if encoded in the same operon or transcriptional unit) for the two sequence motifs, the higher the probability that the query enzymes are a pair of single-action glycosyltransferases. Thus, one of ordinary skill in the art would appreciate that given the following motifs, one would be able to ascertain and ascribe a probable heparin synthase function to a newly discovered enzyme and then test this ascribed function in a manner to confirm the enzymatic activity. Thus, single dual-action enzymes possessing enzymatic activity to produce heparin/heparosan and having at least one of the two disclosed motifs are contemplated as being encompassed by the presently claimed and disclosed invention.

```
Motif I: (SEQ ID NO: 63)
QTYXN(L/I)EX4DDX(S/T)(S/T)D(K/N)(T/S)X6IAX(S/T)

(S/T)(S/T)(K/R)V(K/R)X6NXGXYX16FQDXDDX(C/S)H(H/P)

ERIXR

Motif II: (SEQ ID NO: 64)
(K/R)DXGKFIX12-17DDDI(R/I)YPXDYX3MX40-50 VNXLGTGTV
```

Motif I corresponds to the GlcUA transferase portion of the enzyme, while Motif II corresponds to the GlcNAc transferase portion of the enzyme. With respect to the motifs:

X=any residue parentheses enclose a subset of potential residues [separated by a slash] that may be at a particular position (e.g., —(K/R) indicates that either K or R may be found at the position—i.e., there are semiconserved residues at that position.

The consensus X spacing is shown with the number of residues in subscript (e.g., X12-17), but there are weaker constraints on these particular residues, thus spacing may be longer or shorter. Conserved residues may be slightly different in a few places especially if a chemically similar amino acid is substituted (e.g., K for a R, or E for a D). Overall, at the 90% match level, the confidence in this predictive method is very high, but even a 70-50% match level without excessive gap introduction (e.g., altered spacing between conserved residues) or rearrangements (miss-positioning with respect to order of appearance in the amino to carboxyl direction) would also be considered to be within the scope of these motifs. One of ordinary skill in the art, given the present specification, general knowledge of the art, as well as the extensive literature of sequence similarity and sequence statistics (e.g., the BLAST information website at www.ncbi.nlm.mih.gov), would appreciate the ability of a practitioner to identify potential new heparin/heparosan synthases based upon sequence similarity or adherence to the motifs presented herein and thereafter test for functionality by means of heterozologous expression, to name but one example.

pmHS1 and PmHS2 Polymer Grafting and Use of Chimeric or Hybrid or Mutant Transferases As mentioned hereinabove, it was first discovered and disclosed that pmHAS-catalyzed synthesis in vitro was unique in comparison to all other existing HA synthases of *Streptococcus*, bacteria, humans or an algal virus. Specifically, recombinant pmHAS can elongate exogenously supplied functional acceptors (described herein) into longer glycosaminoglycans. The pmHAS synthase adds monosaccharides one at a time in a step-wise fashion to the growing chain. The pmHAS exquisite sugar transfer specificity results in the repeating sugar backbone of the GAG chain. The pmCS enzyme, which is 90% identical at the amino acid level to pmHAS, performs the same synthesis reactions but incorporates GalNAc instead of GlcNAc. The pmHS1 and PmHS2 enzymes can also add heparosan chains onto exogenous supplied functional acceptors such as long or short heparosan polymers.

The *Pasteurella* GAG synthases (pmHAS, pmCS, pmHS1 and PmHS2) are very specific glycosyltransferases with respect to the sugar transfer reaction: usually only the authentic sugar is added onto acceptors. The epimers or closely structurally related molecules (e.g., UDP-glucose) are not utilized. However, these GAG synthases from *Pasteurella* do utilize heterologous acceptor sugars. For example, pmHAS elongates short chondroitin acceptors with HA chains. Additionally, pmHS1 adds heparosan chains onto HA acceptor oligosaccharides. Thus, a diverse range of hybrid of chimeric or hybrid GAG oligosaccharides can be made with the disclosed GAG synthases (i.e., pmHAS, pmCS, pmHS1, and PmHS2). The chemoenzymatic methodology can be used in either a liquid-phase synthesis of soluble, free sugars or in a solid-phase synthesis to build sugars on surfaces (as disclosed hereinafter).

Synthase activity assays (2.5 hours, 30°) with subsequent paper chromatography separations and liquid scintillation counting of the origin zone. Typical reaction buffer (Tris & Mn ion; DeAngelis & White 2001) contained both radioactive UDP-GlcNAc and UDP-GlcUA and various acceptor sugars (as noted in table). Unless noted, the HA was from testicular Haase digestions (Leech means leech HAase). Hep2 or Hep2 are synthetic heparosan disaccharide or trisaccharide analogs, respectively (Haller & Boons, 2001). Recombinant *E. coli* derived membranes from cell with plasmids containing pmHS1 gene or no insert (vector). With no membranes and no acceptor sugar, the background was 70 and 35 dpm, respectively.

Thus, chimeric or hybrid GAGS can be made using the *Pasteurella* GAG synthases of the presently claimed and disclosed invention. As shown in Table VIII, synthetic di- and tri-saccharides of heparosan, and HA can be elongated. Naturally derived HA tetramers can also be elongated. The reducing end is not required to be in a free state (aglycons are not a problem), therefore, the reducing end can serve as the tether site onto a surface, drug, or other synthetic or natural molecule. Exemplary compounds that can be made using the *Pasteurella* GAGs of the presently claimed and disclosed invention include, but are not limited to:

HA-C CS-HA C-HA HA-HP C-HP HA-C-HA CS-HA-C C-HA-C

HA-C-HP CS-HA-HP C-HA-HP and so forth, and one of ordinary skill in the art given this specification would appreciate and be able to construct any number of chimeric or hybrid GAG molecules using the *Pasteurella* GAG synthases disclosed and claimed herein. With respect to the above-referenced chimeric or hybrid GAGs, HA=hyaluronan; C=chondroitin; CS=chondroitin sulfate; and HP=heparosan or heparin like molecules.

TABLE VIII

Acceptor Sugar Usage of pmHS1 Test

| | PmHS1 | | Vector | |
|---|---|---|---|---|
| Acceptor Sugar | $^3$H-GlcNAc | $^{14}$C-GlcUA (dpm) | $^3$H-GlcNAc | $^{14}$C-GlcUA (dpm) |
| None | 690 | 580 | 55 | 60 |
| Type D (0.38 μg) sonicated | 4400 | 4500 | 80 | 60 |
| Heparin (10 μg) porcine | 570 | 560 | 50 | 65 |
| HA4 (12.5 μg) | 5900 | 6500 | 85 | 65 |
| HA4 (0.5 μg) | 2200 | 2600 | 60 | 75 |
| HA4-10 (25 μg) | 7400 | 6900 | 75 | 70 |
| HA4-10 (1 μg) | 2300 | 2200 | 120 | 70 |
| HA4 leech (12.5 μg) | 880 | 670 | 45 | 85 |
| HA8-14 leech (25 μg) | 1100 | 1000 | 70 | 90 |

TABLE VIII-continued

| Acceptor Sugar Usage of pmHS1 Test | | | | |
|---|---|---|---|---|
| | PmHS1 | | Vector | |
| Acceptor Sugar | $^{3}$H-GlcNAc (dpm) | $^{14}$C-GlcUA | $^{3}$H-GlcNAc (dpm) | $^{14}$C-GlcUA |
| Hep2 (1 μg) | 1800 | 1700 | 70 | 95 |
| Hep3 (25 μg) | 5800 | 5600 | 55 | 75 |
| Hep3 (1 μg) | 9700 | 10000 | 45 | 90 |

The C-terminal halves of pmHAS and pmCS (the putative GlcUA-transferase) can be switched and the sugar-transfer specificity for GlcNAc and GalNAc is not disturbed. This finding suggested that the hexosamine specificity determinants of the enzymes between GlcNAc- and GlcUA-transfer are located in their amino-terminal halves. To define the critical residues or regions that specify sugar transfer, further domain swapping were performed by PCR-overlap-extension.

Certain chimeric or hybrid constructs, such as pm-EG and pm-IK, are not dual-action enzymes and do not have either pmHAS or pmCS activities. But pm-FH, which possesses pmCS residues 1-258, is an active pmCS, although its remaining part is from pmHAS residues 266-703. When more of the pmCS sequence is replaced by pmHAS sequence as in pm-JL enzyme construct (which possesses pmCS residues 1-214 at the amino-terminal and pmHAS residues 222-703 at the carboxyl-terminal), the enzyme is converted into a catalyst with HAS activity. The conversion of GalNAc-transferring activity into GlcNAc-transferring activity indicated that residues 222-265 of pmHAS and probably the corresponding residues 215-258 of pmCS play critical role in the selectivity between binding and/or transferring of GalNAc and GlcNAc substrate.

Site-directed mutagenesis of region HAS222-265/CS215-258: none of the residues tested in this region are sufficient alone to switch the sugar transfer specificity between pmHAS and pmCS. In the above identified regions, there are 14 residues that are different between pmHAS and pmCS. We checked the primary sequences of the predicted chondroitin synthases from several independent type F *Pasteurella multocida* in the region of 215 to 258. Based on the comparison of these amino acid sequences, most of the differences between pmHAS and pmCS are conserved among those independent strains (FIG. 1). To identify possible critical individual residues that might be important for the selectivity between GalNAc and GlcNAc substrate, we utilized site-directed mutagenesis to change a single or multiple residues in this region. We used either pmHAS1-703 DNA (for I243-, I243/G244/L245-containing mutants) or pmCS$^{1-704}$ DNA (for Y216-, L220-, or C221-containing mutants) as templates and replaced the target residue(s) with the corresponding one(s) in the other enzyme (FIG. 1). Results from enzymatic assays showed that all pmCS$^{1-704}$ mutants transfer GalNAc instead of GlcNAc and all pmHAS$^{1-703}$ mutants transfer GlcNAc instead of GalNAc. This finding indicates that none of the residues that we tested here are sufficient alone to switch the sugar transfer specificity between pmHAS and pmCS.

Domain Swapping Between pmHAS and pmCS: pmcs$^{1-214}$-HAS$^{222-266}$-CS$^{258-704}$ Transfers Both GlcNAc and GalNAc and GlcN Based on the above studies, we hypothesized that additional residues in the 44-residues region were important for the selectivity between GalNAc and GlcNAc transferase. To prove our hypothesis, this region was swapped between pmHAS$^{1-703}$ and pmCS$^{1-704}$ by PCR-overlap-extension. Pm-EG and pPmF4A (a library clone containing pmCS gene locus) DNAs were used to create pmCS$^{1-214}$-HAS$^{222-265}$-CS$^{258-704}$. Pm-FH and pPm7A (a library clone containing pmHAS gene locus) DNAs were used to create pmHAS$^{1-221}$-CS$^{215-258}$-HAS$^{266-703}$ (FIG. 2). PmHAS$^{1-221}$-CS$^{215-258}$-HAS$^{266-703}$ did not express. Interestingly, pmCS$^{1-214}$-HAS$^{222-265}$-CS$^{258-704}$ could transfer both GlcNAc and GalNAc with preference for UDP-GalNAc as judged by HAS assay and CS assay, supporting our conclusion that this region in pmHAS and pmCS plays a critical role in determination of sugar substrate specificity. We also obtained a pmCS$^{1-214}$-HAS$^{222-265}$-CS$^{258-704}$ clone that possesses an additional mutation of I243V; this clone lost GlcNAc-transferring activity and was switched back into a chondroitin synthase. This finding suggests that I243 in pmHAS, and probably V236 in pmCS, plays important yet unknown roles in the determination of sugar substrate specificity.

In order to examine whether pmCS$^{1-214}$-HAS$^{222-265}$-CS$^{258-704}$ could transfer sugars other than GlcNAc and GalNAc, different sugar substrates, including UDP-glucose, UDP-galactose, UDP-mannose, UDP-xylose and UDP-glucosamine (GlcN), along with isotope-labeled GlcUA and HA oligosaccharide acceptor, were included when performing the polymerization assay. The results demonstrated that pmCS$^{1-214}$-HAS$^{222-265}$-CS$^{258-704}$ will use UDP-GlcNAc, UDP-GalNAc, or UDP-glucosamine Table IX. This observation indicated that although swapping of the small region between pmCS and pmHAS resulted in relaxation of substrate selectivity, the enzyme is not so promiscuous that all UDP-sugars will substitute.

Figure 3:
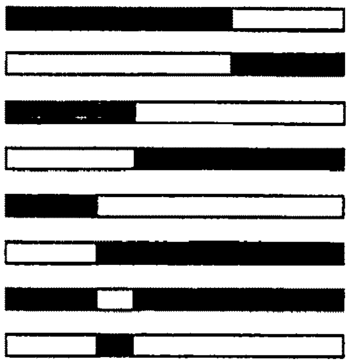
FIG. 3 depicts a summary of enzyme activities of chimeric proteins. The enzymes are drawn as bars. Black bars represent pmCS. White bars represent pmHAS. +, active; –, inactive. PmCHC represents pmCS$^{1-214}$-HAS$^{222-265}$-CS$^{258-704}$. The roles of the two domains are confirmed and we have localized a 44-residue region critical for distinguishing C4 epimers of the hexosamine precursor.

The possibility that the chimeric or hybrid enzyme could synthesize hybrid polymers with a blend of HA- and chondroitin-like sugars was also exploited. Reactions containing $^{3}$H-UDP-GalNAc, $^{14}$C-UDP-GlcNAc, UDP-GlcUA and HA acceptor were performed. The ratio of the incorporation of $^{3}$H-GalNAc and $^{14}$C-GlcNAc changed according to the UDP-sugar ratio in the reaction mixture included in the reaction. Gel filtration analysis of the polymerization products demonstrated that the molecules contain both $^{3}$H and $^{14}$C. The characterization of all the chimeric or hybrid proteins is summarized in FIG. 3. In addition, similar strategies for mutagenesis of PmHS1 and PmHS2 or production of chimeric or hybrid enzymes from portions thereof are expected to produce novel, useful catalysts.

Truncation analysis of pmHAS has identified a carboxyl-terminal region that appears to be responsible for the membrane association of pmHAS. Site-directed mutagenesis studies focused on several conserved motifs indicated that these conserved residues are critical for function. PmHAS and PmCS each contain two separate glycosyltransferase sites (Jing and DeAngelis, 2003). Thus the novel "one polypeptide, two active sites" theory has been confirmed. A 44-residue region of the enzymes has been demonstrated to be critical for sugar-transfer specificity. Based on this discovery, an enzyme that can transfer GalNAc, GlcN, and GlcNAc has been engineered.

TABLE IX

Sugar substrate specificity of pmCS$^{1-214}$-HAS$^{222-265}$-CS$^{258-704}$

| substrate sugar | incorporation |
|---|---|
| UDP-GalNAc | 100% |
| UDP-GlcNAc | 28% |
| UDP-Glucosamine | 2% |

TABLE IX-continued

| Sugar substrate specificity of pmCS$^{1-214}$-HAS$^{222-265}$-CS$^{258-704}$ | |
|---|---|
| substrate sugar | incorporation |
| UDP-Galactose | not detectable |
| UDP-Glucose | not detectable |
| UDP-Mannose | not detectable |
| UDP-Xylose | not detectable |

Standard polymerization assays were performed in the presence of isotope-labeled GlcUA, HA oligosaccharide acceptor, and one of the following sugar substrates. The sugar incorporation was indicated as the percentage of the incorporation of UDP-GalNAc. PmCS$^{1-214}$-HAS$^{222-265}$-CS$^{258-704}$ can transfer GalNAc, GlcNAc, and Glucosamine.

Type A *Pasteurella multocida* produces a hyaluronan [HA] capsule to enhance infection. The 972-residue hyaluronan synthase, pmHAS, polymerizes the linear HA polysaccharide chain composed of GlcNAc and GlcUA. PmHAS possesses two separate glycosyltransferase sites. Protein truncation studies demonstrated that residues 1-117 can be deleted without affecting catalytic activity. The carboxyl-terminal boundary of the GlcUA-transferase resides within residues 686-703. Both sites contain a DXD motif. All four aspartate residues are essential for HA synthase activity. D247 and D249 mutants possessed only GlcUA-transferase activity while D527 and D529 mutants possessed only GlcNAc-transferase activity. These results further confirm our previous assignment of the active sites within the synthase polypeptide. The WGGED sequence motif appears to be involved in GlcNAc-transferase activity because E396 mutants and D370 mutants possessed only GlcUA-transferase activity.

Type F *P. multocida* synthesizes an unsulfated chondroitin GalNAc and GlcUA capsule. Domain swapping between pmHAS and the homologous chondroitin synthase, pmCS, was performed. A chimeric or hybrid enzyme consisting of residues 1-427 of pmHAS and residues 421-704 of pmCS was an active HA synthase. On the other hand, the converse chimeric or hybrid enzyme consisting of residues 1-420 of pmCS and residues 428-703 of pmHAS was an active chondroitin synthase. Overall, these findings support the model of two independent transferase sites within a single polypeptide as well as further delineate the site boundaries.

pmHAS utilizes two separate glycosyltransferase sites to catalyze the transfer of GlcNAc and GlcUA to form the HA polymer. Within the pmHAS sequence, there is a pair of duplicated domains which are similar to the "Domain A" proposed by Saxena. Both domains of pmHAS possess a short sequence motif containing DGS that is conserved among many β-glycosyltransferases. Changing the aspartate in either motif to asparagines, glutamate, or lysine significantly reduced or eliminated the HAS activity. However, the D196 mutants and the D477 mutants maintain high level of GlcUA-transferase and GlcNAc-transferase activity, respectively.

pmCS contains 965 amino acid residues and is about 90% identical to pmHAS. A soluble recombinant *Eschedchia coli*-derived pmCS$^{1-704}$ catalyzes the repetitive addition of sugars from UDP-GalNAc and UDP-GlcUA to chondroitin oligosaccharide acceptors in vitro.

In order to analyze the contribution of the amino terminal region of pmHAS, various recombinant truncated polypeptides were produced (pmHAS$^{46-703}$, pmHAS$^{72-703}$, pmHAS$^{96-703}$ and pmHAS$^{118-703}$) in *E. coli*. The truncated versions pmHAS$^{46-703}$ and pmHAS$^{72-703}$ were as active as pmHAS$^{1-703}$, a soluble polypeptide with complete HAS activity. PmHAS$^{96-703}$ expressed at a very low level compared with other constructs but was active. PmHAS$^{118-703}$ expressed better than pmHAS$^{96-703}$ and still elongated HA chains. Therefore, it is probable that further deletion beyond residue 72 affected the overall folding efficiency of the entire polypeptide. Observation of lower molecular weight degradation bands derived from pmHAS$^{118-703}$ on Western blots also suggests that improper folding occurs to some extent. Overall, these findings suggest that the amino-terminal 117 residues are not required for HA synthase activity.

pmHAS$^{1-850}$ loses its GlcUA-transferase activity. To further delineate the GlcUA-transferase domain within the carboxyl terminal region, two slightly longer mutants, pmHAS$^{1-668}$ and pmHAS$^{1-686}$ were created. Both mutants also could not polymerize HA due to the loss of GlcUA-transferase activity, indicating that the carboxyl-terminal boundary of the GlcUA-transferase resides between residues 686 and 703. Similar analyses of PmHS1 (Kane et al., 2006) suggest that residues ~1-77 and ~601-651 are indispensable for catalytic activity (these truncations have been assigned SEQ ID NOS: 71 and 70, respectively).

Monodisperse Glycosaminoglycan Polymer Synthesis

The size of the hyaluronan [HA] polysaccharide dictates its biological effect in many cellular and tissue systems based on many reports in the literature. However, no source of very defined, uniform HA polymers with sizes greater than 2 to 5 kDa is currently available. This situation is complicated by the observation that long and short HA polymers appear to have antagonistic or inverse effects on some biological systems. Therefore, HA preparations containing a mixture of both size populations may yield contradictory or paradoxical results. One embodiment of the novel method of the present invention produces HA with very narrow, monodisperse size distributions that are referred to herein as "selectHA."

The *Pasteurella* bacterial HA synthase enzyme, PmHAS, catalyzes the synthesis of HA polymers utilizing monosaccharides from UDP-sugar precursors in vivo and in vitro. PmHAS will also elongate exogenously supplied HA oligosaccharide acceptors in vitro; in fact, HA oligosaccharides substantially boost the overall incorporation rate. A purified recombinant, PmHAS derivative was employed herein to produce either native composition HA or derivatized HA. The same general behavior was exhibited by PmCS and PmHS1 and PmHS2; the presence of acceptors stimulated polymerization.

HA polymers of a desired size were constructed by controlling stoichiometry (i.e., ratio of precursors and acceptor molecules). The polymerization process is synchronized in the presence of acceptor, thus all polymer products are very similar. In contrast, without the use of an acceptor, the polymer products are polydisperse in size. In the present examples, stoichiometrically controlled synchronized synthesis reactions yielded a variety of HA preparations in the range of ~15 kDa to about 1.5 MDa. Each specific size class had a polydispersity value in the range of 1.01 for polymers up to 0.5 MDa or ~1.2 for polymers of ~1.5 MDa (1 is the ideal monodisperse size distribution) as assessed by size exclusion chromatography/multi-angle laser light scattering analysis. The selectHA preparations migrate on electrophoretic gels (agarose or polyacrylamide) as very tight bands. Similarly, PmCS and PmHS1 will produce defined monodisperse polymers in reactions with acceptor.

The use of a modified acceptor allows the synthesis of selectHA polymers containing radioactive (e.g., 3H, 125I), fluorescent (e.g., fluorescein, rhodamine), detection (i.e., NMR or X-ray), affinity (e.g., biotin) or medicant tags. In this scheme, each molecule has a single detection agent located at the reducing terminus. Alternatively, the use of radioactive UDP-sugar precursors allows the synthesis of uniformly labeled selectHA polymers with very high specific activities.

Overall, the selectHA reagents should assist in the elucidation of the numerous roles of HA in health and disease due to their monodisperse size distributions and defined compositions. It must be emphasized that unpredicted kinetic properties of the *Pasteurella* GAG synthases in a recombinant virgin state in the presence of defined, unnatural reaction conditions facilitates targeted size range production of monodisperse polymers that are not synthesizable by previously reported methods.

Affect of HA acceptor on pmHAS-catalyzed polymerization. HA polymerization reactions were performed with purified pmHAS and UDP-sugar precursors under various conditions, and the reaction products were analyzed by agarose gel or acrylamide gel electrophoresis. The size distribution of HA products obtained were observed to be quite different based on the presence or absence of the HA4 acceptor in the reaction (Jing and DeAngelis, 2004). When 30 mM of UDP-sugars were present as well as 0.03 ug/ul of HA4, pmHAS synthesized smaller chains with a narrow size distribution. The Mn determined by MALLS is 551.5 kDa and its polydispersity (Mw/Mn) is 1.006 (Jing and DeAngelis, 2004). However, without HA4, pmHAS synthesized a more polydisperse product with the same amount of precursor sugars. The Mn determined by MALLS is 1.53 MDa and its polydispersity (Mw/Mn) is 1.169.

To verify whether pmHAS can utilize HA acceptors of various sizes, parallel assays were set up using the same starting conditions, and at various times additional UDP-sugars were added to the reaction. The result indicated that intermediate products were utilized as starting material for later chain elongation by pmHAS.

Figure 4:
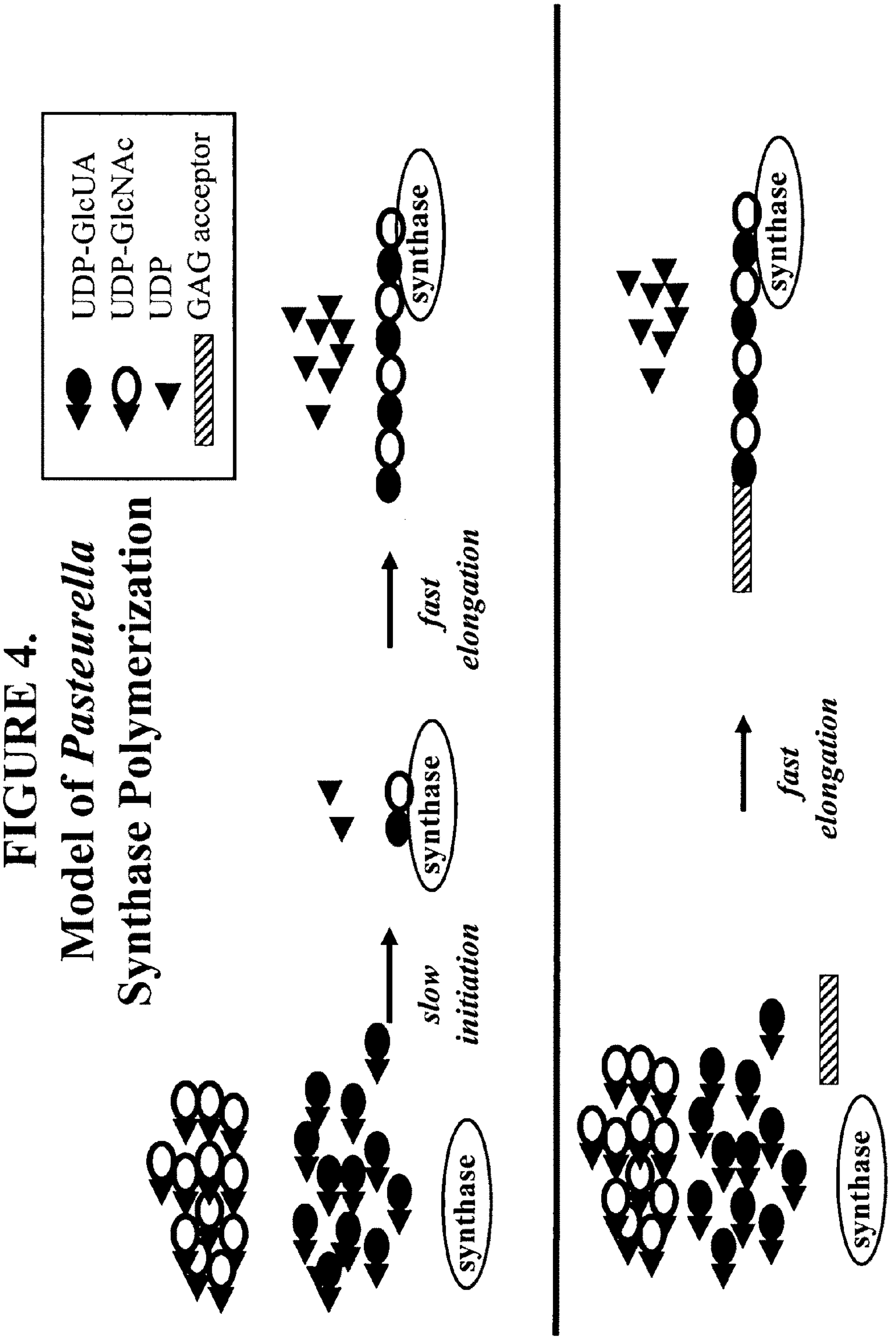
FIG. 4 is a graphical representation of a model of *Pasteurella* synthase polymerization. It is important to note that other uronic acid or hexosamine precursors may be combined or substituted as well. In addition, other acceptor molecules can substitute as the primer for reaction synchronization and size control.
Figure 5:
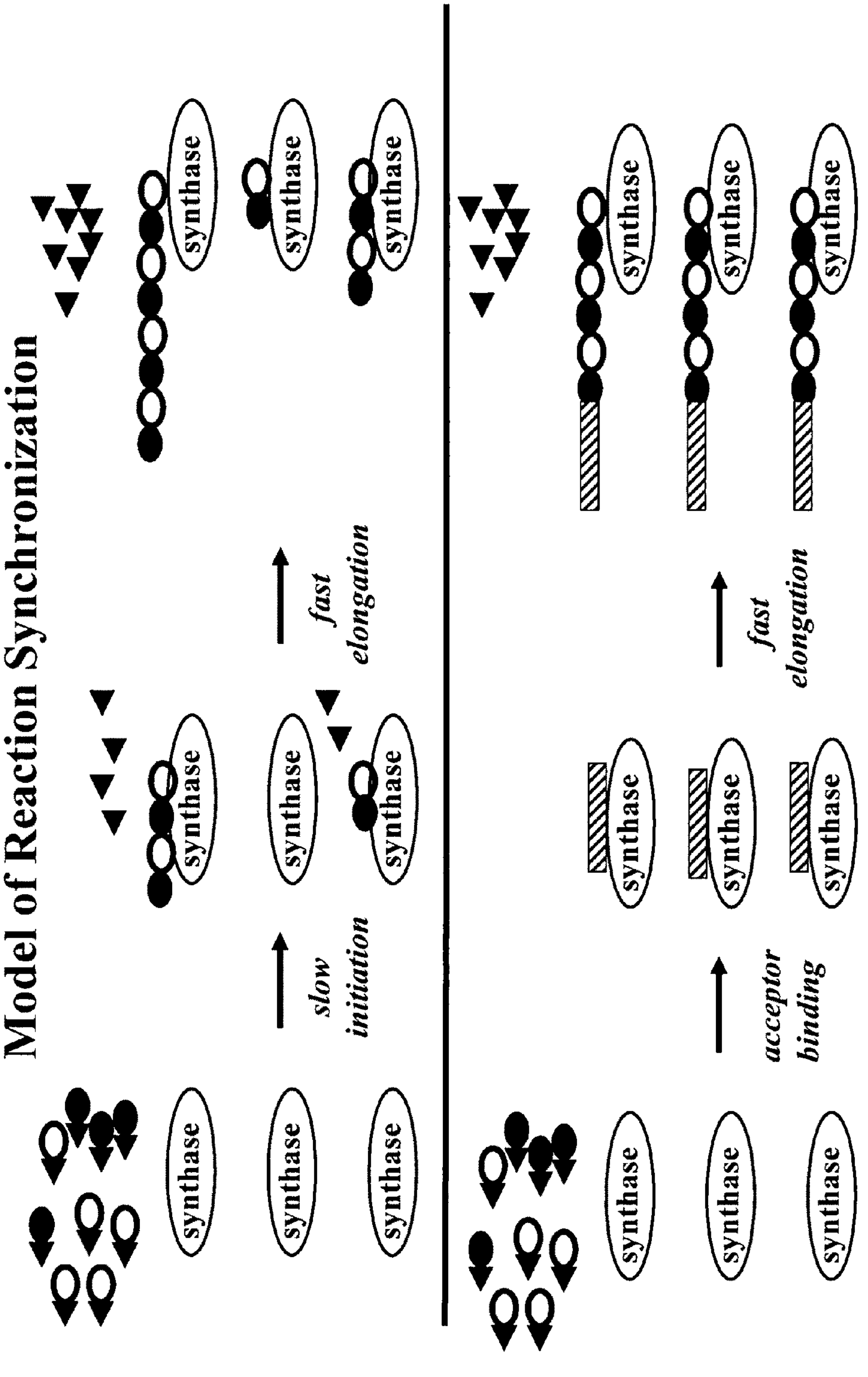
FIG. 5 is a graphical representation of a model of reaction synchronization.

Size control of HA. The polymerization by pmHAS in the presence of HA acceptor is a synchronized process, and thus a more defined HA preparation can be obtained with pmHAS. This synchronization is probably due to the difference in rate or efficiency of new chain initiation versus chain elongation as speculated earlier in DeAngelis, 1999 and depicted in FIG. 4 model. The addition of acceptor appears to bypass the slower initiation step; thus all chains are elongated in parallel resulting in a more homogenous final population (Jing and DeAngelis, 2004). A model demonstrating *Pasteurella* synthase reaction synchronization mediated by acceptor usage is shown in FIG. 5.

Figure 8:
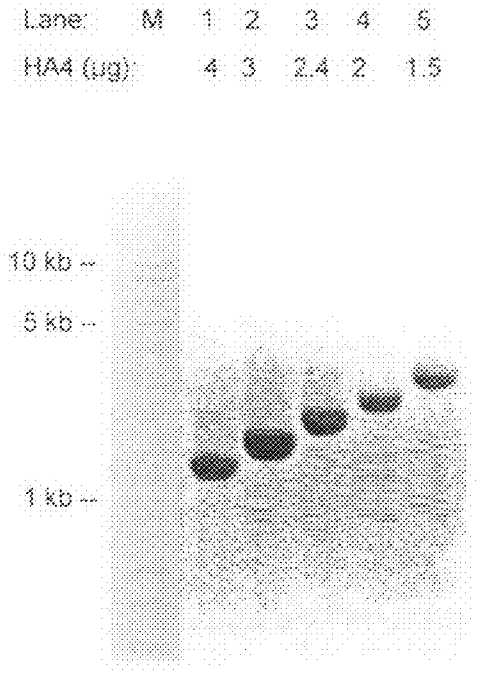
FIG. 8 is a graphical representation illustrating control of HA product size by acceptor concentration. 100 μl of reactions were setup with 0.7 μg/μl of pmHAS, 32 mM of UDP-GlcNAc, 32 mM of UDP-GlcUA and decreasing amount of HA4. HA were purified, and 1 μg of each sample were loaded on a 1.2% agarose gel (A). The molecular mass of HA were determined by MALLS and the results were listed in the table (B). The item numbers in the table correspond to lane number in Panel A. M, Bioline DNA HyperLadder.

The synthase enzyme will preferentially add available UDP-sugar precursors to the acceptor termini. If there are many acceptors, thus many termini, then a limited amount of UDP-sugars will be distributed among many molecules and thus result in many short polymer chain extensions. Conversely, if there are few acceptors, thus few termini, then the limited amount of UDP-sugars will be distributed among few molecules and thus result in a few long polymer chain extensions (modeled in FIG. 6). It has previously been observed that chain initiation is the rate-limiting step for pmHAS, and the enzyme prefers to transfer sugars onto existing HA chains when acceptor is included in the reaction. If the polymerization is indeed a synchronized process, then the amount of HA4 should affect the final size of the HA product when the same amount of UDP-sugar is present. To test this speculation, assays were performed with various levels of HA4 with fixed amount of UDP-sugar and pmHAS (FIG. 8A). To determine the size and polydispersity of these HA products, HA polymer sizes were determined by size exclusion chromatography—Multi Angle Laser Light Scattering (SEC-MALLS, FIG. 8B). Using the same strategy HA was generated from 27 kDa to 1.3 MDa with polydispersity ranging from 1.001 to 1.2. FIG. 8 demonstrates the monodispersity of the various HA polymers resulting from reaction synchronization. This range has been extended from 5 kDa to ~2.5 MDa.

Figure 9:
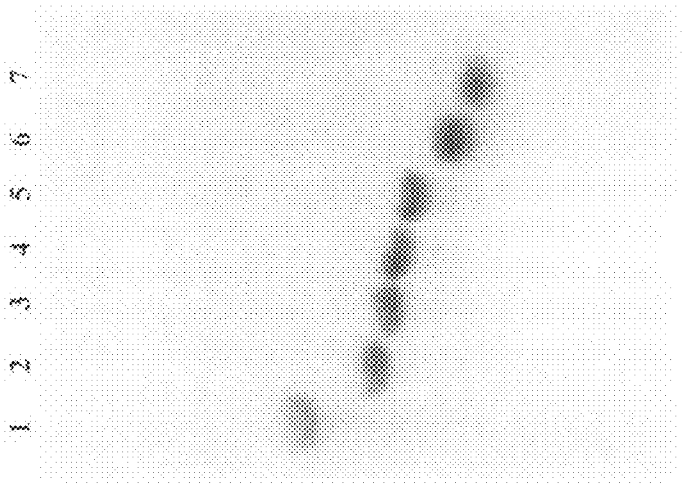
FIG. 9 is an electrophoresis gel illustrating in vitro synthesis of fluorescent HA. 20 μl of reactions were setup with 2 μg/μl of pmHAS various amounts of fluorescent HA4 and UDP-sugars. Reaction products were analyzed with 0.8% agarose gel electrophoresis and viewed under UV light.

In vitro synthesis of fluorescent HA. The in vitro technology for the production of monodisperse glycosaminoglycans also allows the use of modified acceptor to synthesize HA polymers containing various types of foreign moieties. An example is shown using fluorescent HA4 to produce fluorescent monodisperse HA of various sizes (FIG. 9). Similarly, radioactive (e.g., $^{3}H$, $^{125}I$), affinity (e.g., biotin), detection (e.g., probe for NMR or X-ray uses or a reporter enzyme), or medicant tagged glycosaminoglycan polymers are possible with the appropriate modified acceptor. However, the invention is not limited to the tags described herein, and other tags known to a person having ordinary skill in the art may be utilized in accordance with the present invention.

Figure 10:
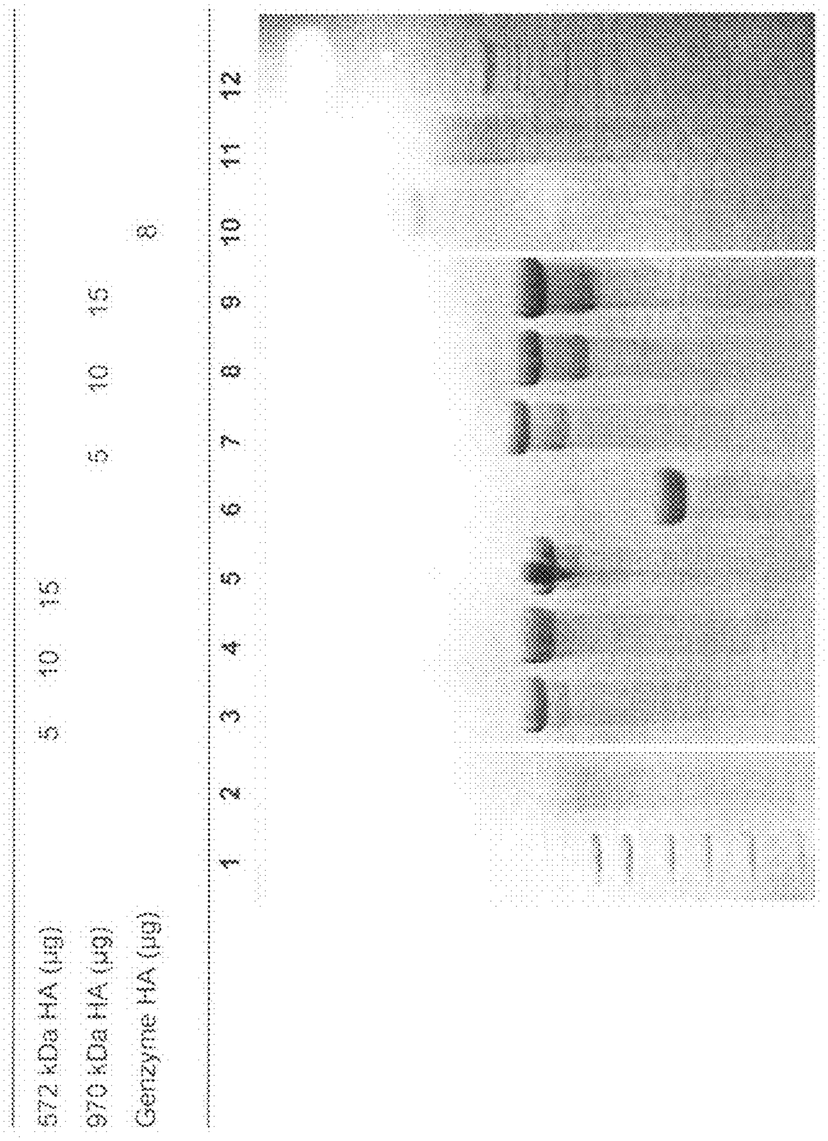
FIG. 10 is an electrophoresis gel illustrating utilization of large HA acceptors. Reactions were carried out at 30° C. for 48 hours. The 60 μl reaction contained 0.28 μg/μl of pmHAS, 3.3 mM UDP-GlcNAc, 3.3 mM UDP-GlcUA and without (lane 2) or with various amounts of acceptors (lanes 3-5, 7-9 and 10). 1.0 μl of each reaction was loaded on 0.7% agarose gel and stained with STAINS-ALL. Lane 1, BIORAD kb ladder (top band is 15 kb). Lane 6, 0.5 μg of 970 kDa HA starting acceptor. Lane 11, 3 μg of Genzyme HA starting acceptor. Lane 12, Invitrogen DNA HyperLadder (top band is 48.5 kB).

In addition to the small sugar chains (e.g., tetrasaccharide HA4), larger HA polymers can be used as starting acceptor for pmHAS; the enzyme will elongate existing chains with more sugars. Experiments were performed using 575 kDa HA and 970 kDa HA (synthesized in vitro with pmHAS and HA4 as acceptor, using the previously described methods) and a commercially available HA sample (~2 MDa; Genzyme) as acceptors. The results indicate that the existing HA chains were further elongated (FIG. 10). For example, the ~2 MDa starting material in lane 11 was elongated to produce the larger (i.e., slower migrating) material in lane 10. Therefore, a method for creating higher value longer polymers is also described by the present invention. The length of the final product can be controlled stoichiometrically as shown in lanes 7-9; a lower starting acceptor concentration (lane 7) results in longer chains because the same limited amount of UDP-sugars is consumed, making a few long chains instead of many shorter chains (lane 9). PmHS1 similarly can elongate longer polymer acceptors; for example, a ~50 kDa polymer served as an acceptor (Kane et al., 2006).

The molecular weights of naturally existing HA polymers usually range from hundreds of thousands up to several millions of Daltons. For research requiring smaller HA polymers, enzymatic degradation is usually the first choice. However, this process is not satisfactory because it is time-consuming and the final yield of the targeted HA size fraction is low, and demanding chromatography is required. With the in vitro synthesis techniques of the present invention, HA as small as 10 kDa can be generated with polydispersity around 1.001.

High molecular HAs are commercially available from animal or bacterial sources. Problems with those include possible contaminants leading to immunological responses as well as broad size distribution (Soltes etc., 2002). Polydispersities (Mw/Mn) are commonly higher than 1.5. Conclusions drawing from experimental data during biological research with these HA could be misleading. Thus there exists a need for uniform HA to perform biological study, as agreed by Uebelhart and Williams (1999).

To determine the exact average molecular mass of HA, MALLS is usually the choice. Yet many people have the need to quickly estimate the mass. For this purpose, some groups investigated the correlation of HA migration on agarose gel with DNA (Lee and Cowman, 1994). The drawback of this method is that, first, the HA samples used were not uniform, and second, the migration of HA and DNA on agarose gel changes differently with the change of the concentration of agarose gel. The in vitro generated HA of defined size distribution provide excellent series of standards for this purpose (FIG. 11).

In general, the unique technologies of the present invention allow the generation of a variety of defined, monodisperse HA tools for elucidating the numerous roles of HA in health and disease due to their monodisperse size distributions and defined compositions.

In addition to making HA polymers, the relaxed acceptor specificity of pmHAS allows the use of various chondroitin acceptors. This allows the production of monodisperse hybrid GAGs that have utility in medicine including tissue engineering and surgical aids. In particular, new protein-free proteoglycans are now possible that do not have antigenicity or allergenicity concerns compared to animal-derived products.

Figure 12:
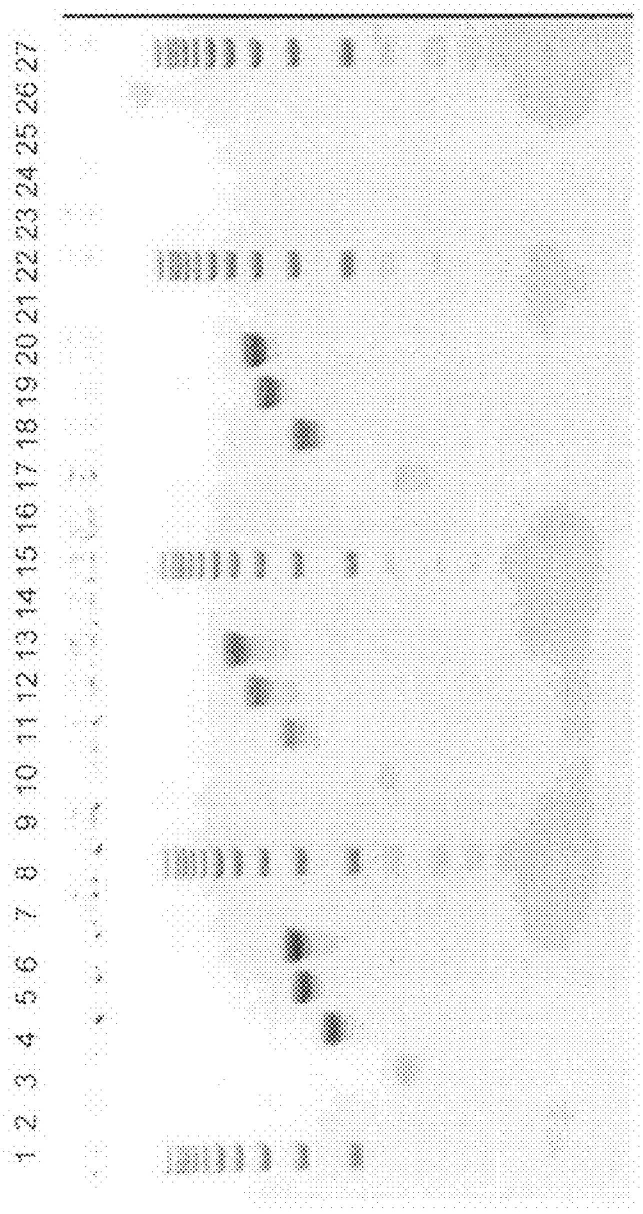
FIG. 12 is an electrophoresis gel illustrating various mondisperse chondroitin sulfate HA hybrid GAGs. The 1% agarose gel stained with STAINS-ALL shows a variety of chondroitin sulfates (either A, B or C) that were elongated with pmHAS, thus adding HA chains. Lanes 1, 8, 15, 22 and 27 contain the Kilobase DNA ladder; lanes 2 and 7 contain starting CSA, while lanes 3-6 contain CSA-HA at 2 hrs, 4 hrs, 6 hrs and O/N, respectively; lanes 9 and 14 contain starting CSB, while lanes 10-13 contain CSB-HA at 2 hrs, 4 hrs, 6 hrs and O/N, respectively; lanes 16 and 21 contain starting CSC, while lanes 17-20 contain CSC-HA at 2 hrs, 4 hrs, 6 hrs and O/N, respectively; lanes 23-26 contain no acceptor at 2 hrs, 4 hrs, 6 hrs and O/N, respectively.

In FIG. 12, various monodisperse chondroitin sulfate HA hybrid GAGs are created by elongating a variety of chondroitin sulfates (A, B, and C) with pmHAS, thus adding HA chains. Various amounts of HA were added to the preparations (at various times during reaction as noted) by adding more UDP-sugars. For example, lanes 3-6 show hybrids with a constant amount of chondroitin sulfate and increasing HA chain lengths. The starting chondroitin sulfates stain weakly here, and the band position is marked with an arrow. Without the acceptor (lanes 23-26), no such defined bands are seen; after a long period, some HA polymer shows up (lane 26) which results from de novo initiation without acceptor.

Figure 13:
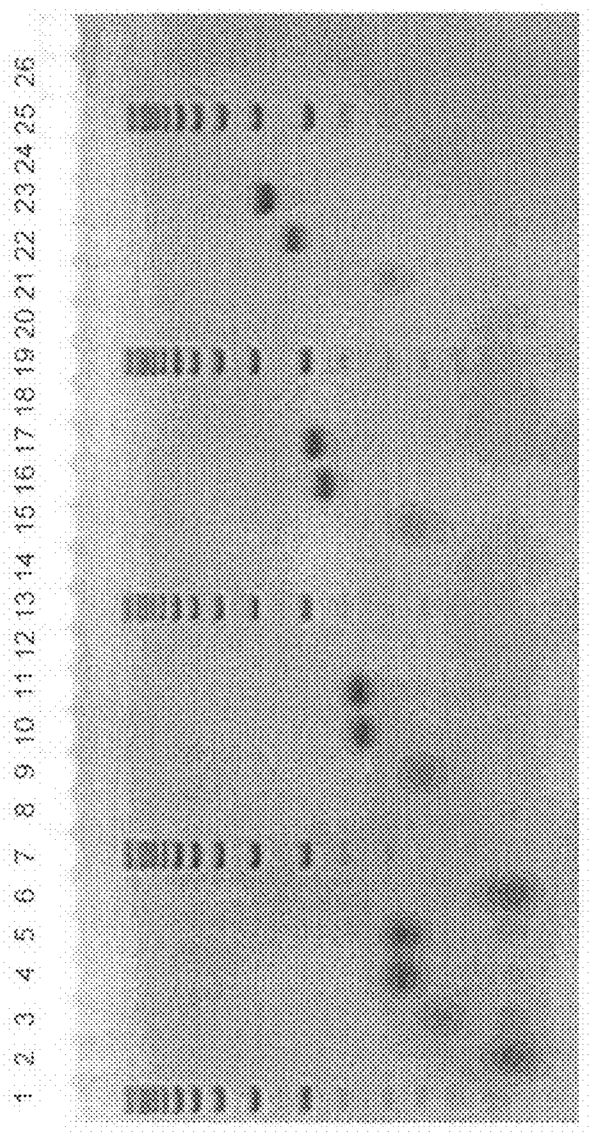
FIG. 13 is an electrophoresis gel illustrating control of hybrid GAG size by stoichiometric control. The 1% agarose gel stained with STAINS-ALL shows chondroitin sulfate A that was elongated with pmHAS, thus adding HA chains. Lanes 1, 7, 13, 19 and 25 contain the Kilobase ladder; lanes 2 and 6 contain 225 μg starting CSA, while lanes 3-5 contain 225 μg CSA-HA at 2 hrs, 6 hrs and O/N, respectively; lanes 8 and 12 contain 75 μg starting CSA, while lanes 9-11 contain 75 μg CSA-HA at 2 hrs, 6 hrs and O/N, respectively; lanes 14 and 18 contain 25 μg starting CSA, while lanes 15-17 contain 25 μg CSA-HA at 2 hrs, 6 hrs and O/N, respectively; lanes 20 and 24 contain 8.3 μg starting CSA, while lanes 21-23 contain 8.3 μg CSA-HA at 2 hrs, 6 hrs and O/N, respectively.

In FIG. 13, chondroitin sulfate A was elongated with pmHAS, thus adding HA chains. Various amounts of HA were added to the preparations by controlling the level of chondroitin acceptor (thus changing the UDP-sugar/acceptor ratio) as well as adding more UDP-sugars during the reaction. By changing the UDP-sugar/acceptor ratio, stoichiometric control of the hybrid GAG size was demonstrated.

In addition to extension with a HA synthase, other GAG synthases may be used in the methods of the present invention. For example, a chondroitin synthase such as but not limited to pmCS can be used to elongate an existing chondroitin sulfate polymer or HA polymer to produce defined hybrid GAG molecules of various structures. Again, these molecules may have use as surgical aids or tissue engineering scaffolds.

Figure 14:
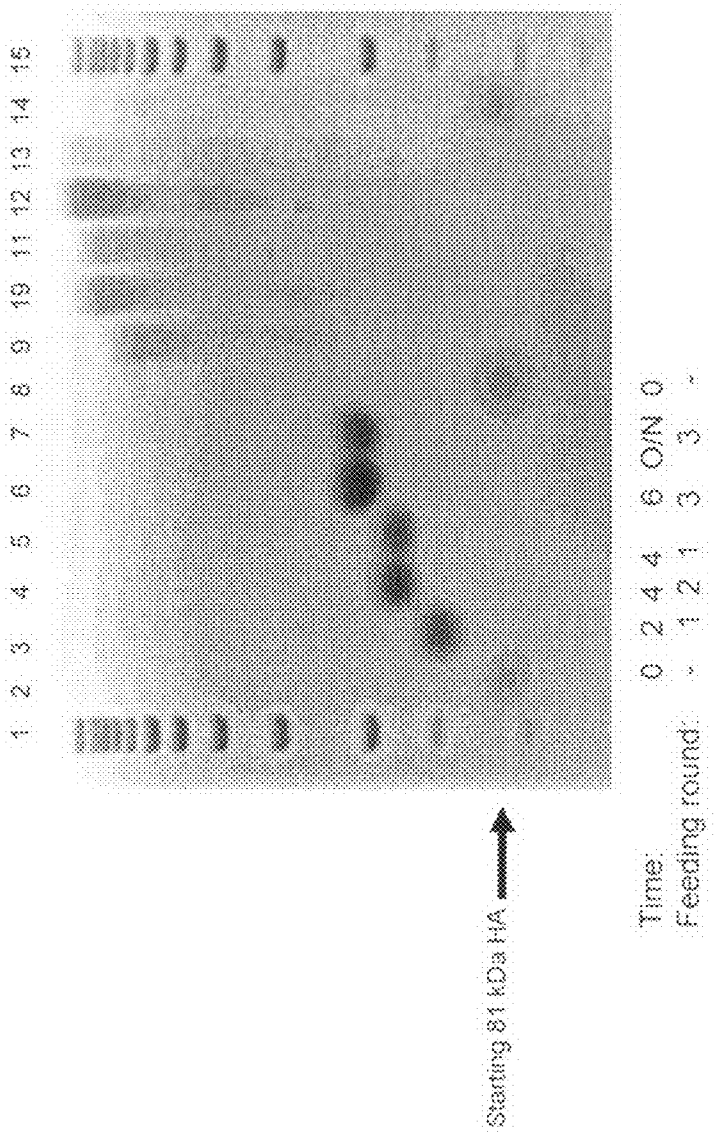
FIG. 14 is an electrophoresis gel illustrating extension of HA with chondroitin chains using pmCS. The 1.2% agarose gel stained with STAINS-ALL shows a reaction with pmCS and UDP-GlcUA, UDP-GalNAc with either an 81 kDa HA acceptor (lanes 3-7) or no acceptor (lanes 9-13). Some reactions were "fed" UDP-sugar during the reaction at various times. Lanes 1 and 15 contain the Kilobase DNA standard. Lanes 2, 8 and 14 contain starting 81 kDa HA. Lanes 3-7: contain HA acceptor +HA-C at 2 hr, 4 hr, 4 hr (set O/N in incubator without 4 hr feeding), 6 hr and O/N, respectively. Lanes 9-13: contain no acceptor (minus) −HA-C at 2 hr, 4 hr, 4 hr (set O/N in incubator without 4 hr feeding), 6 hr and O/N, respectively.

In FIG. 14, pmCS and UDP-GlcUA, UDP-GalNAc were reacted with either a 81 kDa HA acceptor (migration position marked with arrow; lanes 3-7) or no acceptor (lanes 9-13). Various lengths of chondroitin were added to the HA chains (at longer times with more UDP-sugars producing longer hybrid chains). Without the acceptor, no such defined bands were seen; after a long period, some long pure chondroitin polymer shows up which results from de novo initiation without acceptor.

Figure 15:
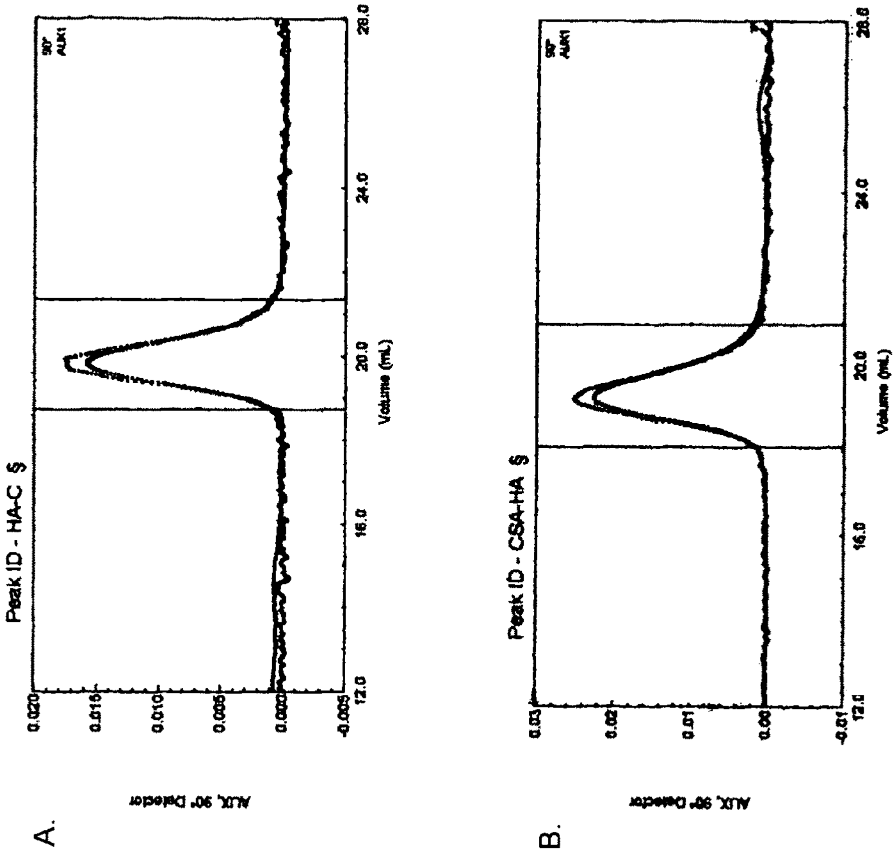
FIG. 15 illustrates size exclusion (or gel filtration) chromatography analysis coupled with multi-angle laser light scattering detection, which confirms the monodisperse nature of polymers created by the present invention. In A, HA (starting MW 81 kDa) extended with chondroitin chains using pmCS (same sample used in FIG. 14, lane #7, overnight [O/N] extension) was analyzed; the material was 280,000 Mw and polydispersity (Mw/Mn) was 1.003+/−0.024. Chondroitin sulfate extended with HA chains using pmHAS (same sample used in FIG. 13, lane #23) was analyzed and shown in the bottom chromatogram; the material was 427,000 Mw and polydispersity (Mw/Mn) was 1.006+/−0.024.

In FIG. 15, Size exclusion (or gel filtration) chromatography analysis coupled with multi-angle laser light scattering detection confirms the monodisperse nature of polymers created by the present invention. In the FIG. 15A, HA (starting MW 81 kDa) extended with chondroitin chains using pmCS (same sample used in FIG. 14, lane #7, overnight [O/N] extension) was analyzed; the material was 280,000 Mw and polydispersity (Mw/Mn) was 1.003+/−0.024. Chondroitin sulfate HA extended with HA chains using pmHAS (same sample used in FIG. 12, lane #23) was analyzed and shown in FIG. 15B; the material was 427,000 Mw and polydispersity (Mw/Mn) was 1.006+/−0.024.

Figure 16:
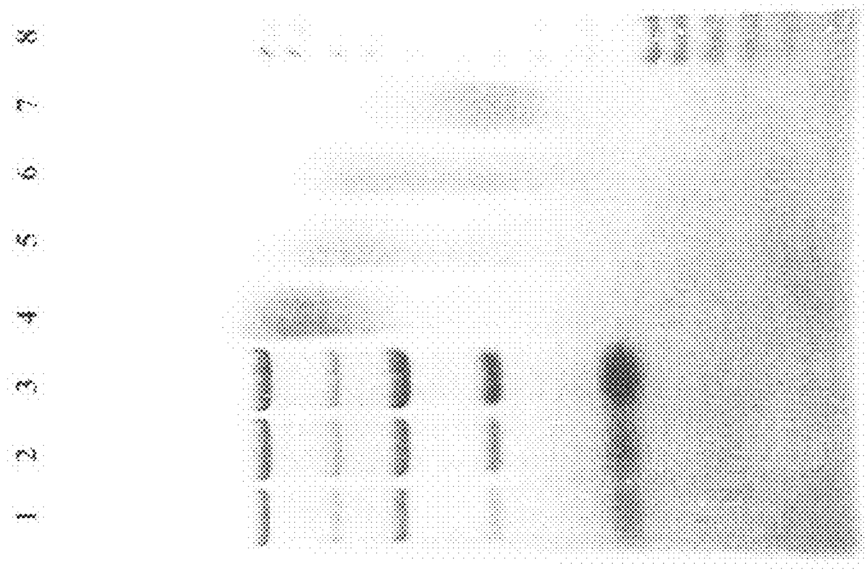
FIG. 16 is an 0.7% agarose gel detected with Stains-all that compares the monodisperse, 'select HA' to commercially produced HA samples. The defined nature of 'selectHA' (the products in lanes 1-3) are evident compared to other extracted commercial HA in lanes 4-7 (DNA standard, lane 8).

In FIG. 16, a 0.7% agarose gel detected with Stains-all compares the monodisperse, 'select HA' to commercially produce HA samples is shown. In lanes 1-3, the mixture of various monodisperse HAs made by the present invention (separate reaction products that were recombined to run all in one lane; sizes from top to bottom of lane: 1.27 MDa, 946 kDa, 575 kDa, 284 kDa, 27 kDa) run as discrete, tight bands. In contrast, in lanes 4-7, the commercially produced HA samples run as polydisperse smears (lane 4, 1.1 MDa; 5, 810 kDa; 6, 587 kDa; 7, 350 kDa). Remarkably, the monodisperse HA bands look almost as narrow as the single-molecule species of DNA present in lane 8 (BIOLINE standard).

Next, it was demonstrated that the catalytic utility of PmHS1 and PmHS2 are very distinct as measured by various criteria, including their ability to produce polymers either with monodisperse size distributions or with unnatural sugar compositions.

Figure 17:
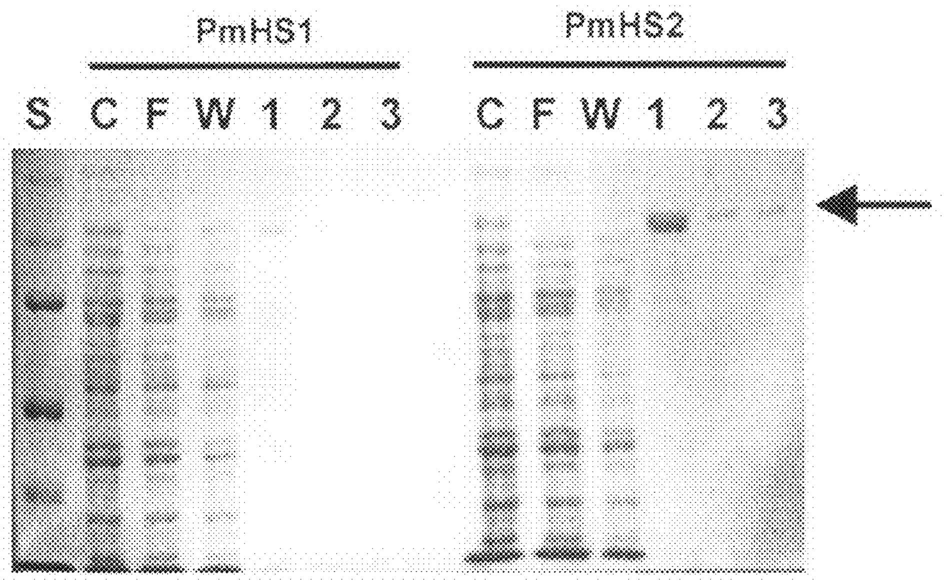
FIG. 17 is a gel analysis of recombinant heparosan synthase proteins (maltose binding protein (MBP)-PmHS fusions). This Coomassie Blue-stained polyacrylamide gel (8%) depicts substantial purification of the two enzymes by affinity chromatography on immobilized amylose. Lanes: S, molecular mass standards (top to bottom 150, 100, 75, 50, 37 kDa); C, starting *E. coli* lysate; F, flow through; W, wash; 1, 2, 3, eluted fractions from amylose column. The bands marked with an arrow are the appropriate molecular weight for the MBP-PmHS fusion constructs (~113 kDa) and are immunoreactive with anti-PmHS peptide antibody (data not shown). The eluted protein possesses heparosan polymerization activity; the majority of lower molecular weight bands are degradation products that are immunoreactive with anti-heparosan synthase and anti-maltose binding protein antibodies.

The maltose binding protein/heparosan synthase fusion constructs (Sismey-Ragatz et al., 2007) had greatly increased protein expression in comparison to the earlier generation thioredoxin PmHS1 fusion construct (Kane et al., 2006). The MBP also allowed for efficient purification as depicted in FIG. 17; in contrast, the thioredoxin affinity handle was observed to leach substantial amounts of target protein thus thwarting purification attempts (data not shown). Furthermore, both MBP-PmHS constructs possessed increased stability at useful reaction temperatures (e.g., active at pH 7.2 at 30° C. for 24 hrs).

Previous studies on the efficiency of cognate acceptor utilization by the crude native sequence enzymes suggested that these relatively homologous *Pasteurella* synthases had different catalytic properties; acceptor stimulated PmHS1 sugar incorporation ~7- to 25-fold (by serving as a primer to circumvent the slow initiation step) while PmHS2 is boosted only ~2.5-fold (DeAngelis et al., 2002 and 2004). These levels of acceptor stimulation were also observed for the purified fusion enzymes. In polymerization assays without acceptor, it also appears that purified PmHS2 has ~2-fold higher level of de novo initiation of sugar chains compared to purified PmHS1 (~5.2 versus ~2.6 pmoles monosaccharide transferred/min/μg protein). On the other hand, it appears that PmHS1 has an elongation rate which is ~3-fold faster than PmHS2 (~76 versus ~28 pmoles monosaccharide transferred/min/μg protein).

Figure 18:
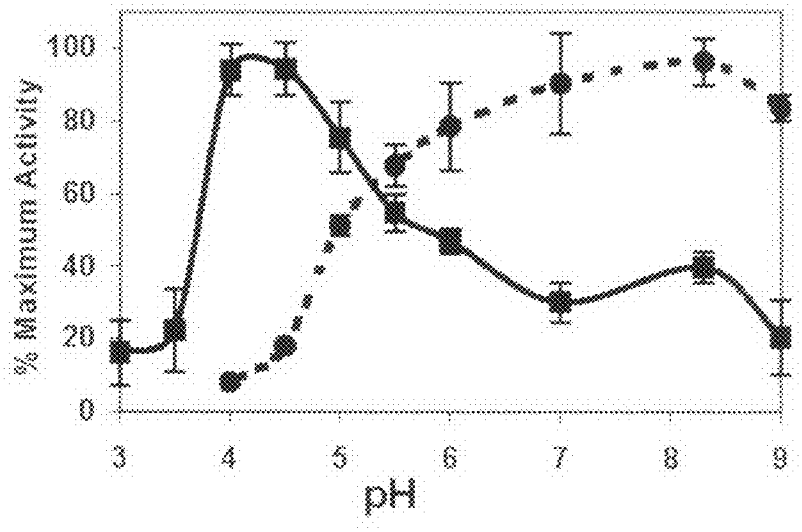
FIG. 18 depicts pH dependence of PmHS1 and PmHS2 polymerization activity. The incorporation of [$^3$H]GlcUA into a polysaccharide catalyzed by either PmHS1 or PmHS2 (~1.5 μg) was measured in polymerization reactions buffered at different pH values. Sodium acetate was used for pH 3-7 and Tris HCl was used for pH 7-9. The assay with the maximal activity was set to 100% to normalize the plot. Three independent reactions were performed; standard deviation is shown. PmHS1 (dotted line, circles) operates best at neutral pH, but PmHS2 (solid line, squares) works faster at acidic pH.

The pH profiles as determined by polymerization assays were also different; the purified PmHS1 catalyst preferred a neutral pH while purified PmHS2 preferred acidic (pH ~4-5) conditions (FIG. 18). This result of differential activity was not expected considering that the protein sequences of PmHS1 and PmHS2 are relatively homologous. Simplistically, based on expected amino acid side-chain $pK_a$ values it may be likely that one or more histidine residues in PmHS2 (but not present in PmHS1) is protonated at the lower pH, thus gaining a positive charge, making a better contact or providing improved electrostatic steering for a negatively charged substrate (either a heparosan oligosaccharide or a UDP-sugar). Alternatively, one or more glutamate or aspartate residues in PmHS2 (but not PmHS1) are protonated at lower pH, thus neutralized, reducing potential electrostatic repulsion of a negatively charged substrate. It is important to note that even though PmHS2 prefers the acidic pH for maximal activity, this catalyst is not very stable in those conditions. The PmHS2 protein did not demonstrate noticeable additional proteolysis at low pH as assessed by western blotting (not shown), thus the loss of activity must be due to denaturing via an unfolding event.

The size of acceptor oligosaccharide preferred by each of the synthases was also examined. The heparosan tetrasaccharide was about ~150-fold and ~8-fold better than the corresponding disaccharide for PmHS1 or for PmHS2, respectively. In addition, the synthetic glycoside, AFA, was also a useful acceptor for PmHS1 and PmHS2. These findings suggest that the size of the active site pockets of the heparosan synthases may be similar to those hypothesized for the acceptor sites of PmHAS; a site that appears to bind 3 or 4 monosaccharides is hypothesized to make contact with the nascent HA chain. Simpler glycosides are also good acceptors for PmHS1 or PmHS2.

Figure 6:
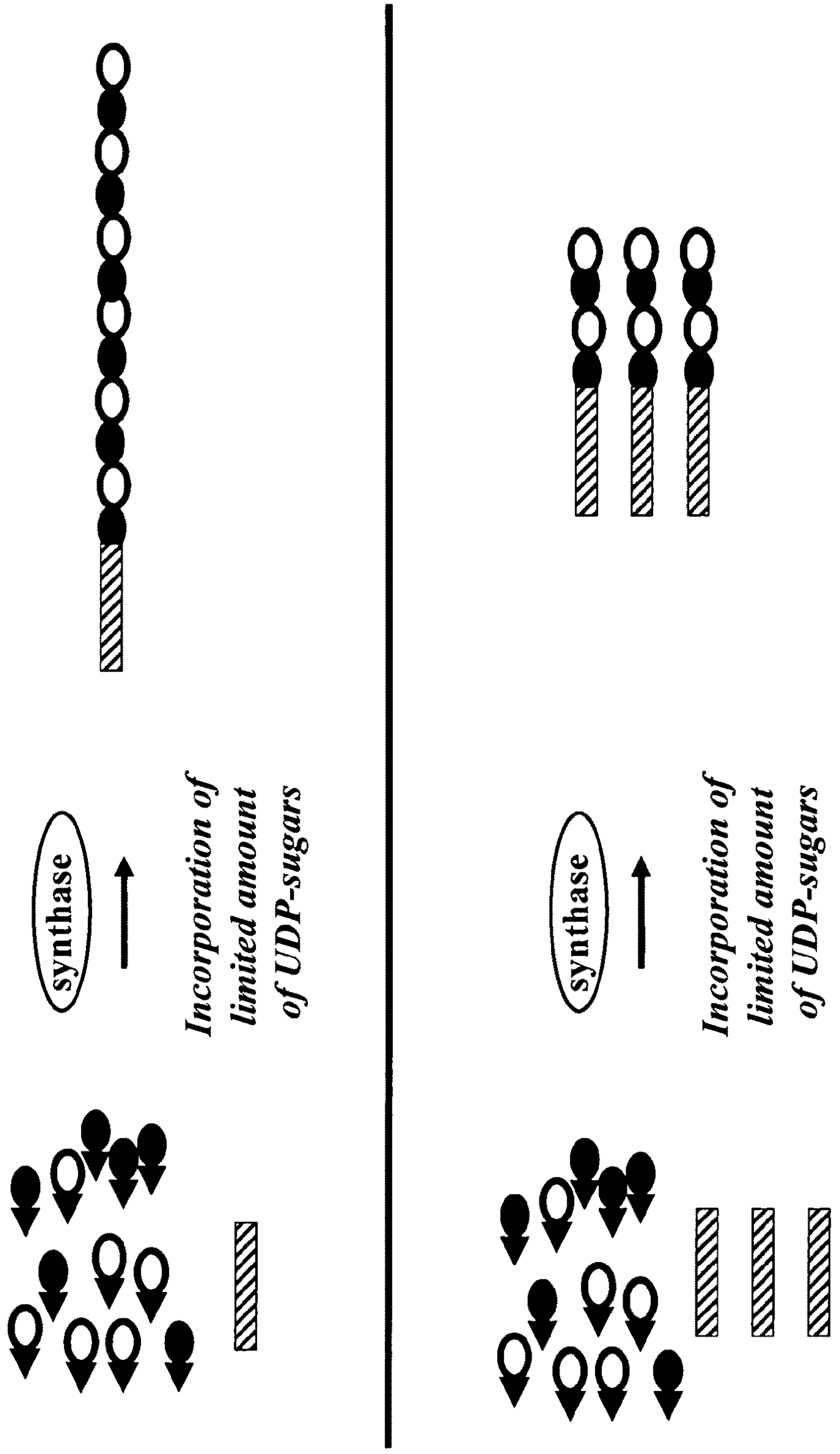
FIG. 6 is a graphical representation of a model of stoichiometric control of polymer size.
Figure 7:
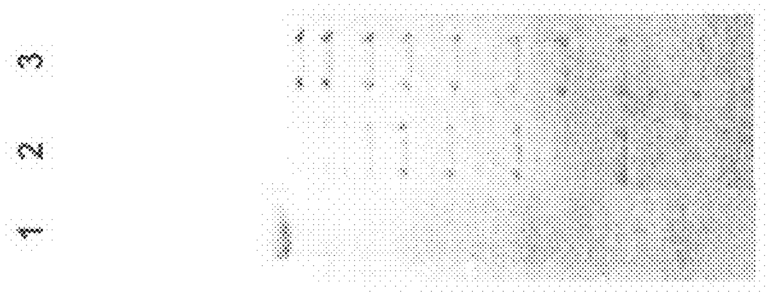
FIG. 7 is an electrophoresis gel illustrating that in vitro generated HA can reach the molecular mass of 1.3 MDa. Lane 2, Bio-Rad 1 kilobase DNA ruler with the top band of 15 kb. Lane 3, Bioline DNA hyperLadder with the top band of 10 kb.
Figure 19:
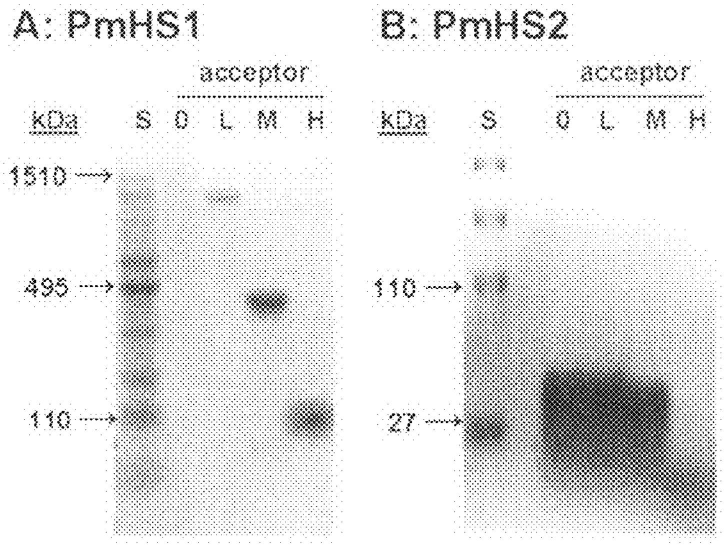
FIG. 19 is an agarose gel analysis of monodisperse heparosan polymers. Increasing amounts of heparosan oligosaccharide (n=2, 3) acceptor (lanes: 0, none; Low, 0.23 nM; Medium, 2.3 nM; High, 22 nM final conc.) were added to 40 μl reactions containing 5 mM UDP-GlcUA, 5 mM UDP-GlcNAc and 13 μg of heparosan synthase catalyst. Polymer (20 μl portion) was analyzed by agarose gel electrophoresis with Stains-All detection. Panel A: PmHS1, 1.2% gel (S, Select-HA™ LoLadder and HiLadder). Panel B: PmHS2, 3% gel (S, Select-HA™ LoLadder). All polymers were sensitive to heparin lyase III (not shown). The average molecular masses were determined by SEC-MALLS. PmHS1 forms products with a narrow size distribution (polydispersity $M_w/M_n$=1.06 to 1.18; for reference, the value of an ideal monodisperse polymer is 1) and may be readily stoichiometrically controlled (as indicated by the three different size bands of 800 kDa, 380 kDa, and 100 kDa (L, M and H lanes, respectively)). On the other hand, PmHS2 in the presence of acceptor makes somewhat more polydisperse samples ($M_w/M_n$=1.1 to 1.63) with lower molecular weight (28 kDa, 24 kDa and 8 kDa (L, M and H lanes, respectively)) and it is more difficult to control of the final polymer size.

Monodisperse Heparosan—Synchronized polymerization reactions should result in monodisperse heparosan polymers as previously observed for PmHAS, as described herein. The formation of heparosan with narrow size distribution is dependent on the ability of the glycosyltransferase to be primed by acceptors (thus avoiding a slow de novo initiation event yielding out of step elongation events) and efficiently transfer monosaccharides from UDP-sugars (FIG. 4-6). It is likely that PmHS1 catalyzes the synthesis of higher molecular weight monodisperse polymer when compared to PmHS2 due to its better ability to utilize and rapidly elongate exogenously supplied acceptors. As determined by agarose gel and SEC-MALLS analyses (FIG. 19), PmHS1 produced various sizes of monodisperse high molecular weight heparosan (~70% average yield based on starting UDP-sugars) while under identical conditions PmHS2 did not. Such monodisperse heparosan polymer may serve as the starting material for the creation of defined molecules that are more predictable with respect to biological responses and potency.

Production of Glycosaminoglycan Polymers with Unnatural Structures

The testing of a variety of different UDP-sugar donor substrates is a means to determine the tolerance of the synthase active sites for a variety of donor and acceptor functional groups. Characterizing donor preference is obvious, but in the case of a polymer with repeating saccharide units, once a sugar is added onto the non-reducing terminus of the nascent chain, the unnatural sugar then serves as an acceptor substrate. Therefore, a successful analog must be able to play multiple roles to produce a polysaccharide chain.

Figure 20:
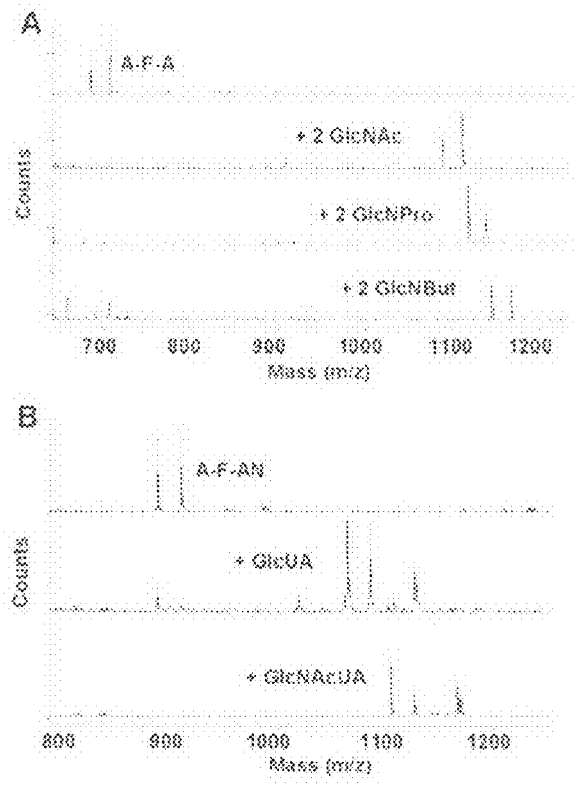
FIG. 20 depicts mass spectral analyses of PmHS2-catalyzed single sugar addition of UDP-sugar analogs. The usage of UDP-substrates was detected by the formation of the target compound with the appropriate negative ion molecular mass by MALDI-ToF MS. In each spectrum, the larger molecular weight peak (+22 Da) corresponds to the addition of sodium instead of a proton to the carboxylate. Panel A: PmHS2 (~1-2 μg, 8 μl reaction, 30° C., ~6-12 hrs) catalyzed the transfer of monosaccharide from various UDP-hexosamines (UDP-GlcNAc, UDP-GlcNPro or UDP-GlcNBut; ~1-3 mM final) to a synthetic GlcUA-terminated acceptor, A-F-A (~0.6 mM; predicted 683.13 Da, observed 683.13 Da) to form longer molecules (A-F-A+2 GlcNAc product, predicted 1089.29 Da, observed 1089.12 Da; A-F-A+2 GlcNPro product, predicted 1117.32 Da, observed 1117.88 Da; A-F-A+2 GlcNBut product, predicted 1145.35 Da, observed 1145.19 Da). Panel B: PmHS2 was tested with UDP-uronic acids (UDP-GlcUA or UDP-GlcNAcUA) and a synthetic GlcNAc-terminated acceptor, A-F-AN (predicted 886.21 Da, observed 886.09 Da), using the same conditions described above (A-F-AN+ GlcUA product, predicted 1062.24 Da, observed 1062.03 Da; A-F-AN+2 GlcNAcUA product, predicted 1103.25 Da, observed 1103.10 Da). PmHS2 can mis-incorporate a variety of unnatural analogs.

MALDI-ToF MS analyses and radiolabeled sugar incorporation assays revealed that PmHS2 has the ability to catalyze the incorporation of several unnatural donor sugar analogs while PmHS1 appears much more strict (Table X, FIG. 20). The GlcNAc-transferase site of PmHS2 will accept different acyl chain lengths at the C2 position as long as the amine is acylated, but does not appear to tolerate substitution at the C3 or C5 positions. Interestingly, UDP-GlcNPro, the UDP-GlcNAc analog with an extra methylene group in the acyl chain, is preferred by both enzymes more than the authentic substrate; perhaps a hydrophobic pocket is responsible for this catalyst/substrate contact. However, this pocket must have limited dimensions because UDP-GlcNBut, a molecule with two more additional methylene units than the authentic donor, is a worse substrate. Other hydrophobic moieties with different structures are expected to serve as donors as well. By analogy, a hydrophobic pocket on glycosaminoglycan binding proteins or receptors such as the HA-binding site of TSG-6 (Blundell et al., 2005) may bind with higher affinity to polymers containing hexosamines with longer acyl chains, thus new sugar ligand derivatives with more potent inhibition or signaling effects may be possible.

TABLE X

Donor Substrate Usage by PmHS1 and by PmHS2.

| UDP-Sugar Analog | PmHS1 substitutes for: UDP-GlcUA? | PmHS1 substitutes for: UDP-GlcNAc? | PmHS2 substitutes for: UDP-GlcUA? | PmHS2 substitutes for: UDP-GlcNAc? |
|---|---|---|---|---|
| UDP-GlcN | n.a. | – | n.a. | – |
| UDP-GlcNAcUA | – | – | + | – |
| UDP-GlcdiNAc | n.a. | – | n.a. | – |
| UDP-GlcdiNAcUA | – | – | + | – |
| UDP-GlcNBut | n.a. | – | n.a. | + |
| UDP-GlcNPro | n.a. | +++ | n.a. | +++ |

Each UDP-sugar analog was tested for its ability to substitute for UDP-GlcNAc or UDP-GlcUA by radiolabeled sugar polymerization assays and paper chromatography. An authentic UDP-sugar and the appropriate second UDP-sugar analog (e.g., UDP-GlcUA and a potential UDP-GlcNAc substitute) were co-incubated with enzyme. The rates for the combination of both authentic donors, UDP-GlcNAc and UDP-GlcUA, are set to 100%; analogs are presented as +++ = >200%, ++ = 100-11%, + = 10-1%, – = <~0.2%, n.a., not applicable. All positive compounds were verified by single sugar addition assays with mass spectrometry (FIG. 20) except for UDP-GlcdiNAcUA due to low transfer efficiency. Overall, PmHS2 can mis-incorporate several analogs, but PmHS1 appears to have more restricted donor usage.

The GlcUA-transferase site of PmHS2, but not PmHS1, is tolerant of extra chemical groups at the C2 or C3 positions (Table X). The UDP-GlcNAcUA analog possesses within a single pyranose unit both the C6 carboxylate and the C2 acetylated amide groups (normally found separately on two adjacent pyranose units in native heparosan). It was observed that the PmHS2 enzyme only utilizes this analog to substitute for the uronic acid unit of the disaccharide repeat, and not the hexosamine (Table X). At this time, it is difficult to predict if this analog fails as a hexosamine because it is a poor donor and/or a poor acceptor. Preparative syntheses employing PmHS2 catalyst with no acceptor gave average polymer yields of ~60% or ~22% for authentic heparosan versus unnatural GlcNAcUA-containing heparosan, respectively. Higher concentrations of UDP-sugar precursor helped compensate for the slower incorporation rates of some unnatural analogs.

The relaxed specificity of PmHS2 could be due to different active site geometry or different surrounding residues than PmHS1, which facilitates the favorable binding interactions and/or avoids certain hindrances (e.g., steric, electrostatic) with the analogs. Overall, these results help to elucidate the nature of the synthase active site without an experimentally determined three-dimensional enzyme structure.

From previous work and here with purified PmHS1 and PmHS2, the isomeric state of the C4 hydroxyl of the UDP-sugar precursors appears to be critical for these synthases because the C4 epimers of the authentic substrates, UDP-GalNAc and UDP-GalUA, are not functional analogs in the polymerization assay (not shown). This observed stringency is probably due to the importance of the hydroxyls forming the glycosidic linkages of the heparosan chain, (-GlcUA-β1,4-GlcNAc-α1,4-), residing in the correct orientation for catalytic residues to couple the saccharide units.

The evolutionary history of PmHS1 and PmHS2 is not yet known. Two opposing hypotheses are possible: (I) the "traditional" scenario where a gene encoding a substrate selective PmHS1 progenitor was duplicated and the resulting PmHS2 ancestor, unfettered from its normal duty of making heparosan, became less specific for a potential hitherto unknown function, or (II) a more recently recognized scenario (Jensen, 1976) where a gene encoding a nonspecific PmHS2 progenitor was duplicated resulting in a PmHS1 ancestor that became more substrate specific in order to make heparosan. As PmHS2 (but not PmHS1) occurs in many Type A and Type F strains (HA or chondroitin capsule producers, respectively), model II may be more likely. More DNA sequence information from other isolates and species may be required to establish whether PmHS1 or PmHS2 was the primordial enzyme. Pathogenic bacteria are under extreme selective pressure from host defenses thus the potential to alter capsule composition and maintain virulence is a valuable asset.

Figure 21:
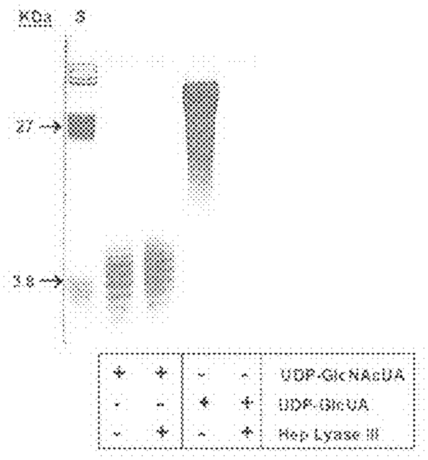
FIG. 21 depicts heparin lyase challenge of native and analog polymers. Two different polymers were synthesized with PmHS2 using UDP-GlcNAc and one of the indicated UDP-uronic acids (either UDP-GlcNAcUA analog or natural UDP-GlcUA). Half of the polymer sample was subjected to heparin lyase III treatment overnight before analysis on a 15% polyacrylamide gel (S, Select-HA™ LoLadder and nanoHA$_{10-20}$™ ladder; key sizes denoted in kDa). The GlcNAcUA-containing polymer was resistant to digestion while the native heparosan was totally degraded.

The promiscuity of PmHS2 makes it a useful catalyst for preparing glycosaminoglycan polymer analogs with new biological or chemical properties. For example, unnatural polymers containing the GlcNAcUA monomer are not digested by heparin lyase III, an enzyme known to digest most other heparinoids (FIG. 21). Depending on the substitutions, similar heparinoids may have a slower turnover rate potentially making it a longer acting therapeutic. These new polymers should also prove to be very useful in the pursuit of understanding the structure/function relationships of the polymer and the interaction of heparinoids with various binding proteins including receptors, growth factors, and coagulation factors.

Figure 22:
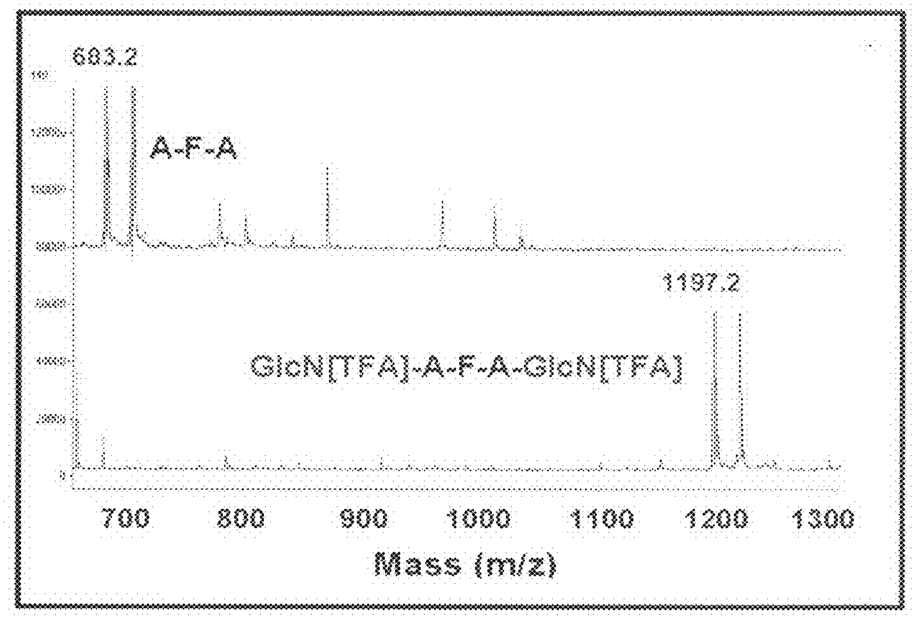
FIG. 22 depicts mass spectral analyses of PmHS2-catalyzed single sugar addition of UDP-GlcN[TFA]. PmHS2 (~1-2 μg, 8 μl reaction, 30° C., ~6-12 hrs) catalyzed the addition of GlcNTFA to the nonreducing termini of a GlcUA-terminated synthetic glycoside acceptor, A-FA (~0.6 mM) (Eq.3). This was detected by MALDI-ToF MS and is evident by the formation of a peak with the expected larger mass (predicted exact mass 1197.18; observed mass 1197.21). The same type of result was observed for PmHAS.
Figure 23:
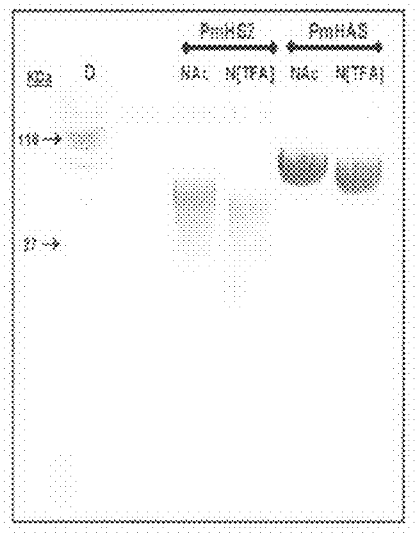
FIG. 23 depicts PAGE analyses of GlcN[TFA] containing polymers synthesized by PmHS2 and PmHAS. PmHS2 or PmHAS (~12 and 100 μg) respectively, were incubated with 25 mM UDP-GlcUA and either UDP-GlcNAc (NAc) or UDP-GlcN[TFA] (N[TFA]) at 30° C., overnight. Reactions were run on polyacrylamide gels (12%) and polymers were detected by Alcian Blue stain. Natural and unnatural polymers were synthesized by the *Pasteurella* enzymes with approximately equal sizes and yields. (D; DNA standard; the position of the HA standards 110 and 27 kDa are depicted with arrows).

Single sugar addition and polymerization assays confirmed that both PmHAS and PmHS2 would utilize the UDP-GlcN[TFA] (UDP-N-(trifluoroacetyl)glucosamine) as a hexosamine donor substitute (FIGS. 22 and 23). In contrast, PmHS1, recombinant *Xenopus* HAS and recombinant *Streptococcus* HAS did not effectively transfer UDP-GlcN[TFA] (>0.01% for PmHS1, ~1.0% for *Xenopus* and streptococcal HAS). This data indicates again that PmHS2 has relaxed specificity at the C-2 position in the GlcNAc transferase site and reveals for the first time that PmHAS will also tolerate unnatural groups at the C-2 position. The relative efficiency of catalyst to transfer UDP-GlcN[TFA] was assessed by radiolabel incorporation and PAGE.

Figure 24:
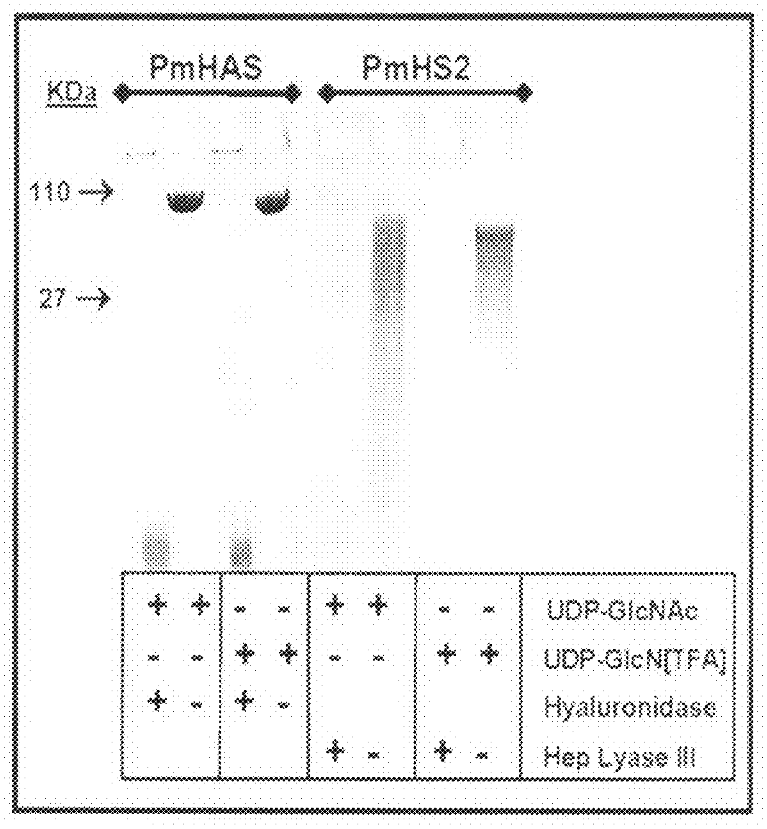
FIG. 24 depicts lyase challenge of Natural and GlcN[TFA] containing polymers. Two different polymers were synthesized with PmHS2 or PmHAS using UDP-GlcUA and one of the indicated UDP-hexosamine sugars (either UDP-GlcN[TFA] analog or natural UDP-GlcNAc). Half of the polymer sample was subjected to hyaluronidase or heparosan lyase III treatment. Key sizes denoted in kDa. The GlcN[TFA]-containing polymers were not resistant to digestion.

GAGs mediate many of their biological effects via interactions with proteins. Here, the binding properties and the sensitivity to degradation enzymes of the unnatural GlcN[TFA] polymer in comparison to the natural HA polymer were tested. One of the major HA binding proteins is CD44, a glycoprotein expressed on most cell surfaces and facilitates many signaling events as well as the cellular intake of HA. Only a portion of the CD44 protein (residues 1-199) was used in this study; this domain contains the link module which facilitates HA binding. HABP or aggrecan also specifically binds to HA and is a huge proteoglycan complex found in cartilage. Aggrecan is composed of three gobular domains and two extended regions, but in this assay, only the link module in the gobular 1 domain (HA binding region) was tested for binding. ELISA binding assays indicated that the GlcN[TFA] polymer binds at least 100-fold more weakly to both HA binding proteins, HABP and CD44, compared to HA polymer of similar size. Unlike PmHAS, which will bind and extend a GlcN[TFA] polymer, these HA binding proteins will not tolerate a TFA group at the C-2 position. Digestion experiments using Heparin Lyase III and hyaluronidase determined that the GlcN[TFA]-containing GAG polymers are susceptible to degradation by the appropriate enzyme and thus, recognized by these distinct degradative enzymes (FIG. 24).

Figure 25:
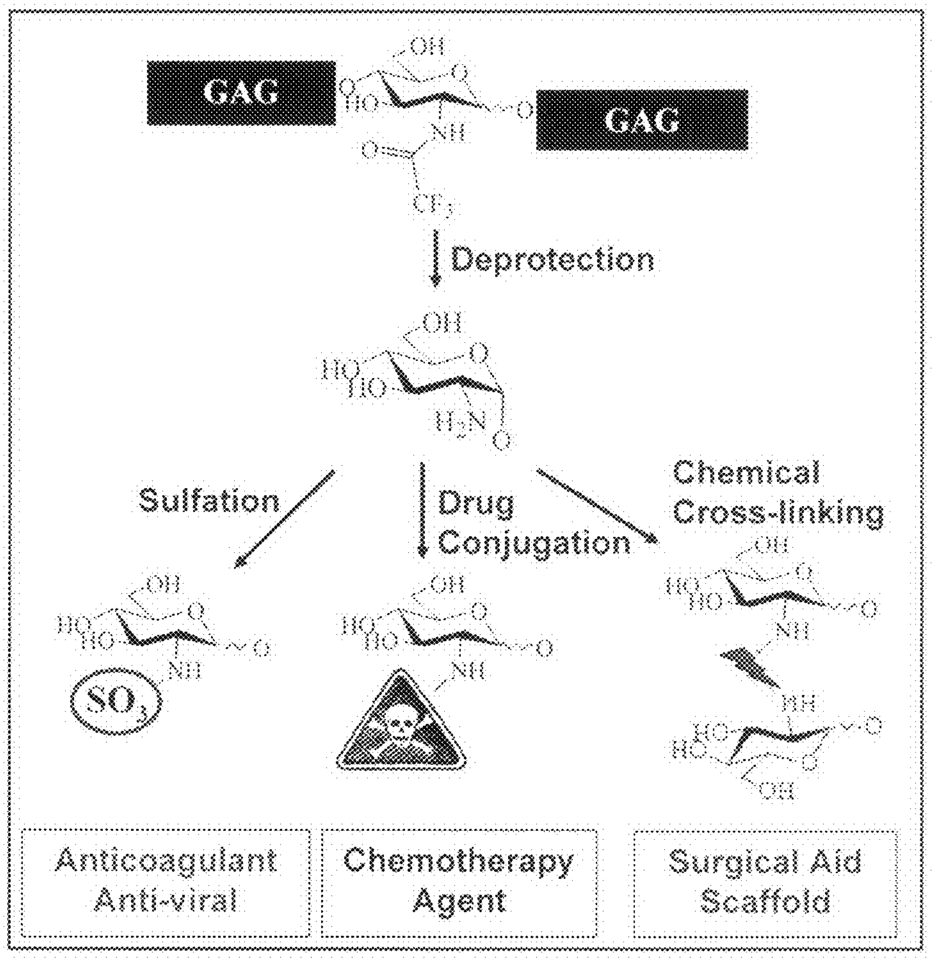
FIG. 25 is a diagram of GlcN[TFA] deprotection and potential medical applications. The GlcN[TFA] sugar can be added to any position within a polymer or oligosaccharide. The TFA group on the hexoasmine sugar can be deprotected with base treatment. This produces a primary amine that is potentially the site for N-sulfation, coupling to drugs and cross-linking site to form a gel; these applications are examples, and other chemistries and theraputics may also be employed.

Removal of natural acetyl groups from GAGs usually requires extreme conditions (hydrazine at 100° C. for hours) that often results in cleavage and sugar ring perturbations. The use of the TFA group provides a specific method for N-deacetylation under milder basic conditions. The electronegative fluorine atoms remove electron density from the amide bond thus weakening it. The deprotected amine can hypothetically be conjugated very effectively with any amine-reactive moiety or chemically cross linked to form a gel (FIG. 25). Furthermore, the amino group is the natural target for the N-sulfation enzyme, which will help to facilitate the bioenzymatic production of heparin.

TABLE XI

| Unnatural UDP-Sugar Substrate Utilization | |
|---|---|
| UDP-Sugar | PmHAS |
| U-GlcN | N |
| U-GlcNAcUA | N |
| U-GlcNAcNAc | N |
| U-GlcdiNAcUA | N |
| U-GlcN[TFA] | Y** (0.6%) |
| U-GlcNBut | Y** (2%) |
| U-GlcNPro | Y** (100%) |

**Acts like GlcNAc

TABLE XII

| | PmHS1 Substitutes for: | | PmHS2 Substitutes for? | | PmHAS Substitutes for? | |
|---|---|---|---|---|---|---|
| UDP-Sugar analogs | UDP-GlcUA? | UDP-GlcNAc? | UDP-GlcUA? | UDP-GlcNAc? | UDP-GlcUA? | UDP-GlcNAc? |
| UDP-2-deoxy-2-fluoro-GlcUA | + | n.a. | + | n.a. | + | n.a. |
| UDP-2-deoxy-6-fluoro-GlcNAc | n.a. | +++ | n.a. | +++ | n.a. | + |
| UDP-6,6'-difluoro-GlcNAc | n.a. | + | n.a. | + | n.a. | − |

Other UDP-sugar donors that substitute for the authentic uronic acid or hexosamine also are incorporated by PmHAS, PmHS1 or PmHS2 (see Tables X-XII). For example, the resulting GAG-like polymers with fluorine-containing analogs (Table XII) will differ in chemical properties and biological activities.

There are a multitude of roles for GAGs in the body. Some cellular or molecular systems will recognize and/or metabolize the GAG-analogs in a different fashion than the natural sugars or other related analogs; this avenue allows targeting or selectivity in a therapeutic treatment.

For the analogs in the Table XII, another biomedical application is the preparation of new NMR (nuclear magnetic resonance) or MRI (magnetic resonance imaging) probes. The fluorine atom, $^{19}F$, is a very useful since it has good spectral properties and the normal animal or human body contains very little of this atom. GAGs with $^{19}F$ will be readily tracked in the body; if a tissue or cell binds and/or internalizes the probe, it may be detected by this non-invasive procedure. For example, a diseased or cancerous cell that preferentially binds the probe will have more $^{19}F$ signal. Likewise, the use of other NMR-active tags will be similarly possible when incorporated into the GAG chain. $^{18}F$, the positron emitting radioactive atom, could also be used in a similar fashion, and is tracked using a PET scanner.

Biomaterials and Methods of Making Same

Biomaterials also play a pivotal role in the field of tissue engineering. Biomimetic synthetic polymers have been created to elicit specific cellular functions and to direct cell-cell interactions both in implants that are initially cell-free, which may serve as matrices to conduct tissue regeneration, and in implants to support cell transplantation. Biomimetic approaches have been based on polymers endowed with bioadhesive receptor-binding peptides and mono- and oligosaccharides. These materials have been patterned in two- and three-dimensions to generate model multicellular tissue architectures, and this approach may be useful in future efforts to generate complex organizations of multiple cell types. Natural polymers have also played an important role in these efforts, and recombinant polymers that combine the beneficial aspects of natural polymers with many of the desirable features of synthetic polymers have been designed and produced. Biomaterials have been employed to conduct and accelerate otherwise naturally occurring phenomena, such as tissue regeneration in wound healing in the otherwise healthy subject; to induce cellular responses that might not be normally present, such as healing in a diseased subject or the generation of a new vascular bed to receive a subsequent cell transplant; and to block natural phenomena, such as the immune rejection of cell transplants from other species or the transmission of growth factor signals that stimulate scar formation.

Approximately 10 years ago, the concept of bioadhesion was introduced into the pharmaceutical literature and has since stimulated much research and development both in academia and in industry. The first generation of bioadhesive drug delivery systems (BBDS) were based on so-called mucoadhesive polymers, i.e., natural or synthetic macromolecules, often already well accepted and used as pharmaceutical excipients for other purposes, which show the remarkable ability to 'stick' to humid or wet mucosal tissue surfaces. While these novel dosage forms were mainly expected to allow for a possible prolongation, better localization or intensified contact to mucosal tissue surfaces, it had to be realized that these goals were often not so easily accomplished, at least not by means of such relatively straightforward technology. However, although not always convincing as a glue, some of the mucoadhesive polymers were found to display other, possibly even more important biological activities, namely to inhibit proteolytic enzymes and/or to modulate the permeability of usually tight epithelial tissue barriers. Such features were found to be particularly useful in the context of peptide and protein drug delivery.

The primary goal of bioadhesive controlled drug delivery is to localize a delivery device within the body to enhance the drug absorption process in a site-specific manner. Bioadhesion is affected by the synergistic action of the biological environment, the properties of the polymeric controlled release device, and the presence of the drug itself. The delivery site and the device design are dictated by the drug's molecular structure and its pharmacological behavior.

For example, one embodiment of the present invention is the use of sutures or bandages with heparosan-chains grafted on the surface or throughout the material in combination with the fibrinogen glue. The immobilized heparosan does not diffuse away as in current formulations, but rather remains at the wound site.

Organic materials have also been postulated for use as bioadhesives. Bioadhesive lattices of water-swollen poly (acrylic acid) nano- and microparticles have been synthesized using an inverse (W/O) emulsion polymerization method. They are stabilized by a co-emulsifier system consisting of SPAN™80 and TWEEN™ 80 dispersed in aliphatic hydrocarbons. The initial polymerization medium contains emulsion droplets and inverse micelles which solubilize a part of the monomer solution. The polymerization is then initiated by free radicals, and particle dispersions with a narrow size distribution are obtained. The particle size is dependent on the type of radical initiator used. With water-soluble initiators, for example ammonium persulfate, microparticles are obtained in the size range of 1 to 10 micrometer, indicating that these microparticles originate from the emulsion droplets since the droplet sizes of the W/O emulsion show similar distribution. When lipophilic radical initiators, such as azobis-isobutyronitrile, are used, almost exclusively nanoparticles are generated with diameters in the range of 80 to 150 nm, due to the limited solubility of oligomeric poly(acrylic acid) chains in the lipophilic continuous phase. These poly (acrylic acid) micro- and nanoparticles yielded excellent bioadhesive properties in an in-vitro assay and may, therefore, be suitable for the encapsulation of peptides and other hydrophilic drugs.

In the present invention, HA, heparosan or chondroitin chains would be the natural substitute for poly(acrylic-acid) based materials. These GAGs are negatively-charged polymers as is poly(acrylic-acid), but glycosaminoglycans are naturally occurring molecules in the vertebrate body and would not invoke an immune response like a poly(acrylic-acid) material.

The interest in realizing 'true' bioadhesion continues: instead of mucoadhesive polymers, plant or bacterial lectins, i.e., adhesion molecules which specifically bind to sugar moieties of the epithelial cell membrane are now widely being investigated as drug delivery adjuvants. These second-generation bioadhesives not only provide for cellular binding, but also for subsequent endo- and transcytosis. This makes the novel, specifically bioadhesive molecules particularly interesting for the controlled delivery of DNA/RNA molecules in the context of antisense or gene therapy.

For the efficient delivery of peptides, proteins, and other biopharmaceuticals by nonparenteral routes, in particular via the gastrointestinal, or GI, tract, novel concepts are needed to overcome significant enzymatic and diffusional barriers. In this context, bioadhesion technologies offer some new perspectives. The original idea of oral bioadhesive drug delivery systems was to prolong and/or to intensify the contact between controlled-release dosage forms and the stomach or gut mucosa. However, the results obtained during the past decade using existing pharmaceutical polymers for such purposes were rather disappointing. The encountered difficulties were mainly related to the physiological peculiarities of GI mucus. Nevertheless, research in this area has also shed new light on the potential of mucoadhesive polymers. First, one important class of mucoadhesive polymers, poly(acrylic acid), could be identified as a potent inhibitor of proteolytic enzymes. Second, there is increasing evidence that the interaction between various types of bio(muco)adhesive polymers and epithelial cells has direct influence on the permeability of mucosal epithelia. Rather than being just adhesives, mucoadhesive polymers may therefore be considered as a novel class of multifunctional macromolecules with a number of desirable properties for their use as biologically active drug delivery adjuvants.

In order to overcome the problems related to GI mucus and to allow longer lasting fixation within the GI lumen, bioadhesion probably may be better achieved using specific bioadhesive molecules. Ideally, these bind to surface structures of the epithelial cells themselves rather than to mucus by receptor-ligand-like interactions. Such compounds possibly can be found in the future among plant lectins, novel synthetic polymers, and bacterial or viral adhesion/invasion factors. Apart from the plain fixation of drug carriers within the GI lumen, direct bioadhesive contact to the apical cell membrane possibly can be used to induce active transport processes by membrane-derived vesicles (endo- and transcytosis). The nonspecific interaction between epithelia and some mucoadhesive polymers induces a temporary loosening of the tight intercellular junctions, which is suitable for the rapid absorption of smaller peptide drugs along the paracellular pathway. In contrast, specific endo- and transcytosis may ultimately allow the selectively enhanced transport of very large bioactive molecules (polypeptides, polysaccharides, or polynucleotides) or drug carriers across tight clusters of polarized epi- or endothelial cells, whereas the formidable barrier function of such tissues against all other solutes remains intact.

Bioadhesive systems are presently playing a major role in the medical and biological fields because of their ability to maintain a dosage form at a precise body-site for a prolonged period of time over which the active principle is progressively released. Additional uses for bioadhesives include: bioadhesives/mucoadhesives in drug delivery to the gastrointestinal tract; nanoparticles as a gastroadhesive drug delivery system; mucoadhesive buccal patches for peptide delivery; bioadhesive dosage forms for buccai/gingival administration; semisolid dosage forms as buccal bioadhesives; bioadhesive dosage forms for nasal administration; ocular bioadhesive delivery systems; nanoparticles as bioadhesive ocular drug delivery systems; and bioadhesive dosage forms for vaginal and intrauterine applications.

The bioadhesive may also contain liposomes. Liposomes are unilamellar or multilamellar lipid vesicles which entrap a significant fraction of aqueous solution. The vesicular microreservoirs of liposomes can contain a variety of water-soluble materials, which are thus suspended within the emulsion. The preparation of liposomes and the variety of uses of liposomes in biological systems has been disclosed in U.S. Pat. Nos. 4,708,861; 4,224,179; and 4,235,871. Liposomes are generally formed by mixing long chain carboxylic acids, amines, and cholesterol, as well as phospholipids, in aqueous buffers. The organic components spontaneously form multilamellar bilayer structures called liposomes. Depending on their composition and storage conditions, liposomes exhibit varying stabilities. Liposomes serve as models of cell membranes and also are used as drug delivery systems.

Most attempts to use liposomes as drug delivery vehicles have envisioned liposomes as entities which circulate in blood, to be taken up by certain cells or tissues in which their degradation would slowly release their internal aqueous drug-containing contents. In an effort to aid in their up-take by a given target tissue, some liposomes have been Atailored@ by binding specific antibodies or antigens to the outer surface. Liposomes have also been devised as controlled release systems for the delivery of their contents in vivo. Compositions in which liposomes containing biologically active agents are maintained and immobilized in polymer matrices, such as methylcellulose, collagen and agarose, for sustained release of the liposome contents, are described in U.S. Pat. No. 4,708,861 to Popescu et al.

In this manner, the present invention contemplates a bioadhesive comprising HA or chondroitin or heparin produced from pmHAS, pmCS, pmHS1, or PmHS2. The present invention also contemplates a composition containing a bioadhesive comprising HA or chondroitin or heparin produced from pmHAS, pmCS, pmHS1, or PmHS2 and an effective amount of a medicament, wherein the medicament can be entrapped or grafted directly within the HA or chondroitin or heparin bioadhesive or be suspended within a liposome which is entrapped or grafted within the HA or chondroitin or heparin bioadhesive. These compositions are especially suited to the controlled release of medicaments.

Such compositions are useful on the tissues, skin, and mucus membranes (mucosa) of an animal body, such as that of a human, to which the compositions adhere. The compositions so adhered to the mucosa, skin, or other tissue slowly release the treating agent to the contacted body area for relatively long periods of time, and cause the treating agent to be sorbed (absorbed or adsorbed) at least at the vicinity of the contacted body area. Such time periods are longer than the time of release for a similar composition that does not include the HA bioadhesive.

The treating agents useful herein are selected generally from the classes of medicinal agents and cosmetic agents. Substantially any agent of these two classes of materials that is a solid at ambient temperatures may be used in a composition or method of the present invention. Treating agents that are liquid at ambient temperatures, e.g., nitroglycerine, can be used in a composition of this invention, but are not preferred because of the difficulties presented in their formulation. The treating agent may be used singly or as a mixture of two or more such agents.

One or more adjuvants may also be included with a treating agent, and when so used, an adjuvant is included in the meaning of the phrase treating agent or medicament. Exemplary of useful adjuvants are chelating agents such as EDTA that bind calcium ions and assist in passage of medicinal agents through the mucosa and into the blood stream. Another illustrative group of adjuvants are the quaternary nitrogen-containing compounds such as benzalkonium chloride that also assist medicinal agents in passing through the mucosa and into the blood stream.

The treating agent is present in the compositions of this invention in an amount that is sufficient to prevent, cure and/or treat a condition for a desired period of time for which the composition of this invention is to be administered, and such an amount is referred herein as an effective amount. As is well known, particularly in the medicinal arts, effective amounts of medicinal agents vary with the particular agent involved, the condition being treated and the rate at which the composition containing the medicinal agent is eliminated from the body, as well as varying with the animal in which it is being used, and the body weight of that animal. Consequently, effective amounts of treating agents may not be defined for each agent. Thus, an effective amount is that amount which in a composition of this invention provides a sufficient amount of the treating agent to provide the requisite activity of treating agent in or on the body of the treated animal for the desired period of time, and is typically less than that amount usually used.

Inasmuch as amounts of particular treating agents in the blood stream that are suitable for treating particular conditions are generally known, as are suitable amounts of treating agents used in cosmetics, it is a relatively easy laboratory task to formulate a series of controlled release compositions of this invention containing a range of such treating agent for a particular composition of this invention.

The second principle ingredient of this embodiment of the present invention is a bioadhesive comprising an amount of hyaluronic acid (HA) from pmHAS or chondroitin from PmCS or heparin from pmHS1 or PmHS2. Such a glycosaminoglycan bioadhesive made from a HA or chondroitin or heparin chain directly polymerized onto a molecule with the desired pharmacological property or a HA or chondroitin or heparin chain polymerized onto a matrix or liposome which in turn contains or binds the medicament.

Woodfield et al. (2002) describe that articular cartilage lesions resulting from trauma or degenerative diseases are commonly encountered clinical problems. It is well-established that adult articular cartilage has limited regenerative capacity, and, although numerous treatment protocols are currently employed clinically, few approaches exist that are capable of consistently restoring long-term function to damaged articular cartilage. Tissue engineering strategies that focus on the use of three-dimensional scaffolds for repairing articular cartilage lesions offer many advantages over current treatment strategies. Appropriate design of biodegradable scaffold conduits (either preformed or injectable) allow for the delivery of reparative cells bioactive factors, or gene factors to the defect site in an organized manner. This review seeks to highlight pertinent design considerations and limitations related to the development, material selection, and processing of scaffolds for articular cartilage tissue engineering, evidenced over the last decade. In particular, considerations for novel repair strategies that use scaffolds in combination with controlled release of bioactive factors or gene therapy.

The various glycosaminoglycans produced by the methods of the present invention, especially the hybrid or chimeric polymers, are promising materials for incorporation, either directly or indirectly, into a scaffold for cell growth and implantation. In addition, the polymers may be attached to surfaces or devices via acceptor moiety or a direct chain interaction.

Bello et al. (2001) describe that tissue-engineered skin is a significant advance in the field of wound healing and was developed due to limitations associated with the use of autografts. These limitations include the creation of a donor site which is at risk of developing pain, scarring, infection and/or slow healing. A number of products are commercially available and many others are in development. Cultured epidermal autografts can provide permanent coverage of large area from a skin biopsy. However, 3 weeks are needed for graft cultivation. Cultured epidermal allografts are available immediately and no biopsy is necessary. They can be cryopreserved and banked, but are not currently commercially available. A nonliving allogeneic acellular dermal matrix with intact basement membrane complex (Alloderm) is immunologically inert. It prepares the wound bed for grafting allowing improved cultured allograft 'take' and provides an intact basement membrane. A nonliving extracellular matrix of collagen and chondroitin-6-sulfate with silicone backing (Integra) serves to generate neodermis. A collagen and glycosaminoglycan dermal matrix inoculated with autologous fibroblasts and keratinocytes has been investigated but is not commercially available. It requires 3 to 4 weeks for cultivation. Dermagraft consists of living allogeneic dermal fibroblasts grown on degradable scaffold. It has good resistance to tearing. An extracellular matrix generated by allogeneic human dermal fibroblasts (TransCyte) serves as a matrix for neodermis generation. Apligraf is a living allogeneic bilayered construct containing keratinocytes, fibroblasts and bovine type I collagen. It can be used on an outpatient basis and avoids the need for a donor site wound. Another living skin equivalent, composite cultured skin (OrCel), consists of allogeneic fibroblasts and keratinocytes seeded on opposite sides of bilayered matrix of bovine collagen. There are limited clinical data available for this product, but large clinical trials are ongoing. Limited data are also available for 2 types of dressing material derived from pigs: porcine small intestinal submucosa acellular collagen matrix (Oasis) and an acellular xenogeneic collagen matrix (E-Z-Derm). Both products have a long shelf life. Other novel skin substitutes are being investigated. The potential risks and benefits of using tissue-engineered skin need to be further evaluated in clinical trials but it is obvious that they offer a new option for the treatment of wounds.

The various glycosaminoglycans produced by the methods of the present invention, especially the hybrid or chimeric polymers, are promising components for tissue engineered organs including skin.

Vlodavsky et al. (1996) disclose that heparan sulfate proteoglycans (HSPGs) are ubiquitous macromolecules associated with the cell surface and extracellular matrix (ECM) of a wide range of cells of vertebrate and invertebrate tissues. The basic HSPG structure consists of a protein core to which several linear heparan sulfate (HS) chains are covalently attached. The polysaccharide chains are typically composed of repeating hexuronic and D-glucosamine disaccharide units that are substituted to a varying extent with N- and O-linked sulfate moieties and N-linked acetyl groups. Beside serving as a scaffold for the attachment of various ECM components (e.g., collagen, laminin, fibronectin), the binding of HS to certain proteins has been suggested to induce a conformational change which may lead to the exposure of novel reactive determinants or conversely stabilize an inert protein configuration. Of particular significance is the interaction of HS with fibroblast growth factors (FGFs), mediating their sequestration, stabilization and high affinity receptor binding and signaling. Cellular responses to FGFs may hence be modulated by metabolic inhibitors of HS synthesis and sulfation, HS-degrading enzymes, and synthetic mimetics of heparin/HS. HS is involved in basic FGF (bFGF) receptor binding and mitogenic activity and its modulation by species of heparin, HS, and synthetic polyanionic 'heparin-mimicking' compounds. The results are discussed in relation to the current thoughts on the dual involvement of low and high affinity receptor sites in the growth promoting and angiogenic activities of bFGF and other heparin-binding growth factors.

The mimetics based on the various glycosaminoglycans produced by the methods of the present invention, including the hybrid or chimeric polymers, are promising due to their inherent abilities to interact, trigger, or bind a variety of molecules including cytokines, receptors, and growth factors. These GAG molecules should thus serve as modulators of cell behavior and/or growth via numerous natural pathways in mammals and humans.

Iivanainen et al. (2003) disclose that dynamic interactions between endothelial cells and components of their surrounding extracellular matrix are necessary for the invasion, migration, and survival of endothelial cells during angiogenesis. These interactions are mediated by matrix receptors that initiate intracellular signaling cascades in response to binding to specific extracellular matrix molecules. The interactions between endothelial cells and their environment are also modulated by enzymes that degrade different matrix components and thus enable endothelial invasion. Recent reports on gene targeting in mice have confirmed the role of two classes of matrix receptors, integrins and cell surface heparan sulfate proteoglycans, and a group of matrix degrading proteolytic enzymes, matrix metalloproteinases, in angiogenesis. The significance of endothelial cell-matrix interactions is further supported by several ongoing clinical trials that analyze the effects of drugs blocking this interaction on angiogenesis-dependent growth of human tumors.

The mimetics based on various glycosaminoglycans produced by the methods of the present invention, including the hybrid or chimeric polymers, are promising due to their inherent abilities to intearct, trigger, or bind a variety of molecules including cytokines, receptors, and growth factors. These molecules should thus serve as modulators of cell behavior and/or growth.

Song et al. (2002) teach that glypicans are a family of heparan sulfate proteoglycans that are bound to the cell surface by a glycosyl-phosphatidylinositol anchor. Six members of this family have been identified in mammals. In general, glypicans are highly expressed during development, and their expression pattern suggests that they are involved in morphogenesis. One member of this family, glypican-3, is mutated in the Simpson-Golabi-Behmel syndrome. This syndrome is characterized by overgrowth and various developmental abnormalities that indicate that glypican-3 inhibits proliferation and cell survival in the embryo. It has consequently been proposed that glypicans can regulate the activity of several growth factors that play a critical role in morphogenesis. Defined heparosan derivatives could be used to modulate such activities.

The various glycosaminoglycans produced by the methods of the present invention, especially the hybrid or chimeric polymers, are promising materials for incorporation, either directly or indirectly, onto cell surfaces. The polymers may be attached to cell surfaces or devices via acceptor moiety (for example, but not by way of limitation, a lipid conjugate).

The monodisperse heparosan of the present invention is also a starting material for sulfated heparin-based anticoagulants, antivirals, proliferation modulators, etc. Size defined molecules as well as analogs should allow a multitude of therapeutics to be created with potential for enhanced activity and better control.

Materials and Methods

Membrane preparations containing recombinant pmHAS (GenBank AF036004) (SEQ. ID NOS:1 and 2) were isolated from *E. coli* SURE(pPmHAS). Membrane preparations containing native pmHAS were obtained from the *P. multocida* strain P-1059 (ATCC #15742). pmHAS was assayed in 50 mM Tris, pH 7.2, 20 mM $MnC1_2$, and UDP-sugars (UDP-[$^{14}$C]GlcUA, 0.3 μCi/mmol, NEN and UDP-GlcNAc) at 30C. The reaction products were analyzed by various chromatographic methods as described below. Membrane preparations containing other recombinant HAS enzymes, Group A streptococcal HasA or *Xenopus* DG42 produced in the yeast *Saccharomyces cerevisiae*, were prepared.

Uronic acid was quantitated by the carbazole method. Even-numbered HA oligosaccharides [$(GlcNAc\text{-}GlcUA)_n$] were generated by degradation of HA (from Group A *Streptococcus*) with either bovine testicular hyaluronidase Type V (n=2-5) or *Streptomyces* hyaluroniticus HA lyase (n=2 or 3) in 30 mM sodium acetate, pH 5.2, at 30° overnight. The latter enzyme employs an elimination mechanism to cleave the chain resulting in an unsaturated GlcUA residue at the non-reducing terminus of each fragment. For further purification and desalting, some preparations were subjected to gel filtration with P-2 resin (BioRad) in 0.2 M ammonium formate and lyophilization. Odd-numbered HA oligosaccharides [$GlcNAc(GlcUA\text{-}GlcNAc)_n$] ending in a GlcNAc residue were prepared by mercuric acetate-treatment of partial HA digests generated by HA lyase (n=2-7). The masses of the HA oligosaccharides were verified by matrix-assisted laser desorption ionization time-of-flight mass spectrometry. Sugars in water were mixed with an equal volume of 5 mg/ml 6-azo-2-thiothymine in 50% acetonitrile/0.1% trifluoroacetic acid, and rapidly air-dried on the target plate. The negative ions produced by pulsed nitrogen laser irradiation were analyzed in linear mode (20 kV acceleration; Perceptive Voyager).

Other oligosaccharides that are structurally similar to HA were also tested in HAS assays. The structure of heparosan pentamer derived from the *E. coli* K5 capsular polysaccharide is α4GlcUA-β4GlcNAc; this carbohydrate has the same composition as HA but the glycosidic linkages between the monosaccharides are different. The chitin-derived oligosaccharides, chitotetraose and chitopentaose, are β4GlcNAc polymers made of 4 or 5 monosaccharides, respectively.

Various oligosaccharides were radiolabeled by reduction with 4 to 6 equivalents of sodium borotritide (20 mM, NEN; 0.2 μCi/mmol) in 15 mM NaOH at 30 C for 2 hrs. $^3$H-oligosaccharides were desalted on a P-2 column in 0.2 M ammonium formate to remove unincorporated tritium and lyophilized. Some labeled oligosaccharides were further purified preparatively by paper chromatography with Whatman 1 developed in pyridine/ethyl acetate/acetic acid/$H_2O$ (5:5:1:3) before use as an acceptor.

Paper chromatography with Whatman 3M developed in ethanol/1M ammonium acetate, pH 5.5 (65:35) was used to separate high molecular weight HA product (which remains at the origin) from UDP-sugars and small acceptor oligosaccharides. In the conventional HAS assay, radioactive UDP-sugars are polymerized into HA. To obtain the size distribution of the HA polymerization products, some samples were also separated by gel filtration chromatography with Sephacryl S-200 (Pharmacia) columns in 0.2 M NaCl, 5 mM Tris, pH 8. Columns were calibrated with dextran standards. The identity of the polymer products was assessed by sensitivity to specific HA lyase and the requirement for the simultaneous presence of both UDP-sugar precursors during the reaction. Thin layer chromatography [TLC] on high performance silica plates with application zones (Whatman) utilizing butanol/acetic acid/water (1.5:1:1 or 1.25:1:1) development solvent separated $^3$H-labeled oligosaccharides in reaction mixes. Radioactive molecules were visualized after impregnation with EnHance spray (NEN) and fluorography at ~80°.

Membrane preparations containing recombinant full length pmHAS, $pmHAS^{437-972}$, $pmHAS^{437-756}$, $pmHAS^{1-756}$, $pmHAS^{1-567}$ and $pmHAS^{152-756}$ were isolated from *E. coli* as described. For soluble truncated pmHAS proteins, $pmHAS^{1-703}$, $pmHAS^{1-650}$, and $pmHAS^{1-703}$-derived mutants, cells were extracted with B-Per™ II Bacterial Protein Extraction Reagent (Pierce) according to the manufacturer's instruction except that the procedure was performed at 7° in the presence of protease inhibitors. Membrane preparations of *P. multocida* P-1059 (ATCC 15742) were made as described.

The size of GAG polymers was analyzed by chromatography on a Phenomenex PolySep-GFC-P 3000, P 4000 or P5000 column (300×7.8 mm) eluted with 0.2 M sodium nitrate at 0.6 ml/min on a Waters 600E system. The column was standardized with various size fluorescent dextrans (580, 50, and 12 kDa). Radioactive components were detected with a LB508 Radioflow Detector (EG & G Berthold) and Zinsser cocktail (1.8 ml/min). In comparison to the full HAS assay using paper chromatography described above, these 3 minute reactions contained twice the UDP-sugar concentrations, 0.06 μCi UDP-[$^{14}$C]GlcUA, and 0.25 μg even-numbered GAG oligosaccharide. Also, addition of ethylenediamine tetracetic acid (final conc. 22 mM) and boiling (2 min) was employed to terminate the reactions instead of addition of SDS.

A lambda library of Sau3A partially digested Type F *P. multocida* P-4679 DNA (~4-9 kb average length insert) was made using the BamHI-cleaved Zap Express vector system (Stratagene). The plaque lifts were screened by hybridization (5×SSC, 50° C.; 16 hrs) with the digoxigenin-labeled probe using the manufacturer guidelines for colorimetric development. *E. Coli* XLI-Blue MRF was co-infected with the purified, individual positive lambda clones and ExAssist helper phage to yield phagemids. The resulting phagemids were transfected into *E. coli* XLOLR cells to recover the plasmids. Sequence analysis of the plasmids revealed a novel open reading frame, which was called pmCS, with high homology to pmHAS. This same method was utilized to identify a novel open reading frame, which was called pmHS1 (DNA sequence facilities at Oklahoma State University and University of Oklahoma HSC). The ORF was amplified and sequenced from several highly encapsulated isolates (see hereinbelow); very similar sequences were obtained.

In previous studies with pmHAS, it was found that a functional, soluble enzyme would be created if a portion of the carboxyl terminus was truncated by molecular genetic means. Therefore, a portion of the pmCS ORF (residues 1-704) in the insert of one of the excised lambda clones, pPmF4A, was amplified by 20 cycles of PCR with Taq polymerase. The sense primer corresponded to the sequence at the deduced amino terminus of the ORF and the antisense primer encoded the new carboxyl terminus followed by an artificial stop codon. The resulting PCR product was purified and concentrated using GeneClean. This insert was cloned using the pETBlue-1 Acceptor system (Novagen) according to the manufacturer's instructions. The Taq-generated single A overhang is used to facilitate the cloning of the open reading frame downstream of the T7 promoter and the ribosome binding site of the vector. The ligated products were transformed into *E. coli* NovaBlue and plated on LB carbenicillin (50 μg/ml) under conditions for blue/white screening. White or light blue colonies were analyzed by restriction digestion. A clone containing a plasmid with the desired truncated ORF, pPm-$CS^{1-704}$, was transformed into *E. coli* Tuner, the T7 RNA polymerase-containing expression host, and maintained on LB media with carbenicillin and chloramphenicol (34 μg/ml) at 30° C. Log phase cultures were induced with β-isopropylthiogalactoside (0.2 mM final) for 5 hrs. The cells were harvested by centrifugation, frozen, and extracted for 20 min with a mild detergent (bPer II reagent, Pierce) at 7° in the presence of a broad-range protease inhibitor cocktail. The cells were removed by centrifugation and the soluble extract was used as the source of CS enzyme for in vitro assays.

Truncated polypeptides were generated by amplifying the pPm7A insert by 13 cycles of PCR with Taq polymerase (Fisher) and synthetic oligonucleotide primers corresponding to various portions of the pmHAS open reading frame. Except for the construction of $pmHAS^{1-686}$ and $pmHAS^{1-668}$, the primers contained EcoRI and PstI restriction sites to facilitate cloning into the expression plasmid pKK223-3 (tac promoter; Pharmacia). The resulting recombinant constructs were transformed into *E. coli* TOP 10F cells (Invitrogen) and maintained on Luria-Bertani media with ampicillin selection. The DNA encoding $pmHAS^{1-686}$ and $pmHAS^{1-668}$ were cloned into pETBlue-1 plasmid and expressed in Tuner (DE3)pLacI cells (Novagen) according to manufacturing instructions; these cells were maintained on Luria-Bertani media with carbenicillin and chloramphenicol selection.

Point mutations were made using the QuickChange site-directed mutagenesis method (Stratagene) with the plasmid pKK223/$pmHAS^{1-703}$ DNA as template. The sequences of the mutant open reading frames were verified by automated DNA sequencing (Oklahoma State University Recombinant DNA/Protein Resource Facility).

Recombinant *E. coli* were grown in Luria-Bertani media with drug selection until $OD_{600}$ was 0.3-0.6 when cells were induced with 0.5 mM isopropyl-1-thio-β-D-galactoside. Cells were harvested 5 hours after induction. For soluble truncated proteins and $pmHAS^{1-703}$-derived mutants expressed in *E. coli* TOP10F' cell, cells were extracted with B-Per™ II Bacterial Protein Extraction Reagent (an octylthioglucoside-based solution; Pierce) according to the manufacturer's instruction except that the procedure was performed at 7° in the presence of protease inhibitors. For proteins expressed in Tuner(DE3)pLacI, lysis by ultrasonication followed by subcellular fractionation was performed and the supernatant after centrifugation at 100,000×g was used.

Five assays were designed to detect either (a) the polymerization of long HA chains, (b) the addition of a single GlcNAc to a GlcUA-terminated HA oligosaccharide acceptor, (c) the addition of a single GlcUA to a GlcNAc-terminated HA oligosaccharide acceptor, (d) the polymerization of long chondroitin chains, or (e) the addition of a single GalNAc to a GlcUA-terminated HA oligosaccharide acceptor. The first three assays were described hereinabove. For the chondroitin synthase assay, the same conditions as the HA synthase assay were used except that the other hexosamine precursor, UDP-GalNAc, was employed and there is no ammonium sulfate or ethylene glycol in the assay system. GalNAc-transferase activity was assayed under the same conditions as the GlcNAc-transferase assay except that 0.3 mM UDP-[$^3$H]GalNAc (0.2 μCi; NEN) was used instead of UDP-[$^3$H]GlcNAc. Reactions were terminated by the addition of SDS to 2% (w/v). The reaction products were separated from substrates by descending paper (Whatman 3M) chromatography with ethanol/1 M ammonium acetate, pH 5.5, development solvent (65:35 for the HAS, chondroitin synthase, and GlcUA-transferase assays; 75:25 for GlcNAc-transferase and GalNAc-transferase assay). All assays were adjusted to be linear with regard to incubation time and to protein concentration. Radiolabeled products were quantitated by liquid scintillation counting (Biosafe II, Research Products International).

The pmHAS polypeptides in membranes and extracts were analyzed using standard 8% polyacrylamide SDS gels and Western blotting utilizing a monospecific antibody directed against a synthetic peptide corresponding to residues 526 to 543 of pmHAS (acetyl-LDSDDYLEPDAVELCLKE-amide; i.e., residues 526-543 of SEQ ID NO:2) as described hereinabove.

The DNA encoding different segments of pmHAS-D or pmCS were generated by amplifying the pPm7A insert or pPmF4A insert, respectively, by 15 cycles of PCR with Taq polymerase (Fisher) and synthetic oligonucleotide primers corresponding to various portions of the pmHAS-D or pmCS open reading frame. Each internal primer contained overlaps with the other segment to allow joining of the two desired segments. The forward and reverse primers for pmHAS residue 1-427 (A segment) were P1=5'-ATGAACACATTATCACAAGCAATAAAAGC-3' (SEQ ID NO:49) and P2=5'-GCGAATCTTCTATTGGTAAAAGYTTTC-3' (SEQ ID NO:50) (Y=C/T, respectively. The forward and reverse primers for pmCS residue 421-704 (C segment) were P3=5'-CTTTTACCAATAGAAGATTCGCATAT-3' (SEQ ID NO:51) and P4=5'-GAAGACGTCTTAGGCATCTTTATTCTGAATGAG-3' (SEQ ID NO:52), respectively. The forward and reverse primers for pmCS residue 1-420 (D segment) were P1 and P2. The forward and reverse primers for pmHAS residue 428-703 (B segment) were P3 and P5=5'-GGGAATTCTGCAGTTAAATATCTTTTAAGATATCAATCTCTTC-3' (SEQ ID NO:53), respectively. The chimeric or hybrid synthases were created by 15 cycles of PCR with the gel-purified (GeneClean; Bio101) segments and outer primers (pm-AC used A and C segments with primer P1 and P4; pm-BD used B and D segments with primer P1 and P5). The purified PCR products were cloned into pETBlue-1 vector and the chimeric or hybrid proteins were expressed in Tuner(DE3)pLacI cells (Novagen). The complete open reading frames of multiple clones of both constructs were sequenced. A pmAC construct that was perfect, was found but both of the two pmBD constructs that we had sequenced completely had secondary undesired mutations (#1, E695 and 1697F; #2, 1302V). However, these mutations were in different locations and the enzyme transferase activities were identical. Several other pmBD clones have the identical phenotype but their complete sequences were not determined.

Analysis of Genomic DNA and Isolation of Capsule Biosynthesis Locus DNA—Preliminary data from Southern blot analysis using pmHAS-based hybridization probes [12] suggested that the Type A synthase and the putative Type D synthase were not very similar at the DNA level. However, PCR suggested that the UDP-glucose dehydrogenase genes, which encode an enzyme that produces the UDP-GlcUA precursor required for both HA and heparin biosynthesis, were very homologous. In most encapsulated bacteria, the precursor-forming enzymes and the transferases are located in the same operon. To make a hybridization probe predicted to detect the capsule locus, Type D chromosomal DNA served as a template in PCR reactions utilizing degenerate oligonucleotide primers (sense: GARTTYBTIMRIGARGGIMRGCIYTITAYGAY (SEQ ID NO:54); antisense: RCARTAICClCCRTAICCRAAISWXGGRTTRTTRTARTG (SEQ ID NO:55), where I=inosine; R=A or G; S=C or G; W=A or T; Y=C or T) corresponding to a conserved central region in many known UDP-glucose dehydrogenase genes. The ~0.3-kb amplicon was generated using Taq DNA polymerase (Fisher), gel-purified, and labeled with digoxigenin (High Prime system, Boehringer Mannheim).

Expression of Recombinant *P. multocida* Heparosan Synthase. The pmHS1 ORF (617 amino acids) was amplified from the various Type D genomic DNA template by 18 cycles of PCR with Taq polymerase. For constructing the full-length enzyme, the sense primer (ATGAGCTTATTTAAACGTGCTACTGAGC—SEQ ID NO:54) corresponded to the sequence at the deduced amino terminus of the ORF and the antisense primer (TTTACTCGTTATAAAAAGATAAACACGGAATAAG—SEQ ID NO:55) encoded the carboxyl terminus including the stop codon. In addition, a truncated version of pmHS1 was produced by PCR with the same sense primer but a different antisense primer (TATATTTACAGCAGTATCATTTTCTAAAGG—SEQ ID NO:56) to yield a predicted 501-residue protein, DcbF (SEQ ID NO:57) (GenBank Accession Number AAK17905); this variant corresponds to residues 1-497 of pmHS1 followed by the residues TFRK. The current optimal constructs are fusions to the maltose-binding protein (pMAL-c vector, New England Biolabs; Sismey-Ragatz et al., 2007).

Construction and Purification of Recombinant Maltose Binding Fusion Construct Proteins—PmHS1 and PmHS2 were both expressed as a carboxyl terminal fusion to maltose binding protein (MBP) using the pMAL-c2X vector (New England BioLabs, Beverly, Mass.). Polymerase chain reaction was employed to subclone the open reading frames from our previous pETBlue-1 constructs (DeAngelis & White, 2002 & 2004). For PmHS1, new unique flanking restriction sites (BamHI and HindIII) were added with the primers used for amplification (15 cycles: 94° C., 30 sec; 52° C., 30 sec; 72° C., 2 min) with Taq DNA polymerase. For PmHS2, restriction sites (BamHI and PstI) were added with the primers used for amplification (21 cycles: 94° C., 30 sec; 52° C., 30 sec; 72° C., 3.5 min) with Pfu DNA polymerase (Stratagene, La Jolla, Calif.). The amplicons were gel purified, restriction digested with both appropriate enzymes (Promega, Madison, Wis.), and ligated to similarly double-cut pMAL-c2X plasmid. *E. coli* ONE SHOT® Top 10F' (Invitrogen, Carlsbad, Calif.) was used for the initial transformation on LB ampicillin (100 μg/ml) plates and grown at 30° C. To facilitate extracting the enzymes, the expression host *E. coli* XJa (Zymo Research, Orange, Calif.), which encodes a phage lysin enzyme, was employed allowing for simple freeze/thaw lysis. Cultures were grown in Superior Broth (AthenaES, Baltimore, Md.) at 30° C. with ampicillin (100 μg/ml), and L-arabinose (3.25 mM; to induce the lysin enzyme). At mid-log phase, isopropyl β-D-1-thiogalactopyranoside (IPTG) (0.2 mM final) was added to induce fusion protein production. One hour after induction, the cultures were supplemented with fructose (12.8 mM final) and grown for ~5-12 hours before harvesting by centrifugation at 4° C. The bacteria were resuspended in 20 mM Tris, pH 7.2, and protease inhibitors (p-[4-2-aminoethyl] benzenesulfonyl fluoride hydrochloride, pepstatin, benzamidine, N-[N-(L-3-trans-carboxyoxirane-2-carbonyl)-L-leucyl]-agmatine, leupeptin) on ice, frozen and thawed twice allowing lysin to degrade the cell walls. The lysates was clarified by centrifugation. The synthases were affinity purified via the MBP unit using amylose resin (New England BioLabs). After washing extensively with column buffer (20 mM Tris, pH 7.2, 200 mM NaCl, 1 mM EDTA), the protein was eluted in column buffer containing 10 mM maltose.

Polymerization Assays—Radiolabeled sugar incorporation assays using UDP-[$^3$H]GlcUA or UDP-[$^3$H]GlcNAc (Perkin Elmer NEN, Boston, Mass.) were employed to monitor substrate usage and pH dependence. Polymerization reactions (40 μl) typically contained 50 mM Tris, pH 7.2, 1 mM $MnCl_2$, 0.5-1.0 mM UDP-GlcNAc, 0.5-1 mM UDP-GlcUA, 0.1 mCi UDP-[$^3$H]sugar and ~4-5 mg of enzyme (unless noted). The reactions were typically incubated at 30° C. for 15 to 30 min then stopped with SDS (2% final). Descending paper chromatography was used to separate unincorporated UDP sugars from the polymer product (i.e. sugars longer than ~14 sugars). Three separate experiments were completed for each data set and each assay was verified to be in the linear range with respect to time and enzyme concentration. Less than 5% of the UDP-sugar was consumed. For acceptor usage tests, a "no acceptor" control was performed for all assays in order to determine the de novo initiation heparosan synthesis for each enzyme; this value was subtracted from the value attained in parallel assays with an acceptor. For initial tests querying the ability of a synthase to mis-incorporate a non-authentic UDP-sugar donor, the test compound was used at ~0.5-1.5 mM in the presence of carrier-free UDP-[$^3$H]GlcUA or UDP-[$^3$H]GlcNAc (0.1 μCi) without acceptor for 12-48 hours. Subsequent assays to obtain relative kinetic rates employed radiolabeled authentic UDP-sugar diluted to 0.6 mM for 90 or 180 min.

Monodisperse Heparosan Synthesis—A mixture of heparosan tetrasaccharide and hexasaccharide (~1:4 by mass, respectively) acceptors was used to prime synthesis of narrow size distribution heparosan polymers. The length of the chain was controlled by altering the stoichiometry of the UDP-sugar to acceptor as for the non-homologous PmHAS, the *Pasteurella* HA synthase. These reactions typically contained 5-25 mM UDP-sugars in the same reaction buffer used for polymerization assays and were incubated overnight at 30° C.

Single Sugar Addition Assays—Tests were performed under the same buffer conditions as polymerization assays, but contained only a single UDP-sugar substrate (~1-3 mM final) and an appropriately terminated acceptor (e.g., heparosan oligosaccharide, A-F-A or A-F-A-N). The incorporation of sugar from the donor substrate was detected by the increase in mass to the appropriate predicted molecular weight product by MALDI-TOF MS.

Sugar Analysis Techniques—The sizes of the heparosan polymers were analyzed with agarose gels (1.2-3%, 1×TAE buffer, 30 V for 5-6 hours) and Stains-All (1-ethyl-2-[3-(1-ethylnaphtho[1,2-d]thiazolin-2-ylidene)-2-methylpropenyl] naphtho-[1,2-d]thiazolium bromide) detection or with polyacrylamide gels (15%, 29:1 monomer:bis, 1×TBE, 250 V for 30 min) and Alcian Blue staining. The size distribution of the polymers was determined by high performance size exclusion chromatography-multi angle laser light scattering.

The HA4 molecule was converted into a fluorescent derivative in two steps. First, reductive amination of HA4 with cyanoborohydride and excess diaminobutane in 0.1 M borate buffer, pH 8.5, was used to make an amino-HA4 derivative that was purified by gel filtration on P2 resin. Second, the amino-HA4 was derivatized with the N-hydroxysuccinimide ester of Oregon green 488 (Molecular Probes) and the Fluor-HA4 was purified by preparative normal-phase thin layer chromatography (silica developed with 2:1:1 n-butanol/acetic acid/water).

Heparosan oligosaccharide acceptor preparation. A ~55 kDa heparosan polysaccharide acceptor was used as a positive control and a normalization factor for many experiments. Heparosan oligosaccharides $(GlcUA\text{-}GlcNAc)_n$-(GlcUA-anhydromannitol), n=1, 2 or 3) were prepared by partial deacetylation with base, nitrous acid hydrolysis, and reduction; these polymers contain intact non-reducing termini, but an anhydromannitol group at the reducing end. The fragments were purified by gel filtration on a P2 column (BioRad, Hercules, Calif.) in 0.2 M ammonium formate, followed by normal phase thin layer chromatography (TLC) on silica plates (Whatman, Clifton, N.J.) with n-butanol/acetic acid/water (1:1:1). The bands were detected by staining of side lanes with napthoresorcinol. The size and purity of oligosaccharides were verified by matrix assisted laser desorption ionization time of flight mass spectrometry (MALDI-ToF MS). Fluorescein di-β-D-glucuronide (A-F-A; Molecular Probes, Eugene, Oreg.), a commercially available synthetic acceptor that mimics a glycosaminoglycan trisaccharide that was identified in previous work with the *Pasteurella* HA synthase (Williams et al, 2006), was used as the starting material to prepare the A-F-A-N (GlcUA-F-GlcUA-GlcNAc) and the N-A-F-A-N (GlcNAc-GlcUA-F-GlcUA-GlcNAc) acceptors using UDP-GlcNAc with PmHS2. These longer acceptors were purified by TLC (silica plates and n-butanoVacetic acid/water, 2:1:1).

Catalyst preparation and in vitro synthesis. The catalyst, pmHAS1-703 or pmCS1-704, are soluble purified *E. coli*-derived recombinant protein. The enzyme in the octyl-thioglucoside extracts of the cell paste was purified by chromatography on Toyopearl Red AF resin (Tosoh) using salt elution (50 mM HEPES, pH 7.2, 1 M ethylene glycol with 0 to 1.5 M NaCl gradient in 1 hour). The fractions containing the synthase protein (~90% pure by SDS-PAGE/Coomassie-staining) were concentrated by ultrafiltration and exchanged into reaction buffer.

Analysis of in vitro synthesized Glycosaminoglycans (GAGs). GAGs were analyzed on agarose gels as described in Lee and Cowman. In brief, agarose gels (0.7-1.2%) in 1×TAE buffer were run at 40V. Gels are stained with Stains-All dye (0.005% w/v in ethanol) overnight and destained with water. GAG was analyzed on acrylamide gels (15-20%) as described in Ikegami-Kawai and Takahashi. To purify GAGs, the synthase was removed by choloroform extraction or thin layer chromatography, and GAGs were precipitated as described above or with three volumes of ethanol followed by redissolving in water. Alternatively, the unincorporated precursor sugars were removed by ultrafiltration with Microcon units (Millipore). The concentration was determined by carbazole assay (ref) and a glucuronic acid standard.

Gel filtration/multi-angle laser light scattering analysis was used to determine the absolute molecular weights. Polymers were separated on tandem Toso Biosep TSK-GEL columns (6000PWXL followed by 4000PWXL; each 7.8 mm 30 cm; Japan or equivalent) eluted in 50 mM sodium phosphate, 150 mM NaCl, pH 7 at 0.5 mL/min. The eluant flowed through an Optilab DSP interferometric refractometer and then a Dawn DSF laser photometer (632.8 nm; Wyatt Technology, Santa Barbara, Calif.) in the multi-angle mode. The manufacturer's software package was used to determine the absolute average molecular weight using a dn/dC coefficient of 0.153.

TABLE XIII

| Mutation/Truncation | SEQ ID NO: |
|---|---|
| $pmHAS^{1\text{-}650}$ | 10 |
| $pmHAS^{1\text{-}703}$ D477N | 11 |
| $pmHAS^{1\text{-}703}$ D196N | 12 |
| $pmHAS^{437\text{-}972}$ | 13 |
| $pmHAS^{437\text{-}756}$ | 14 |
| $pmHAS^{152\text{-}756}$ | 15 |
| $pmHAS^{1\text{-}703}$ D196E | 16 |
| $pmHAS^{1\text{-}703}$ D196K | 17 |
| $pmHAS^{1\text{-}703}$ D477E | 18 |
| $pmHAS^{1\text{-}703}$ D477K | 19 |
| $pmHAS^{1\text{-}756}$ | 20 |
| $pmHAS^{1\text{-}567}$ | 21 |
| $pmHAS^{1\text{-}704}$ | 22 |
| $pmHAS^{46\text{-}703}$ | 23 |
| $pmHAS^{72\text{-}703}$ | 24 |
| $pmHAS^{96\text{-}703}$ | 25 |
| $pmHAS^{118\text{-}703}$ | 26 |
| $pmHAS^{1\text{-}668}$ | 27 |
| $pmHAS^{1\text{-}686}$ | 28 |
| $pmHAS^{1\text{-}703}$ D247E | 29 |
| $pmHAS^{1\text{-}703}$ D247N | 30 |
| $pmHAS^{1\text{-}703}$ D247K | 31 |
| $pmHAS^{1\text{-}703}$ D249E | 32 |
| $pmHAS^{1\text{-}703}$ D249N | 33 |
| $pmHAS^{1\text{-}703}$ D249K | 34 |
| $pmHAS^{1\text{-}703}$ D527N | 35 |
| $pmHAS^{1\text{-}703}$ D527E | 36 |
| $pmHAS^{1\text{-}703}$ D527K | 37 |
| $pmHAS^{1\text{-}703}$ D529E | 38 |
| $pmHAS^{1\text{-}703}$ D529N | 39 |
| $pmHAS^{1\text{-}703}$ D529K | 40 |
| $pmHAS^{1\text{-}703}$ E369D | 41 |
| $pmHAS^{1\text{-}703}$ E369Q | 42 |
| $pmHAS^{1\text{-}703}$ E369H | 43 |
| $pmHAS^{1\text{-}703}$ D370E | 44 |
| $pmHAS^{1\text{-}703}$ D370N | 45 |
| $pmHAS^{1\text{-}703}$ D370K | 46 |

The pmHAS mutants and truncations have been described previously in parent application U.S. Pat. No. 7,223,751, issued to DeAngelis et al. on May 29, 2007, the contents of which has previously been incorporated herein by reference. For ease of reference, Table XIII is provided; such Table lists each mutant/truncation and its corresponding SEQ ID NO.

Although the foregoing invention has been described in detail by way of illustration and example for purposes of clarity of understanding, it will be obvious to those skilled in the art that certain changes and modifications may be practiced without departing from the spirit and scope thereof, as described in this specification and as defined in the appended claims below.

REFERENCES

The following references, to the extent that they provide exemplary procedural or other details supplementary to those set forth herein, are specifically incorporated herein by reference in their entirety as though set forth herein particular.

Asplund, T., J. Brinck, M. Suzuki, M. J. Briskin, and P. Heldin. (1998) *Biochim. Biophys. Acta.* 1380, 377-388.
Ausubel, F. M., R. Brent, R. E. Kingston, D. D. Moore, J. G. Seidman, J. A. Smith, and K. Struhl. (1995) *Short Protocols in Molecular Biology,* 3rd Ed., John Wiley & Sons Inc., New York.
Bello, Y M, Falabelia, A F, and Eagistein, W H. (2001) *Am J Clin Dermatol,* 2:305-313.
Bernfield, M., Gotte, M., Park, P. W., Reizes, O., Fitzgerald, M. L. Licecum, J. and Zako, M. (1999) *Annu Rev Biochem* 68, 729-777
Bertram, J., M. Stratz, and P. Durre. *J. Bact.* (1991); 173: 443-8.
Bitter, T. and H. M. Muir., (1962) *Anal. Biochem.* 4, 330-334.
Blundell, C. D., Almond, A., Mahoney, D. J., DeAngelis, P. L., Cambell, I. D. and Day, A. J., (2005) J. Biol Chem 280, 18189-18201
Bradford, M. M., (1976) *Anal. Biochem.* 72, 248-254.
Breton, C. and A. Imberty. (1999) *Curr. Opin. Struc. Biol.* 9, 563-571.
Busch, C., F. Hofmann, J. Seizer, S. Munro, S. Jeckel, and K. Aktories. (1998) *J. Biol. Chem.,* 273, 19566-19572.
Busse, M. and M. Kusche-Gullberg, J. Biol Chem, 2003. 278(42): p. 41333-7
Campbell, R. E., S. C. Mosimann, I. van de Rijn, M. E. Tanner, and N. C. J. Strynadke. (2000) *Biochemistry* 39, 7012-7023.
Capila, I. and Linhardt, R. J. (2002) Angew Chem Int Ed Engl 41, 319-412
Carter, G. R. and E. Annau. (1953) *Am. J. Vet. Res.* 14, 475-478.
Charnock, S. J. and G. J. Davies. (1999) *Biochemistry,* 38, 6380-6385.
Chen, M., Bridges, A. and Liu, J. (2006) Biochemistry 45, 12358-12365
Chen, W Y. and Abstangelo G. (1999) *Wound Repair Regen,* 7, 79-89.
Chung, J. Y., I. Wilkie, J. D. Boyce, K. M. Townsend, A. J. Frost, M. Ghoddusi, and B. Adler. (2001) *Infect. Immun.,* 69, 2487-2492.
Corpet, F. (1998) *Nucleic Acids Res.* 16, 10881-10890.
Crater, D. L., and I. van de Rijn. (1995) *J. Biol. Chem.* 270, 18452-18458.
DeAngelis, P. L., Oatman, L. C. and Gay, D. F. (2003) J. Biol Chem 278, 35199-35203
DeAngelis, P. L., J. Papaconstantinou, and P. H. Weigel. *J. Biol. Chem.,* 268, 14568-14571, 1993.
DeAngelis, P. L., J. Papaconstantinou, and P. H. Weigel. *J. Biol. Chem.,* 268, 19181-19184, 1993.
DeAngelis, P. L. and P. H. Weigel. *Biochemistry,* 33, 9033-9039, 1994.
DeAngelis, P. L., W. Jing, M. V. Graves, D. E. Burbank, and J. L. Van Elten. *Science,* 278, 1800-1803, 1997.
DeAngelis, P. L. *Cell. Mol. Life. Sci.,* 56, 670-682, 1999.
DeAngelis, P. L. *Glycobiology.* 12(1):9R-16R. Review. 2002.
DeAngelis, P. L., and C. L. White. *J. Biol. Chem.* 277(9): 7209-13, 2002.
DeAngelis, P. L. and White, C. L. (2004) J. Bacteriol 186, 8529-8532
DeAngelis, P. L. *Anal. Biochem.* 284(1):167-9, 2000.
DeAngelis, P. L. and A. J. Padgett-McCue. *J. Biol. Chem.* 275(31):24124-9, 2000.
DeAngelis, P. L. *J. Biol. Chem.* 274(37); 26557-62, 1999.
DeAngelis P. L. *Microb. Pathog.* 24(4):203-9, 1998.
DeAngelis, P. L., W. Jing, R. R. Drake, and A. M. Achyuthan. *J. Biol. Chem.* 273(14):8454-8, 1998.
DeAngelis, P. L., W. Jing, M. V. Graves, D. E. Burbank, and J. L. Van Etten. *Science.* 278(5344):1800-3, 1997.
DeAngelis, P. L., and A. M. Achyuthan. *J. Biol. Chem.* 271 (39):23657-60, 1996.
DeAngelis, P. L. *Biochemistry.* 35(30):9768-71, 1996.
DeAngelis, P. L., Oatman, L. C. and Gay, D. F. (2003) *J. Biol. Chem.,* 278.
DeAngelis, P. L. (2002) Anatomical Record, 206, 317-326
DeLuca, S, and J. E. Silbert. (1968) *J. Biol. Chem.* 243, 2725-2729.
Doughtery, B. A., and I. van de Rijn. (1994) J. Biol. Chem., 269, 169-175.
Drake, C. R., I. S. Roberts, B. Jann, K. Jann, and G. J. Boulnois (1990) *FEMS Microbiol. Lett.,* 54, 227-230.
Duncan, G., C. McCormick, and F. Tufaro. (2001) *J. Clin. Invest,* 108, 511-516.
Duncan, M. B., Liu, M., Fox, C. and Liu, J., (2006) Biochem Biophys Res Commun 339(4), 1232
Esko, J. D. and U. Lindahl. (2001) *J. Clin. Invest.* 108, 169-173.
Finke, A., D. Bronne, A. V. Nikolaev, B. Jann, and K. Jann. (1991) *J. Bacteriol.,* 173, 4088-4094.
Gastinel, L. N., C. Cambillau, and Y. Bourne. (1999) *EMBO J.* 18, 3546-3557.
Gastinel, L. N., C. Bignon, A. K. Misra, O. Hindsgaul, J. H. Shaper, and D. H. Joziasse. (2001) *EMBO J.* 20, 638-649.
Gherezghiher, T., M. C. Koss, R. E. Nordquist, and C. P. Wilkinson. (1987) *J. Chromatogr.* 413, 9-15.
Gietz, R. D., R. H. Schiestl, A. R. Willems, and R. A. Woods. (1995) *Yeast* 11, 355-360.
Griffiths, G., N. J. Cook, E. Gottfridson, T. Lind, K. Lidholt, and I. S. Roberts. *J. Biol. Chem.,* 273, 11752-11757, 1998.
Hagopian, A. and E. H. Eylar. *Arch. Biochim. Biophys.,* 128, 422-433.
Hall, N. A. and A. D. Patrick. (1989) *Anal. Biochem.* 178, 378-384.
Hansen, L. M. and D. C. Hirch. (1989) *Vet. Microbiol.* 21, 177-184.
Hardingham, T. E. and A. J. Fosang. (1992) *FASEB J.* 6, 861-870.
Harmon, B. G., J. Glisson, K. S. Latimer, W. L. Stephens, and J. C. Nunnally. (1991) *Am. J. Vet Res.* 52, 1507-1511.
Hascall, V. C. and G. K. Hascall. (1981) in *Cell Biology of Extracellular Matrix* (Hay, E. D., ed) pp. 39-78, Plenum Publishing Corp. New York.
Heldermon, C., P. L. DeAngelis, and P. H. Weigel. (2001) *J. Biol. Chem.,* 276, 2037-2046.
Hempel, J., J. Perozich, H. Romavacek, A. Hinich, I. Kuo, and D. S. Feingold. (1994) *Protein Sci.* 3, 1074-1080.
Hodson, N., G. Griffiths, N. Cook, M. Pourhossein, E. Gottfridson, T. Lind, K. Lindholt, and I. S. Roberts. (2000) J. Biol. Chem., 275, 27311-27315.
Hofmann, K. and W. Stoffel. (1993) *Biol. Chem.* Hoppe-Seyler 347, 166 (abstr.)
Iivanainen, E., Kahari, V M., Heino, J., and Elenius, K. (2003) *Microsc Res Tech,* 60:13-22.
Ikegami-Kawai, M. and Takahashi, T. (2002) *Analytical Biochem,* 311(2), 157-165.
Itano, N., T. Sawai, M. Yoshida, P. Lenas, Y. Yamada, M. Imagawa, T. Shinomura, M. Hamaguchi, Y. Yoshida, Y.

Ohnuki, S. Miyauchi, A. P. Spicer, J. A. McDonald, and K. Kimata. (1999) *J. Biol. Chem.* 274(35), 25085-25092.
Jensen, R. A. (1976) Annu Rev Microbiol 30, 409-425
Jing, W. and P. L. DeAngelis. *Glycobiology.* 10(9):883-9, 2000.
Jing W. and DeAngelis, P. L., (2004) J Biol Chem 279, 42345-42349
Jing, W. and P. L. DeAngelis, Glycobiology, 2003, 13(10): p. 661R-71R.
Kane, T. A., White, C. L. and DeAngelis, P. L. (2006) J. Biol Chem 281, 33192-33197
Kim, B. T., et al., Proc Natl Acad Sci USA, 2001. 98(13): p. 7176-81.
Kitagawa, H., T. Uyama, and K. Sugahara. (2001) *J. Biol. Chem.,* 276, 38721-38726.
Kitagawa, H., et al., J. Biol Chem, 2007. 282(11): p. 8533-44.
Knudson, C. B. and W. Knudson (1993) *FASEB. J.* 7, 1233-1241.
Koyama, M., W. Helbert, T. Imai, J. Sugiyama, and B. Henrissat. (1997) *Proc. Natl. Acad. Sci. U.S.A.* 94, 9091-9095.
Kroll, J. S., B. Loynds, L. N. Brophy, and E. R. Moxon. (1990) *Mol. Microbiol.* 4, 1853-1862.
Kumari, K. and P. H. Weigel. (1997) *J. Biol. Chem.,* 272, 32539-32546.
Laurent, T. C., and J. R. E. Fraser. (1992) *FASEB J.* 6, 2397-2404.
Lee, C. J. (1987) *Mol. Immunol.,* 24, 1005-1019.
Lee, H G and Cowman, M K (1994) *Analytical Biochem.* 219(2), 278-287.
Li, J., D. M. Rancour, M. L. Allende, C. A. Worth, D. S. Darling, J. B. Gilbert, A. K. Menon and W. W. Young Jr. (2001) *Glycobiology,* 11, 217-229.
Lidholt, K. (1997) *Biochem. Soc. Trans.* 25, 866-870.
Lidholt, K. and M. Fjelstad. (1997) *J. Biol. Chem.* 272, 2682-2687.
Lidholt, K. and U. Lindahl. (1992) *Biochem J.* 287, 21-29.
Lindahl, U. and M. Hook. (1978) *Annu. Rev. Biochem.* 47, 385-417.
Lind, T., U. Lindahl, and K. Lidholt. (1993) *J. Biol. Chem.* 268, 20705-20708.
Lind, T. et al., (1998) *J. Biol. Chem.* 273, 11752-11757.
Liu, Z., Zhang, J., Chen, X. and Wang, P. G., (2002) Chembiochem 3(4), 348-355
Ludwigs, U., A. Elgavish, J. D. Esko, E. Meexan, and L. Roden. *Biochem. J.,* 245, 795-804, 1987.
Marks, D. L., M. Dominguez, K. Wu, and R. E. Pagano. (2001) *J. Biol. Chem.* 276, 26492-26498.
Markovitz, A., J. A. Cifonelli, and A. Dorfman. (1959) *J. Biol. Chem.* 234, 2343-2350.
May, B. J., Q. Zhang, L. Li, M. L. Paustian, T. S. Whittam, and V. Kapur. (2001) *Proc. Natl. Acad. Sci. U.S.A.* 98, 3460-3465.
Meyer, M. F., and G. Kreii (1996) *Proc. Natl. Acad. Sci. U.S.A.* 93, 4543-4547.
Morera, S., A. Imberty, U. Aschke-Sannenborn, P. S. Freemont, J. Janin, and W. Ruger. (1999) *J. Mol. Biol.* 311, 569-577.
Morera, S. L. Lariviere, J. Kurzeck, U. Aschke-Sannenborn, P. S. Freemont, J. Janin, and W. Ruger. (2001) *J. Mol. Biol.,* 311, 569-577.
Ohya, T. and Y. Kaneko. (1970) *Biochim. Biophys. Acta* 198, 607-609.
Pedersen, L. C., K. Tsuchida, H. Kitagawa, K. Sugahara, T. A. Darden, and M. Negishi. (2000) *J. Biol. Chem.,* 275, 34580-34585.
Persson, K., H. D. Ly, M. Dieckelmann, W. W. Wakarchuk, S. G. Withers, and N. C. J. Strynadka. (2001) *Nat. Struct. Biol.* 8, 166-175.
Petit, C., G. P. Rigg, C. Pazzani, A. Smith, V. Sieberth, M. Stevens, G. Boulnois, K. Jann, and I. S. Roberts. *Mol. Microbiol.,* 17, 611-620.
Prehm, P. (1983) *Biochem. J.* 211, 181-189.
Prehm, P. (1983) *Biochem. J.* 211, 191-198.
Pummill, P. E., et al., Biochim Biophys Acta, 2007. 1770(2): p. 286-90.
Pummill, P. E., E. S. Kempner and P. L. DeAngelis, J. Biol Chem, 2001. 276(43): p. 39832-5.
Pummill, P. E., and P. L. DeAngelis. *J. Biol. Chem.* 277(24): 21610-6, 2002.
Pummill P. E., A. M. Achyuthan, and P. L. DeAngelis. *J. Biol. Chem.* 273(9):4976-81, 1998.
Quinn, A. W., and K. P. Sing. (1957) *Proc. Soc. Exp. Biol. Med.* 95, 290-294.
Radominska, A. and R. R. Drake. (1994) *Methods Enzymol.* 230, 330-339.
Rahemtulla, F. and S. Lovtrup. (1975) *Comp. Biochem. Physiol.* 50B, 631-635.
Ramakrishnan, B. and P. Qasba. (2001) *J. Mol. Biol.* 310, 205-218.
Rejzek, M., Mukhopadhyay, B, Wenzel, C. Q., Lam. J. S, and Field, R. A., (2007) Carbohydr Res 342, 460-466
Rimler, R. B. (1994) *Vet Rec.* 134, 191-192.
Rimler, R. B. and K. R. Rhodes. (1987) *J. Clin. Microbiol.* 25, 615-618.
Rimler, R. B. (1994) *Vet. Rec.* 134, 191-192.
Rimler, R. B., K. B. Register, T. Magyar, and M. R. Ackermann. (1995) *Vet. Microbiol.* 47, 287-294.
Roberts, I. S. (1996) *Annu. Rev. Microbiol.* 50, 285-315.
Roberts, I. S., R. Mountford, R. Hodge, K. B. Jann, and G. Boulnois. (1988) *J. Bacteriol.* 170, 1305-1310.
Roden, L. (1980) in *The Biochemistry of Glycoproteins and Proteoglycans* (Lennarz, W. J., ed) pp. 267-371, Plenum Publishing Corp. New York.
Rodriguez, M. L, B. Jann, and K. Jann. (1988) *Eur. J. Biochem.* 177, 117-124.
Rohozinski, J., L. E. Girton, and J. L. Van Etten. *Virology* 168, 363 (1989).
Rosa, F., T. D. Sargent, M. L. Rebbert, G. S. Michaels, M. Jamrich, H. Grunz, E. Jonas, J. A. Winkles, and I. B. Dawid. (1988) *Dev. Biol.* 129, 114-123.
Rosner, H., H. D. Grimmecke, Y. A. Knirel, and A. S. Shashkov. (1992) *Carbohydr. Res.* 223, 329-333.
Sala, R. F., et al., Carbohydr Res. 1998. 306(1-2): p. 127-36.
Sambrook, J., E. F. Fritshc, and T. Maniatis. *Molecular Cloning: A Laboratory Manual,* $2^{nd}$ edn. Cold Spring Harbor, N.Y.: Cold Spring Laboratory Press. 1989.
Saxena, I. M., R. M. Brown, M. Fevre, R. A. Geremia, and B. Henrissat. *J. Bacterol.,* 177, 1419-1424, 1995.
Semino, C. E. and P. W. Robbins. (1995) *Proc. Natl. Acad. Sci. U.S.A.* 92, 3498-3501.
Semino, C. E., C. A. Specht, A. Raimondi, and P. W. Robbins. (1996) *Proc. Natl. Acad. Sci. U.S.A.* 93, 4548-4553.
Senay, C., et al., EMBO Rep, 2000. 1(3): p. 286-6.
Soltes, L., Mendichi, R., Lath, D., Mach, M. and Bakos, D. (2002) *Biomed. Chromatogr.* 16, 459-462.
Song, H H. and Films, J. (2002) *Biochim Biophys Acta,* 1573: 241-246.
Spicer, A. P. and J. A. McDonald. (1998), *J. Biol. Chem.* 273(4), 1923-1932.
Spicer, A. P. and T. K. Nguyen, Biochem Soc Trans, 1999. 27(2): p. 109-15.

Stoolmiller, A. C. and A. Dorfman. (1969) *J. Biol. Chem.* 244, 236-346.
Sugahara, K. and Kitagawa, H. (2002) IUBMB Life 54, 163-175
Sugahara, K., N. B. Schwartz and A. Dorfman. (1979) *J. Biol. Chem.* 254, 6252-6261.
Sunthankar, P. I. Pastuszak, A. Rooke, A. D. Elbein, I. van de Rijn, W. M. Canfield, and R. R. Drake. (1998) *Anal. Biochem.,* 258(2): 195-201.
Suzuki, M., et al., Biochem J, 1995. 307 (Pt3): p 817-21.
Svanborg-Eden, C., L. Hagberg, R. Hull, S. Hull, K. E. Magnusson, and L. Tarbouriech, N., S. J. Chamock, and G. J. Davies. (2001) *J. Mol. Biol.* 314, 655-661.
Taylor, K. A., and J. G. Buchanan-Smith. (1992) *Anal. Biochem.* 201, 190-196.
Telser, A., H. C. Robinson, and A. Dorfman. (1965) *Proc. Natl. Acad. Sci. U.S.A.* 54, 912-919.
Tengblad, A. (1980) *Biochem. J.* 185, 101-105.
Tlapak-Simmons, V. L., E. S. Kempner, B. A. Baggenstoss, and P. H. Weigel. (1998) *J. Biol. Chem.,* 273, 26100-26109.
Tlapak-Simmons, V. L., B. A. Baggenstoss, K. Kumari, C. Heldermon, and P. H. Weigel. (1999) *J. Biol. Chem.* 274, 4246-4253.
Townsend, K. M., J. D. Boyce, J. Y. Chung, A. J. Frost, and B. Adler. (2001) *J. Clin. Microbiol.,* 39, 924-929.
Tracy, B. S., et al., *J. Biol Chem* 2007. 282(1): p. 337-44.
Tsuchida, K., T. Lind, H. Kitagawa, U. Lindahl, K. Sugahara, and K. Lindholt. (1999) *Eur. J. Biochem.* 264, 461-467.
Uebelhart, D. and Williams, J M. (1999) *Curr. Opin in Rhematology,* 11, 427.
Unligil, U. M. and J. M. Rini. (2000) *Curr. Opin. Struct Biol.* 10, 510-517.
Unligil, U. M., S. Zhou, S. Yuwaraj, M. Sarkar, H. Schachter, and J. M. Rini. (2000) *EMBO J.* 19, 5269-5280.
van de Rijn, I. and R. R. Drake (1992) *J. Biol. Chem.* 267, 24302-24306.
van de Rijn, I. and R. E. Kessler. (1980) *Infect. Immun.* 27, 444-448.
Van Etten, J. L., D. E. Burbank, A. M. Schuster, and R. H. Meints, *Virology,* 140, 135 (1985).
Vann, W. F., M. A. Schmidt, B. Jann, and K. Jann. (1981) *Eur. J. Biochem.* 116, 359-364.
Varki, A. (1996) *Proc. Natl. Acad. Sci. U.S.A.* 93, 4523-4525.
Vimr, E. R., W. Aaronson, and R. P. Silver. (1989) *J. Bacteriol.* 171, 1106-1117.
Vlodavsky, I Miao, H Q, Medalion, B., Danager, P., and Ron, D. (1996) *Cancer Metastasis,* 15:177-186.
Vrielink, A., W. Ruger, H. P. C. Driessen, and P. S. Freemont. (1994) *EMBO J.* 15, 3413-3422.
Weigel, P. H., V. C. Hascall, and M. Tammi. *J. Biol. Chem.,* 272, 13997-14000, 1997.
Wessels, M. R., A. E. Moses, J. B. Goldberg, and T. J. DiCesare. (1991) *Proc. Natl. Acad. Sci. U.S.A.* 88, 8317-8321.
Wiggins, C. A. R., and S. Munro. (1998) *Proc. Natl. Acad. Sci. U.S.A.* 95, 7945-7950.
Williams, K. J., Halkes, K. M., Kamerling, J. P. and DeAngelis, P. L., (2006) J. Biol Chem 281, 5391-5397
Wilson, K. Preparation of genomic DNA from bacteria. In: Ausbel F M, Brent R, Kingston R E, et al., Eds. *Current Protocols in Molecular Biology*. New York: Wiley Interscience Publishing, 1987: 2.4.1-2.4.5.
Woodfield, T B, Bezemer, J M, Pieper, J S, van Blitterswijk, C A, and Riesle, J. (2002) *Crit. Rev Eukaryot Gene Expr,* 12:209-236.
Yamada, T., T. Higashiyama, and T. Fukuda, *Appl. Environ. Microbiol.* 57, 3433 (1991).
Yoshida, M., N. Itano, Y. Yamada, and K. Kimata. *J. Biol. Chem.,* 275, 497-506, 2000.
Zak, B. M., Crawford, B. E. and Esko, J. D. (2002) Biochim Biophys Acta 1573, 346-355

What is claimed is:

1. A method for enzymatically producing defined glycosaminoglycan polymers comprising the steps of:

providing at least one functional acceptor, wherein the functional acceptor comprises at least two sugar units, and wherein at least one of the at least two sugar units is selected from the group consisting of uronic acid, a uronic acid analog comprising a substitution at at least one of the C2 and C3 positions thereof, a hexosamine and a hexosamine analog comprising a substitution at at least one of the C2 and C6 positions thereof;

providing a recombinant heparosan synthase having an empty acceptor site and being capable of elongating the at least one functional acceptor in a controlled and/or repetitive fashion to form extended glycosaminoglycan molecules, and wherein the recombinant heparosan synthase is selected from the group consisting of:

(a) a recombinant heparosan synthase having an amino acid sequence as set forth in one of SEQ ID NOS: 6, 8, 66, 70 and 71;

(b) a recombinant heparosan synthase encoded by the nucleotide sequence of one of SEQ ID NOS: 5, 7 and 65;

(c) a recombinant heparosan synthase encoded by a nucleotide sequence that is at least 90% identical to at least one of SEQ ID NOS: 5, 7 and 65;

(d) a recombinant heparosan synthase encoded by a nucleic acid capable of hybridizing to the complement of the polynucleotide of at least one of SEQ ID NOS: 5, 7 and 65 under hybridization conditions comprising hybridization at a temperature of 68° C. in 5×SSC/5× Denhardt's solution/1.0% SDS, followed with washing in 3×SSC at 42° C.;

(e) a recombinant heparosan synthase encoded by a nucleic acid capable of hybridizing to the complement of a polynucleotide encoding an amino acid sequence as set forth in at least one of SEQ ID NOS: 6, 8, 66, 70 and 71 under hybridization conditions comprising hybridization at a temperature of 68° C. in 5×SSC/5× Denhardt's solution/1.0% SDS, followed with washing in 3×SSC at 42° C.; and providing at least one of a UDP-sugar and a UDP-sugar analog in a stoichiometric ratio to the at least one functional acceptor such that the recombinant heparosan synthase elongates the at least one functional acceptor to provide glycosaminoglycan polymers wherein the glycosaminoglycan polymers have a desired size distribution such that the glycosaminoglycan polymers are substantially monodisperse in size such that the glycosaminoglycan polymers have a polydispersity value in a range of from 1.0 to 1.5, and wherein the desired size distribution is obtained by controlling the stoichiometric ratio of UDP-sugar to functional acceptor.

2. The method of claim 1 wherein uronic acid is further defined as a uronic acid selected from the group consisting of GlcUA, iduronic acid (idoUA) and GalUA; hexosamine is further defined as a hexosamine selected from the group consisting of GlcNAc, GalNAc, GlcN GalN; the uronic acid analog is further defined as a uronic acid analog selected from the group consisting of GlcNAcUA, GlcdiNAcUA, and 2-deoxy-2-fluoro-GlcUA; and the hexosamine analog is further defined as a hexosamine analog selected from the group consisting of GlcN, GlcNAcNAc, GlcN[TFA], GlcNBut, GlcNPro, and 6-F-6-deoxyGlcNAc.

3. The method of claim 1, further comprising the step of providing a divalent metal ion, wherein the divalent metal ion is selected from the group consisting of manganese, magnesium, cobalt, nickel and combinations thereof, and wherein the method is carried out in a buffer having a pH from about 4 to about 9.

4. The method of claim 1 wherein at least one of:

(a) the substantially monodisperse glycosaminoglycan polymers have a molecular weight in a range of from about 3.5 kDa to about 0.5 MDa, and have a polydispersity value in a range of from about 1.0 to about 1.1;

(b) the substantially monodisperse glycosaminoglycan polymers have a molecular weight in a range of from about 0.5 MDa to about 4.5 MDa, and have a polydispersity value in a range of from about 1.0 to about 1.5; and (c) the substantially monodisperse glycosaminoglycan polymers have a molecular weight in a range of from about 0.5 MDa to about 4.5 MDa, and have a polydispersity value in a range of from about 1.0 to about 1.2.

5. The method of claim 1 wherein the at least one functional acceptor further comprises a moiety selected from the group consisting of a fluorescent tag, a radioactive tag or therapeutic, an affinity tag, a detection probe, a medicant, a biologically active agent, a therapeutic agent, and combinations thereof.

6. The method of claim 1 wherein the at least one of a UDP-sugar and a UDP-sugar analog is radioactive or nuclear magnetic resonance-active.

7. A method for enzymatically producing defined glycosaminoglycan polymers comprising the steps of:

providing at least one functional acceptor, wherein the functional acceptor has at least one sugar unit selected from the group consisting of uronic acid a uronic acid analog comprising a substitution at at least one of the C2 and C3 positions thereof, a hexosamine and a hexosamine analog comprising a substitution at at least one of the C2 and C6 positions thereof;

providing a recombinant heparosan synthase having an empty acceptor site and being capable of elongating the at least one functional acceptor in a controlled and/or repetitive fashion to form extended glycosaminoglycan molecules, and wherein the recombinant heparosan synthase is selected from the group consisting of:

(a) a recombinant heparosan synthase having an amino acid sequence as set forth in one of SEQ ID NOS: 6, 8, 66, 70 and 71;

(b) a recombinant heparosan synthase encoded by the nucleotide sequence of one of SEQ ID NOS: 5, 7 and 65;

(c) a recombinant heparosan synthase encoded by a nucleotide sequence that is at least 90% identical to at least one of SEQ ID NOS: 5, 7 and 65;

(d) a recombinant heparosan synthase encoded by a nucleic acid capable of hybridizing to the complement of the polynucleotide of at least one of SEQ ID NOS: 5, 7 and 65 under hybridization conditions comprising hybridization at a temperature of 68° C. in 5×SSC/5× Denhardt's solution/1.0% SDS, followed with washing in 3×SSC at 42° C.;

(e) a recombinant heparosan synthase encoded by a nucleic acid capable of hybridizing to the complement of a polynucleotide encoding an amino acid sequence as set forth in at least one of SEQ ID NOS: 6, 8, 66, 70 and 71 under hybridization conditions comprising hybridization at a temperature of 68° C. in 5×SSC/5× Denhardt's solution/1.0% SDS, followed with washing in 3×SSC at 42° C.; and providing at least one of a UDP-sugar and a UDP-sugar analog in a stoichiometric ratio to the at least one functional acceptor such that the recombinant heparosan synthase elongates the at least one functional acceptor to provide glycosaminoglycan polymers wherein the glycosaminoglycan polymers have a desired size distribution such that the glycosaminoglycan polymers are substantially monodisperse in size such that the glycosaminoglycan polymers have a polydispersity value in a range of from 1.0 to 1.5, and wherein the desired size distribution is obtained by controlling the stoichiometric ratio of UDP-sugar to functional acceptor.

8. The method of claim 7 wherein the functional acceptor comprises a glycoside of uronic acid.

9. The method of claim 7 wherein the at least one functional acceptor further comprises a moiety selected from the group consisting of a fluorescent tag, a radioactive tag or therapeutic, an affinity tag, a detection probe, a medicant, a biologically active agent, a therapeutic agent, and combinations thereof.

10. The method of claim 1 wherein the functional acceptor is at least one of:

(a) a heparosan oligosaccharide, polysaccharide or polymer;

(b) a heparin oligosaccharide, polysaccharide or polymer;

(c) a heparan oligosaccharide, polysaccharide or polymer;

(d) an acceptor comprising a glycoside of uronic acid; and (e) a sulfated or modified oligosaccharide, polysaccharide or polymer.

11. The method of claim 1, wherein the UDP-sugar is selected from the group consisting of UDP-GlcUA, UDP-GalUA UDP-GlcNAc, UDP-Glc, UDP-GalNAc, UDP-GlcN, UDP-GalN, and the UDP-sugar analog is selected from the group consisting of UDP-GlcN, UDP-GlcNAcUA, UDP- GlcNAcNAc, UDP-GlcdiNAcUA, UDP-GlcN[TFA], UDP-GlcNBut, UDP-GlcNPro, UDP-6-F-6-deoxyGlcNAc, and UDP-2-F-2-deoxyGlcUA.

12. The method of claim 7, wherein the UDP-sugar is selected from the group consisting of UDP-GlcUA, UDP-GalUA UDP-GlcNAc, UDP-Glc, UDP-GalNAc, UDP-GlcN, UDP-GalN, and the UDP-sugar analog is selected from the group consisting of UDP-GlcN, UDP-GlcNAcUA, UDP-GlcNAcNAc, UDP-GlcdiNAcUA, UDP-GlcN[TFA], UDP-GlcNBut, UDP-GlcNPro, UDP-6-F-6-deoxyGlcNAc, and UDP-2-F-2-deoxyGlcUA.

13. A method for enzymatically producing defined glycosaminoglycan polymers comprising the steps of:

providing at least one functional acceptor, wherein the functional acceptor has at least one sugar unit selected from the group consisting of uronic acid, a uronic acid analog comprising a substitution at at least one of the C2 and C3 positions thereof, a hexosamine and a hexosamine analog comprising a substitution at at least one of the C2 and C6 positions thereof;

providing a recombinant heparosan synthase having an empty acceptor site and being capable of elongating the at least one functional acceptor in a controlled and/or repetitive fashion to form extended glycosaminoglycan molecules, and wherein the recombinant heparosan synthase is a single dual-action enzyme possessing GlcUA-transferase and GlcNAc-transferase activities and comprises the motifs of SEQ ID NOS:63 and 64; and providing at least one of a UDP-sugar and a UDP-sugar analog in a stoichiometric ratio to the at least one functional acceptor such that the recombinant heparosan synthase elongates the at least one functional acceptor to provide glycosaminoglycan polymers wherein the glycosaminoglycan polymers have a desired size distribution such that the glycosaminoglycan polymers are substantially monodisperse in size such that the glycosaminoglycan polymers have a polydispersity value in a range of from 1.0 to 1.5, and wherein the desired size distribution is obtained by controlling the stoichiometric ratio of UDP-sugar to functional acceptor.

14. The method of claim 13 wherein the functional acceptor comprises a glycoside of uronic acid.

15. The method of claim 13 wherein the at least one functional acceptor further comprises a moiety selected from the group consisting of a fluorescent tag, a radioactive tag or therapeutic, an affinity tag, a detection probe, a medicant, a biologically active agent, a therapeutic agent, and combinations thereof.

16. The method of claim 13 wherein the functional acceptor is at least one of:

(a) a heparosan oligosaccharide, polysaccharide or polymer;
(b) a heparin oligosaccharide, polysaccharide or polymer;
(c) a heparan oligosaccharide, polysaccharide or polymer;
(d) an acceptor comprising a glycoside of uronic acid; and
(e) a sulfated or modified oligosaccharide, polysaccharide or polymer.

17. The method of claim 13, wherein the UDP-sugar is selected from the group consisting of UDP-GlcUA, UDP-GalUA UDP-GlcNAc, UDP-Glc, UDP-GalNAc, UDP-GlcN, UDP-GalN, and the UDP-sugar analog is selected from the group consisting of UDP-GlcN, UDP-GlcNAcUA, UDP-GlcNAcNAc, UDP-GlcdiNAcUA, UDP-GlcN[TFA], UDP-GlcNBut, UDP-GlcNPro, UDP-6-F-6-deoxyGlcNAc, and UDP-2-F-2-deoxyGlcUA.

* * * * *

UNITED STATES PATENT AND TRADEMARK OFFICE

CERTIFICATE OF CORRECTION

PATENT NO. : 8,088,604 B2
APPLICATION NO. : 11/906704
DATED : January 3, 2012
INVENTOR(S) : Paul L. DeAngelis et al.

It is certified that error appears in the above-identified patent and that said Letters Patent is hereby corrected as shown below:

On the title page, under “Related U.S. Application Data” (63)
Line 1: Delete “No. 11/165,379,” and replace with -- No. 11/651,379, --

In the Specification:
Column 12, line 32: Delete “cloning” and replace with -- clotting --
Column 55, line 25: Delete “buccai/gingival” and replace with -- buccal/gingival --
Column 61, line 3: Delete “E. Coli” and replace with -- E. coli --
Column 63, line 27: Delete “GARTTYBTIMRIGARGGIM-” and replace with -- GARTTYBTIMRIGARGGIAA- --
Column 63, line 29: Delete “ICC1CCRTAICCRAAISWXGGRTTRTTRTARTG” and replace with -- ICCICCRTAICCRAAISWXGGRTTRTTRTARTG --

In the References:
Column 67, line 13: Delete “Falabelia,” and replace with -- Falabella, --
Column 67, line 13: Delete “Eagistein,” and replace with -- Eaglstein, --
Column 67, line 28: Delete “Seizer,” and replace with -- Selzer, --
Column 67, line 60: Delete “Elten.” and replace with -- Etten. --
Column 68, line 25: After “1232” insert -- -1237 --
Column 69, line 55: Delete “Kreii” and replace with -- Kreil --
Column 70, line 62: Delete “Films,” and replace with -- Filmus, --
Column 71, line 1: Delete “Stool miller,” and replace with -- Stoolmiller, --
Column 71, line 12: Delete “Chamock,” and replace with -- Charnock, --

In the Claims:
Column 215, line 23: Delete “(idoUA)” and replace with -- (IdoUA) --

Signed and Sealed this
First Day of May, 2012

David J. Kappos
*Director of the United States Patent and Trademark Office*